(12) United States Patent
Aldred et al.

(10) Patent No.: US 10,663,455 B2
(45) Date of Patent: May 26, 2020

(54) TRANSCRIPTION BIOMARKERS OF BIOLOGICAL RESPONSES AND METHODS OF USE

(71) Applicant: SwitchGear Genomics, Inc., Menlo Park, CA (US)

(72) Inventors: Shelley Force Aldred, Hayward, CA (US); Nathan D. Trinklein, Redwood City, CA (US); Michael Rose, Walnut Creek, CA (US); Patrick Collins, Millbrae, CA (US)

(73) Assignee: ACTIVE MOTIF, INC., Carlsbad, CA (US)

( * ) Notice: Subject to any disclaimer, the term of this patent is extended or adjusted under 35 U.S.C. 154(b) by 423 days.

(21) Appl. No.: 15/457,999

(22) Filed: Mar. 13, 2017

(65) Prior Publication Data
US 2017/0191987 A1  Jul. 6, 2017

Related U.S. Application Data

(62) Division of application No. 14/329,984, filed on Jul. 13, 2014, now Pat. No. 9,663,823, which is a division of application No. 12/586,131, filed on Sep. 16, 2009, now Pat. No. 8,815,779.

(51) Int. Cl.
| | |
|---|---|
| *C12Q 1/68* | (2018.01) |
| *G01N 33/50* | (2006.01) |
| *C12Q 1/6886* | (2018.01) |
| *C12Q 1/6883* | (2018.01) |
| *C12Q 1/6876* | (2018.01) |
| *C12N 15/10* | (2006.01) |

(52) U.S. Cl.
CPC ..... *G01N 33/5011* (2013.01); *C12N 15/1037* (2013.01); *C12Q 1/6876* (2013.01); *C12Q 1/6883* (2013.01); *C12Q 1/6886* (2013.01); *C12Q 2600/136* (2013.01); *C12Q 2600/158* (2013.01)

(58) Field of Classification Search
CPC .......................... C12Q 1/6886; C12Q 1/6876
See application file for complete search history.

(56) References Cited

U.S. PATENT DOCUMENTS

| | | | |
|---|---|---|---|
| 5,143,854 A | 9/1992 | Pirrung et al. |
| 5,242,974 A | 9/1993 | Holmes |
| 5,252,743 A | 10/1993 | Barrett et al. |
| 5,292,658 A | 3/1994 | Cormier et al. |
| 5,324,633 A | 6/1994 | Fodor et al. |
| 5,384,261 A | 1/1995 | Winkler et al. |
| 5,424,186 A | 6/1995 | Fodor et al. |
| 5,445,934 A | 8/1995 | Fodor et al. |
| 5,451,683 A | 9/1995 | Barrett et al. |
| 5,482,867 A | 1/1996 | Barrett et al. |
| 5,491,074 A | 2/1996 | Aldwin et al. |
| 5,527,681 A | 6/1996 | Holmes |
| 5,550,215 A | 8/1996 | Holmes |
| 5,571,639 A | 11/1996 | Hubbell et al. |
| 5,578,832 A | 11/1996 | Trulson et al. |
| 5,593,839 A | 1/1997 | Hubbell et al. |
| 5,599,695 A | 2/1997 | Pease et al. |
| 5,624,711 A | 4/1997 | Sundberg et al. |
| 5,625,048 A | 4/1997 | Tsien et al. |
| 5,631,734 A | 5/1997 | Stern et al. |
| 5,677,195 A | 10/1997 | Winkler et al. |
| 5,708,153 A | 1/1998 | Dower et al. |
| 5,744,305 A | 4/1998 | Fodor et al. |
| 5,770,358 A | 6/1998 | Dower et al. |
| 5,789,162 A | 8/1998 | Dower et al. |
| 5,795,716 A | 8/1998 | Chee |
| 5,800,992 A | 9/1998 | Fodor et al. |
| 5,807,522 A | 9/1998 | Brown et al. |
| 5,831,070 A | 11/1998 | Pease et al. |
| 5,837,832 A | 11/1998 | Chee et al. |
| 5,854,004 A | 12/1998 | Czernilofsky et al. |
| 5,856,101 A | 1/1999 | Hubbell et al. |
| 5,858,659 A | 1/1999 | Sapolsky et al. |
| 5,871,928 A | 2/1999 | Fodor et al. |
| 5,888,765 A | 3/1999 | Patterson et al. |
| 5,936,324 A | 8/1999 | Montagu |
| 5,968,740 A | 10/1999 | Fodor et al. |
| 5,974,164 A | 10/1999 | Chee |
| 5,981,185 A | 11/1999 | Matson et al. |

(Continued)

FOREIGN PATENT DOCUMENTS

| | | |
|---|---|---|
| EP | 1176196 A1 | 1/2002 |
| EP | 1447413 A2 | 8/2004 |

(Continued)

OTHER PUBLICATIONS

Liu, J. et al., "Identification of cell type-specific promoter elements associated with the rat tyrosine hydroxylase gene using transgenic founder analysis", Molecular Brain Research, 50 '1997), p. 33-42.
Liu, X., et al., "Bioprospector: discovering conserved DNA motifs in upstream regulatory regions of co-expressed genes", Pacific Symposium on Biocomputing, 6 (2001), 127-138.
Lonnerberg, P. et al., "Cell Type-specific Regulation of Choline Acetyltransferase Gene Expression", The Journal of Biological Chemistry, 271 (Dec. 27, 1996), 33358-33365.
Lunyak, V.V., et al., "REST and Peace for the Neuronal-Specific Transcriptional Program", Ann. N.Y. Acad. Sci., 1014 (2004) 110-120.
Mazumder, B., et al., "Translational control by the 3.-UTR: the ends specify the means", Trends in Biochemical Sciences, 28 (Feb. 2003), 91-98.

(Continued)

*Primary Examiner* — Antonio Galisteo Gonzalez
(74) *Attorney, Agent, or Firm* — John Storella, P.C.

(57) ABSTRACT

This invention provides transcription regulatory control sequences, the activity of which function as biomarkers for a variety of biological responses. This invention also provides expression constructs in which a biomarker transcription regulatory sequence is operably linked with a sequence for a reporter. Cells that comprise these expression constructs can be used in assays to identify conditions that modulate activity of the biological response.

31 Claims, 102 Drawing Sheets

Specification includes a Sequence Listing.

(56) References Cited

U.S. PATENT DOCUMENTS

| | | |
|---|---|---|
| 5,981,956 A | 11/1999 | Stern |
| 6,025,601 A | 2/2000 | Trulson et al. |
| 6,033,860 A | 3/2000 | Lockhart et al. |
| 6,040,193 A | 3/2000 | Winkler et al. |
| 6,054,270 A | 4/2000 | Southern |
| 6,090,555 A | 7/2000 | Fiekowsky et al. |
| 6,110,426 A | 8/2000 | Shalon et al. |
| 6,200,760 B1 | 3/2001 | Dannenberg et al. |
| 6,232,107 B1 | 5/2001 | Bryan et al. |
| 6,242,211 B1 | 6/2001 | Peterson et al. |
| 6,261,776 B1 | 7/2001 | Pirrung et al. |
| 6,291,183 B1 | 9/2001 | Pirrung et al. |
| 6,537,746 B2 | 3/2003 | Arnold et al. |
| 6,544,790 B1 | 4/2003 | Sabatini |
| 6,605,431 B1 | 8/2003 | Gourse et al. |
| 6,610,482 B1 | 8/2003 | Fodor et al. |
| 6,630,324 B1 | 10/2003 | Barski et al. |
| 6,670,129 B2 | 12/2003 | Webb et al. |
| 6,713,665 B2 | 3/2004 | Crane et al. |
| 6,951,757 B2 | 10/2005 | Sabatini |
| 7,058,515 B1 | 6/2006 | Selifonov et al. |
| 7,060,459 B2 | 6/2006 | Saus |
| 7,067,649 B2 | 6/2006 | Harats |
| 7,084,267 B1 | 8/2006 | Keith |
| H2191 H | 6/2007 | Wang |
| 8,815,779 B2 | 8/2014 | Aldred et al. |
| 2002/0006664 A1 | 1/2002 | Sabatini |
| 2003/0008283 A1 | 1/2003 | Li |
| 2003/0211481 A1 | 11/2003 | Erives et al. |
| 2004/0005577 A1 | 1/2004 | Rosen et al. |
| 2004/0043468 A1 | 3/2004 | Mauro et al. |
| 2004/0091866 A1 | 5/2004 | Giordano et al. |
| 2004/0129543 A1 | 7/2004 | Voltz et al. |
| 2004/0146964 A1 | 7/2004 | Maxwell et al. |
| 2004/0219543 A1 | 11/2004 | Wirtz |
| 2005/0074827 A1 | 4/2005 | Muh et al. |
| 2005/0084848 A1 | 4/2005 | Phillips |
| 2006/0183115 A1 | 8/2006 | Wang |
| 2006/0263764 A1 | 11/2006 | Pachuk |
| 2007/0072175 A1 | 3/2007 | Cooper et al. |
| 2007/0161031 A1 | 7/2007 | Trinklein et al. |
| 2007/0243176 A1 | 10/2007 | Escobedo et al. |
| 2007/0258895 A1 | 11/2007 | Wang |
| 2008/0044436 A1 | 2/2008 | Hum et al. |
| 2008/0220983 A1 | 9/2008 | Trinklein et al. |
| 2009/0018031 A1 | 1/2009 | Trinklein et al. |
| 2009/0035216 A1 | 2/2009 | Svenson et al. |

FOREIGN PATENT DOCUMENTS

| | | |
|---|---|---|
| WO | 9106677 | 5/1991 |
| WO | 2000074725 A1 | 12/2000 |
| WO | 2002031111 A3 | 10/2002 |
| WO | 2003031568 A2 | 8/2003 |
| WO | 2003072035 A2 | 9/2003 |
| WO | 2001057190 A3 | 11/2006 |
| WO | 2008073303 A3 | 11/2008 |
| WO | 2011034935 A3 | 10/2011 |

OTHER PUBLICATIONS

Metzen, E., et al., "Intracellular localization of human HIF-1a hydroxylases: implications for oxygen sensing", J. Cell Sci., 116 (2003), 1319-1326.

Metzen, E., et al., "Regulation of the prolyl hydroxylase domain protein 2 (phd2/egln-1) gene: identification of a functional hypoxia-responsive element", Biochem. J., 387 (2005), 711-717.

Meyer, S., et al., "Messenger RNA Turnover in Eukaryotes: Pathways and Enzymes", Critical Reviews in Biochemistry and Molecular Biology, 39 (2004), 197-216.

Min, Nan et al., "5' Upstream DNA sequence of the rat tyrosine hydroxylase gene directs high-level and tissue-specific expression to catecholaminergic neurons in the central nervous system of transoenic mice", Molecular Brain Research, 27 (1994), o. 281-289.

Mullner, E.W., et al., "A Stem-Loop in the 3' Untranslated Region Mediates Iron-Dependent Regulation of Transferrin Receptor mRNA Stability in the Cytoplasm", Cell, 53 (Jun. 3, 1988), 815-825.

Murray, J.I., et al., "Diverse and Specific Gene Expression Responses to Stresses in Cultured Human Cells", Biology of the Cell, 15 (May 2004), 2361-2374.

Myers, R.M., et al., Fine Structure Genetic Analysis of a 6-Globin Promoter, Science, 232 (May 2, 1986), 613-618.

National Institutes of Health, Mammalian Gene Collection, home page [online], [retrieved on May 22, 2008]. Retrieved the Internet: (2008), 2 p.

National Institutes of Health, NCBI RefSeq, home page [online], [retrieved on Mar. 14, 2008]. Retrieved from the Internet: http://www.ncbi.nlm.nih.gov/RefSeq/> (2008), 4 p.

National Institutes of Health, NCBI RefSeq, home page, Release 28 [online], [retrieved on Mar. 14, 2008]. Retrieved from Internet: (2008), 4 p.

National Institutes of Health, NCBI RefSeq, home page, Release 29 [online], [retrieved on May 22, 2008]. Retrieved from Internet: (2008), 3 p.

Wilusz, C.J., et al., "Bringing the role of mRNA decay in the control of gene expression into focus", Trends in Genetics, 20 (Oct. 2004), 491-497.

Ogbourne, S., et al., "Transcriptional control and the role of silencers in transcriptional regulation in eukaryotes", J., 331 (1998), 1-14.

Okazaki, Y. et al., Analysis of the mouse transcriptome based on functional annotation of 60,770 full-length cDNAs, Nature, 420 (2002), p. 563-573.

WIPO; PCT/US2010/048950—ISR/Written Opinion/Preliminary Report on Patentability, dated Aug. 11, 2011, 17 pgs.

Perier, R.C., et al., "The Eukaryotic Promoter Database EPD", Nucleic Acids Research, 26 (1998), 353-357.

Pesole, G., et al., "UTRdb and UTRsite: specialized databases of sequences and functional elements of 5' and 3' regions of eukaryotic mRNAs. Update 2002", Nucleic Acids Research, 30 (2002), 335-340.

Pirkkala, L., et al., "Roles of the heat shock transcription factors in regulation of the heat shock response and beyond", FASEB Journal, 15 (May 2001), 1118-1131.

Praz, V., et al., "The Eukaryotic Promoter Database, EPD: new entry types and links to gene expression data", Nucleic Research, 30 (2002), 322-324.

Pujol A, "Characterization of the Adrenoleukodystrophy-Related (ALDR, ABCD2) Gene Promoter: Inductibility by Retinoic Acid and Forskolin", Genomics, Academic Press, vol. 70, No. 1, (Nov. 15, 2000), 131-139.

Rimokh, R., et al., "Rearrangement of CCND1 (BCL1/PRAD1) 3' Untranslated Region in Mantle-Cell Lymphomas and t(11q13)-Associated Leukemias", Blood, 83 (Jun. 15, 1994), 3689-3696.

Rozen, S et al., "Primer3 on the WWW for General Users and for Biologist Programmers", Methods in Molecular Biology, 132 (2000), 365-386.

Schoenherr, C.J., et al., "Identification of potential target genes for the neuron-restrictive silencer factor", Proc. Natl. Acad. Sci. USA, 93 (1996), 9881-9886.

Schoenher, C.J., et al., "The Neuron-Restrictive Silencer Factor (NRSF): A Coordinate Repressor of Multiple Neuron-Specific Genes", Science, 267 (Mar. 3, 1995), 1360-1363.

Score, sequence listing for Cooper et al., U.S. Patent Application Publication No. 2007/0072175 [online]. [retrieved on Mar. 9, 2010]. Retrieved from the Internet: , 5 p.

Semenza, G L, "Hypoxia response elements in the aldolase A, enolase 1, and lactate dehydrogenase A gene promoters contain essential binding sites for hypoxia-inducible factor 1", Journal of Biological Chemistry, American Society for Biochemistry and Molecular Biology, vol. 271, No. 51, (Dec. 20, 1996), 32529-32537.

Suzuki, Y., et al., "DB-MS: DataBase of human Transcriptional Start Sites and full-length cDNAs", Nucleic Acids Research, 30 (2002), 328-331.

(56) References Cited

OTHER PUBLICATIONS

Suzuki, Y., et al., "DBTSS: DataBase of Transcriptional Start Sites: progress report 2004", Nucleic Acids Research, 32 (2004), D78-D81.
Suzuki, Y., et al., "Identification and Characterization of the Potential Promoter Regions of 1031 Kinds of Human Genes", Genome Research, 11 (2001), 677-684.
Suzuki-Yagawa, Y., et al., "The ts13 Mutation in the TAFII250 Subunit (CCG1) of TFIID Directly Affects Transcription of D-Type Cyclin Genes in Cells Arrested in G1 at the Nonpermissive Temperature", Molecular and Cellular Biology, 17 (Jun. 1997), 3284-3294.
Tarnasky, H., et al., "A novel testis-specific gene, SPAG4, whose product interacts specifically with outer dense fiber protein ODF27, maps to human chromosome 20q11.2", Cytogenet. Cell Genet., 81 (1998), 65-67.
Tatarelli, C., et al., "Characterization of the Human TESTIN Gene Localized in the FRA7G Region at 7q31.2", Genomics, 68 (2000), 1-12.
The ENCODE Project Consortium, "Identification and analysis of functional elements in 1% of the human genome by the ENCODE pilot project", Nature, 447 (Jun. 2007), 799-816.
The ENCODE Project Consortium, "The ENCODE (Encyclopedia of DNA Elements) Project", Science, 306 (Oct. 22, 2004), 636-640.
The FANTOM Consortium and the RIKEN Genomic Exploration Research Group Phase I & II Team, "Analysis of the mouse transcriptome based on functional annotations of 60,770 full-length cDNAs", Nature, 420 (Dec. 5, 2002), 563-573.
The Gene Ontology, home page [online], [retrieved on Mar. 14, 2008]. Retrieved from the Internet: (2008), 2 p.
The I.M.A.G.E. Consortium, home page [online], [retrieved on Jun. 12, 2008]. Retrieved from the Internet: http://image.llnl.gov/> (2008), 1 p.
The MGC Project Team, "The Status, Quality, and Expansion of the NIH Full-Length cDNA Project: The Mammalian Gene Collection (MGC)", Genome Research, 14 (2004), 2121-2127.
Theodorakis, N.G., et al,. Posttranscriptional Regulation of hsp70 Expression in Human Cells: Effects of Heat Shock, Inhibition of Protein Synthesis, and Adenovirus Infection on Translation and mRNA Stability, Molecular and Cellular Biology, 7 (Dec. 1987), 4357-4368.
Xie, X, et al., "Systematic discovery of regulatory motifs in human promoters and 3' UTRs by comparison of several mammals", Nature, 434 (Mar. 17, 2005), 338-345.
Yang, A., et al., "p63, a p53 Homolog at 3q27-29, Encodes Multiple Products with Transactivating, Death-Inducing, and Dominant-Negative Activities", Molecular Cell, 2 (Sep. 1998), 305-316.
Yasumoto, K-I. et al. "Role of the intracellular localization 1-55 of HIF-prolyl hydroxylases", Biochim. Biophy. Acta, Feb. 2009(available on line), vol. 1793, pp. 792-797. See abstract, fig. 1 and materials and methods.]].
Trinklein, N.D., et al., "Integrated analysis of experimental data sets reveals many novel promoters in 1% of the human genome", Genome Research, 17 (2007), 720-731.
Trinklein, N.D., et al., "The Role of Heat Shock Transcription Factor 1 in the Genome-wide Regulation of the Mammalian Heat Shock Response", Molecular Biology of the Cell, 15 (Mar. 2004), 1254-1261.
Trinklein, N.D., et al., "Transcriptional regulation and binding of heat shock factor 1 and heat shock factor 2 to 32 human heat shock genes during thermal stress and differentiation", Cell Stress & Chaperones, 9 (2004), 21-28.
Ahituv, N., et al., "Exploiting human-fish genome comparisons for deciphering gene regulation", Human Molecular Genetics, 13 (2004), 261-266.
Bailey, T.L., et al., "Fitting a Mixture Model by Expectation Maximization to Discover Motifs in Biopolymers", Proceedings of the Second International Conference on Intelligent Systems for Molecular Biology, AAAI Press (Aug. 1994), 28-36.

Trinklein, Nathan D., et al., "Identification and Functional Analysis of Human Transcriptional Promoters", Genome Res., 13 (2003), o. 308-312.
Bertone, P., et al., "Global Identification of Human Transcribed Sequences with Genome Tiling Arrays", Science, 306 (Dec. 24, 2004), 2242-2246.
Blais, A., et al., "Hitting their targets: an emerging picture of E2F and cell cycle control", Current Opinion in Genetics & Development, 14 (2004), 527-532.
Brudno, M., et al., "LAGAN and Multi-LAGAN: Efficient Tools for Large-Scale Multiple Alignment of Genomic DNA", Genome Research, 13 (2003), 721-731.
Buckland, P.R., et al., "Stong Bias in the Location of Functional Promoter Polymorphisms", Human Mutation, 26 (2005), 214-223.
Butler, J.E.F., et al., "The RNA polymerase II core promoter: a key component in the regulation of gene expression", Genes & Development, 16 (2002), 2583-2592.
Carlson, C.S., et al., "Polymorphisms within the C-Reactive Protein (CRP) Promoter Region Are Associated with Plasma CRP Levels", Am. J. Hum. Genet., 77 (2005), 64-77.
Casey, J.L., et al., Two genetic loci participate in the regulation by iron of the gene for the human transferrin receptor, Proc. Natl. Acad. Sci. USA, 85 (Mar. 1998) 1787-1791.
Collins, F.S., et al., "A point mutation in the Aγ-globin gene promoter in Greek hereditary persistence of fetal haemoglobin", Nature, 33 (Jan. 24, 1985), 325-326.
Conne, B., et al., "The 3' untranslated region of messenger RNA: A molecular 'hotspot' for pathology?", Nature Medicine, 6 (Jun. 2000), 637-641.
Cooper, G.M., et al., "Distribution and intensity of constraint in mammalian genomic sequence", Genome Research, 15 (2005), 901-913.
Cooper, Sara J., et al., "Comprehensive analysis of transcriptional promoter structure and function in 1% of the human genome", Genome Res. 2006 16: 1-10.
Wang, E.H., "Promoter-Selective Transcriptional Defect in Cell Cycle Mutant ts13 Rescued by hTAFII1250", Science, 263 (Feb. 11, 1994), 811-814.
Davuluri, R.V., et al., "CART Classification of Human 5' UTR Sequences", Genome Research, 10 (Nov. 2000), 1807-1816.
Dixon, W.J., "Analysis of Extreme Values", The Annals of Mathematical Statistics, 21 (1950), 488-506.
European Patent Application No. 08726512.0, Search Report dated Nov. 11, 2010, 7 p.
European Patent Office Annex to Communication Pursuant to Article 94(3) EPC—Examination of EP Application No. 10 817 769.2-1404, Aug. 29, 2016, 6 pgs.
European Patent Office Annex to Communication Pursuant to Article 94(3) EPC—Examination of EP Application No. 10 817 769.2-1404; May 29, 2015, 9 pgs.
European Patent Office Annex to Communication Pursuant to Article 94(3) EPC—Examination of EP Application No. 10 817 769.2-1404, Jan. 2, 2016, 4 pgs.
European Patent Office Annex to Communication Pursuant to Article 94(3) EPC—Examination of EP Application No. 10 817 769.5-1404, Feb. 20, 2017, 7 pgs.
European Patent Office Communication Pursuant to Article 94(3) EPC—Examination of EP Application No. 10 317 769.2-1404, Jul. 11, 2017, 6 pgs.
European Patent Office, European Application No. 10817769, Supplementary European Search Report dated Dec. 12, 2012, 13 pgs.
Evans, W.E., et al., "Pharmacogenomics: Translating Functional Genomics into Rational Therapeutics", Science, 286 (1999), 487-491.
Fodor, S.P.A., et al., "Light-Directed, Spatially Addressable Parallel Chemical Synthesis", Science, 251 (Feb. 15, 1991), 767-773.
Gao, Fen-Biao et al., "Selection of a subset of mRNAs from combinatorial 3' untranslated region libraries using neuronal RNA-binding protein Hel-N1", Proc. Natl. Acad. Sci. USA, 91 '1994), p. 11207-11211.
Gentles, A.J., et al., Why are human G-protein-coupled receptors predominantly intronless?, Trends in Genetics, 15 (Feb. 1999), 47-49.

(56) References Cited

OTHER PUBLICATIONS

Guillemin, K. et al., "The Hypoxic Response: Huffing and HIFing", Cell, 89 (1997), p. 9-12.

Hattori, M., et al., "*Homo sapiens* genomic DNA, chromosome Un, clone:CMC-190A2, telomere region, complete sequence", NCBI Sequence Viewer, Entrez, Accession AP006221, National Institutes of Health (1993) [online], [retrieved Jan. 24, 2008]. Retrieved from the Internet , 12 p.

Hentschel, C.C., et al., "The Organization and Expression of Histone Gene Families", Cell, 25 (Aug. 1981), 301-313.

Weiler, J., et al., "Hybridisation based DNA screening on peptide nucleic acid (PNA) oligomer arrays", Nucleic Acids Research, 25 (1997), 2792-2799.

Weiss, I.M., et al., "Erythroid Cell-Specific mRNA Stability Elements in the a2-Globin 3' Nontranslated Region", Molecular and Cellular Biology, 15 (May 1995), 2457-2465.

Howard, M.L., et al, "cis-Regulatory control circuits in development", Developmental Biology, 271 (2004), 109-118.

Wilson, et al., "A Novel Cell Line, MDA-kb2, That Stably Expresses an Androgent and Glucocorticoid-Responsive Reporter for the Detection of Hormone Receptor Agonists and Antagonists," Toxicological Sciences, 66 (2002), 69-81.

Imanishi, T., et al., "Integrative Annotation of 21,037 Human Genes Validated by Full-Length cDNA Clones", PLoS Biology, 2 (Jun. 2004), 0856-0875.

Kamura, N., et al., "Selection of 5'-untranslated sequences that enhance initiation of translation in a cell-free protein synthesis system from wheat embryos" Bioorganic & Medicinal Chemistry Letters, 15 (2005), 5402-5406.

Kanamori, H., et al., "Differential Display Combined with a Regulated Transient Expression System", Bio Techniques, 26 (Jun. 1999), 1018-1020.

Kapranov, P., et al., "Large-Scale Transcriptional Activity in Chromosomes 21 and 22", Science, 296 (May 3, 2002), 916-919.

Karolchik, D., et al., "The UCSC Genome Browser Database", Nucleic Acids Research, 31 (2003), 51-54.

Kaul, R.K., et al., "*Homo sapiens* chromosome 1 clone RP4-700A9, complete sequence", NCBI Sequence Viewer, Accession AC099680, National Institutes of Health (2002) [online], [retrieved Sep. 6, 2011]. Retrieved from the Internet , 25 p.

Kim, N., et al., "A Novel Member of the Leukocyte Receptor Complex Regulates Osteoclast Differentiation", J. Exp. Med., 195 (Jan. 21, 2002), 201-209.

Kim, T.H., et al., "Direct isolation and identification of promoters in the human genome", Genome Research, 15 (2005), 830-839.

Kimmel, A.R., et al., "Preparation of cDNA and the Generation of cDNA Libraries: Overview", Methods in Enzymology, 152 (1987), 307-316.

Krumm, A., et al., "Promoter-proximal pausing of RNA polymerase II defines a general rate-limiting step after transcription initiation", Genes & Development, 9 (1995), 559-572.

Krumm, A., et al., "The block to transcriptional elongation within the human c-myc gene is determined in the promoter-proximal region", Genes & Development, 6 (1992), 2201-2213.

Kulozik, A.E., et al., "Thalassemia Intermedia: Moderate Reduction of 13 Globin Gene Transcriptional Activity by a Novel Mutation of the Proximal CACCC Promoter Element", Blood, 77 (May 1, 1991), 2054-2058.

Landry J.R., et al., "Complex controls: the role of alternative promoters in mammalian genomes", Trends in Genetics, 19 (Nov. 2003), 640-648.

Le, P.P., et al., "Glucocorticoid Receptor-Dependent Gene Regulatory Networks", PLoS Genetics, 1 (Aug. 2005), 0159-0170.

Lewis, Benjamin P., et al., "Prediction of Mammalian MicroRNA Targets", Cell, 115 (2003), p. 787-798.

FIG. 1A  TABLE 1 TRANSCRIPTIONAL BIOMARKER FUNCTIONAL DATA
PART 1
SECTION 1:

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS* |
|---|---|---|---|---|---|---|
| 1 | EGLN1 | SEQ ID NO. 1 | 732.385 | 1154.843 | 1.577 | HYPOX_DFO_HCT116 |
| 2 | EGLN1 | SEQ ID NO. 1 | 8.435 | 292.298 | 34.654 | HYPOX_DFO_HT1080 |
| 3 | EGLN1 | SEQ ID NO. 1 | 732.385 | 1989.674 | 2.717 | HYPOX_O2_HCT116 |
| 4 | EGLN1 | SEQ ID NO. 1 | 8.435 | 231.019 | 27.389 | HYPOX_O2_HT1080 |
| 5 | LDHA | SEQ ID NO. 2 | 1306.69 | 9656.519 | 7.39 | HYPOX_DFO_HCT116 |
| 6 | LDHA | SEQ ID NO. 2 | 106.747 | 2987.773 | 27.989 | HYPOX_DFO_HT1080 |
| 7 | LDHA | SEQ ID NO. 2 | 1306.69 | 4101.176 | 3.139 | HYPOX_O2_HCT116 |
| 8 | LDHA | SEQ ID NO. 2 | 106.747 | 1712.725 | 16.045 | HYPOX_O2_HT1080 |
| 9 | GAPDH | SEQ ID NO. 3 | 567 | 1030.545 | 1.818 | HYPOX_DFO_HCT116 |
| 10 | GAPDH | SEQ ID NO. 3 | 208.992 | 956.212 | 4.575 | HYPOX_DFO_HT1080 |
| 11 | GAPDH | SEQ ID NO. 3 | 567 | 1038.687 | 1.832 | HYPOX_O2_HCT116 |
| 12 | GAPDH | SEQ ID NO. 3 | 208.992 | 672.815 | 3.219 | HYPOX_O2_HT1080 |
| 13 | ALDOA | SEQ ID NO. 4 | 3644.442 | 13844.666 | 3.799 | HYPOX_DFO_HCT116 |
| 14 | ALDOA | SEQ ID NO. 4 | 686.221 | 2889.334 | 4.21 | HYPOX_DFO_HT1080 |
| 15 | ALDOA | SEQ ID NO. 4 | 3644.442 | 10296.92 | 2.825 | HYPOX_O2_HCT116 |
| 16 | ALDOA | SEQ ID NO. 4 | 686.221 | 1461.874 | 2.13 | HYPOX_O2_HT1080 |
| 17 | ALDOC | SEQ ID NO. 5 | 2899.764 | 4431.376 | 1.528 | HYPOX_DFO_HCT116 |
| 18 | ALDOC | SEQ ID NO. 5 | 92.432 | 574.525 | 6.216 | HYPOX_DFO_HT1080 |
| 19 | ALDOC | SEQ ID NO. 5 | 2899.764 | 4376.288 | 1.509 | HYPOX_O2_HCT116 |
| 20 | ALDOC | SEQ ID NO. 5 | 92.432 | 365.504 | 3.954 | HYPOX_O2_HT1080 |
| 21 | HK2 | SEQ ID NO. 6 | 2427.986 | 13969.978 | 5.754 | HYPOX_DFO_HCT116 |
| 22 | HK2 | SEQ ID NO. 6 | 19.517 | 1560.932 | 79.976 | HYPOX_DFO_HT1080 |
| 23 | HK2 | SEQ ID NO. 6 | 2427.986 | 10507.561 | 4.328 | HYPOX_O2_HCT116 |
| 24 | HK2 | SEQ ID NO. 6 | 19.517 | 928.374 | 47.566 | HYPOX_O2_HT1080 |

*FIG. 1B* -- TABLE 1 TRANSCRIPTIONAL BIOMARKER FUNCTIONAL DATA
SECTION 1

| LINE_ID | GENE_SYMBOL | SEQUENCE_ID_LISTING | PROM_ACTIVITY_N O_INDUCTION | PROM_ACTIVITY_WI TH_INDUCTION | INDUCTION RATIO | INDUCTION_CONDITIONS* |
|---|---|---|---|---|---|---|
| 25 | TFRC | SEQ ID NO. 7 | 3880.483 | 13834.58 | 3.565 | HYPOX_DFO_HCT116 |
| 26 | TFRC | SEQ ID NO. 7 | 408.651 | 1834.062 | 4.488 | HYPOX_DFO_HT1080 |
| 27 | TFRC | SEQ ID NO. 7 | 3880.483 | 7869.671 | 2.028 | HYPOX_O2_HCT116 |
| 28 | TFRC | SEQ ID NO. 7 | 408.651 | 963.829 | 2.359 | HYPOX_O2_HT1080 |
| 29 | CA9 | SEQ ID NO. 8 | 112.752 | 200.984 | 1.783 | HYPOX_DFO_HCT116 |
| 30 | CA9 | SEQ ID NO. 8 | 1.258 | 123.533 | 98.237 | HYPOX_DFO_HT1080 |
| 31 | CA9 | SEQ ID NO. 8 | 112.752 | 565.723 | 5.017 | HYPOX_O2_HCT116 |
| 32 | CA9 | SEQ ID NO. 8 | 1.258 | 87.797 | 69.819 | HYPOX_O2_HT1080 |
| 33 | PGK1 | SEQ ID NO. 9 | 633.088 | 5453.643 | 8.614 | HYPOX_DFO_HCT116 |
| 34 | PGK1 | SEQ ID NO. 9 | 151.596 | 669.957 | 4.419 | HYPOX_DFO_HT1080 |
| 35 | PGK1 | SEQ ID NO. 9 | 633.088 | 2931.336 | 4.63 | HYPOX_O2_HCT116 |
| 36 | PGK1 | SEQ ID NO. 9 | 151.596 | 274.798 | 1.813 | HYPOX_O2_HT1080 |
| 37 | ENO2 | SEQ ID NO. 10 | 915.281 | 1522.224 | 1.663 | HYPOX_DFO_HCT116 |
| 38 | ENO2 | SEQ ID NO. 10 | 144.329 | 1429.9 | 9.907 | HYPOX_DFO_HT1080 |
| 39 | ENO2 | SEQ ID NO. 10 | 915.281 | 2657.514 | 2.903 | HYPOX_O2_HCT116 |
| 40 | ENO2 | SEQ ID NO. 10 | 144.329 | 954.14 | 6.611 | HYPOX_O2_HT1080 |
| 41 | PDK1 | SEQ ID NO. 11 | 32.378 | 151.803 | 4.688 | HYPOX_DFO_HCT116 |
| 42 | PDK1 | SEQ ID NO. 11 | 0.776 | 58.13 | 74.927 | HYPOX_DFO_HT1080 |
| 43 | PDK1 | SEQ ID NO. 11 | 32.378 | 136.252 | 4.208 | HYPOX_O2_HCT116 |
| 44 | PDK1 | SEQ ID NO. 11 | 0.776 | 23.971 | 30.897 | HYPOX_O2_HT1080 |
| 45 | MIF | SEQ ID NO. 12 | 52.071 | 269.38 | 5.173 | HYPOX_DFO_HCT116 |
| 46 | MIF | SEQ ID NO. 12 | 1.698 | 22.283 | 13.119 | HYPOX_DFO_HT1080 |
| 47 | MIF | SEQ ID NO. 12 | 52.071 | 222.386 | 4.271 | HYPOX_O2_HCT116 |
| 48 | MIF | SEQ ID NO. 12 | 1.698 | 21.16 | 12.458 | HYPOX_O2_HT1080 |

FIG. 1C -- TABLE 1 TRANSCRIPTIONAL BIOMARKER FUNCTIONAL DATA
SECTION 1

| LINE_ID | GENE_SYMBOL | SEQUENCE_ID_LISTING | PROM_ACTIVITY_NO_INDUCTION | PROM_ACTIVITY_WITH_INDUCTION | INDUCTION_RATIO | INDUCTION_CONDITIONS* |
|---|---|---|---|---|---|---|
| 49 | HIG2 | SEQ ID NO. 13 | 2563.952 | 8013.064 | 3.125 | HYPOX_DFO_HCT116 |
| 50 | HIG2 | SEQ ID NO. 13 | 232.211 | 1351.21 | 5.819 | HYPOX_DFO_HT1080 |
| 51 | HIG2 | SEQ ID NO. 13 | 2563.952 | 9981.119 | 3.893 | HYPOX_O2_HCT116 |
| 52 | HIG2 | SEQ ID NO. 13 | 232.211 | 666.439 | 2.87 | HYPOX_O2_HT1080 |
| 53 | ANKRD37 | SEQ ID NO. 14 | 2361.653 | 13975.168 | 5.918 | HYPOX_DFO_HCT116 |
| 54 | ANKRD37 | SEQ ID NO. 14 | 32.418 | 1760.782 | 54.315 | HYPOX_DFO_HT1080 |
| 55 | ANKRD37 | SEQ ID NO. 14 | 2361.653 | 9515.659 | 4.029 | HYPOX_O2_HCT116 |
| 56 | ANKRD37 | SEQ ID NO. 14 | 32.418 | 897.264 | 27.678 | HYPOX_O2_HT1080 |
| 57 | P4HA2 | SEQ ID NO. 15 | 1104.155 | 2048.364 | 1.855 | HYPOX_DFO_HCT116 |
| 58 | P4HA2 | SEQ ID NO. 15 | 31.08 | 239.969 | 7.721 | HYPOX_DFO_HT1080 |
| 59 | P4HA2 | SEQ ID NO. 15 | 1104.155 | 2901.76 | 2.628 | HYPOX_O2_HCT116 |
| 60 | P4HA2 | SEQ ID NO. 15 | 31.08 | 223.71 | 7.193 | HYPOX_O2_HT1080 |
| 61 | YEATS2 | SEQ ID NO. 16 | 889.621 | 1044.798 | 1.174 | HYPOX_DFO_HCT116 |
| 62 | YEATS2 | SEQ ID NO. 16 | 68.812 | 150.291 | 2.184 | HYPOX_DFO_HT1080 |
| 63 | YEATS2 | SEQ ID NO. 16 | 889.621 | 2879.097 | 3.236 | HYPOX_O2_HCT116 |
| 64 | YEATS2 | SEQ ID NO. 16 | 68.812 | 217.153 | 3.156 | HYPOX_O2_HT1080 |
| 65 | HK1 | SEQ ID NO. 17 | 201.908 | 388.148 | 1.922 | HYPOX_DFO_HCT116 |
| 66 | HK1 | SEQ ID NO. 17 | 20.592 | 66.208 | 3.215 | HYPOX_DFO_HT1080 |
| 67 | HK1 | SEQ ID NO. 17 | 201.908 | 454.671 | 2.252 | HYPOX_O2_HCT116 |
| 68 | HK1 | SEQ ID NO. 17 | 20.592 | 89.461 | 4.344 | HYPOX_O2_HT1080 |
| 69 | ENO1 | SEQ ID NO. 18 | 2508.594 | 12447.003 | 4.962 | HYPOX_DFO_HCT116 |
| 70 | ENO1 | SEQ ID NO. 18 | 733.645 | 3491.341 | 4.759 | HYPOX_DFO_HT1080 |
| 71 | ENO1 | SEQ ID NO. 18 | 2508.594 | 6152.489 | 2.453 | HYPOX_O2_HCT116 |
| 72 | ENO1 | SEQ ID NO. 18 | 733.645 | 2120.542 | 2.89 | HYPOX_O2_HT1080 |

FIG. 1D -- TABLE 1 TRANSCRIPTIONAL BIOMARKER FUNCTIONAL DATA

SECTION 2:

| LINE_ID | GENE_SYMBOL | SEQUENCE_ID_LISTING | PROM_ACTIVITY_N O_INDUCTION | PROM_ACTIVITY_WI TH_INDUCTION | INDUCTION RATIO | INDUCTION_CONDITIONS* |
|---|---|---|---|---|---|---|
| 73 | ASB2 | SEQ ID NO. 19 | 1.209 | 3.222 | 2.664 | ER |
| 74 | SYT8 | SEQ ID NO. 20 | 0.907 | 5.032 | 5.551 | ER |
| 75 | KRT13 | SEQ ID NO. 21 | 1.427 | 8.421 | 5.9 | ER |
| 76 | NULL | SEQ ID NO. 22 | 17.172 | 40.397 | 2.353 | ER |
| 77 | MNT | SEQ ID NO. 23 | 0.981 | 3.42 | 3.487 | ER |
| 78 | C14orf133 | SEQ ID NO. 24 | 51.361 | 82.648 | 1.609 | ER |
| 79 | C1orf151 | SEQ ID NO. 25 | 14.024 | 34.468 | 2.458 | ER |
| 80 | TFAP2C | SEQ ID NO. 26 | 1.041 | 3.039 | 2.92 | ER |
| 81 | OAT | SEQ ID NO. 27 | 9.629 | 80.616 | 8.372 | ER |
| 82 | DDAH2 | SEQ ID NO. 28 | 1.245 | 6.579 | 5.283 | ER |
| 83 | SLC25A36 | SEQ ID NO. 29 | 0.845 | 2.971 | 3.515 | ER |
| 84 | NULL | SEQ ID NO. 30 | 59.787 | 282.204 | 4.72 | ER |
| 85 | MICALL2 | SEQ ID NO. 31 | 4.538 | 23.994 | 5.288 | ER |

*FIG. 1E* -- TABLE 1 TRANSCRIPTIONAL BIOMARKER FUNCTIONAL DATA
SECTION 3:

| LINE_ID | GENE_SYMBOL | SEQUENCE_ID_LISTING | PROM_ACTIVITY_N O_INDUCTION | PROM_ACTIVITY_WI TH_INDUCTION | INDUCTION RATIO | INDUCTION_CONDITIONS* |
|---|---|---|---|---|---|---|
| 86 | PMEPA1 | SEQ ID NO. 32 | 1.42 | 5.92 | 4.18 | AR |
| 87 | EGLN3 | SEQ ID NO. 33 | 2.47 | 6.46 | 2.61 | AR |
| 88 | DSEL | SEQ ID NO. 34 | 0.52 | 15.34 | 29.31 | AR |
| 89 | NAT1 | SEQ ID NO. 35 | 4.04 | 11.6 | 2.87 | AR |
| 90 | KLK2 | SEQ ID NO. 36 | 0.05 | 2.41 | 48.83 | AR |
| 91 | C1orf21 | SEQ ID NO. 37 | 0.2 | 3.84 | 19.06 | AR |
| 92 | SGK1 | SEQ ID NO. 38 | 0.79 | 4.5 | 5.68 | AR |
| 93 | TIPARP | SEQ ID NO. 39 | 1.12 | 7.91 | 7.06 | AR |
| 94 | PRKCD | SEQ ID NO. 40 | 4.05 | 19.99 | 4.94 | AR |
| 95 | PMEPA1 | SEQ ID NO. 41 | 1.19 | 5.49 | 4.63 | AR |
| 96 | CDC42EP3 | SEQ ID NO. 42 | 0.24 | 2.49 | 10.3 | AR |
| 97 | FMBP1L | SEQ ID NO. 43 | 0.24 | 4.55 | 19.04 | AR |
| 98 | UAP1 | SEQ ID NO. 44 | 1.79 | 5.81 | 3.25 | AR |
| 99 | JAG1 | SEQ ID NO. 45 | 0.55 | 11.01 | 19.88 | AR |
| 100 | BARD1 | SEQ ID NO. 46 | 1.75 | 4.84 | 2.76 | AR |

*FIG. 1F* -- TABLE 1 TRANSCRIPTIONAL BIOMARKER FUNCTIONAL DATA
SECTION 4:

| LINE_ID | GENE_SYMBOL | SEQUENCE_ID_LISTING | PROM_ACTIVITY_NO_INDUCTION | PROM_ACTIVITY_WITH_INDUCTION | INDUCTION_RATIO | INDUCTION_CONDITIONS* |
|---|---|---|---|---|---|---|
| 101 | NULL | SEQ ID NO. 47 | 1.16 | 3.971 | 3.424 | P53 |
| 102 | KANK1 | SEQ ID NO. 48 | 0.793 | 5.275 | 6.651 | P53 |
| 103 | DDI2 | SEQ ID NO. 49 | 31.304 | 128.359 | 4.1 | P53 |
| 104 | E2F7 | SEQ ID NO. 50 | 1.768 | 11.073 | 6.263 | P53 |
| 105 | VWA5A | SEQ ID NO. 51 | 0.994 | 2.229 | 2.242 | P53 |
| 106 | NULL | SEQ ID NO. 52 | 0.483 | 2.843 | 5.887 | P53 |
| 107 | CDKN1A | SEQ ID NO. 53 | 41.286 | 114.848 | 2.782 | P53 |
| 108 | TRAF6 | SEQ ID NO. 54 | 8.431 | 14.494 | 1.719 | P53 |
| 109 | NULL | SEQ ID NO. 55 | 3.02 | 17.518 | 5.8 | P53 |
| 110 | TP73 | SEQ ID NO. 56 | 1.331 | 19.66 | 14.766 | P53 |
| 111 | TP53INP1 | SEQ ID NO. 57 | 301.135 | 1137.284 | 3.777 | P53 |
| 112 | SERPINE1 | SEQ ID NO. 58 | 5.233 | 23.067 | 4.408 | P53 |
| 113 | ARG2 | SEQ ID NO. 59 | 2.54 | 12.893 | 5.076 | P53 |
| 114 | GPX1 | SEQ ID NO. 60 | 3.612 | 9.722 | 2.692 | P53 |

*FIG. 1G* -- TABLE 1 TRANSCRIPTIONAL BIOMARKER FUNCTIONAL DATA
SECTION 5:

| LINE_ID | GENE_SYMBOL | SEQUENCE_ID_LISTING | PROM_ACTIVITY_N O_INDUCTION | PROM_ACTIVITY_WI TH_INDUCTION | INDUCTION RATIO | INDUCTION_CONDITIONS* |
|---|---|---|---|---|---|---|
| 115 | LSS | SEQ ID NO. 61 | 9.095 | 52.188 | 5.738 | SREBP_LOV |
| 116 | LSS | SEQ ID NO. 61 | 9.095 | 4.087 | 0.449 | SREBP_SYNTH |
| 117 | LSS | SEQ ID NO. 61 | 9.095 | 42.583 | 4.682 | SREBP_U18666A |
| 118 | HMGCS1 | SEQ ID NO. 62 | 11.3 | 43.771 | 3.874 | SREBP_LOV |
| 119 | HMGCS1 | SEQ ID NO. 62 | 11.3 | 8.584 | 0.76 | SREBP_SYNTH |
| 120 | HMGCS1 | SEQ ID NO. 62 | 11.3 | 33.317 | 2.948 | SREBP_U18666A |
| 121 | LDLR | SEQ ID NO. 63 | 0.528 | 4.194 | 7.942 | SREBP_LOV |
| 122 | LDLR | SEQ ID NO. 63 | 0.528 | 0.127 | 0.241 | SREBP_SYNTH |
| 123 | LDLR | SEQ ID NO. 63 | 0.528 | 2.365 | 4.479 | SREBP_U18666A |
| 124 | INSIG1 | SEQ ID NO. 64 | 18.688 | 58.689 | 3.14 | SREBP_LOV |
| 125 | INSIG1 | SEQ ID NO. 64 | 18.688 | 8.012 | 0.429 | SREBP_SYNTH |
| 126 | INSIG1 | SEQ ID NO. 64 | 18.688 | 43.001 | 2.301 | SREBP_U18666A |
| 127 | HMGCR | SEQ ID NO. 65 | 9.276 | 34.599 | 3.73 | SREBP_LOV |
| 128 | HMGCR | SEQ ID NO. 65 | 9.276 | 4.883 | 0.526 | SREBP_SYNTH |
| 129 | HMGCR | SEQ ID NO. 65 | 9.276 | 29.572 | 3.188 | SREBP_U18666A |
| 130 | ACSL5 | SEQ ID NO. 66 | 0.876 | 1.878 | 2.145 | SREBP_LOV |
| 131 | ACSL5 | SEQ ID NO. 66 | 0.876 | 1.246 | 1.423 | SREBP_SYNTH |
| 132 | ACSL5 | SEQ ID NO. 66 | 0.876 | 1.474 | 1.683 | SREBP_U18666A |
| 133 | NULL | SEQ ID NO. 67 | 10.538 | 19.205 | 1.822 | SREBP_LOV |
| 134 | NULL | SEQ ID NO. 67 | 10.538 | 4.796 | 0.455 | SREBP_SYNTH |
| 135 | NULL | SEQ ID NO. 67 | 10.538 | 20.415 | 1.937 | SREBP_U18666A |
| 136 | NSDHL | SEQ ID NO. 68 | 36.05 | 94.957 | 2.634 | SREBP_LOV |
| 137 | NSDHL | SEQ ID NO. 68 | 36.05 | 28.552 | 0.792 | SREBP_SYNTH |
| 138 | NSDHL | SEQ ID NO. 68 | 36.05 | 85.634 | 2.375 | SREBP_U18666A |
| 139 | DHCR24 | SEQ ID NO. 69 | 1.468 | 7.337 | 4.998 | SREBP_LOV |
| 140 | DHCR24 | SEQ ID NO. 69 | 1.468 | 0.52 | 0.354 | SREBP_SYNTH |
| 141 | DHCR24 | SEQ ID NO. 69 | 1.468 | 4.608 | 3.139 | SREBP_U18666A |
| 142 | FASN | SEQ ID NO. 70 | 20.017 | 96.388 | 4.815 | SREBP_LOV |
| 143 | FASN | SEQ ID NO. 70 | 20.017 | 12.38 | 0.618 | SREBP_SYNTH |
| 144 | FASN | SEQ ID NO. 70 | 20.017 | 63.245 | 3.16 | SREBP_U18666A |
| 145 | PGD | SEQ ID NO. 71 | 12.135 | 23.703 | 1.954 | SREBP_LOV |
| 146 | PGD | SEQ ID NO. 71 | 12.135 | 9.875 | 0.814 | SREBP_SYNTH |
| 147 | PGD | SEQ ID NO. 71 | 12.135 | 21.95 | 1.809 | SREBP_U18666A |
| 148 | ID1 | SEQ ID NO. 72 | 26.773 | 90.093 | 3.365 | SREBP_LOV |
| 149 | ID1 | SEQ ID NO. 72 | 26.773 | 16.24 | 0.607 | SREBP_SYNTH |
| 150 | ID1 | SEQ ID NO. 72 | 26.773 | 81.934 | 3.06 | SREBP_U18666A |
| 151 | DHCR7 | SEQ ID NO. 73 | 2.292 | 11.562 | 5.044 | SREBP_LOV |
| 152 | DHCR7 | SEQ ID NO. 73 | 2.292 | 1.427 | 0.623 | SREBP_SYNTH |
| 153 | DHCR7 | SEQ ID NO. 73 | 2.292 | 11.65 | 5.083 | SREBP_U18666A |

*FIG. 1H* -- TABLE 1 TRANSCRIPTIONAL BIOMARKER FUNCTIONAL DATA
SECTION 5

| LINE_ID | GENE_SYMBOL | SEQUENCE_ID_LISTING | PROM_ACTIVITY_NO_INDUCTION | PROM_ACTIVITY_WITH_INDUCTION | INDUCTION_RATIO | INDUCTION_CONDITIONS* |
|---|---|---|---|---|---|---|
| 154 | FDPS | SEQ ID NO. 74 | 7.185 | 23.308 | 3.244 | SREBP_LOV |
| 155 | FDPS | SEQ ID NO. 74 | 7.185 | 4.27 | 0.594 | SREBP_SYNTH |
| 156 | FDPS | SEQ ID NO. 74 | 7.185 | 20.148 | 2.804 | SREBP_U18666A |
| 157 | FASN | SEQ ID NO. 75 | 22.43 | 93.388 | 4.164 | SREBP_LOV |
| 158 | FASN | SEQ ID NO. 75 | 22.43 | 11.78 | 0.525 | SREBP_SYNTH |
| 159 | FASN | SEQ ID NO. 75 | 22.43 | 50.082 | 2.233 | SREBP_U18666A |
| 160 | MVD | SEQ ID NO. 76 | 7.236 | 59.473 | 8.219 | SREBP_LOV |
| 161 | MVD | SEQ ID NO. 76 | 7.236 | 4.733 | 0.654 | SREBP_SYNTH |
| 162 | MVD | SEQ ID NO. 76 | 7.236 | 39.052 | 5.397 | SREBP_U18666A |
| 163 | SQLE | SEQ ID NO. 77 | 8.145 | 36.969 | 4.539 | SREBP_LOV |
| 164 | SQLE | SEQ ID NO. 77 | 8.145 | 2.952 | 0.362 | SREBP_SYNTH |
| 165 | SQLE | SEQ ID NO. 77 | 8.145 | 27.994 | 3.437 | SREBP_U18666A |
| 166 | IDI1 | SEQ ID NO. 78 | 25.019 | 84.405 | 3.374 | SREBP_LOV |
| 167 | IDI1 | SEQ ID NO. 78 | 25.019 | 16.67 | 0.666 | SREBP_SYNTH |
| 168 | IDI1 | SEQ ID NO. 78 | 25.019 | 59.197 | 2.366 | SREBP_U18666A |

FIG. 1I -- TABLE 1 TRANSCRIPTIONAL BIOMARKER FUNCTIONAL DATA
SECTION 6:

| LINE_ID | GENE_SYMBOL | SEQUENCE_ID_LISTING | PROM_ACTIVITY_NO_INDUCTION | PROM_ACTIVITY_WITH_INDUCTION | INDUCTION_RATIO | INDUCTION_CONDITIONS* |
|---|---|---|---|---|---|---|
| 169 | AIM2 | SEQ ID NO. 79 | 19.656 | 83.528 | 4.25 | STAT_IFNA |
| 170 | AIM2 | SEQ ID NO. 79 | 19.656 | 289.257 | 14.716 | STAT_IFNG |
| 171 | TMEM140 | SEQ ID NO. 80 | 58.845 | 542.663 | 9.222 | STAT_IFNA |
| 172 | TMEM140 | SEQ ID NO. 80 | 58.845 | 707.901 | 12.03 | STAT_IFNG |
| 173 | PARP12 | SEQ ID NO. 81 | 5.477 | 37.459 | 6.84 | STAT_IFNA |
| 174 | PARP12 | SEQ ID NO. 81 | 5.477 | 13.947 | 2.547 | STAT_IFNG |
| 175 | BTC | SEQ ID NO. 82 | 3.858 | 51.865 | 13.445 | STAT_IFNA |
| 176 | BTC | SEQ ID NO. 82 | 3.858 | 9.144 | 2.371 | STAT_IFNG |
| 177 | NULL | SEQ ID NO. 83 | 553.985 | 815.222 | 1.472 | STAT_IFNA |
| 178 | NULL | SEQ ID NO. 83 | 553.985 | 879.604 | 1.588 | STAT_IFNG |
| 179 | IL4I1 | SEQ ID NO. 84 | 2.606 | 11.031 | 4.232 | STAT_IFNA |
| 180 | IL4I1 | SEQ ID NO. 84 | 2.606 | 5.441 | 2.087 | STAT_IFNG |
| 181 | IRF7 | SEQ ID NO. 85 | 432.776 | 1805.48 | 4.172 | STAT_IFNA |
| 182 | IRF7 | SEQ ID NO. 85 | 432.776 | 1119.382 | 2.587 | STAT_IFNG |
| 183 | EIF2AK2 | SEQ ID NO. 86 | 25.921 | 513.496 | 19.81 | STAT_IFNA |
| 184 | EIF2AK2 | SEQ ID NO. 86 | 25.921 | 92.338 | 3.562 | STAT_IFNG |
| 185 | CASP7 | SEQ ID NO. 87 | 254.479 | 1063.833 | 4.18 | STAT_IFNA |
| 186 | CASP7 | SEQ ID NO. 87 | 254.479 | 1059.063 | 4.162 | STAT_IFNG |
| 187 | CHMP5 | SEQ ID NO. 88 | 80.529 | 193.176 | 2.399 | STAT_IFNA |
| 188 | CHMP5 | SEQ ID NO. 88 | 80.529 | 118.97 | 1.477 | STAT_IFNG |
| 189 | RUNX1 | SEQ ID NO. 89 | 21.879 | 37.16 | 1.698 | STAT_IFNA |
| 190 | RUNX1 | SEQ ID NO. 89 | 21.879 | 382.492 | 17.482 | STAT_IFNG |
| 191 | ZC3HAV1 | SEQ ID NO. 90 | 93.614 | 571.207 | 6.102 | STAT_IFNA |
| 192 | ZC3HAV1 | SEQ ID NO. 90 | 93.614 | 792 | 8.46 | STAT_IFNG |
| 193 | PML | SEQ ID NO. 91 | 60.959 | 620.577 | 10.18 | STAT_IFNA |
| 194 | PML | SEQ ID NO. 91 | 60.959 | 203.412 | 3.337 | STAT_IFNG |
| 195 | TNFSF10 | SEQ ID NO. 92 | 1.914 | 21.688 | 11.332 | STAT_IFNA |
| 196 | TNFSF10 | SEQ ID NO. 92 | 1.914 | 6.894 | 3.602 | STAT_IFNG |
| 197 | ACTA2 | SEQ ID NO. 93 | 47.901 | 75.99 | 1.586 | STAT_IFNA |
| 198 | ACTA2 | SEQ ID NO. 93 | 47.901 | 252.117 | 5.263 | STAT_IFNG |
| 199 | ERAP1 | SEQ ID NO. 94 | 58.867 | 204.741 | 3.478 | STAT_IFNA |
| 200 | ERAP1 | SEQ ID NO. 94 | 58.867 | 133.037 | 2.26 | STAT_IFNG |
| 201 | BCL6 | SEQ ID NO. 95 | 94.574 | 145.049 | 1.534 | STAT_IFNA |
| 202 | BCL6 | SEQ ID NO. 95 | 94.574 | 530.532 | 5.61 | STAT_IFNG |
| 203 | LOC441108 | SEQ ID NO. 96 | 8.789 | 137.783 | 15.676 | STAT_IFNA |
| 204 | LOC441108 | SEQ ID NO. 96 | 8.789 | 83.891 | 9.545 | STAT_IFNG |
| 205 | PSMB9 | SEQ ID NO. 97 | 1.828 | 25.902 | 14.17 | STAT_IFNA |
| 206 | PSMB9 | SEQ ID NO. 97 | 1.828 | 103.313 | 56.518 | STAT_IFNG |

FIG. 1J -- TABLE 1 TRANSCRIPTIONAL BIOMARKER FUNCTIONAL DATA

SECTION 7:

| LINE_ID | GENE_SYMBOL | SEQUENCE_ID_LISTING | PROM_ACTIVITY_NO_INDUCTION | PROM_ACTIVITY_WITH_INDUCTION | INDUCTION_RATIO | INDUCTION_CONDITIONS* |
|---|---|---|---|---|---|---|
| 207 | HIST1H3B | SEQ ID NO. 98 | 0.652 | 1.484 | 2.276 | CREB_FSK |
| 208 | HIST1H3B | SEQ ID NO. 98 | 0.652 | 1.301 | 2.763 | CREB_PMA |
| 209 | PCNA | SEQ ID NO. 99 | 6.328 | 10.501 | 1.659 | CREB_FSK |
| 210 | PCNA | SEQ ID NO. 99 | 6.328 | 27.293 | 4.313 | CREB_PMA |
| 211 | GTF2E1 | SEQ ID NO. 100 | 3.16 | 5.271 | 1.668 | CREB_FSK |
| 212 | GTF2E1 | SEQ ID NO. 100 | 3.16 | 6.486 | 2.053 | CREB_PMA |
| 213 | PPP1R15A | SEQ ID NO. 101 | 2.109 | 6.238 | 2.958 | CREB_FSK |
| 214 | PPP1R15A | SEQ ID NO. 101 | 2.109 | 15.03 | 7.127 | CREB_PMA |
| 215 | GADD45B | SEQ ID NO. 102 | 8.541 | 13.563 | 1.588 | CREB_FSK |
| 216 | GADD45B | SEQ ID NO. 102 | 8.541 | 32.725 | 3.831 | CREB_PMA |
| 217 | SGK1 | SEQ ID NO. 103 | 1.557 | 3.279 | 2.105 | CREB_FSK |
| 218 | SGK1 | SEQ ID NO. 103 | 1.557 | 4.745 | 3.047 | CREB_PMA |
| 219 | SNF1LK | SEQ ID NO. 104 | 9.029 | 24.785 | 2.745 | CREB_FSK |
| 220 | SNF1LK | SEQ ID NO. 104 | 9.029 | 25.6 | 2.835 | CREB_PMA |
| 221 | CYR61 | SEQ ID NO. 105 | 2.649 | 6.489 | 2.449 | CREB_FSK |
| 222 | CYR61 | SEQ ID NO. 105 | 2.649 | 8.97 | 3.386 | CREB_PMA |
| 223 | CREM | SEQ ID NO. 106 | 0.197 | 0.47 | 2.385 | CREB_FSK |
| 224 | CREM | SEQ ID NO. 106 | 0.197 | 0.831 | 4.218 | CREB_PMA |
| 225 | NDUFV1 | SEQ ID NO. 107 | 2.194 | 4.297 | 1.959 | CREB_FSK |
| 226 | NDUFV1 | SEQ ID NO. 107 | 2.194 | 3.789 | 1.727 | CREB_PMA |
| 227 | ID2 | SEQ ID NO. 108 | 1.466 | 1.918 | 1.308 | CREB_FSK |
| 228 | ID2 | SEQ ID NO. 108 | 1.466 | 6.304 | 4.3 | CREB_PMA |
| 229 | FN1 | SEQ ID NO. 109 | 0.405 | 0.902 | 2.227 | CREB_FSK |
| 230 | FN1 | SEQ ID NO. 109 | 0.405 | 3.046 | 7.522 | CREB_PMA |
| 231 | DNAJB11 | SEQ ID NO. 110 | 1.89 | 3.401 | 1.8 | CREB_FSK |
| 232 | DNAJB11 | SEQ ID NO. 110 | 1.89 | 3.228 | 1.708 | CREB_PMA |
| 233 | PPARGC1A | SEQ ID NO. 111 | 0.295 | 0.62 | 2.103 | CREB_FSK |
| 234 | PPARGC1A | SEQ ID NO. 111 | 0.295 | 1.107 | 3.758 | CREB_PMA |

*FIG. 1K* -- TABLE 1 TRANSCRIPTIONAL BIOMARKER FUNCTIONAL DATA
SECTION 8:

| LINE_ID | GENE_SYMBOL | SEQUENCE_ID_LISTING | PROM_ACTIVITY_N O_INDUCTION | PROM_ACTIVITY_WI TH_INDUCTION | INDUCTION RATIO | INDUCTION_CONDITIONS* |
|---|---|---|---|---|---|---|
| 235 | COMT | SEQ ID NO. 112 | 0.716 | 1.056 | 1.476 | GR_CORT |
| 236 | COMT | SEQ ID NO. 112 | 0.716 | 1.412 | 1.974 | GR_DEX |
| 237 | COMT | SEQ ID NO. 112 | 0.716 | 1.221 | 1.706 | GR_PRED |
| 238 | NULL | SEQ ID NO. 113 | 0.94 | 2.551 | 2.713 | GR_CORT |
| 239 | NULL | SEQ ID NO. 113 | 0.94 | 3.253 | 3.46 | GR_DEX |
| 240 | NULL | SEQ ID NO. 113 | 0.94 | 3.481 | 3.702 | GR_PRED |
| 241 | CYP3A43 | SEQ ID NO. 114 | 0.614 | 0.957 | 1.559 | GR_CORT |
| 242 | CYP3A43 | SEQ ID NO. 114 | 0.614 | 1.866 | 3.039 | GR_DEX |
| 243 | CYP3A43 | SEQ ID NO. 114 | 0.614 | 1.703 | 2.774 | GR_PRED |
| 244 | NULL | SEQ ID NO. 115 | 0.255 | 0.611 | 2.4 | GR_CORT |
| 245 | NULL | SEQ ID NO. 115 | 0.255 | 1.116 | 4.386 | GR_DEX |
| 246 | NULL | SEQ ID NO. 115 | 0.255 | 0.666 | 2.618 | GR_PRED |
| 247 | BAIAP2 | SEQ ID NO. 116 | 1.017 | 2.5 | 2.457 | GR_CORT |
| 248 | BAIAP2 | SEQ ID NO. 116 | 1.017 | 5.467 | 5.373 | GR_DEX |
| 249 | BAIAP2 | SEQ ID NO. 116 | 1.017 | 4.83 | 4.747 | GR_PRED |
| 250 | RNASE2 | SEQ ID NO. 117 | 0.387 | 0.535 | 1.383 | GR_CORT |
| 251 | RNASE2 | SEQ ID NO. 117 | 0.387 | 5.642 | 14.581 | GR_DEX |
| 252 | RNASE2 | SEQ ID NO. 117 | 0.387 | 1.204 | 3.112 | GR_PRED |
| 253 | NULL | SEQ ID NO. 118 | 0.095 | 0.429 | 4.516 | GR_CORT |
| 254 | NULL | SEQ ID NO. 118 | 0.095 | 1.627 | 17.138 | GR_DEX |
| 255 | NULL | SEQ ID NO. 118 | 0.095 | 1.144 | 12.049 | GR_PRED |
| 256 | NKPD1 | SEQ ID NO. 119 | 2.933 | 16.5 | 5.626 | GR_CORT |
| 257 | NKPD1 | SEQ ID NO. 119 | 2.933 | 32.967 | 11.241 | GR_DEX |
| 258 | NKPD1 | SEQ ID NO. 119 | 2.933 | 36.324 | 12.385 | GR_PRED |
| 259 | MARK3 | SEQ ID NO. 120 | 0.312 | 0.448 | 1.438 | GR_CORT |
| 260 | MARK3 | SEQ ID NO. 120 | 0.312 | 1.236 | 3.963 | GR_DEX |
| 261 | MARK3 | SEQ ID NO. 120 | 0.312 | 1.269 | 4.063 | GR_PRED |

*FIG. 1L* -- TABLE 1 TRANSCRIPTIONAL BIOMARKER FUNCTIONAL DATA
SECTION 8

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS* |
|---|---|---|---|---|---|---|
| 262 | PREPL | SEQ ID NO. 121 | 0.145 | 0.255 | 1.761 | GR_CORT |
| 263 | PREPL | SEQ ID NO. 121 | 0.145 | 0.693 | 4.794 | GR_DEX |
| 264 | PREPL | SEQ ID NO. 121 | 0.145 | 0.384 | 2.656 | GR_PRED |
| 265 | SLC38A4 | SEQ ID NO. 122 | 0.041 | 0.335 | 8.123 | GR_CORT |
| 266 | SLC38A4 | SEQ ID NO. 122 | 0.041 | 2.143 | 51.936 | GR_DEX |
| 267 | SLC38A4 | SEQ ID NO. 122 | 0.041 | 1.137 | 27.566 | GR_PRED |
| 268 | MEST | SEQ ID NO. 123 | 3.089 | 4.859 | 1.573 | GR_CORT |
| 269 | MEST | SEQ ID NO. 123 | 3.089 | 8.897 | 2.88 | GR_DEX |
| 270 | MEST | SEQ ID NO. 123 | 3.089 | 7.63 | 2.47 | GR_PRED |
| 271 | SLC19A2 | SEQ ID NO. 124 | 6.66 | 19.273 | 2.894 | GR_CORT |
| 272 | SLC19A2 | SEQ ID NO. 124 | 6.66 | 24.721 | 3.712 | GR_DEX |
| 273 | SLC19A2 | SEQ ID NO. 124 | 6.66 | 18.987 | 2.851 | GR_PRED |
| 274 | MT2A | SEQ ID NO. 125 | 56.855 | 130.707 | 2.299 | GR_CORT |
| 275 | MT2A | SEQ ID NO. 125 | 56.855 | 121.445 | 2.136 | GR_DEX |
| 276 | MT2A | SEQ ID NO. 125 | 56.855 | 133.159 | 2.342 | GR_PRED |
| 277 | SDPR | SEQ ID NO. 126 | 0.608 | 2.959 | 4.865 | GR_CORT |
| 278 | SDPR | SEQ ID NO. 126 | 0.608 | 6.022 | 9.9 | GR_DEX |
| 279 | SDPR | SEQ ID NO. 126 | 0.608 | 4.037 | 6.636 | GR_PRED |

*FIG. 1M* -- TABLE 1 TRANSCRIPTIONAL BIOMARKER FUNCTIONAL DATA
SECTION 9:

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS* |
|---|---|---|---|---|---|---|
| 280 | PLA2G2A | SEQ ID NO. 127 | 0.188 | 0.302 | 1.608 | PPAR_ALPHA |
| 281 | PLA2G2A | SEQ ID NO. 127 | 0.062 | 0.064 | 1.038 | PPAR_DELTA |
| 282 | PLA2G2A | SEQ ID NO. 127 | 0.154 | 1.071 | 6.931 | PPAR_GAMMA |
| 283 | FABP1 | SEQ ID NO. 128 | 0.577 | 1.279 | 2.219 | PPAR_ALPHA |
| 284 | FABP1 | SEQ ID NO. 128 | 0.043 | 0.033 | 0.761 | PPAR_DELTA |
| 285 | FABP1 | SEQ ID NO. 128 | 0.182 | 0.552 | 3.032 | PPAR_GAMMA |
| 286 | LIPC | SEQ ID NO. 129 | 0.073 | 0.085 | 1.158 | PPAR_ALPHA |
| 287 | LIPC | SEQ ID NO. 129 | 0.009 | 0.008 | 0.909 | PPAR_DELTA |
| 288 | LIPC | SEQ ID NO. 129 | 0.027 | 0.069 | 2.559 | PPAR_GAMMA |
| 289 | AQP7 | SEQ ID NO. 130 | 0.074 | 0.1 | 1.34 | PPAR_ALPHA |
| 290 | AQP7 | SEQ ID NO. 130 | 0.018 | 0.014 | 0.737 | PPAR_DELTA |
| 291 | AQP7 | SEQ ID NO. 130 | 0.109 | 0.434 | 3.981 | PPAR_GAMMA |
| 292 | C9orf25 | SEQ ID NO. 131 | 1.57 | 1.739 | 1.107 | PPAR_ALPHA |
| 293 | C9orf25 | SEQ ID NO. 131 | 0.192 | 0.408 | 2.125 | PPAR_DELTA |
| 294 | C9orf25 | SEQ ID NO. 131 | 0.829 | 1.04 | 1.255 | PPAR_GAMMA |
| 295 | RPS3A | SEQ ID NO. 132 | 0.233 | 0.495 | 2.128 | PPAR_ALPHA |
| 296 | RPS3A | SEQ ID NO. 132 | 0.079 | 0.076 | 0.96 | PPAR_DELTA |
| 297 | RPS3A | SEQ ID NO. 132 | 0.101 | 0.557 | 5.512 | PPAR_GAMMA |
| 298 | ECH1 | SEQ ID NO. 133 | 0.32 | 1.127 | 3.523 | PPAR_ALPHA |
| 299 | ECH1 | SEQ ID NO. 133 | 0.015 | 0.02 | 1.346 | PPAR_DELTA |
| 300 | ECH1 | SEQ ID NO. 133 | 0.043 | 0.212 | 4.933 | PPAR_GAMMA |

FIG. 1N -- TABLE 1 TRANSCRIPTIONAL BIOMARKER FUNCTIONAL DATA
SECTION 10:

| LINE_ID | GENE_SYMBOL | SEQUENCE_ID_LISTING | PROM_ACTIVITY_N O_INDUCTION | PROM_ACTIVITY_WI TH_INDUCTION | INDUCTION RATIO | INDUCTION_CONDITIONS* |
|---|---|---|---|---|---|---|
| 301 | ABCA1 | SEQ ID NO. 134 | 0.288 | 0.502 | 1.74 | RAR_BETA |
| 302 | HOXA1 | SEQ ID NO. 135 | 0.066 | 0.099 | 1.515 | RAR_BETA |
| 303 | NUB1 | SEQ ID NO. 136 | 0.686 | 1.692 | 2.464 | RAR_BETA |
| 304 | PKD1 | SEQ ID NO. 137 | 0.018 | 0.032 | 1.77 | RAR_BETA |

FIG. 10 -- TABLE 1 TRANSCRIPTIONAL BIOMARKER FUNCTIONAL DATA
SECTION 11:

| LINE_ID | GENE_SYMBOL | SEQUENCE_ID_LISTING | PROM_ACTIVITY_N O_INDUCTION | PROM_ACTIVITY_WI TH_INDUCTION | INDUCTION_ RATIO | INDUCTION_CONDITIONS* |
|---|---|---|---|---|---|---|
| 305 | YIPF5 | SEQ ID NO. 138 | 159.088 | 180.629 | 1.135 | NFKB |
| 306 | IRF1 | SEQ ID NO. 139 | 19.14 | 224.79 | 11.745 | NFKB |
| 307 | TNFAIP3 | SEQ ID NO. 140 | 14.284 | 72.734 | 5.092 | NFKB |
| 308 | NFKB1 | SEQ ID NO. 141 | 7.148 | 60.486 | 8.461 | NFKB |
| 309 | RELB | SEQ ID NO. 142 | 12.045 | 95.231 | 7.906 | NFKB |
| 310 | TP53 | SEQ ID NO. 143 | 113.43 | 173.202 | 1.527 | NFKB |
| 311 | IL8 | SEQ ID NO. 144 | 1.075 | 35.046 | 32.611 | NFKB |
| 312 | VCAM1 | SEQ ID NO. 145 | 1.87 | 10.87 | 5.814 | NFKB |
| 313 | CCL5 | SEQ ID NO. 146 | 9.502 | 43.622 | 4.591 | NFKB |
| 314 | MT2A | SEQ ID NO. 146 | 118.861 | 293.325 | 2.468 | NFKB |
| 315 | SELE | SEQ ID NO. 147 | 0.746 | 20.008 | 26.817 | NFKB |
| 316 | TNF | SEQ ID NO. 148 | 26.761 | 41.369 | 1.546 | NFKB |
| 317 | CD40 | SEQ ID NO. 149 | 0.966 | 28.883 | 29.908 | NFKB |
| 318 | STAT5A | SEQ ID NO. 150 | 10.915 | 34.258 | 3.139 | NFKB |
| 319 | CSF1 | SEQ ID NO. 151 | 3.521 | 37.765 | 10.725 | NFKB |
| 320 | NFKBIA | SEQ ID NO. 152 | 34.253 | 70.096 | 2.046 | NFKB |
| 321 | NFKB2 | SEQ ID NO. 153 | 5.167 | 45.614 | 8.829 | NFKB |
| 322 | TAP1 | SEQ ID NO. 154 | 29.246 | 62.573 | 2.139 | NFKB |

FIG. 1P -- TABLE 1 TRANSCRIPTIONAL BIOMARKER FUNCTIONAL DATA
SECTION 12:

| LINE_ID | GENE_SYMBOL | SEQUENCE_ID_LISTING | PROM_ACTIVITY_N O_INDUCTION | PROM_ACTIVITY_WI TH_INDUCTION | INDUCTION RATIO | INDUCTION_CONDITIONS* |
|---|---|---|---|---|---|---|
| 323 | CEACAM1 | SEQ ID NO. 155 | 0.338 | 3.039 | 8.982 | HEATSHOCK |
| 324 | PTCD1 | SEQ ID NO. 156 | 0.242 | 3.188 | 13.192 | HEATSHOCK |
| 325 | DNAJB6 | SEQ ID NO. 157 | 76.04 | 263.214 | 3.462 | HEATSHOCK |
| 326 | GML | SEQ ID NO. 158 | 0.398 | 19.155 | 48.033 | HEATSHOCK |
| 327 | HSPD1 | SEQ ID NO. 159 | 39.523 | 190.072 | 4.809 | HEATSHOCK |
| 328 | SLC35F2 | SEQ ID NO. 160 | 0.339 | 2.618 | 7.715 | HEATSHOCK |
| 329 | APTX | SEQ ID NO. 161 | 39.683 | 141.938 | 3.577 | HEATSHOCK |
| 330 | HSPE1 | SEQ ID NO. 162 | 34.034 | 138.525 | 4.07 | HEATSHOCK |
| 331 | CAPZB | SEQ ID NO. 163 | 0.973 | 1.845 | 1.897 | HEATSHOCK |
| 332 | HNRNPA2B1 | SEQ ID NO. 164 | 271.363 | 439.445 | 1.619 | HEATSHOCK |
| 333 | RAB39 | SEQ ID NO. 165 | 0.233 | 1.361 | 5.831 | HEATSHOCK |
| 334 | ST13 | SEQ ID NO. 166 | 23.905 | 87.572 | 3.663 | HEATSHOCK |
| 335 | XPNPEP3 | SEQ ID NO. 167 | 59.06 | 149.475 | 2.531 | HEATSHOCK |
| 336 | HSPA1A | SEQ ID NO. 168 | 7.946 | 892.531 | 112.325 | HEATSHOCK |
| 337 | HSP90AB1 | SEQ ID NO. 169 | 20.038 | 178.812 | 8.924 | HEATSHOCK |

FIG. 1Q -- TABLE 1 TRANSCRIPTIONAL BIOMARKER FUNCTIONAL DATA
SECTION 13:

| LINE_ID | GENE_SYMBOL | SEQUENCE_ID_LISTING | PROM_ACTIVITY_N O_INDUCTION | PROM_ACTIVITY_WI TH_INDUCTION | INDUCTION RATIO | INDUCTION_CONDITIONS* |
|---|---|---|---|---|---|---|
| 338 | NR4A1 | SEQ ID NO. 170 | 15.285 | 110.453 | 7.226 | SRF |
| 339 | ING4 | SEQ ID NO. 171 | 1.007 | 1.585 | 1.573 | SRF |
| 340 | NLRP1 | SEQ ID NO. 172 | 6.368 | 16.172 | 2.54 | SRF |
| 341 | FOSB | SEQ ID NO. 173 | 0.807 | 3.736 | 4.63 | SRF |
| 342 | MYH9 | SEQ ID NO. 174 | 3.859 | 26.688 | 6.916 | SRF |

* INDUCTION CONDITION DESCRIPTION

HYPOX_DFO_HCT116= Biological response to hypoxia in HCT116 cells using deferoxamine (DFO) as the inducer
HYPOX_DFO_HT1080= Biological response to hypoxia in HT1080 cells using deferoxamine (DFO) as the inducer
HYPOX_O2_HCT116= Biological response to hypoxia in HCT116 cells using 1% oxygen as the inducing condition
HYPOX_O2_HT1080= Biological response to hypoxia in HT1080 cells using 1% oxygen as the inducing condition
ER= Biological response to estrogen using beta estradiol as the inducing condition
AR= Biological response to androgen using methyltrienolone as the inducing condition
P53= Biological response to p53 activation using nutlin as the inducing condition
SREBP_LOV= Biological response to cholesterol biosynthesis inhibition using lovastatin as the inducing condition
SREBP_SYNTH= Biological response to cholesterol biosynthesis activation using synthecol as the inducing condition
SREBP_U18666A= Biological response to cholesterol biosynthesis inhibition using U18666A as the inducing condition
STAT_IFNA= Biological response to interferons using interferon alpha as the inducing condition
STAT_IFNG= Biological response to interferons using interferon gamma as the inducing condition
CREB_FSK= Biological response to cyclic AMP signaling using forskolin as the inducing condition
CREB_PMA= Biological response to cyclic AMP signaling using phorbol 12-myristate 13-acetate (PMA) as the inducing condition
GR_CORT= Biological response to glucocorticoids using cortisone as the inducing condition
GR_DEX= Biological response to glucocorticoids using dexamethasone as the inducing condition
GR_PRED= Biological response to glucocorticoids using prednisone as the inducing condition
PPAR_ALPHA= Biological response to PPAR alpha using WY14643 as the inducing condition
PPAR_DELTA= Biological response to PPAR delta using GW501516 as the inducing condition
PPAR_GAMMA= Biological response to PPAR gamma using ciglitazone as the inducing condition
RAR_BETA= Biological response to RAR beta using adapalene as the inducing condition
NFKB= Biological response to NFKB activation using TNF alpha as the inducing condition
HEATSHOCK= Biological response to heat shock using 43 degrees celcius as the inducing condition
SRF= Biological response to serum using 20% serum as the inducing condition

FIG. 1R -- TABLE 1 TRANSCRIPTIONAL BIOMARKER FUNCTIONAL DATA
PART II: SUPPLEMENTAL TRANSCRIPTIONAL BIOMARKER FUNCTIONAL DATA

SECTION 3A

| LINE_ID | GENE_SYMBOL | SEQUENCE_ID_LISTING | PROM_ACTIVITY_N O_INDUCTION | PROM_ACTIVITY_WI TH_INDUCTION | PROM_ACTIVITY_WI _RATIO | INDUCTION INDUCTION_CONDITIONS* |
|---|---|---|---|---|---|---|
| 343 | GSTT2 | SEQ ID NO. 175 | 0.05 | 0.19 | 3.71 | AR |
| 344 | DNM1L | SEQ ID NO. 176 | 3.05 | 3.08 | 1.01 | AR |
| 345 | PFTK1 | SEQ ID NO. 177 | 0.07 | 0.36 | 5.33 | AR |
| 346 | SOCS2 | SEQ ID NO. 178 | 0.05 | 0.09 | 1.88 | AR |
| 347 | TRPV3 | SEQ ID NO. 179 | 1.02 | 0.38 | 0.37 | AR |
| 348 | GREB1 | SEQ ID NO. 180 | 0.06 | 0.28 | 4.65 | AR |
| 349 | UHRF2 | SEQ ID NO. 181 | 6.93 | 4.83 | 0.7 | AR |
| 350 | PYCR1 | SEQ ID NO. 182 | 0.02 | 0.05 | 2.18 | AR |
| 351 | MBOAT2 | SEQ ID NO. 183 | 0.08 | 0.25 | 3.2 | AR |
| 352 | SLC39A10 | SEQ ID NO. 184 | 0.48 | 0.82 | 1.72 | AR |
| 353 | NDRG1 | SEQ ID NO. 185 | 4.41 | 15.92 | 3.61 | AR |
| 354 | CAMKK2 | SEQ ID NO. 186 | 0.06 | 0.34 | 5.91 | AR |
| 355 | PIK3R1 | SEQ ID NO. 187 | 0.03 | 0.04 | 1.41 | AR |
| 356 | PIK3AP1 | SEQ ID NO. 188 | 0.14 | 0.52 | 3.59 | AR |
| 357 | IHPK1 | SEQ ID NO. 189 | 0.43 | 1.48 | 3.47 | AR |
| 358 | MID1 | SEQ ID NO. 190 | 0.09 | 0.17 | 1.79 | AR |
| 359 | ACO2 | SEQ ID NO. 191 | 11.54 | 8.55 | 0.74 | AR |
| 360 | FAM115A | SEQ ID NO. 192 | 0.32 | 1.52 | 4.8 | AR |
| 361 | RAB4A | SEQ ID NO. 193 | 0.76 | 0.67 | 0.89 | AR |
| 362 | PIK3CB | SEQ ID NO. 194 | 0.05 | 0.13 | 2.49 | AR |
| 363 | SEC24B | SEQ ID NO. 195 | 0.25 | 0.24 | 0.96 | AR |
| 364 | PTPRM | SEQ ID NO. 196 | 0.1 | 1.4 | 13.74 | AR |
| 365 | MRPS28 | SEQ ID NO. 197 | 0.01 | 0.01 | 1.31 | AR |
| 366 | ACAD8 | SEQ ID NO. 198 | 0.71 | 1.19 | 1.67 | AR |
| 367 | PPFIBP2 | SEQ ID NO. 199 | 0.04 | 0.45 | 12.4 | AR |
| 368 | ATP2B1 | SEQ ID NO. 200 | 0.37 | 1.78 | 4.8 | AR |
| 369 | MLPH | SEQ ID NO. 201 | 0.16 | 0.53 | 3.23 | AR |
| 370 | PDS5B | SEQ ID NO. 202 | 2.3 | 2.71 | 1.18 | AR |
| 371 | DNAJB9 | SEQ ID NO. 203 | 14.91 | 13.96 | 0.94 | AR |
| 372 | RALB | SEQ ID NO. 204 | 0.23 | 1.75 | 7.52 | AR |
| 373 | C15orf23 | SEQ ID NO. 205 | 5.42 | 5.3 | 0.98 | AR |
| 374 | ORM2 | SEQ ID NO. 206 | 0.04 | 0.08 | 1.85 | AR |
| 375 | CXCR7 | SEQ ID NO. 207 | 0.21 | 0.19 | 0.91 | AR |
| 376 | KLK3 | SEQ ID NO. 208 | 0.06 | 0.39 | 6.49 | AR |
| 377 | FKBP5 | SEQ ID NO. 209 | 0.04 | 0.04 | 1.05 | AR |
| 378 | CAMKK2 | SEQ ID NO. 210 | 0.07 | 0.51 | 6.89 | AR |
| 379 | C14orf4 | SEQ ID NO. 211 | 4.14 | 1.36 | 0.33 | AR |
| 380 | PGC | SEQ ID NO. 212 | 0.02 | 0.08 | 3.99 | AR |
| 381 | CDC42EP3 | SEQ ID NO. 213 | 0.03 | 0.07 | 2.44 | AR |
| 382 | QAT | SEQ ID NO. 213 | 0.77 | 9.16 | 11.83 | AR |

*FIG. 1S* -- TABLE 1 TRANSCRIPTIONAL BIOMARKER FUNCTIONAL DATA
SECTION 3A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS* |
|---|---|---|---|---|---|---|
| 383 | CDK5RAP1 | SEQ ID NO. 214 | 24.6 | 17.66 | 0.72 | AR |
| 384 | LRRN1 | SEQ ID NO. 215 | 0.19 | 1.3 | 7.02 | AR |
| 385 | HELZ | SEQ ID NO. 216 | 3.39 | 2.09 | 0.62 | AR |
| 386 | RNF19A | SEQ ID NO. 217 | 1.13 | 3.77 | 3.35 | AR |
| 387 | C1orf26 | SEQ ID NO. 218 | 9.96 | 14.43 | 1.45 | AR |
| 388 | KCTD3 | SEQ ID NO. 219 | 0.36 | 0.65 | 1.82 | AR |
| 389 | CCNH | SEQ ID NO. 220 | 1.3 | 1.27 | 0.98 | AR |
| 390 | HMGCR | SEQ ID NO. 220 | 5.81 | 8.94 | 1.54 | AR |
| 391 | CAMKK2 | SEQ ID NO. 221 | 0.11 | 0.1 | 0.89 | AR |
| 392 | NSMAF | SEQ ID NO. 222 | 0.51 | 0.29 | 0.57 | AR |
| 393 | ATAD2 | SEQ ID NO. 223 | 0.08 | 0.1 | 1.21 | AR |
| 394 | PAK1IP1 | SEQ ID NO. 224 | 1.33 | 1.3 | 0.97 | AR |
| 395 | PFTK1 | SEQ ID NO. 225 | 0.06 | 0.07 | 1.19 | AR |
| 396 | GNGT1 | SEQ ID NO. 226 | 0.02 | 0.04 | 2.61 | AR |
| 397 | SYTL2 | SEQ ID NO. 227 | 0.54 | 0.31 | 0.57 | AR |
| 398 | SAT1 | SEQ ID NO. 228 | 0.08 | 0.25 | 3.05 | AR |
| 399 | AKAP9 | SEQ ID NO. 229 | 1.17 | 2.21 | 1.89 | AR |
| 400 | TRIP5 | SEQ ID NO. 230 | 3.74 | 2.65 | 0.71 | AR |
| 401 | PLOD3 | SEQ ID NO. 231 | 17.4 | 10.84 | 0.62 | AR |
| 402 | NULL | SEQ ID NO. 232 | 8.38 | 7.55 | 0.9 | AR |
| 403 | NULL | SEQ ID NO. 233 | 3.8 | 3.33 | 0.88 | AR |
| 404 | HERPUD2 | SEQ ID NO. 234 | 1.07 | 2.09 | 1.95 | AR |
| 405 | NCAPG2 | SEQ ID NO. 235 | 7.4 | 8.41 | 1.14 | AR |
| 406 | TRIP6 | SEQ ID NO. 236 | 0.06 | 0.31 | 4.8 | AR |
| 407 | MUB1 | SEQ ID NO. 236 | 21.62 | 24.91 | 1.15 | AR |
| 408 | BRCA2 | SEQ ID NO. 237 | 1.63 | 1.77 | 1.09 | AR |
| 409 | TP53INP1 | SEQ ID NO. 237 | 38.4 | 15.35 | 0.4 | AR |
| 410 | SGK1 | SEQ ID NO. 238 | 0.05 | 0.08 | 1.63 | AR |

FIG. 1T -- TABLE 1 TRANSCRIPTIONAL BIOMARKER FUNCTIONAL DATA
SECTION 7A

| LINE_ID | GENE_SYMBOL | SEQUENCE_ID_LISTING | PROM_ACTIVITY_N_O_INDUCTION | PROM_ACTIVITY_WI_TH_INDUCTION | INDUCTION_RATIO | INDUCTION_CONDITIONS* |
|---|---|---|---|---|---|---|
| 411 | EIF3H | SEQ ID NO. 239 | 0.333 | 0.364 | 1.096 | CREB_FSK |
| 412 | EIF3H | SEQ ID NO. 239 | 0.333 | 0.413 | 1.24 | CREB_PMA |
| 413 | WBP11 | SEQ ID NO. 240 | 2.67 | 3.077 | 1.152 | CREB_FSK |
| 414 | WBP11 | SEQ ID NO. 240 | 2.67 | 2.764 | 1.035 | CREB_PMA |
| 415 | LARP7 | SEQ ID NO. 241 | 0.015 | 0.015 | 0.969 | CREB_FSK |
| 416 | LARP7 | SEQ ID NO. 241 | 0.015 | 0.024 | 1.577 | CREB_PMA |
| 417 | HISPPD1 | SEQ ID NO. 242 | 1.535 | 1.611 | 1.049 | CREB_FSK |
| 418 | HISPPD1 | SEQ ID NO. 242 | 1.535 | 1.248 | 0.813 | CREB_PMA |
| 419 | ANKRD42 | SEQ ID NO. 243 | 2.033 | 1.831 | 0.9 | CREB_FSK |
| 420 | ANKRD42 | SEQ ID NO. 243 | 2.033 | 3.1 | 1.525 | CREB_PMA |
| 421 | LMLN | SEQ ID NO. 244 | 0.271 | 0.297 | 1.1 | CREB_FSK |
| 422 | LMLN | SEQ ID NO. 244 | 0.271 | 0.342 | 1.263 | CREB_PMA |
| 423 | HIST1H2AH | SEQ ID NO. 245 | 1.672 | 2.164 | 1.294 | CREB_FSK |
| 424 | HIST1H2AH | SEQ ID NO. 245 | 1.672 | 2.31 | 1.381 | CREB_PMA |
| 425 | TTC35 | SEQ ID NO. 246 | 0.175 | 0.238 | 1.359 | CREB_FSK |
| 426 | TTC35 | SEQ ID NO. 246 | 0.175 | 0.233 | 1.329 | CREB_PMA |
| 427 | HIST1H2BK | SEQ ID NO. 247 | 2.742 | 4.9 | 1.787 | CREB_FSK |
| 428 | HIST1H2BK | SEQ ID NO. 247 | 2.742 | 7.958 | 2.903 | CREB_PMA |
| 429 | HIST2H2AC | SEQ ID NO. 248 | 3.986 | 4.97 | 1.247 | CREB_FSK |
| 430 | HIST2H2AC | SEQ ID NO. 248 | 3.986 | 5.603 | 1.405 | CREB_PMA |
| 431 | HIST2H2BE | SEQ ID NO. 249 | 9.397 | 10.733 | 1.142 | CREB_FSK |
| 432 | HIST2H2BE | SEQ ID NO. 249 | 9.397 | 18.537 | 1.973 | CREB_PMA |
| 433 | SRA1 | SEQ ID NO. 250 | 0.432 | 0.52 | 1.203 | CREB_FSK |
| 434 | SRA1 | SEQ ID NO. 250 | 0.432 | 0.773 | 1.791 | CREB_PMA |
| 435 | MRPS18B | SEQ ID NO. 251 | 2.137 | 2.289 | 1.071 | CREB_FSK |
| 436 | MRPS18B | SEQ ID NO. 251 | 2.137 | 2.347 | 1.098 | CREB_PMA |
| 437 | ALS2 | SEQ ID NO. 252 | 0.217 | 0.169 | 0.778 | CREB_FSK |
| 438 | ALS2 | SEQ ID NO. 252 | 0.217 | 0.152 | 0.702 | CREB_PMA |
| 439 | BLOC1S2 | SEQ ID NO. 253 | 2.085 | 2.353 | 1.128 | CREB_FSK |
| 440 | BLOC1S2 | SEQ ID NO. 253 | 2.085 | 2.486 | 1.192 | CREB_PMA |
| 441 | KIAA0859 | SEQ ID NO. 254 | 9.587 | 6.669 | 0.696 | CREB_FSK |
| 442 | KIAA0859 | SEQ ID NO. 254 | 9.587 | 7.689 | 0.802 | CREB_PMA |
| 443 | MFAP3 | SEQ ID NO. 255 | 14.586 | 17.903 | 1.227 | CREB_FSK |
| 444 | MFAP3 | SEQ ID NO. 255 | 14.586 | 20.17 | 1.383 | CREB_PMA |
| 445 | MULL | SEQ ID NO. 256 | 0.013 | 0.021 | 1.596 | CREB_FSK |
| 446 | MULL | SEQ ID NO. 256 | 0.013 | 0.017 | 1.297 | CREB_PMA |
| 447 | CCDC59 | SEQ ID NO. 257 | 2.007 | 1.436 | 0.715 | CREB_FSK |
| 448 | CCDC59 | SEQ ID NO. 257 | 2.007 | 2.124 | 1.058 | CREB_PMA |
| 449 | DLL3 | SEQ ID NO. 258 | 0.26 | 0.213 | 0.813 | CREB_FSK |
| 450 | DLL3 | SEQ ID NO. 258 | 0.26 | 0.529 | 2.034 | CREB_PMA |
| 451 | BTG2 | SEQ ID NO. 259 | 0.297 | 0.55 | 1.855 | CREB_FSK |
| 452 | BTG2 | SEQ ID NO. 259 | 0.297 | 0.858 | 2.892 | CREB_PMA |
| 453 | IQCG | SEQ ID NO. 260 | 0.283 | 0.345 | 1.218 | CREB_FSK |
| 454 | IQCG | SEQ ID NO. 260 | 0.283 | 0.563 | 2.005 | CREB_PMA |
| 455 | AZI2 | SEQ ID NO. 261 | 1.678 | 1.943 | 1.158 | CREB_FSK |
| 456 | AZI2 | SEQ ID NO. 261 | 1.678 | 1.741 | 1.037 | CREB_PMA |

FIG. 1U -- TABLE 1 TRANSCRIPTIONAL BIOMARKER FUNCTIONAL DATA
SECTION 7A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS* |
|---|---|---|---|---|---|---|
| 457 | APBB3 | SEQ ID NO. 262 | 0.457 | 0.556 | 1.216 | CREB_FSK |
| 458 | APBB3 | SEQ ID NO. 262 | 0.457 | 0.579 | 1.267 | CREB_PMA |
| 459 | FLAD1 | SEQ ID NO. 263 | 5.43 | 6.988 | 1.287 | CREB_FSK |
| 460 | FLAD1 | SEQ ID NO. 263 | 5.43 | 7.692 | 1.417 | CREB_PMA |
| 461 | ZC3H10 | SEQ ID NO. 264 | 13.979 | 15.245 | 1.091 | CREB_FSK |
| 462 | ZC3H10 | SEQ ID NO. 264 | 13.979 | 13.345 | 0.955 | CREB_PMA |
| 463 | AREG | SEQ ID NO. 265 | 0.066 | 0.129 | 1.951 | CREB_FSK |
| 464 | AREG | SEQ ID NO. 265 | 0.066 | 0.352 | 5.346 | CREB_PMA |
| 465 | SGK1 | SEQ ID NO. 265 | 0.215 | 0.336 | 1.563 | CREB_FSK |
| 466 | SGK1 | SEQ ID NO. 265 | 0.215 | 0.498 | 2.317 | CREB_PMA |
| 467 | UCP1 | SEQ ID NO. 266 | 0.024 | 0.039 | 1.674 | CREB_FSK |
| 468 | UCP1 | SEQ ID NO. 266 | 0.024 | 0.05 | 2.115 | CREB_PMA |
| 469 | TIPARP | SEQ ID NO. 266 | 0.006 | 0.004 | 0.736 | CREB_FSK |
| 470 | TIPARP | SEQ ID NO. 266 | 0.006 | 0.008 | 1.399 | CREB_PMA |
| 471 | INSIG1 | SEQ ID NO. 266 | 0.075 | 0.147 | 1.958 | CREB_FSK |
| 472 | INSIG1 | SEQ ID NO. 266 | 0.075 | 0.155 | 2.069 | CREB_PMA |
| 473 | ACOX3 | SEQ ID NO. 267 | 0.011 | 0.01 | 0.936 | CREB_FSK |
| 474 | ACOX3 | SEQ ID NO. 267 | 0.011 | 0.021 | 2.001 | CREB_PMA |
| 475 | NR4A3 | SEQ ID NO. 268 | 0.014 | 0.018 | 1.293 | CREB_FSK |
| 476 | NR4A3 | SEQ ID NO. 268 | 0.014 | 0.024 | 1.773 | CREB_PMA |
| 477 | NEDD9 | SEQ ID NO. 269 | 0.215 | 0.478 | 2.219 | CREB_FSK |
| 478 | NEDD9 | SEQ ID NO. 269 | 0.215 | 0.602 | 2.798 | CREB_PMA |
| 479 | NR4A1 | SEQ ID NO. 269 | 3.508 | 5.55 | 1.582 | CREB_FSK |
| 480 | NR4A1 | SEQ ID NO. 269 | 3.508 | 45.412 | 12.946 | CREB_PMA |
| 481 | SLC2A3 | SEQ ID NO. 270 | 0.014 | 0.019 | 1.368 | CREB_FSK |
| 482 | SLC2A3 | SEQ ID NO. 270 | 0.014 | 0.033 | 2.354 | CREB_PMA |
| 483 | HMGCR | SEQ ID NO. 270 | 0.605 | 0.532 | 0.88 | CREB_FSK |
| 484 | HMGCR | SEQ ID NO. 270 | 0.605 | 0.629 | 1.041 | CREB_PMA |
| 485 | ACOX3 | SEQ ID NO. 271 | 0.976 | 1.273 | 1.304 | CREB_FSK |
| 486 | ACOX3 | SEQ ID NO. 271 | 0.976 | 2.873 | 2.943 | CREB_PMA |
| 487 | NR4A1 | SEQ ID NO. 272 | 0.056 | 0.085 | 1.515 | CREB_FSK |
| 488 | NR4A1 | SEQ ID NO. 272 | 0.056 | 0.178 | 3.166 | CREB_PMA |
| 489 | BCL2 | SEQ ID NO. 273 | 0.055 | 0.071 | 1.294 | CREB_FSK |
| 490 | BCL2 | SEQ ID NO. 273 | 0.055 | 0.069 | 1.262 | CREB_PMA |
| 491 | DNAJB9 | SEQ ID NO. 274 | 8.925 | 10.912 | 1.223 | CREB_FSK |
| 492 | DNAJB9 | SEQ ID NO. 274 | 8.925 | 9.244 | 1.036 | CREB_PMA |
| 493 | TSC22D4 | SEQ ID NO. 275 | 0.972 | 0.719 | 0.74 | CREB_FSK |
| 494 | TSC22D4 | SEQ ID NO. 275 | 0.972 | 1.03 | 1.059 | CREB_PMA |
| 495 | POR | SEQ ID NO. 276 | 5.132 | 5.131 | 1 | CREB_FSK |
| 496 | POR | SEQ ID NO. 276 | 5.132 | 5.127 | 0.999 | CREB_PMA |
| 497 | NULL | SEQ ID NO. 277 | 0.071 | 0.065 | 0.912 | CREB_FSK |
| 498 | NULL | SEQ ID NO. 277 | 0.071 | 0.074 | 1.039 | CREB_PMA |
| 499 | POP7 | SEQ ID NO. 278 | 14.814 | 13.407 | 0.905 | CREB_FSK |
| 500 | POP7 | SEQ ID NO. 278 | 14.814 | 12.91 | 0.871 | CREB_PMA |
| 501 | NULL | SEQ ID NO. 279 | 1.671 | 1.915 | 1.146 | CREB_FSK |
| 502 | NULL | SEQ ID NO. 279 | 1.671 | 1.39 | 0.832 | CREB_PMA |

FIG. 1V -- TABLE 1 TRANSCRIPTIONAL BIOMARKER FUNCTIONAL DATA
SECTION 7A

| LINE_ID | GENE_SYMBOL | SEQUENCE_ID_LISTING | PROM_ACTIVITY_N O_INDUCTION | PROM_ACTIVITY_WITH_INDUCTION | INDUCTION_RATIO | INDUCTION_CONDITIONS* |
|---|---|---|---|---|---|---|
| 503 | TRIM56 | SEQ ID NO. 280 | 0.158 | 0.233 | 1.473 | CREB_FSK |
| 504 | TRIM56 | SEQ ID NO. 280 | 0.158 | 0.213 | 1.347 | CREB_PMA |
| 505 | REPIN1 | SEQ ID NO. 281 | 0.091 | 0.056 | 0.612 | CREB_FSK |
| 506 | REPIN1 | SEQ ID NO. 281 | 0.091 | 0.087 | 0.952 | CREB_PMA |
| 507 | INHBA | SEQ ID NO. 282 | 0.067 | 0.16 | 2.401 | CREB_FSK |
| 508 | INHBA | SEQ ID NO. 282 | 0.067 | 1.446 | 21.645 | CREB_PMA |
| 509 | BIRC3 | SEQ ID NO. 283 | 0.378 | 0.44 | 1.161 | CREB_FSK |
| 510 | BIRC3 | SEQ ID NO. 283 | 0.378 | 19.858 | 52.47 | CREB_PMA |
| 511 | APTX | SEQ ID NO. 284 | 0.019 | 0.032 | 1.704 | CREB_FSK |
| 512 | APTX | SEQ ID NO. 284 | 0.019 | 0.205 | 10.794 | CREB_PMA |
| 513 | CCND1 | SEQ ID NO. 285 | 0.069 | 0.091 | 1.326 | CREB_FSK |
| 514 | CCND1 | SEQ ID NO. 285 | 0.069 | 0.154 | 2.241 | CREB_PMA |
| 515 | BMF | SEQ ID NO. 286 | 0.095 | 0.113 | 1.19 | CREB_FSK |
| 516 | BMF | SEQ ID NO. 286 | 0.095 | 0.109 | 1.151 | CREB_PMA |
| 517 | BRCA1 | SEQ ID NO. 287 | 0.35 | 0.728 | 2.08 | CREB_FSK |
| 518 | BRCA1 | SEQ ID NO. 287 | 0.35 | 0.822 | 2.346 | CREB_PMA |
| 519 | PCNP | SEQ ID NO. 288 | 1.592 | 1.795 | 1.127 | CREB_FSK |
| 520 | PCNP | SEQ ID NO. 288 | 1.592 | 1.493 | 0.938 | CREB_PMA |
| 521 | APTX | SEQ ID NO. 289 | 1.145 | 1.721 | 1.503 | CREB_FSK |
| 522 | APTX | SEQ ID NO. 289 | 1.145 | 1.711 | 1.493 | CREB_PMA |
| 523 | BMF | SEQ ID NO. 290 | 0.121 | 0.137 | 1.133 | CREB_FSK |
| 524 | BMF | SEQ ID NO. 290 | 0.121 | 0.179 | 1.437 | CREB_PMA |
| 525 | RECQL5 | SEQ ID NO. 291 | 0.293 | 0.327 | 1.116 | CREB_FSK |
| 526 | RECQL5 | SEQ ID NO. 291 | 0.293 | 0.507 | 1.731 | CREB_PMA |
| 527 | EIF2B1 | SEQ ID NO. 292 | 0.119 | 0.163 | 1.363 | CREB_FSK |
| 528 | EIF2B1 | SEQ ID NO. 292 | 0.119 | 0.188 | 1.575 | CREB_PMA |
| 529 | CCNL1 | SEQ ID NO. 293 | 0.008 | 0.011 | 1.367 | CREB_FSK |
| 530 | CCNL1 | SEQ ID NO. 293 | 0.008 | 0.012 | 1.446 | CREB_PMA |
| 531 | TNF | SEQ ID NO. 294 | 0.009 | 0.031 | 3.402 | CREB_FSK |
| 532 | TNF | SEQ ID NO. 294 | 0.009 | 0.048 | 5.323 | CREB_PMA |
| 533 | GTF2H1 | SEQ ID NO. 295 | 3.722 | 4.634 | 1.245 | CREB_FSK |
| 534 | GTF2H1 | SEQ ID NO. 295 | 3.722 | 9.793 | 2.631 | CREB_PMA |
| 535 | GADD45G | SEQ ID NO. 296 | 0.005 | 0.007 | 1.548 | CREB_FSK |
| 536 | GADD45G | SEQ ID NO. 296 | 0.005 | 0.007 | 1.596 | CREB_PMA |
| 537 | HSPA5 | SEQ ID NO. 297 | 0.056 | 0.075 | 1.343 | CREB_FSK |
| 538 | HSPA5 | SEQ ID NO. 297 | 0.056 | 0.081 | 1.453 | CREB_PMA |
| 539 | DDIT3 | SEQ ID NO. 298 | 14.752 | 15.287 | 1.036 | CREB_FSK |
| 540 | DDIT3 | SEQ ID NO. 298 | 14.752 | 53.538 | 3.629 | CREB_PMA |
| 541 | CCNG2 | SEQ ID NO. 299 | 0.062 | 0.096 | 1.554 | CREB_FSK |
| 542 | CCNG2 | SEQ ID NO. 299 | 0.062 | 0.214 | 3.464 | CREB_PMA |
| 543 | RGS2 | SEQ ID NO. 300 | 0.007 | 0.008 | 1.244 | CREB_FSK |
| 544 | RGS2 | SEQ ID NO. 300 | 0.007 | 0.011 | 1.658 | CREB_PMA |
| 545 | PTP4A1 | SEQ ID NO. 301 | 3.951 | 7.155 | 1.811 | CREB_FSK |
| 546 | PTP4A1 | SEQ ID NO. 301 | 3.951 | 6.324 | 1.601 | CREB_PMA |
| 547 | MAFF | SEQ ID NO. 302 | 1.975 | 2.722 | 1.378 | CREB_FSK |
| 548 | MAFF | SEQ ID NO. 302 | 1.975 | 4.366 | 2.211 | CREB_PMA |

FIG. 1W -- TABLE 1 TRANSCRIPTIONAL BIOMARKER FUNCTIONAL DATA
SECTION 7A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS* |
|---|---|---|---|---|---|---|
| 549 | CCND1 | SEQ ID NO. 303 | 0.597 | 1.117 | 1.871 | CREB_FSK |
| 550 | CCND1 | SEQ ID NO. 303 | 0.597 | 2.637 | 4.419 | CREB_PMA |
| 551 | NF1 | SEQ ID NO. 304 | 0.066 | 0.064 | 0.978 | CREB_FSK |
| 552 | NF1 | SEQ ID NO. 304 | 0.066 | 0.069 | 1.054 | CREB_PMA |
| 553 | INHA | SEQ ID NO. 305 | 0.044 | 0.067 | 1.547 | CREB_FSK |
| 554 | INHA | SEQ ID NO. 305 | 0.044 | 0.113 | 2.589 | CREB_PMA |
| 555 | NFKBIB | SEQ ID NO. 306 | 0.267 | 0.349 | 1.308 | CREB_FSK |
| 556 | NFKBIB | SEQ ID NO. 306 | 0.267 | 0.589 | 2.208 | CREB_PMA |
| 557 | MYC | SEQ ID NO. 307 | 0.341 | 0.354 | 1.038 | CREB_FSK |
| 558 | MYC | SEQ ID NO. 307 | 0.341 | 0.769 | 2.259 | CREB_PMA |
| 559 | DUSP1 | SEQ ID NO. 308 | 0.012 | 0.014 | 1.164 | CREB_FSK |
| 560 | DUSP1 | SEQ ID NO. 308 | 0.012 | 0.017 | 1.479 | CREB_PMA |
| 561 | ETS2 | SEQ ID NO. 309 | 0.809 | 1.028 | 1.27 | CREB_FSK |
| 562 | ETS2 | SEQ ID NO. 309 | 0.809 | 1.429 | 1.767 | CREB_PMA |
| 563 | HDAC6 | SEQ ID NO. 310 | 0.618 | 0.724 | 1.157 | CREB_FSK |
| 564 | HDAC6 | SEQ ID NO. 310 | 0.618 | 0.937 | 1.517 | CREB_PMA |
| 565 | DUSP4 | SEQ ID NO. 311 | 0.241 | 0.24 | 0.997 | CREB_FSK |
| 566 | DUSP4 | SEQ ID NO. 311 | 0.241 | 0.734 | 3.046 | CREB_PMA |
| 567 | APTX | SEQ ID NO. 311 | 1.85 | 3.261 | 1.762 | CREB_FSK |
| 568 | APTX | SEQ ID NO. 311 | 1.85 | 2.025 | 1.094 | CREB_PMA |
| 569 | PCNA | SEQ ID NO. 312 | 0.745 | 1.419 | 1.904 | CREB_FSK |
| 570 | PCNA | SEQ ID NO. 312 | 0.745 | 0.89 | 1.195 | CREB_PMA |
| 571 | PTP4A1 | SEQ ID NO. 313 | 0.353 | 0.584 | 1.654 | CREB_FSK |
| 572 | PTP4A1 | SEQ ID NO. 313 | 0.353 | 0.915 | 2.591 | CREB_PMA |
| 573 | PIM1 | SEQ ID NO. 314 | 1.98 | 3.29 | 1.661 | CREB_FSK |
| 574 | PIM1 | SEQ ID NO. 314 | 1.98 | 2.217 | 1.12 | CREB_PMA |
| 575 | HTT | SEQ ID NO. 315 | 17.284 | 18.652 | 1.079 | CREB_FSK |
| 576 | HTT | SEQ ID NO. 315 | 17.284 | 22.117 | 1.28 | CREB_PMA |
| 577 | JUND | SEQ ID NO. 316 | 0.09 | 0.094 | 1.05 | CREB_FSK |
| 578 | JUND | SEQ ID NO. 316 | 0.09 | 0.108 | 1.198 | CREB_PMA |
| 579 | IFRD1 | SEQ ID NO. 317 | 0.032 | 0.052 | 1.615 | CREB_FSK |
| 580 | IFRD1 | SEQ ID NO. 317 | 0.032 | 0.064 | 1.97 | CREB_PMA |
| 581 | IGFBP1 | SEQ ID NO. 318 | 0.155 | 0.159 | 1.022 | CREB_FSK |
| 582 | IGFBP1 | SEQ ID NO. 318 | 0.155 | 0.288 | 1.853 | CREB_PMA |
| 583 | PDK4 | SEQ ID NO. 319 | 0.027 | 0.042 | 1.546 | CREB_FSK |
| 584 | PDK4 | SEQ ID NO. 319 | 0.027 | 0.061 | 2.223 | CREB_PMA |
| 585 | IFRD1 | SEQ ID NO. 320 | 0.069 | 0.172 | 2.501 | CREB_FSK |
| 586 | IFRD1 | SEQ ID NO. 320 | 0.069 | 0.157 | 2.231 | CREB_PMA |
| 587 | FGF6 | SEQ ID NO. 321 | 0.083 | 0.081 | 0.982 | CREB_FSK |
| 588 | FGF6 | SEQ ID NO. 321 | 0.083 | 0.085 | 1.03 | CREB_PMA |
| 589 | CDK5 | SEQ ID NO. 322 | 0.136 | 0.241 | 1.774 | CREB_FSK |
| 590 | CDK5 | SEQ ID NO. 322 | 0.136 | 0.176 | 1.301 | CREB_PMA |
| 591 | CKS2 | SEQ ID NO. 323 | 8.077 | 11.347 | 1.405 | CREB_FSK |
| 592 | CKS2 | SEQ ID NO. 323 | 8.077 | 28.302 | 3.504 | CREB_PMA |
| 593 | NEDD9 | SEQ ID NO. 324 | 0.052 | 0.061 | 1.171 | CREB_FSK |
| 594 | NEDD9 | SEQ ID NO. 324 | 0.052 | 0.106 | 2.02 | CREB_PMA |

FIG. 1X -- TABLE 1 TRANSCRIPTIONAL BIOMARKER FUNCTIONAL DATA
SECTION 7A

| LINE_ID | GENE_SYMBOL | SEQUENCE_ID_LISTING | PROM_ACTIVITY_N O_INDUCTION | PROM_ACTIVITY_WI TH_INDUCTION | INDUCTION RATIO | INDUCTION_CONDITIONS* |
|---|---|---|---|---|---|---|
| 595 | CDKN2B | SEQ ID NO. 325 | 0.83 | 1.378 | 1.66 | CREB_FSK |
| 596 | CDKN2B | SEQ ID NO. 325 | 0.83 | 4.764 | 5.739 | CREB_PMA |
| 597 | EXO1 | SEQ ID NO. 326 | 0.11 | 0.17 | 1.544 | CREB_FSK |
| 598 | EXO1 | SEQ ID NO. 326 | 0.11 | 1.35 | 12.25 | CREB_PMA |
| 599 | SSSCA1 | SEQ ID NO. 327 | 0.085 | 0.114 | 1.334 | CREB_FSK |
| 600 | SSSCA1 | SEQ ID NO. 327 | 0.085 | 0.164 | 1.925 | CREB_PMA |
| 601 | JUN | SEQ ID NO. 328 | 0.037 | 0.066 | 1.79 | CREB_FSK |
| 602 | JUN | SEQ ID NO. 328 | 0.037 | 0.173 | 4.694 | CREB_PMA |
| 603 | PTGS2 | SEQ ID NO. 329 | 0.094 | 0.111 | 1.174 | CREB_FSK |
| 604 | PTGS2 | SEQ ID NO. 329 | 0.094 | 0.454 | 4.81 | CREB_PMA |
| 605 | AGT | SEQ ID NO. 330 | 0.092 | 0.196 | 2.134 | CREB_FSK |
| 606 | AGT | SEQ ID NO. 330 | 0.092 | 0.495 | 5.393 | CREB_PMA |
| 607 | ADRB1 | SEQ ID NO. 331 | 0.007 | 0.01 | 1.441 | CREB_FSK |
| 608 | ADRB1 | SEQ ID NO. 331 | 0.007 | 0.018 | 2.438 | CREB_PMA |
| 609 | ADM | SEQ ID NO. 332 | 0.012 | 0.014 | 1.156 | CREB_FSK |
| 610 | ADM | SEQ ID NO. 332 | 0.012 | 0.017 | 1.332 | CREB_PMA |
| 611 | LDHA | SEQ ID NO. 332 | 0.007 | 0.01 | 1.422 | CREB_FSK |
| 612 | LDHA | SEQ ID NO. 332 | 0.007 | 0.019 | 2.733 | CREB_PMA |
| 613 | FOS | SEQ ID NO. 333 | 0.007 | 0.007 | 1.075 | CREB_FSK |
| 614 | FOS | SEQ ID NO. 333 | 0.007 | 0.015 | 2.236 | CREB_PMA |
| 615 | NOS2A | SEQ ID NO. 334 | 0.053 | 0.08 | 1.498 | CREB_FSK |
| 616 | NOS2A | SEQ ID NO. 334 | 0.053 | 0.239 | 4.479 | CREB_PMA |
| 617 | HK2 | SEQ ID NO. 334 | 0.014 | 0.019 | 1.388 | CREB_FSK |
| 618 | HK2 | SEQ ID NO. 334 | 0.014 | 0.022 | 1.658 | CREB_PMA |
| 619 | EGF | SEQ ID NO. 335 | 0.509 | 0.523 | 1.028 | CREB_FSK |
| 620 | EGF | SEQ ID NO. 335 | 0.509 | 1.267 | 2.491 | CREB_PMA |
| 621 | IL6 | SEQ ID NO. 336 | 0.888 | 0.715 | 0.804 | CREB_FSK |
| 622 | IL6 | SEQ ID NO. 336 | 0.888 | 7.269 | 8.181 | CREB_PMA |
| 623 | CYCS | SEQ ID NO. 337 | 6.803 | 8.264 | 1.215 | CREB_FSK |
| 624 | CYCS | SEQ ID NO. 337 | 6.803 | 17.06 | 2.508 | CREB_PMA |
| 625 | NR3C1 | SEQ ID NO. 338 | 0.006 | 0.008 | 1.445 | CREB_FSK |
| 626 | NR3C1 | SEQ ID NO. 338 | 0.006 | 0.012 | 2.11 | CREB_PMA |
| 627 | PC | SEQ ID NO. 339 | 0.345 | 0.332 | 2.414 | CREB_FSK |
| 628 | PC | SEQ ID NO. 339 | 0.345 | 0.877 | 2.547 | CREB_PMA |
| 629 | PLAUR | SEQ ID NO. 340 | 0.036 | 0.055 | 1.53 | CREB_FSK |
| 630 | PLAUR | SEQ ID NO. 340 | 0.036 | 0.374 | 10.448 | CREB_PMA |
| 631 | EMD | SEQ ID NO. 341 | 1.41 | 2.551 | 1.809 | CREB_FSK |
| 632 | EMD | SEQ ID NO. 341 | 1.41 | 1.904 | 1.351 | CREB_PMA |
| 633 | SFRS11 | SEQ ID NO. 342 | 0.009 | 0.009 | 0.99 | CREB_FSK |
| 634 | SFRS11 | SEQ ID NO. 342 | 0.009 | 0.013 | 1.436 | CREB_PMA |
| 635 | SFRS11 | SEQ ID NO. 343 | 0.017 | 0.023 | 1.327 | CREB_FSK |
| 636 | SFRS11 | SEQ ID NO. 343 | 0.017 | 0.024 | 1.408 | CREB_PMA |
| 637 | ATP1A1 | SEQ ID NO. 344 | 0.476 | 0.976 | 2.05 | CREB_FSK |
| 638 | ATP1A1 | SEQ ID NO. 344 | 0.476 | 0.91 | 1.912 | CREB_PMA |
| 639 | ATP1A1 | SEQ ID NO. 345 | 0.04 | 0.061 | 1.529 | CREB_FSK |
| 640 | ATP1A1 | SEQ ID NO. 345 | 0.04 | 0.084 | 2.112 | CREB_PMA |
| 641 | RGS1 | SEQ ID NO. 346 | 0.019 | 0.02 | 1.059 | CREB_FSK |
| 642 | RGS1 | SEQ ID NO. 346 | 0.019 | 0.037 | 1.9 | CREB_PMA |

FIG. 1Y — TABLE 1 TRANSCRIPTIONAL BIOMARKER FUNCTIONAL DATA
SECTION 7A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS* |
|---|---|---|---|---|---|---|
| 643 | ATF3 | SEQ ID NO. 347 | 0.319 | 0.171 | 0.536 | CREB_FSK |
| 644 | ATF3 | SEQ ID NO. 347 | 0.319 | 0.18 | 0.563 | CREB_PMA |
| 645 | BMP8B | SEQ ID NO. 348 | 0.247 | 0.499 | 2.023 | CREB_FSK |
| 646 | BMP8B | SEQ ID NO. 348 | 0.247 | 0.688 | 2.789 | CREB_PMA |
| 647 | MAGOH | SEQ ID NO. 349 | 1.515 | 1.74 | 1.149 | CREB_FSK |
| 648 | MAGOH | SEQ ID NO. 349 | 1.515 | 2.209 | 1.458 | CREB_PMA |
| 649 | PTGER3 | SEQ ID NO. 350 | 0.056 | 0.079 | 1.397 | CREB_FSK |
| 650 | PTGER3 | SEQ ID NO. 350 | 0.056 | 0.143 | 2.53 | CREB_PMA |
| 651 | PMVK | SEQ ID NO. 351 | 0.145 | 0.205 | 1.413 | CREB_FSK |
| 652 | PMVK | SEQ ID NO. 351 | 0.145 | 0.253 | 1.74 | CREB_PMA |
| 653 | ZEB1 | SEQ ID NO. 352 | 0.664 | 0.656 | 0.988 | CREB_FSK |
| 654 | ZEB1 | SEQ ID NO. 352 | 0.664 | 1.146 | 1.726 | CREB_PMA |
| 655 | CREM | SEQ ID NO. 353 | 2.387 | 3.441 | 1.441 | CREB_FSK |
| 656 | CREM | SEQ ID NO. 353 | 2.387 | 4.634 | 1.941 | CREB_PMA |
| 657 | CREM | SEQ ID NO. 354 | 0.079 | 0.288 | 3.633 | CREB_FSK |
| 658 | CREM | SEQ ID NO. 354 | 0.079 | 3.352 | 42.25 | CREB_PMA |
| 659 | GHITM | SEQ ID NO. 355 | 9.601 | 12.339 | 1.285 | CREB_FSK |
| 660 | GHITM | SEQ ID NO. 355 | 9.601 | 16.964 | 1.767 | CREB_PMA |
| 661 | ID11 | SEQ ID NO. 355 | 0.03 | 0.045 | 1.511 | CREB_FSK |
| 662 | ID11 | SEQ ID NO. 355 | 0.03 | 0.049 | 1.653 | CREB_PMA |
| 663 | ID11 | SEQ ID NO. 356 | 0.198 | 0.409 | 2.063 | CREB_FSK |
| 664 | ID11 | SEQ ID NO. 356 | 0.198 | 0.712 | 3.59 | CREB_PMA |
| 665 | RRM1 | SEQ ID NO. 357 | 0.055 | 0.051 | 0.924 | CREB_FSK |
| 666 | RRM1 | SEQ ID NO. 357 | 0.055 | 0.04 | 0.737 | CREB_PMA |
| 667 | GAL | SEQ ID NO. 358 | 0.006 | 0.009 | 1.547 | CREB_FSK |
| 668 | GAL | SEQ ID NO. 358 | 0.006 | 0.012 | 2.197 | CREB_PMA |
| 669 | FAU | SEQ ID NO. 359 | 2.381 | 2.159 | 0.907 | CREB_FSK |
| 670 | FAU | SEQ ID NO. 359 | 2.381 | 1.613 | 0.677 | CREB_PMA |
| 671 | UCP2 | SEQ ID NO. 360 | 0.122 | 0.281 | 2.301 | CREB_FSK |
| 672 | UCP2 | SEQ ID NO. 360 | 0.122 | 0.291 | 2.379 | CREB_PMA |
| 673 | SRPR | SEQ ID NO. 361 | 0.115 | 0.295 | 2.572 | CREB_FSK |
| 674 | SRPR | SEQ ID NO. 361 | 0.115 | 0.248 | 2.162 | CREB_PMA |
| 675 | AQP2 | SEQ ID NO. 362 | 0.094 | 0.072 | 0.761 | CREB_FSK |
| 676 | AQP2 | SEQ ID NO. 362 | 0.094 | 0.137 | 1.454 | CREB_PMA |
| 677 | PWP1 | SEQ ID NO. 363 | 0.034 | 0.038 | 1.126 | CREB_FSK |
| 678 | PWP1 | SEQ ID NO. 363 | 0.034 | 0.048 | 1.404 | CREB_PMA |
| 679 | MAPKAPK5 | SEQ ID NO. 364 | 0.044 | 0.067 | 1.509 | CREB_FSK |
| 680 | MAPKAPK5 | SEQ ID NO. 364 | 0.044 | 0.045 | 1.022 | CREB_PMA |
| 681 | MAPKAPK5 | SEQ ID NO. 365 | 0.408 | 0.487 | 1.194 | CREB_FSK |
| 682 | MAPKAPK5 | SEQ ID NO. 365 | 0.408 | 0.498 | 1.222 | CREB_PMA |
| 683 | ZNF26 | SEQ ID NO. 366 | 0.072 | 0.107 | 1.494 | CREB_FSK |
| 684 | ZNF26 | SEQ ID NO. 366 | 0.072 | 0.071 | 0.99 | CREB_PMA |
| 685 | CNPY2 | SEQ ID NO. 357 | 0.044 | 0.043 | 0.984 | CREB_FSK |
| 686 | CNPY2 | SEQ ID NO. 357 | 0.044 | 0.037 | 0.842 | CREB_PMA |
| 687 | SDS | SEQ ID NO. 358 | 0.391 | 0.381 | 0.974 | CREB_FSK |
| 688 | SDS | SEQ ID NO. 358 | 0.391 | 1.144 | 2.928 | CREB_PMA |
| 689 | SPRY2 | SEQ ID NO. 369 | 0.481 | 0.849 | 1.767 | CREB_FSK |
| 690 | SPRY2 | SEQ ID NO. 369 | 0.481 | 1.29 | 2.684 | CREB_PMA |

FIG. 1Z -- TABLE 1 TRANSCRIPTIONAL BIOMARKER FUNCTIONAL DATA
SECTION 7A

| LINE_ID | GENE_SYMBOL | SEQUENCE_ID_LISTING | PROM_ACTIVITY_N O_INDUCTION | PROM_ACTIVITY_N TH_INDUCTION | PROM_ACTIVITY_WI INDUCTION | INDUCTION RATIO | INDUCTION_CONDITIONS |
|---|---|---|---|---|---|---|---|
| 691 | PCK2 | SEQ ID NO. 370 | 0.009 | 0.013 | 1.437 | CREB_FSK |
| 692 | PCK2 | SEQ ID NO. 370 | 0.009 | 0.01 | 1.044 | CREB_PMA |
| 693 | CHGA | SEQ ID NO. 371 | 0.046 | 0.076 | 1.644 | CREB_FSK |
| 694 | CHGA | SEQ ID NO. 371 | 0.046 | 0.088 | 1.908 | CREB_PMA |
| 695 | RPS6KA5 | SEQ ID NO. 372 | 0.134 | 0.189 | 1.407 | CREB_FSK |
| 696 | RPS6KA5 | SEQ ID NO. 372 | 0.134 | 0.153 | 1.136 | CREB_PMA |
| 697 | NULL | SEQ ID NO. 373 | 0.061 | 0.111 | 1.382 | CREB_FSK |
| 698 | NULL | SEQ ID NO. 373 | 0.081 | 0.347 | 4.306 | CREB_PMA |
| 699 | RRAD | SEQ ID NO. 374 | 0.085 | 0.144 | 1.706 | CREB_FSK |
| 700 | RRAD | SEQ ID NO. 374 | 0.085 | 1.003 | 11.844 | CREB_PMA |
| 701 | TAT | SEQ ID NO. 375 | 0.279 | 0.371 | 1.332 | CREB_FSK |
| 702 | TAT | SEQ ID NO. 375 | 0.279 | 0.884 | 3.17 | CREB_PMA |
| 703 | SSTR2 | SEQ ID NO. 376 | 0.135 | 0.196 | 1.453 | CREB_FSK |
| 704 | SSTR2 | SEQ ID NO. 376 | 0.135 | 0.246 | 1.827 | CREB_PMA |
| 705 | AANAT | SEQ ID NO. 377 | 0.074 | 0.086 | 1.161 | CREB_FSK |
| 706 | AANAT | SEQ ID NO. 377 | 0.074 | 0.175 | 2.374 | CREB_PMA |
| 707 | PER1 | SEQ ID NO. 378 | 0.272 | 0.258 | 0.949 | CREB_FSK |
| 708 | PER1 | SEQ ID NO. 378 | 0.272 | 0.672 | 2.469 | CREB_PMA |
| 709 | TOB1 | SEQ ID NO. 379 | 0.074 | 0.28 | 3.775 | CREB_FSK |
| 710 | TOB1 | SEQ ID NO. 379 | 0.074 | 0.368 | 4.971 | CREB_PMA |
| 711 | PMAIP1 | SEQ ID NO. 380 | 4.989 | 8.736 | 1.761 | CREB_FSK |
| 712 | PMAIP1 | SEQ ID NO. 380 | 4.989 | 20.907 | 4.19 | CREB_PMA |
| 713 | VPS4B | SEQ ID NO. 381 | 0.034 | 0.03 | 0.886 | CREB_FSK |
| 714 | VPS4B | SEQ ID NO. 381 | 0.034 | 0.063 | 1.999 | CREB_PMA |
| 715 | BCKDHA | SEQ ID NO. 382 | 0.948 | 0.944 | 0.996 | CREB_FSK |
| 716 | BCKDHA | SEQ ID NO. 382 | 0.948 | 1.519 | 1.602 | CREB_PMA |
| 717 | GIPR | SEQ ID NO. 383 | 0.138 | 0.184 | 1.337 | CREB_FSK |
| 718 | GIPR | SEQ ID NO. 383 | 0.138 | 3.276 | 23.815 | CREB_PMA |
| 719 | ZNF331 | SEQ ID NO. 384 | 0.846 | 1.174 | 1.388 | CREB_FSK |
| 720 | ZNF331 | SEQ ID NO. 384 | 0.846 | 1.252 | 1.481 | CREB_PMA |
| 721 | OPA3 | SEQ ID NO. 385 | 1.015 | 1.023 | 1.007 | CREB_FSK |
| 722 | OPA3 | SEQ ID NO. 385 | 1.015 | 1.628 | 1.603 | CREB_PMA |
| 723 | ID2 | SEQ ID NO. 386 | 1.208 | 1.413 | 1.174 | CREB_FSK |
| 724 | ID2 | SEQ ID NO. 386 | 1.208 | 0.92 | 0.762 | CREB_PMA |
| 725 | C2orf49 | SEQ ID NO. 387 | 0.025 | 0.026 | 1.033 | CREB_FSK |
| 726 | C2orf49 | SEQ ID NO. 387 | 0.025 | 0.031 | 1.25 | CREB_PMA |
| 727 | CREB1 | SEQ ID NO. 388 | 0.511 | 0.713 | 1.394 | CREB_FSK |
| 728 | CREB1 | SEQ ID NO. 388 | 0.511 | 2.713 | 5.306 | CREB_PMA |
| 729 | ODC1 | SEQ ID NO. 389 | 0.056 | 0.07 | 1.239 | CREB_FSK |
| 730 | ODC1 | SEQ ID NO. 389 | 0.056 | 0.399 | 7.108 | CREB_PMA |
| 731 | ZFP36L2 | SEQ ID NO. 390 | 0.176 | 0.154 | 0.873 | CREB_FSK |
| 732 | ZFP36L2 | SEQ ID NO. 390 | 0.176 | 0.256 | 1.456 | CREB_PMA |
| 733 | TACR1 | SEQ ID NO. 391 | 0.052 | 0.115 | 2.213 | CREB_FSK |
| 734 | TACR1 | SEQ ID NO. 391 | 0.052 | 0.207 | 3.976 | CREB_PMA |
| 735 | NULL | SEQ ID NO. 392 | 0.521 | 0.787 | 1.509 | CREB_FSK |
| 736 | NULL | SEQ ID NO. 392 | 0.521 | 0.709 | 1.359 | CREB_PMA |
| 737 | GCG | SEQ ID NO. 393 | 0.033 | 0.063 | 1.928 | CREB_FSK |
| 738 | GCG | SEQ ID NO. 393 | 0.033 | 0.192 | 5.903 | CREB_PMA |

FIG. 1AA – TABLE 1 TRANSCRIPTIONAL BIOMARKER FUNCTIONAL DATA
SECTION 7A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS |
|---|---|---|---|---|---|---|
| 739 | FN1 | SEQ ID NO. 394 | 0.132 | 0.14 | 1.063 | CREB_FSK |
| 740 | FN1 | SEQ ID NO. 394 | 0.132 | 0.705 | 5.356 | CREB_PMA |
| 741 | FN1 | SEQ ID NO. 395 | 0.039 | 0.062 | 1.613 | CREB_FSK |
| 742 | FN1 | SEQ ID NO. 395 | 0.039 | 0.097 | 2.515 | CREB_PMA |
| 743 | ID1 | SEQ ID NO. 396 | 0.022 | 0.043 | 1.93 | CREB_FSK |
| 744 | ID1 | SEQ ID NO. 396 | 0.022 | 0.032 | 1.446 | CREB_PMA |
| 745 | CEBPB | SEQ ID NO. 397 | 0.014 | 0.053 | 3.665 | CREB_FSK |
| 746 | CEBPB | SEQ ID NO. 397 | 0.014 | 0.071 | 4.937 | CREB_PMA |
| 747 | CRYAA | SEQ ID NO. 398 | 0.016 | 0.03 | 1.86 | CREB_FSK |
| 748 | CRYAA | SEQ ID NO. 398 | 0.016 | 0.063 | 3.86 | CREB_PMA |
| 749 | ADAMTS1 | SEQ ID NO. 399 | 0.042 | 0.083 | 1.958 | CREB_FSK |
| 750 | ADAMTS1 | SEQ ID NO. 399 | 0.042 | 0.096 | 2.263 | CREB_PMA |
| 751 | U2AF1 | SEQ ID NO. 400 | 0.462 | 0.594 | 1.287 | CREB_FSK |
| 752 | U2AF1 | SEQ ID NO. 400 | 0.462 | 0.633 | 1.37 | CREB_PMA |
| 753 | NUP50 | SEQ ID NO. 401 | 0.567 | 0.833 | 1.558 | CREB_FSK |
| 754 | NUP50 | SEQ ID NO. 401 | 0.567 | 0.961 | 1.695 | CREB_PMA |
| 755 | BHLHB2 | SEQ ID NO. 402 | 3.429 | 2.477 | 0.722 | CREB_FSK |
| 756 | BHLHB2 | SEQ ID NO. 402 | 3.429 | 22.411 | 6.536 | CREB_PMA |
| 757 | SNRK | SEQ ID NO. 403 | 0.695 | 1.019 | 1.467 | CREB_FSK |
| 758 | SNRK | SEQ ID NO. 403 | 0.695 | 1.292 | 1.86 | CREB_PMA |
| 759 | ALAS1 | SEQ ID NO. 404 | 1.228 | 1.673 | 1.362 | CREB_FSK |
| 760 | ALAS1 | SEQ ID NO. 404 | 1.228 | 2.732 | 2.224 | CREB_PMA |
| 761 | STK19 | SEQ ID NO. 405 | 0.015 | 0.018 | 1.215 | CREB_FSK |
| 762 | STK19 | SEQ ID NO. 405 | 0.015 | 0.023 | 1.494 | CREB_PMA |
| 763 | STK19 | SEQ ID NO. 406 | 0.016 | 0.017 | 1.065 | CREB_FSK |
| 764 | STK19 | SEQ ID NO. 406 | 0.016 | 0.039 | 2.428 | CREB_PMA |
| 765 | AMD1 | SEQ ID NO. 407 | 0.083 | 0.093 | 1.123 | CREB_FSK |
| 766 | AMD1 | SEQ ID NO. 407 | 0.083 | 0.137 | 1.652 | CREB_PMA |
| 767 | AMD1 | SEQ ID NO. 408 | 0.06 | 0.08 | 1.344 | CREB_FSK |
| 768 | AMD1 | SEQ ID NO. 408 | 0.06 | 0.158 | 2.657 | CREB_PMA |
| 769 | VIP | SEQ ID NO. 409 | 0.03 | 0.056 | 1.896 | CREB_FSK |
| 770 | VIP | SEQ ID NO. 409 | 0.03 | 0.098 | 3.31 | CREB_PMA |
| 771 | CITED2 | SEQ ID NO. 410 | 0.028 | 0.044 | 1.595 | CREB_FSK |
| 772 | CITED2 | SEQ ID NO. 410 | 0.028 | 0.034 | 1.228 | CREB_PMA |
| 773 | SLC7A2 | SEQ ID NO. 411 | 0.192 | 0.489 | 2.545 | CREB_FSK |
| 774 | SLC7A2 | SEQ ID NO. 411 | 0.192 | 0.449 | 2.335 | CREB_PMA |
| 775 | SLC18A1 | SEQ ID NO. 412 | 0.049 | 0.129 | 2.651 | CREB_FSK |
| 776 | SLC18A1 | SEQ ID NO. 412 | 0.049 | 0.114 | 2.344 | CREB_PMA |
| 777 | CEBPD | SEQ ID NO. 413 | 0.081 | 0.079 | 0.97 | CREB_FSK |
| 778 | CEBPD | SEQ ID NO. 413 | 0.081 | 0.185 | 2.281 | CREB_PMA |
| 779 | CRH | SEQ ID NO. 414 | 0.031 | 0.041 | 1.338 | CREB_FSK |
| 780 | CRH | SEQ ID NO. 414 | 0.031 | 0.073 | 2.362 | CREB_PMA |
| 781 | PLAA | SEQ ID NO. 415 | 0.267 | 0.308 | 1.154 | CREB_FSK |
| 782 | PLAA | SEQ ID NO. 415 | 0.267 | 0.552 | 2.067 | CREB_PMA |
| 783 | NFIL3 | SEQ ID NO. 416 | 0.531 | 0.486 | 0.916 | CREB_FSK |
| 784 | NFIL3 | SEQ ID NO. 416 | 0.531 | 1.037 | 1.954 | CREB_PMA |
| 785 | KLF4 | SEQ ID NO. 417 | 1.057 | 1.414 | 1.337 | CREB_FSK |
| 786 | KLF4 | SEQ ID NO. 417 | 1.057 | 2.094 | 1.981 | CREB_PMA |

FIG. 1AB -- TABLE 1 TRANSCRIPTIONAL BIOMARKER FUNCTIONAL DATA
SECTION 7A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS* |
|---|---|---|---|---|---|---|
| 787 | MED27 | SEQ ID NO. 418 | 0.027 | 0.035 | 1.275 | CREB_FSK |
| 788 | MED27 | SEQ ID NO. 418 | 0.027 | 0.03 | 1.121 | CREB_PMA |
| 789 | SMS | SEQ ID NO. 419 | 0.053 | 0.07 | 1.308 | CREB_FSK |
| 790 | SMS | SEQ ID NO. 419 | 0.053 | 0.268 | 5.022 | CREB_PMA |
| 791 | PIGA | SEQ ID NO. 420 | 0.015 | 0.025 | 1.693 | CREB_FSK |
| 792 | PIGA | SEQ ID NO. 420 | 0.015 | 0.025 | 1.681 | CREB_PMA |
| 793 | EFNA1 | SEQ ID NO. 421 | 0.018 | 0.022 | 1.222 | CREB_FSK |
| 794 | EFNA1 | SEQ ID NO. 421 | 0.018 | 0.033 | 1.826 | CREB_PMA |
| 795 | CALCA | SEQ ID NO. 422 | 0.048 | 0.366 | 7.672 | CREB_FSK |
| 796 | CALCA | SEQ ID NO. 422 | 0.048 | 0.132 | 2.766 | CREB_PMA |
| 797 | PC | SEQ ID NO. 423 | 0.294 | 0.301 | 1.023 | CREB_FSK |
| 798 | PC | SEQ ID NO. 423 | 0.294 | 0.613 | 2.083 | CREB_PMA |
| 799 | DIO2 | SEQ ID NO. 424 | 0.108 | 0.118 | 1.084 | CREB_FSK |
| 800 | DIO2 | SEQ ID NO. 424 | 0.108 | 0.164 | 1.507 | CREB_PMA |
| 801 | TIMM13 | SEQ ID NO. 425 | 1.713 | 1.544 | 0.901 | CREB_FSK |
| 802 | TIMM13 | SEQ ID NO. 425 | 1.713 | 2.273 | 1.327 | CREB_PMA |
| 803 | FN1 | SEQ ID NO. 426 | 0.042 | 0.039 | 0.911 | CREB_FSK |
| 804 | FN1 | SEQ ID NO. 426 | 0.042 | 0.074 | 1.743 | CREB_PMA |
| 805 | CHGB | SEQ ID NO. 427 | 0.127 | 0.142 | 1.119 | CREB_FSK |
| 806 | CHGB | SEQ ID NO. 427 | 0.127 | 0.298 | 2.339 | CREB_PMA |
| 807 | NUP50 | SEQ ID NO. 428 | 0.015 | 0.016 | 1.033 | CREB_FSK |
| 808 | NUP50 | SEQ ID NO. 428 | 0.015 | 0.038 | 2.409 | CREB_PMA |
| 809 | AGXT2L1 | SEQ ID NO. 429 | 0.037 | 0.05 | 1.349 | CREB_FSK |
| 810 | AGXT2L1 | SEQ ID NO. 429 | 0.037 | 0.085 | 2.296 | CREB_PMA |
| 811 | HIST1H4E | SEQ ID NO. 430 | 0.217 | 0.209 | 0.962 | CREB_FSK |
| 812 | HIST1H4E | SEQ ID NO. 430 | 0.217 | 0.406 | 1.874 | CREB_PMA |
| 813 | ABT1 | SEQ ID NO. 431 | 0.288 | 0.419 | 1.454 | CREB_FSK |
| 814 | ABT1 | SEQ ID NO. 431 | 0.288 | 0.653 | 2.266 | CREB_PMA |
| 815 | CGA | SEQ ID NO. 432 | 0.238 | 0.611 | 2.563 | CREB_FSK |
| 816 | CGA | SEQ ID NO. 432 | 0.238 | 0.822 | 3.448 | CREB_PMA |
| 817 | PFKFB3 | SEQ ID NO. 433 | 1.2 | 2.058 | 1.714 | CREB_FSK |
| 818 | PFKFB3 | SEQ ID NO. 433 | 1.2 | 6.356 | 5.295 | CREB_PMA |
| 819 | GOT1 | SEQ ID NO. 434 | 0.078 | 0.111 | 1.412 | CREB_FSK |
| 820 | GOT1 | SEQ ID NO. 434 | 0.078 | 0.14 | 1.781 | CREB_PMA |
| 821 | NUP98 | SEQ ID NO. 435 | 0.211 | 0.156 | 0.74 | CREB_FSK |
| 822 | NUP98 | SEQ ID NO. 435 | 0.211 | 0.3 | 1.421 | CREB_PMA |
| 823 | DIO2 | SEQ ID NO. 436 | 0.063 | 0.092 | 1.447 | CREB_FSK |
| 824 | DIO2 | SEQ ID NO. 436 | 0.063 | 0.123 | 1.943 | CREB_PMA |
| 825 | PER1 | SEQ ID NO. 437 | 0.076 | 0.106 | 1.398 | CREB_FSK |
| 826 | PER1 | SEQ ID NO. 437 | 0.076 | 0.178 | 2.348 | CREB_PMA |
| 827 | HES1 | SEQ ID NO. 438 | 0.076 | 0.071 | 0.937 | CREB_FSK |
| 828 | HES1 | SEQ ID NO. 438 | 0.076 | 0.071 | 0.928 | CREB_PMA |
| 829 | PTGS2 | SEQ ID NO. 439 | 0.041 | 0.052 | 1.287 | CREB_FSK |
| 830 | PTGS2 | SEQ ID NO. 439 | 0.041 | 0.603 | 14.869 | CREB_PMA |
| 831 | TNF | SEQ ID NO. 439 | 0.57 | 1.281 | 2.247 | CREB_FSK |
| 832 | TNF | SEQ ID NO. 439 | 0.57 | 5.141 | 10.771 | CREB_PMA |

*FIG. 1AC* -- TABLE 1 TRANSCRIPTIONAL BIOMARKER FUNCTIONAL DATA
SECTION 7A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_ RATIO | INDUCTION_CONDITIONS* |
|---|---|---|---|---|---|---|
| 833 | NULL | SEQ ID NO. 440 | 0.158 | 0.144 | 0.912 | CREB_FSK |
| 834 | NULL | SEQ ID NO. 440 | 0.158 | 0.347 | 2.199 | CREB_PMA |
| 835 | NULL | SEQ ID NO. 441 | 0.039 | 0.059 | 1.515 | CREB_FSK |
| 836 | NULL | SEQ ID NO. 441 | 0.039 | 0.047 | 1.208 | CREB_PMA |
| 837 | PPP1R10 | SEQ ID NO. 442 | 50.517 | 53.471 | 1.058 | CREB_FSK |
| 838 | PPP1R10 | SEQ ID NO. 442 | 50.517 | 93.903 | 1.859 | CREB_PMA |
| 839 | C12orf60 | SEQ ID NO. 443 | 0.712 | 1.029 | 1.444 | CREB_FSK |
| 840 | C12orf60 | SEQ ID NO. 443 | 0.712 | 0.955 | 1.34 | CREB_PMA |
| 841 | C3orf26 | SEQ ID NO. 444 | 1.103 | 1.443 | 1.308 | CREB_FSK |
| 842 | C3orf26 | SEQ ID NO. 444 | 1.103 | 0.779 | 0.706 | CREB_PMA |
| 843 | C19orf47 | SEQ ID NO. 445 | 0.08 | 0.101 | 1.262 | CREB_FSK |
| 844 | C19orf47 | SEQ ID NO. 445 | 0.08 | 0.132 | 1.653 | CREB_PMA |
| 845 | NULL | SEQ ID NO. 446 | 0.007 | 0.009 | 1.246 | CREB_FSK |
| 846 | NULL | SEQ ID NO. 446 | 0.007 | 0.01 | 1.444 | CREB_PMA |
| 847 | C4orf21 | SEQ ID NO. 447 | 0.1 | 0.227 | 2.273 | CREB_FSK |
| 848 | C4orf21 | SEQ ID NO. 447 | 0.1 | 0.152 | 1.519 | CREB_PMA |
| 849 | LARP7 | SEQ ID NO. 448 | 0.009 | 0.011 | 1.212 | CREB_FSK |
| 850 | LARP7 | SEQ ID NO. 448 | 0.009 | 0.015 | 1.597 | CREB_PMA |
| 851 | NULL | SEQ ID NO. 449 | 0.064 | 0.088 | 1.373 | CREB_FSK |
| 852 | NULL | SEQ ID NO. 449 | 0.064 | 0.093 | 1.463 | CREB_PMA |
| 853 | NULL | SEQ ID NO. 450 | 3.47 | 2.508 | 0.723 | CREB_FSK |
| 854 | NULL | SEQ ID NO. 450 | 3.47 | 1.34 | 0.386 | CREB_PMA |
| 855 | FAM119B | SEQ ID NO. 451 | 0.01 | 0.013 | 1.334 | CREB_FSK |
| 856 | FAM119B | SEQ ID NO. 451 | 0.01 | 0.015 | 1.58 | CREB_PMA |
| 857 | RPL23 | SEQ ID NO. 452 | 1.227 | 1.414 | 1.153 | CREB_FSK |
| 858 | RPL23 | SEQ ID NO. 452 | 1.227 | 1.502 | 1.224 | CREB_PMA |
| 859 | BLOC1S2 | SEQ ID NO. 453 | 1.209 | 0.998 | 0.826 | CREB_FSK |
| 860 | BLOC1S2 | SEQ ID NO. 453 | 1.209 | 1.822 | 1.507 | CREB_PMA |

FIG. 1AD -- TABLE 1 TRANSCRIPTIONAL BIOMARKER FUNCTIONAL DATA
SECTION 2A

| LINE_ID | GENE_SYMBOL | SEQUENCE_ID_LISTING | PROM_ACTIVITY_N O_INDUCTION | PROM_ACTIVITY_WI TH_INDUCTION | INDUCTION RATIO | INDUCTION_CONDITIONS* |
|---|---|---|---|---|---|---|
| 861 | ESR1 | SEQ ID NO. 454 | 0.32 | 0.466 | 1.46 | ER |
| 862 | SLC5A11 | SEQ ID NO. 455 | 0.154 | 0.163 | 1.056 | ER |
| 863 | PDCD6 | SEQ ID NO. 456 | 0.164 | 0.199 | 1.212 | ER |
| 864 | SEMA3B | SEQ ID NO. 457 | 0.307 | 0.226 | 0.737 | ER |
| 865 | GUCA2B | SEQ ID NO. 458 | 0.36 | 0.205 | 0.57 | ER |
| 866 | DOK7 | SEQ ID NO. 459 | 0.244 | 0.271 | 1.111 | ER |
| 867 | ZMIZ1 | SEQ ID NO. 460 | 0.86 | 0.751 | 0.873 | ER |
| 868 | S1PR3 | SEQ ID NO. 461 | 0.598 | 0.882 | 1.475 | ER |
| 869 | PCK1 | SEQ ID NO. 462 | 0.199 | 0.197 | 0.991 | ER |
| 870 | ST3GAL4 | SEQ ID NO. 463 | 0.525 | 2.193 | 4.181 | ER |
| 871 | KEAP1 | SEQ ID NO. 464 | 0.439 | 5.478 | 12.468 | ER |
| 872 | ADFP | SEQ ID NO. 465 | 4.773 | 1.603 | 0.336 | ER |
| 873 | FLJ45248 | SEQ ID NO. 466 | 0.255 | 0.304 | 1.192 | ER |
| 874 | SEMA3B | SEQ ID NO. 467 | 0.542 | 1.411 | 2.602 | ER |
| 875 | TTC21A | SEQ ID NO. 468 | 0.204 | 0.242 | 1.184 | ER |
| 876 | SLC7A5 | SEQ ID NO. 469 | 0.393 | 0.669 | 1.703 | ER |
| 877 | SH2B3 | SEQ ID NO. 470 | 0.62 | 1.523 | 2.456 | ER |
| 878 | HMGCS2 | SEQ ID NO. 471 | 0.371 | 0.961 | 2.592 | ER |
| 879 | NULL | SEQ ID NO. 472 | 0.26 | 0.209 | 0.805 | ER |
| 880 | PLXNA1 | SEQ ID NO. 473 | 0.248 | 0.2 | 0.807 | ER |
| 881 | DENMD5B | SEQ ID NO. 474 | 0.818 | 0.749 | 0.916 | ER |
| 882 | NULL | SEQ ID NO. 475 | 0.213 | 0.177 | 0.833 | ER |
| 883 | PRKD | SEQ ID NO. 476 | 0.47 | 1.817 | 3.866 | ER |
| 884 | FLRT2 | SEQ ID NO. 477 | 0.201 | 0.286 | 1.424 | ER |
| 885 | PDLIM2 | SEQ ID NO. 478 | 0.341 | 0.812 | 2.382 | ER |
| 886 | PRELID1 | SEQ ID NO. 479 | 0.413 | 0.477 | 1.155 | ER |
| 887 | CDK6 | SEQ ID NO. 480 | 1.324 | 0.722 | 0.546 | ER |
| 888 | MCF2L | SEQ ID NO. 481 | 0.372 | 0.708 | 1.906 | ER |
| 889 | CYB561 | SEQ ID NO. 482 | 0.996 | 1.115 | 1.12 | ER |
| 890 | PSCA | SEQ ID NO. 483 | 0.293 | 0.408 | 1.393 | ER |
| 891 | NULL | SEQ ID NO. 484 | 0.153 | 0.137 | 0.894 | ER |
| 892 | AREG | SEQ ID NO. 485 | 0.45 | 0.722 | 1.603 | ER |
| 893 | NULL | SEQ ID NO. 486 | 0.234 | 0.55 | 2.351 | ER |
| 894 | CRKL | SEQ ID NO. 487 | 0.613 | 0.563 | 0.918 | ER |
| 895 | CELSR1 | SEQ ID NO. 488 | 0.168 | 0.155 | 0.92 | ER |
| 896 | IL24 | SEQ ID NO. 489 | 2.561 | 1.193 | 0.448 | ER |
| 897 | RPS11 | SEQ ID NO. 490 | 0.262 | 0.381 | 1.455 | ER |
| 898 | NULL | SEQ ID NO. 491 | 0.133 | 0.16 | 1.205 | ER |
| 899 | POLD4 | SEQ ID NO. 492 | 24.371 | 8.243 | 0.338 | ER |
| 900 | C15orf52 | SEQ ID NO. 493 | 0.473 | 1.647 | 3.485 | ER |
| 901 | SLC9A8 | SEQ ID NO. 494 | 16.651 | 13.993 | 0.84 | ER |
| 902 | HLA-F | SEQ ID NO. 495 | 0.217 | 0.223 | 1.026 | ER |
| 903 | LTF | SEQ ID NO. 496 | 0.299 | 0.459 | 1.534 | ER |
| 904 | C3orf23 | SEQ ID NO. 497 | 12.176 | 14.169 | 1.164 | ER |
| 905 | STC2 | SEQ ID NO. 498 | 1.744 | 4.199 | 2.408 | ER |
| 906 | POU6F1 | SEQ ID NO. 499 | 0.326 | 0.512 | 1.571 | ER |
| 907 | TFF1 | SEQ ID NO. 499 | 0.282 | 4.381 | 15.531 | ER |
| 908 | NULL | SEQ ID NO. 500 | 0.208 | 0.136 | 0.655 | ER |

FIG. 1AE -- TABLE 1 TRANSCRIPTIONAL BIOMARKER FUNCTIONAL DATA
SECTION 2A

| LINE_ID | GENE_SYMBOL | SEQUENCE_ID_LISTING | PROM_ACTIVITY_W_O_INDUCTION | PROM_ACTIVITY_WITH_INDUCTION | INDUCTION_RATIO | INDUCTION_CONDITIONS* |
|---|---|---|---|---|---|---|
| 909 | UGT2B17 | SEQ ID NO. 501 | 0.223 | 0.163 | 0.733 | ER |
| 910 | NPTX2 | SEQ ID NO. 502 | 0.549 | 1.685 | 3.072 | ER |
| 911 | Null | SEQ ID NO. 503 | 2.518 | 3.664 | 1.455 | ER |
| 912 | SLC25A34 | SEQ ID NO. 504 | 0.166 | 0.208 | 1.251 | ER |
| 913 | MLN | SEQ ID NO. 505 | 0.325 | 0.409 | 1.258 | ER |
| 914 | MYLK | SEQ ID NO. 506 | 0.449 | 0.559 | 1.245 | ER |
| 915 | C7orf53 | SEQ ID NO. 507 | 0.162 | 0.153 | 0.944 | ER |
| 916 | GAPDH | SEQ ID NO. 508 | 1.303 | 1.388 | 1.065 | ER |
| 917 | MED24 | SEQ ID NO. 509 | 0.143 | 0.132 | 0.921 | ER |
| 918 | PKMOX1 | SEQ ID NO. 510 | 0.143 | 0.205 | 1.433 | ER |
| 919 | Null | SEQ ID NO. 511 | 1.018 | 0.71 | 0.697 | ER |
| 920 | ADAM33 | SEQ ID NO. 512 | 0.16 | 1.651 | 10.294 | ER |
| 921 | LOC124220 | SEQ ID NO. 513 | 0.157 | 0.216 | 1.379 | ER |
| 922 | SPPL2A | SEQ ID NO. 514 | 3.017 | 3.812 | 1.263 | ER |
| 923 | STK11 | SEQ ID NO. 515 | 0.588 | 0.72 | 1.225 | ER |
| 924 | PCYT1A | SEQ ID NO. 516 | 19.836 | 20.516 | 1.034 | ER |
| 925 | EML1 | SEQ ID NO. 517 | 0.182 | 0.126 | 0.691 | ER |
| 926 | CILP2 | SEQ ID NO. 518 | 0.208 | 0.455 | 2.188 | ER |
| 927 | Null | SEQ ID NO. 519 | 0.275 | 0.422 | 1.531 | ER |
| 928 | C10orf197 | SEQ ID NO. 520 | 0.273 | 0.137 | 0.501 | ER |
| 929 | SERBP1 | SEQ ID NO. 521 | 49.333 | 29.218 | 0.592 | ER |
| 930 | FAM83F | SEQ ID NO. 522 | 0.722 | 1.154 | 1.597 | ER |
| 931 | RAB24 | SEQ ID NO. 523 | 7.819 | 11.322 | 1.448 | ER |
| 932 | MT2A | SEQ ID NO. 524 | 75.838 | 54.369 | 0.717 | ER |
| 933 | RPS6KL1 | SEQ ID NO. 525 | 0.24 | 1.377 | 5.729 | ER |
| 934 | TDRKH | SEQ ID NO. 526 | 0.154 | 0.125 | 0.815 | ER |
| 935 | Null | SEQ ID NO. 527 | 0.214 | 1.646 | 7.711 | ER |
| 936 | Null | SEQ ID NO. 528 | 0.136 | 0.131 | 0.959 | ER |
| 937 | Null | SEQ ID NO. 529 | 0.268 | 0.33 | 1.23 | ER |
| 938 | TRAF3IP2 | SEQ ID NO. 530 | 0.24 | 0.211 | 0.879 | ER |
| 939 | DBI | SEQ ID NO. 531 | 1.584 | 1.7 | 1.073 | ER |
| 940 | SCGB1D2 | SEQ ID NO. 532 | 0.108 | 0.211 | 1.947 | ER |
| 941 | RBM35B | SEQ ID NO. 533 | 0.903 | 2.09 | 2.313 | ER |
| 942 | ESR1 | SEQ ID NO. 534 | 0.694 | 1.426 | 2.055 | ER |
| 943 | Null | SEQ ID NO. 535 | 0.265 | 0.845 | 3.19 | ER |
| 944 | NUDT18 | SEQ ID NO. 536 | 0.689 | 0.441 | 0.641 | ER |
| 945 | Null | SEQ ID NO. 537 | 0.303 | 0.353 | 1.17 | ER |
| 946 | CHEDC1 | SEQ ID NO. 538 | 1.011 | 0.167 | 0.165 | ER |
| 947 | Null | SEQ ID NO. 539 | 0.369 | 0.418 | 1.134 | ER |
| 948 | SAMD12 | SEQ ID NO. 540 | 0.345 | 1.708 | 4.946 | ER |
| 949 | TECTB | SEQ ID NO. 541 | 0.14 | 0.138 | 0.989 | ER |
| 950 | COX7A2L | SEQ ID NO. 542 | 8.328 | 8.575 | 1.03 | ER |
| 951 | ATXN7L1 | SEQ ID NO. 543 | 0.171 | 0.217 | 1.267 | ER |
| 952 | Null | SEQ ID NO. 544 | 0.674 | 3.799 | 5.595 | ER |
| 953 | ARL1 | SEQ ID NO. 545 | 0.293 | 6.311 | 21.573 | ER |
| 954 | Null | SEQ ID NO. 546 | 0.164 | 0.148 | 0.9 | ER |
| 955 | PPP1R3B | SEQ ID NO. 547 | 0.725 | 0.568 | 0.784 | ER |
| 956 | GRIN1LA | SEQ ID NO. 548 | 0.171 | 0.242 | 1.42 | ER |

FIG. 1AF – TABLE 1 TRANSCRIPTIONAL BIOMARKER FUNCTIONAL DATA
SECTION 2A

| LINE_ID | GENE_SYMBOL | SEQUENCE_ID_LISTING | PROM_ACTIVITY_N O_INDUCTION | PROM_ACTIVITY_WI TH_INDUCTION | INDUCTION _RATIO | INDUCTION_CONDITIONS |
|---|---|---|---|---|---|---|
| 957 | ADAM8 | SEQ ID NO. 549 | 0.168 | 0.286 | 1.525 | ER |
| 958 | IL20 | SEQ ID NO. 550 | 0.115 | 0.105 | 0.914 | ER |
| 959 | AGT | SEQ ID NO. 551 | 0.383 | 0.955 | 2.492 | ER |
| 960 | FOXN1 | SEQ ID NO. 552 | 0.227 | 0.22 | 0.967 | ER |
| 961 | MECR | SEQ ID NO. 553 | 1.515 | 1.09 | 0.719 | ER |
| 962 | NULL | SEQ ID NO. 554 | 7.992 | 5.216 | 0.653 | ER |
| 963 | PLEKHH1 | SEQ ID NO. 555 | 0.282 | 2.047 | 7.248 | ER |
| 964 | APOA5 | SEQ ID NO. 556 | 0.218 | 0.186 | 0.853 | ER |
| 965 | PDCD6IP | SEQ ID NO. 557 | 15.694 | 15.243 | 0.971 | ER |
| 966 | BCL2 | SEQ ID NO. 558 | 0.132 | 0.253 | 1.918 | ER |
| 967 | TIPARP | SEQ ID NO. 558 | 3.19 | 5.698 | 1.786 | ER |
| 968 | NULL | SEQ ID NO. 559 | 0.269 | 3.924 | 14.599 | ER |
| 969 | GREB1 | SEQ ID NO. 560 | 0.314 | 3.863 | 12.308 | ER |
| 970 | RP1 | SEQ ID NO. 561 | 0.266 | 0.471 | 1.77 | ER |
| 971 | RBL3 | SEQ ID NO. 562 | 3.111 | 2.634 | 0.847 | ER |
| 972 | NULL | SEQ ID NO. 563 | 0.28 | 0.744 | 2.658 | ER |
| 973 | PDZK1 | SEQ ID NO. 564 | 0.427 | 0.686 | 1.609 | ER |
| 974 | LOC283551 | SEQ ID NO. 565 | 0.294 | 11.043 | 37.509 | ER |
| 975 | NULL | SEQ ID NO. 566 | 0.561 | 1.519 | 2.706 | ER |
| 976 | NULL | SEQ ID NO. 567 | 0.39 | 0.55 | 1.409 | ER |
| 977 | UGT2B15 | SEQ ID NO. 568 | 0.183 | 0.255 | 1.403 | ER |
| 978 | LIPC | SEQ ID NO. 568 | 0.157 | 0.179 | 1.137 | ER |
| 979 | NULL | SEQ ID NO. 569 | 0.339 | 0.433 | 1.277 | ER |
| 980 | NULL | SEQ ID NO. 570 | 0.281 | 0.354 | 1.258 | ER |
| 981 | SCD | SEQ ID NO. 571 | 0.235 | 0.242 | 1.031 | ER |
| 982 | NULL | SEQ ID NO. 572 | 0.154 | 0.164 | 1.065 | ER |
| 983 | BCMO1 | SEQ ID NO. 573 | 3.428 | 1.933 | 0.562 | ER |
| 984 | CRB2 | SEQ ID NO. 574 | 0.367 | 0.532 | 1.451 | ER |
| 985 | SLC29A1 | SEQ ID NO. 575 | 0.251 | 0.313 | 1.249 | ER |
| 986 | NULL | SEQ ID NO. 576 | 0.621 | 4.334 | 6.977 | ER |
| 987 | ETNK2 | SEQ ID NO. 577 | 0.186 | 0.254 | 1.365 | ER |
| 988 | TPM3 | SEQ ID NO. 578 | 1.623 | 1.952 | 1.203 | ER |
| 989 | HIST1H4K | SEQ ID NO. 579 | 0.867 | 0.948 | 1.094 | ER |
| 990 | NULL | SEQ ID NO. 580 | 0.728 | 4.399 | 6.043 | ER |
| 991 | CYP1B1 | SEQ ID NO. 581 | 0.196 | 0.195 | 0.993 | ER |
| 992 | AQP7 | SEQ ID NO. 581 | 0.582 | 1.147 | 1.971 | ER |
| 993 | SMARCA3 | SEQ ID NO. 582 | 0.284 | 0.432 | 1.522 | ER |
| 994 | MAL2 | SEQ ID NO. 583 | 0.287 | 0.271 | 0.945 | ER |
| 995 | CARD10 | SEQ ID NO. 584 | 0.24 | 0.241 | 1.007 | ER |
| 996 | NULL | SEQ ID NO. 585 | 0.895 | 0.752 | 0.841 | ER |
| 997 | STS | SEQ ID NO. 586 | 0.209 | 0.319 | 1.526 | ER |
| 998 | SULT1A1 | SEQ ID NO. 587 | 0.282 | 0.259 | 0.919 | ER |
| 999 | CDK5RAP1 | SEQ ID NO. 587 | 104.046 | 111.873 | 1.075 | ER |

*FIG. 1AG* -- TABLE 1 TRANSCRIPTIONAL BIOMARKER FUNCTIONAL DATA
SECTION 2A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS* |
|---|---|---|---|---|---|---|
| 1000 | ZBTB40 | SEQ ID NO. 588 | 1.79 | 2.507 | 1.401 | ER |
| 1001 | GLRX2 | SEQ ID NO. 589 | 0.104 | 0.09 | 0.866 | ER |
| 1002 | ABCD4 | SEQ ID NO. 590 | 4.608 | 3.604 | 0.782 | ER |
| 1003 | SLC35A1 | SEQ ID NO. 591 | 0.161 | 0.317 | 1.976 | ER |
| 1004 | XRCC5 | SEQ ID NO. 592 | 0.763 | 2.243 | 2.941 | ER |
| 1005 | NR1I3 | SEQ ID NO. 593 | 0.084 | 0.079 | 0.94 | ER |
| 1006 | NULL | SEQ ID NO. 594 | 0.225 | 0.526 | 2.34 | ER |
| 1007 | NULL | SEQ ID NO. 595 | 0.119 | 0.126 | 1.06 | ER |
| 1008 | NULL | SEQ ID NO. 596 | 0.348 | 0.748 | 2.148 | ER |
| 1009 | NULL | SEQ ID NO. 597 | 0.322 | 2.042 | 6.347 | ER |
| 1010 | SCNN1A | SEQ ID NO. 598 | 0.25 | 0.347 | 1.386 | ER |
| 1011 | NR1H2 | SEQ ID NO. 599 | 8.07 | 6.057 | 0.75 | ER |
| 1012 | NR2E3 | SEQ ID NO. 600 | 0.263 | 0.222 | 0.846 | ER |
| 1013 | NULL | SEQ ID NO. 601 | 0.141 | 0.125 | 0.888 | ER |
| 1014 | C17orf55 | SEQ ID NO. 602 | 0.384 | 0.608 | 1.583 | ER |
| 1015 | TMPRSS3 | SEQ ID NO. 603 | 0.209 | 0.347 | 1.66 | ER |
| 1016 | HMGCR | SEQ ID NO. 603 | 9.834 | 16.086 | 1.636 | ER |
| 1017 | WISP2 | SEQ ID NO. 604 | 0.204 | 0.191 | 0.936 | ER |
| 1018 | DGAT2 | SEQ ID NO. 605 | 0.158 | 0.19 | 1.197 | ER |
| 1019 | NULL | SEQ ID NO. 606 | 0.209 | 0.292 | 1.397 | ER |
| 1020 | ACP6 | SEQ ID NO. 607 | 0.311 | 3.904 | 12.569 | ER |
| 1021 | NULL | SEQ ID NO. 608 | 0.205 | 0.28 | 1.37 | ER |
| 1022 | PROP1 | SEQ ID NO. 609 | 0.267 | 0.752 | 2.818 | ER |
| 1023 | NULL | SEQ ID NO. 610 | 0.254 | 0.466 | 1.843 | ER |
| 1024 | NULL | SEQ ID NO. 611 | 0.087 | 0.139 | 1.592 | ER |
| 1025 | GREB1 | SEQ ID NO. 612 | 0.193 | 0.372 | 1.927 | ER |
| 1026 | ECE1 | SEQ ID NO. 613 | 0.169 | 0.132 | 0.779 | ER |
| 1027 | NULL | SEQ ID NO. 614 | 0.276 | 0.385 | 1.392 | ER |
| 1028 | SMAD3 | SEQ ID NO. 615 | 0.756 | 0.574 | 0.759 | ER |
| 1029 | DPP9 | SEQ ID NO. 616 | 0.215 | 0.316 | 1.471 | ER |
| 1030 | NULL | SEQ ID NO. 617 | 0.189 | 0.564 | 2.988 | ER |
| 1031 | CCR6 | SEQ ID NO. 618 | 0.152 | 0.204 | 1.347 | ER |
| 1032 | HK1 | SEQ ID NO. 619 | 0.38 | 0.707 | 1.86 | ER |
| 1033 | MANSC1 | SEQ ID NO. 620 | 0.713 | 2.794 | 3.918 | ER |
| 1034 | NULL | SEQ ID NO. 621 | 0.15 | 0.104 | 0.694 | ER |
| 1035 | NULL | SEQ ID NO. 622 | 4.881 | 5.716 | 1.171 | ER |
| 1036 | GREB1 | SEQ ID NO. 623 | 0.326 | 0.31 | 0.951 | ER |
| 1037 | SULT2B1 | SEQ ID NO. 624 | 0.456 | 0.398 | 0.872 | ER |
| 1038 | S100A10 | SEQ ID NO. 625 | 0.579 | 4.323 | 7.473 | ER |
| 1039 | DAAM1 | SEQ ID NO. 626 | 0.163 | 0.227 | 1.391 | ER |
| 1040 | BRF0 | SEQ ID NO. 627 | 57.820 | 52.915 | 0.915 | ER |
| 1041 | LSS | SEQ ID NO. 628 | 0.303 | 0.422 | 2.078 | ER |
| 1042 | PVALB | SEQ ID NO. 629 | 0.166 | 0.2 | 1.205 | ER |
| 1043 | VEPH1 | SEQ ID NO. 630 | 0.097 | 0.163 | 1.685 | ER |
| 1044 | TCEA2 | SEQ ID NO. 631 | 0.212 | 0.297 | 1.401 | ER |
| 1045 | PTGES | SEQ ID NO. 632 | 0.189 | 0.352 | 1.864 | ER |
| 1046 | NKAIN1 | SEQ ID NO. 633 | 0.392 | 0.558 | 1.422 | ER |
| 1047 | SCNN1A | SEQ ID NO. 634 | 0.956 | 2.056 | 2.362 | ER |

FIG. 1AH — TABLE 1 TRANSCRIPTIONAL BIOMARKER FUNCTIONAL DATA
SECTION 2A

| LINE_ID | GENE_SYMBOL | SEQUENCE_ID_LISTING | PROM_ACTIVITY_N O_INDUCTION | PROM_ACTIVITY_WI TH_INDUCTION | INDUCTION _RATIO | INDUCTION_CONDITIONS" |
|---|---|---|---|---|---|---|
| 1048 | Null | SEQ ID NO. 635 | 0.487 | 2.199 | 4.515 | ER |
| 1049 | RAB5B | SEQ ID NO. 636 | 0.175 | 0.451 | 2.586 | ER |
| 1050 | Null | SEQ ID NO. 637 | 4.431 | 5.161 | 1.165 | ER |
| 1051 | FHL1 | SEQ ID NO. 638 | 0.262 | 1.044 | 3.991 | ER |
| 1052 | NEN | SEQ ID NO. 639 | 1.072 | 1.415 | 1.32 | ER |
| 1053 | RELN | SEQ ID NO. 640 | 0.125 | 0.12 | 0.959 | ER |
| 1054 | SLPM5 | SEQ ID NO. 641 | 1.199 | 2.674 | 2.23 | ER |
| 1055 | HIST1H4J | SEQ ID NO. 642 | 0.729 | 0.996 | 1.366 | ER |
| 1056 | Null | SEQ ID NO. 643 | 0.191 | 0.221 | 1.156 | ER |
| 1057 | CPA6 | SEQ ID NO. 644 | 0.697 | 0.518 | 0.743 | ER |
| 1058 | DNAJB6 | SEQ ID NO. 645 | 0.115 | 0.081 | 0.702 | ER |
| 1059 | GDF15 | SEQ ID NO. 646 | 0.089 | 0.079 | 0.895 | ER |
| 1060 | SLC12A7 | SEQ ID NO. 647 | 0.206 | 0.145 | 0.705 | ER |
| 1061 | EPN3 | SEQ ID NO. 648 | 0.447 | 0.468 | 1.048 | ER |
| 1062 | Null | SEQ ID NO. 649 | 0.102 | 0.084 | 0.83 | ER |
| 1063 | HLA-C | SEQ ID NO. 650 | 0.303 | 0.485 | 2.386 | ER |
| 1064 | ECH1 | SEQ ID NO. 650 | 9.752 | 6.208 | 0.637 | ER |
| 1065 | ATAD4 | SEQ ID NO. 651 | 1.063 | 0.898 | 0.845 | ER |
| 1066 | IFT122 | SEQ ID NO. 652 | 0.323 | 0.248 | 1.116 | ER |
| 1067 | FAM134B | SEQ ID NO. 653 | 0.254 | 17.159 | 67.428 | ER |
| 1068 | CYP2C18 | SEQ ID NO. 654 | 0.124 | 0.105 | 0.847 | ER |
| 1069 | Null | SEQ ID NO. 655 | 0.339 | 1.461 | 4.305 | ER |
| 1070 | Null | SEQ ID NO. 656 | 0.29 | 6.685 | 23.035 | ER |
| 1071 | PPP1R13B | SEQ ID NO. 657 | 0.109 | 0.353 | 3.247 | ER |
| 1072 | TBC1D16 | SEQ ID NO. 658 | 0.153 | 0.244 | 1.591 | ER |
| 1073 | Null | SEQ ID NO. 659 | 0.17 | 0.221 | 1.3 | ER |
| 1074 | Null | SEQ ID NO. 660 | 0.131 | 0.167 | 1.275 | ER |
| 1075 | TSNAXIP1 | SEQ ID NO. 661 | 0.326 | 0.299 | 0.917 | ER |
| 1076 | LOC652968 | SEQ ID NO. 662 | 0.463 | 3.787 | 8.178 | ER |
| 1077 | NR2F2 | SEQ ID NO. 663 | 0.17 | 0.164 | 0.968 | ER |
| 1078 | EVL | SEQ ID NO. 664 | 0.126 | 0.143 | 1.117 | ER |
| 1079 | SLC4A2 | SEQ ID NO. 665 | 0.887 | 1.635 | 1.844 | ER |
| 1080 | TRIM25 | SEQ ID NO. 666 | 0.111 | 0.314 | 2.825 | ER |
| 1081 | PPM1J | SEQ ID NO. 667 | 0.474 | 0.645 | 1.36 | ER |
| 1082 | VCPIP1 | SEQ ID NO. 668 | 0.315 | 1.103 | 3.502 | ER |
| 1083 | SAT1 | SEQ ID NO. 668 | 0.486 | 0.861 | 1.774 | ER |
| 1084 | BCL2 | SEQ ID NO. 669 | 0.116 | 0.112 | 0.972 | ER |
| 1085 | EBAG9 | SEQ ID NO. 669 | 1.04 | 1.841 | 1.77 | ER |
| 1086 | CYB561D2 | SEQ ID NO. 670 | 1.557 | 1.803 | 1.158 | ER |
| 1087 | OXT | SEQ ID NO. 671 | 0.275 | 1.66 | 6.034 | ER |
| 1088 | HNRNPH2 | SEQ ID NO. 672 | 36.713 | 60.526 | 1.649 | ER |
| 1089 | Null | SEQ ID NO. 673 | 0.211 | 0.582 | 2.752 | ER |
| 1090 | PSPH | SEQ ID NO. 674 | 0.537 | 0.754 | 1.405 | ER |
| 1091 | AKAP9 | SEQ ID NO. 674 | 10.727 | 11.503 | 1.072 | ER |
| 1092 | FAM3C | SEQ ID NO. 675 | 5.48 | 5.536 | 1.01 | ER |
| 1093 | ECOP | SEQ ID NO. 676 | 0.516 | 2.486 | 4.823 | ER |

FIG. 1AI -- TABLE 1 TRANSCRIPTIONAL BIOMARKER FUNCTIONAL DATA
SECTION 2A

| LINE_ID | GENE_SYMBOL | SEQUENCE_ID_LISTING | PROM_ACTIVITY_N O_INDUCTION | PROM_ACTIVITY_WI TH_INDUCTION | INDUCTION _RATIO | INDUCTION_CONDITIONS* |
|---|---|---|---|---|---|---|
| 1094 | NULL | SEQ ID NO. 677 | 2.146 | 2.648 | 1.234 | ER |
| 1095 | PLOD3 | SEQ ID NO. 677 | 149.686 | 70.232 | 0.469 | ER |
| 1096 | NULL | SEQ ID NO. 677 | 107.518 | 110.548 | 1.028 | ER |
| 1097 | NULL | SEQ ID NO. 677 | 50.51 | 26.013 | 0.515 | ER |
| 1098 | HERPUD2 | SEQ ID NO. 677 | 11.393 | 8.041 | 0.706 | ER |
| 1099 | NULL | SEQ ID NO. 678 | 0.995 | 1.705 | 1.713 | ER |
| 1100 | NCAPG2 | SEQ ID NO. 678 | 81.865 | 55.316 | 0.676 | ER |
| 1101 | NUB1 | SEQ ID NO. 678 | 134.502 | 84.692 | 0.63 | ER |
| 1102 | NULL | SEQ ID NO. 679 | 8.182 | 11.751 | 1.436 | ER |
| 1103 | SLC4A2 | SEQ ID NO. 680 | 6.408 | 5.878 | 0.917 | ER |
| 1104 | NULL | SEQ ID NO. 681 | 3.708 | 4.005 | 1.08 | ER |
| 1105 | REPIN1 | SEQ ID NO. 682 | 6.358 | 12 | 1.888 | ER |
| 1106 | CAT | SEQ ID NO. 683 | 2.808 | 3.588 | 1.278 | ER |
| 1107 | APOA2 | SEQ ID NO. 684 | 0.155 | 0.271 | 1.744 | ER |

FIG. 1AJ -- TABLE 1 TRANSCRIPTIONAL BIOMARKER FUNCTIONAL DATA
SECTION 8A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS |
|---|---|---|---|---|---|---|
| 1108 | RABGGTB | SEQ ID NO. 685 | 0.34 | 0.28 | 0.822 | GR_CORT |
| 1109 | RABGGTB | SEQ ID NO. 685 | 0.34 | 0.151 | 0.445 | GR_DEX |
| 1110 | RABGGTB | SEQ ID NO. 685 | 0.34 | 0.249 | 0.731 | GR_PRED |
| 1111 | CHIC2 | SEQ ID NO. 686 | 6.757 | 7.902 | 1.169 | GR_CORT |
| 1112 | CHIC2 | SEQ ID NO. 686 | 6.757 | 6.961 | 1.03 | GR_DEX |
| 1113 | CHIC2 | SEQ ID NO. 686 | 6.757 | 7.174 | 1.062 | GR_PRED |
| 1114 | MKNK2 | SEQ ID NO. 687 | 0.094 | 0.111 | 1.174 | GR_CORT |
| 1115 | MKNK2 | SEQ ID NO. 687 | 0.094 | 0.126 | 1.329 | GR_DEX |
| 1116 | MKNK2 | SEQ ID NO. 687 | 0.094 | 0.103 | 1.09 | GR_PRED |
| 1117 | RAB11A | SEQ ID NO. 688 | 11.747 | 13.805 | 1.175 | GR_CORT |
| 1118 | RAB11A | SEQ ID NO. 688 | 11.747 | 8.634 | 0.735 | GR_DEX |
| 1119 | RAB11A | SEQ ID NO. 688 | 11.747 | 9.447 | 0.804 | GR_PRED |
| 1120 | TXN | SEQ ID NO. 689 | 70.818 | 61.633 | 0.87 | GR_CORT |
| 1121 | TXN | SEQ ID NO. 689 | 70.818 | 41.811 | 0.59 | GR_DEX |
| 1122 | TXN | SEQ ID NO. 689 | 70.818 | 53.536 | 0.756 | GR_PRED |
| 1123 | RNF11 | SEQ ID NO. 690 | 1.038 | 1.141 | 1.099 | GR_CORT |
| 1124 | RNF11 | SEQ ID NO. 690 | 1.038 | 0.921 | 0.887 | GR_DEX |
| 1125 | RNF11 | SEQ ID NO. 690 | 1.038 | 0.86 | 0.828 | GR_PRED |
| 1126 | TPST2 | SEQ ID NO. 691 | 3.582 | 4.307 | 1.202 | GR_CORT |
| 1127 | TPST2 | SEQ ID NO. 691 | 3.582 | 3.485 | 0.973 | GR_DEX |
| 1128 | TPST2 | SEQ ID NO. 691 | 3.582 | 3.301 | 0.922 | GR_PRED |
| 1129 | IDH1 | SEQ ID NO. 692 | 10.542 | 12.686 | 1.203 | GR_CORT |
| 1130 | IDH1 | SEQ ID NO. 692 | 10.542 | 9.389 | 0.891 | GR_DEX |
| 1131 | IDH1 | SEQ ID NO. 692 | 10.542 | 10.127 | 0.961 | GR_PRED |
| 1132 | BRD2 | SEQ ID NO. 693 | 2.219 | 1.91 | 0.861 | GR_CORT |
| 1133 | BRD2 | SEQ ID NO. 693 | 2.219 | 1.243 | 0.56 | GR_DEX |
| 1134 | BRD2 | SEQ ID NO. 693 | 2.219 | 1.61 | 0.726 | GR_PRED |
| 1135 | IER2 | SEQ ID NO. 694 | 13.834 | 15.584 | 1.126 | GR_CORT |
| 1136 | IER2 | SEQ ID NO. 694 | 13.834 | 10.513 | 0.76 | GR_DEX |
| 1137 | IER2 | SEQ ID NO. 694 | 13.834 | 12.631 | 0.913 | GR_PRED |
| 1138 | HSP90AB1 | SEQ ID NO. 695 | 0.132 | 0.148 | 1.119 | GR_CORT |
| 1139 | HSP90AB1 | SEQ ID NO. 695 | 0.132 | 0.302 | 2.288 | GR_DEX |
| 1140 | HSP90AB1 | SEQ ID NO. 695 | 0.132 | 0.148 | 1.119 | GR_PRED |
| 1141 | COMT | SEQ ID NO. 696 | 5.302 | 6.209 | 1.171 | GR_CORT |
| 1142 | COMT | SEQ ID NO. 696 | 5.302 | 4.192 | 0.791 | GR_DEX |
| 1143 | COMT | SEQ ID NO. 696 | 5.302 | 4.199 | 0.792 | GR_PRED |
| 1144 | RNF10 | SEQ ID NO. 697 | 33.433 | 42.921 | 1.284 | GR_CORT |
| 1145 | RNF10 | SEQ ID NO. 697 | 33.433 | 33.818 | 1.012 | GR_DEX |
| 1146 | RNF10 | SEQ ID NO. 697 | 33.433 | 27.014 | 0.808 | GR_PRED |
| 1147 | WNT5A | SEQ ID NO. 698 | 0.212 | 0.252 | 1.189 | GR_CORT |
| 1148 | WNT5A | SEQ ID NO. 698 | 0.212 | 0.219 | 1.034 | GR_DEX |
| 1149 | WNT5A | SEQ ID NO. 698 | 0.212 | 0.169 | 0.789 | GR_PRED |
| 1150 | BRD2 | SEQ ID NO. 699 | 11.892 | 14.055 | 1.182 | GR_CORT |
| 1151 | BRD2 | SEQ ID NO. 699 | 11.892 | 10.308 | 0.867 | GR_DEX |
| 1152 | BRD2 | SEQ ID NO. 699 | 11.892 | 12.362 | 1.04 | GR_PRED |
| 1153 | SERPINA1 | SEQ ID NO. 700 | 2.899 | 2.49 | 0.859 | GR_CORT |
| 1154 | SERPINA1 | SEQ ID NO. 700 | 2.899 | 1.427 | 0.492 | GR_DEX |
| 1155 | SERPINA1 | SEQ ID NO. 700 | 2.899 | 2.386 | 0.823 | GR_PRED |

*FIG. 1AK* — TABLE 1 TRANSCRIPTIONAL BIOMARKER FUNCTIONAL DATA
SECTION 8A

| LINE_ID | GENE_SYMBOL | SEQUENCE_ID_LISTING | PROM_ACTIVITY_N O_INDUCTION | PROM_ACTIVITY_WI TH_INDUCTION | INDUCTION _RATIO | INDUCTION_CONDITION |
|---|---|---|---|---|---|---|
| 1156 | HERPUD1 | SEQ ID NO. 701 | 2.481 | 3.412 | 1.375 | GR_CORT |
| 1157 | HERPUD1 | SEQ ID NO. 701 | 2.481 | 2.362 | 0.952 | GR_DEX |
| 1158 | HERPUD1 | SEQ ID NO. 701 | 2.481 | 3.102 | 1.25 | GR_PRED |
| 1159 | MKNK2 | SEQ ID NO. 702 | 13.701 | 12.376 | 0.903 | GR_CORT |
| 1160 | MKNK2 | SEQ ID NO. 702 | 13.701 | 11.612 | 0.848 | GR_DEX |
| 1161 | MKNK2 | SEQ ID NO. 702 | 13.701 | 12.157 | 0.887 | GR_PRED |
| 1162 | ADH1C | SEQ ID NO. 703 | 0.24 | 0.222 | 0.928 | GR_CORT |
| 1163 | ADH1C | SEQ ID NO. 703 | 0.24 | 0.139 | 0.579 | GR_DEX |
| 1164 | ADH1C | SEQ ID NO. 703 | 0.24 | 0.188 | 0.783 | GR_PRED |
| 1165 | CKS1B | SEQ ID NO. 704 | 4.002 | 4.638 | 1.159 | GR_CORT |
| 1166 | CKS1B | SEQ ID NO. 704 | 4.002 | 3.669 | 0.917 | GR_DEX |
| 1167 | CKS1B | SEQ ID NO. 704 | 4.002 | 2.454 | 0.613 | GR_PRED |
| 1168 | SERPINA1 | SEQ ID NO. 705 | 0.242 | 0.245 | 1.012 | GR_CORT |
| 1169 | SERPINA1 | SEQ ID NO. 705 | 0.242 | 0.194 | 0.802 | GR_DEX |
| 1170 | SERPINA1 | SEQ ID NO. 705 | 0.242 | 0.216 | 0.893 | GR_PRED |
| 1171 | TPST2 | SEQ ID NO. 706 | 0.594 | 0.626 | 1.054 | GR_CORT |
| 1172 | TPST2 | SEQ ID NO. 706 | 0.594 | 0.428 | 0.721 | GR_DEX |
| 1173 | TPST2 | SEQ ID NO. 706 | 0.594 | 0.57 | 0.959 | GR_PRED |
| 1174 | WNT5A | SEQ ID NO. 707 | 0.537 | 0.656 | 1.22 | GR_CORT |
| 1175 | WNT5A | SEQ ID NO. 707 | 0.537 | 0.445 | 0.829 | GR_DEX |
| 1176 | WNT5A | SEQ ID NO. 707 | 0.537 | 0.505 | 0.941 | GR_PRED |
| 1177 | GNMT | SEQ ID NO. 708 | 0.189 | 0.188 | 0.996 | GR_CORT |
| 1178 | GNMT | SEQ ID NO. 708 | 0.189 | 0.221 | 1.167 | GR_DEX |
| 1179 | GNMT | SEQ ID NO. 708 | 0.189 | 0.199 | 1.054 | GR_PRED |
| 1180 | IER2 | SEQ ID NO. 709 | 2.129 | 2.082 | 0.978 | GR_CORT |
| 1181 | IER2 | SEQ ID NO. 709 | 2.129 | 1.539 | 0.723 | GR_DEX |
| 1182 | IER2 | SEQ ID NO. 709 | 2.129 | 1.998 | 0.938 | GR_PRED |
| 1183 | NULL | SEQ ID NO. 710 | 0.444 | 0.473 | 1.067 | GR_CORT |
| 1184 | NULL | SEQ ID NO. 710 | 0.444 | 0.394 | 0.889 | GR_DEX |
| 1185 | NULL | SEQ ID NO. 710 | 0.444 | 0.351 | 0.791 | GR_PRED |
| 1186 | MTCH2 | SEQ ID NO. 711 | 12.251 | 12.625 | 1.03 | GR_CORT |
| 1187 | MTCH2 | SEQ ID NO. 711 | 12.251 | 8.857 | 0.723 | GR_DEX |
| 1188 | MTCH2 | SEQ ID NO. 711 | 12.251 | 8.297 | 0.677 | GR_PRED |
| 1189 | SCD | SEQ ID NO. 711 | 1.12 | 0.901 | 0.804 | GR_CORT |
| 1190 | SCD | SEQ ID NO. 711 | 1.12 | 0.518 | 0.462 | GR_DEX |
| 1191 | SCD | SEQ ID NO. 711 | 1.12 | 0.804 | 0.718 | GR_PRED |
| 1192 | HSP90AB1 | SEQ ID NO. 712 | 0.042 | 0.047 | 1.12 | GR_CORT |
| 1193 | HSP90AB1 | SEQ ID NO. 712 | 0.042 | 0.03 | 0.721 | GR_DEX |
| 1194 | HSP90AB1 | SEQ ID NO. 712 | 0.042 | 0.037 | 0.889 | GR_PRED |
| 1195 | AS3MT | SEQ ID NO. 713 | 0.577 | 0.584 | 1.012 | GR_CORT |
| 1196 | AS3MT | SEQ ID NO. 713 | 0.577 | 0.409 | 0.708 | GR_DEX |
| 1197 | AS3MT | SEQ ID NO. 713 | 0.577 | 0.537 | 0.931 | GR_PRED |
| 1198 | WNT5A | SEQ ID NO. 714 | 1.604 | 1.349 | 0.841 | GR_CORT |
| 1199 | WNT5A | SEQ ID NO. 714 | 1.604 | 1.028 | 0.641 | GR_DEX |
| 1200 | WNT5A | SEQ ID NO. 714 | 1.604 | 1.109 | 0.691 | GR_PRED |
| 1201 | CPS1 | SEQ ID NO. 715 | 0.074 | 0.081 | 1.103 | GR_CORT |
| 1202 | CPS1 | SEQ ID NO. 715 | 0.074 | 0.066 | 0.902 | GR_DEX |
| 1203 | CPS1 | SEQ ID NO. 715 | 0.074 | 0.08 | 1.086 | GR_PRED |

FIG. 1AL -- TABLE 1 TRANSCRIPTIONAL BIOMARKER FUNCTIONAL DATA
SECTION 8A

| LINE_ID | GENE_SYMBOL | SEQUENCE_ID_LISTING | PROM_ACTIVITY_N O_INDUCTION | PROM_ACTIVITY_W1 TH_INDUCTION | INDUCTION RATIO | INDUCTION_CONDITIONS |
|---|---|---|---|---|---|---|
| 1204 | MYO18A | SEQ ID NO. 716 | 9.392 | 9.32 | 0.992 | GR_CORT |
| 1205 | MYO18A | SEQ ID NO. 716 | 9.392 | 10.515 | 1.12 | GR_DEX |
| 1206 | MYO18A | SEQ ID NO. 716 | 9.392 | 10.712 | 1.141 | GR_PRED |
| 1207 | NULL | SEQ ID NO. 717 | 0.485 | 0.469 | 0.966 | GR_CORT |
| 1208 | NULL | SEQ ID NO. 717 | 0.485 | 0.415 | 0.855 | GR_DEX |
| 1209 | NULL | SEQ ID NO. 717 | 0.485 | 0.584 | 1.203 | GR_PRED |
| 1210 | RGL1 | SEQ ID NO. 718 | 4.551 | 3.846 | 0.845 | GR_CORT |
| 1211 | RGL1 | SEQ ID NO. 718 | 4.551 | 2.675 | 0.588 | GR_DEX |
| 1212 | RGL1 | SEQ ID NO. 718 | 4.551 | 4.021 | 0.884 | GR_PRED |
| 1213 | NULL | SEQ ID NO. 719 | 0.038 | 0.05 | 1.3 | GR_CORT |
| 1214 | NULL | SEQ ID NO. 719 | 0.038 | 0.046 | 1.211 | GR_DEX |
| 1215 | NULL | SEQ ID NO. 719 | 0.038 | 0.053 | 1.397 | GR_PRED |
| 1216 | NULL | SEQ ID NO. 720 | 0.185 | 0.244 | 1.323 | GR_CORT |
| 1217 | NULL | SEQ ID NO. 720 | 0.185 | 0.224 | 1.211 | GR_DEX |
| 1218 | NULL | SEQ ID NO. 720 | 0.185 | 0.269 | 1.459 | GR_PRED |
| 1219 | NULL | SEQ ID NO. 721 | 0.333 | 0.333 | 0.999 | GR_CORT |
| 1220 | NULL | SEQ ID NO. 721 | 0.333 | 0.264 | 0.792 | GR_DEX |
| 1221 | NULL | SEQ ID NO. 721 | 0.333 | 0.318 | 0.953 | GR_PRED |
| 1222 | NULL | SEQ ID NO. 722 | 0.056 | 0.07 | 1.256 | GR_CORT |
| 1223 | NULL | SEQ ID NO. 722 | 0.056 | 0.093 | 1.665 | GR_DEX |
| 1224 | NULL | SEQ ID NO. 722 | 0.056 | 0.069 | 1.23 | GR_PRED |
| 1225 | SMYD4 | SEQ ID NO. 723 | 0.093 | 0.1 | 1.068 | GR_CORT |
| 1226 | SMYD4 | SEQ ID NO. 723 | 0.093 | 0.154 | 1.653 | GR_DEX |
| 1227 | SMYD4 | SEQ ID NO. 723 | 0.093 | 0.116 | 1.238 | GR_PRED |
| 1228 | ATP2B3 | SEQ ID NO. 724 | 0.07 | 0.071 | 1.015 | GR_CORT |
| 1229 | ATP2B3 | SEQ ID NO. 724 | 0.07 | 0.153 | 2.186 | GR_DEX |
| 1230 | ATP2B3 | SEQ ID NO. 724 | 0.07 | 0.081 | 1.143 | GR_PRED |
| 1231 | RGL4 | SEQ ID NO. 725 | 0.209 | 0.287 | 1.373 | GR_CORT |
| 1232 | RGL4 | SEQ ID NO. 725 | 0.209 | 0.29 | 1.387 | GR_DEX |
| 1233 | RGL4 | SEQ ID NO. 725 | 0.209 | 0.25 | 1.199 | GR_PRED |
| 1234 | NULL | SEQ ID NO. 726 | 0.082 | 0.092 | 1.123 | GR_CORT |
| 1235 | NULL | SEQ ID NO. 726 | 0.082 | 0.069 | 0.843 | GR_DEX |
| 1236 | NULL | SEQ ID NO. 726 | 0.082 | 0.062 | 0.76 | GR_PRED |
| 1237 | OBSCN | SEQ ID NO. 727 | 1.47 | 1.491 | 1.015 | GR_CORT |
| 1238 | OBSCN | SEQ ID NO. 727 | 1.47 | 1.261 | 0.858 | GR_DEX |
| 1239 | OBSCN | SEQ ID NO. 727 | 1.47 | 1.62 | 1.102 | GR_PRED |
| 1240 | IFME1 | SEQ ID NO. 728 | 0.131 | 0.154 | 1.176 | GR_CORT |
| 1241 | IFME1 | SEQ ID NO. 728 | 0.131 | 0.175 | 1.341 | GR_DEX |
| 1242 | IFME1 | SEQ ID NO. 728 | 0.131 | 0.175 | 1.343 | GR_PRED |
| 1243 | FLJ45803 | SEQ ID NO. 729 | 0.062 | 0.091 | 1.47 | GR_CORT |
| 1244 | FLJ45803 | SEQ ID NO. 729 | 0.062 | 0.427 | 6.89 | GR_DEX |
| 1245 | FLJ45803 | SEQ ID NO. 729 | 0.062 | 0.19 | 3.073 | GR_PRED |
| 1246 | NULL | SEQ ID NO. 730 | 0.11 | 0.111 | 1.007 | GR_CORT |
| 1247 | NULL | SEQ ID NO. 730 | 0.11 | 0.104 | 0.948 | GR_DEX |
| 1248 | NULL | SEQ ID NO. 730 | 0.11 | 0.136 | 1.235 | GR_PRED |
| 1249 | LAMA3 | SEQ ID NO. 731 | 0.044 | 0.043 | 0.965 | GR_CORT |
| 1250 | LAMA3 | SEQ ID NO. 731 | 0.044 | 0.053 | 1.201 | GR_DEX |
| 1251 | LAMA3 | SEQ ID NO. 731 | 0.044 | 0.053 | 1.204 | GR_PRED |

FIG. 1AM – TABLE 1 TRANSCRIPTIONAL BIOMARKER FUNCTIONAL DATA
SECTION 8A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS |
|---|---|---|---|---|---|---|
| 1252 | LCK6 | SEQ ID NO. 732 | 0.382 | 0.415 | 1.086 | GR_CORT |
| 1253 | LCK6 | SEQ ID NO. 732 | 0.382 | 0.45 | 1.179 | GR_DEX |
| 1254 | LCK6 | SEQ ID NO. 732 | 0.382 | 0.481 | 1.259 | GR_PRED |
| 1255 | HDAC7 | SEQ ID NO. 733 | 0.099 | 0.101 | 1.022 | GR_CORT |
| 1256 | HDAC7 | SEQ ID NO. 733 | 0.099 | 0.099 | 1.006 | GR_DEX |
| 1257 | HDAC7 | SEQ ID NO. 733 | 0.099 | 0.095 | 0.965 | GR_PRED |
| 1258 | ITSN1 | SEQ ID NO. 734 | 0.055 | 0.06 | 1.097 | GR_CORT |
| 1259 | ITSN1 | SEQ ID NO. 734 | 0.055 | 0.081 | 1.491 | GR_DEX |
| 1260 | ITSN1 | SEQ ID NO. 734 | 0.055 | 0.06 | 1.108 | GR_PRED |
| 1261 | PMOD | SEQ ID NO. 735 | 0.331 | 0.73 | 0.878 | GR_CORT |
| 1262 | PMOD | SEQ ID NO. 735 | 0.331 | 0.508 | 0.612 | GR_DEX |
| 1263 | PMOD | SEQ ID NO. 735 | 0.331 | 0.721 | 0.868 | GR_PRED |
| 1264 | DIXDC1 | SEQ ID NO. 736 | 0.08 | 0.124 | 1.54 | GR_CORT |
| 1265 | DIXDC1 | SEQ ID NO. 736 | 0.08 | 0.409 | 5.087 | GR_DEX |
| 1266 | DIXDC1 | SEQ ID NO. 736 | 0.08 | 0.17 | 2.111 | GR_PRED |
| 1267 | NULL | SEQ ID NO. 737 | 0.641 | 0.634 | 0.989 | GR_CORT |
| 1268 | NULL | SEQ ID NO. 737 | 0.641 | 0.702 | 1.095 | GR_DEX |
| 1269 | NULL | SEQ ID NO. 737 | 0.641 | 0.803 | 1.252 | GR_PRED |
| 1270 | NULL | SEQ ID NO. 738 | 0.602 | 0.659 | 1.093 | GR_CORT |
| 1271 | NULL | SEQ ID NO. 738 | 0.602 | 0.486 | 0.806 | GR_DEX |
| 1272 | NULL | SEQ ID NO. 738 | 0.602 | 0.623 | 1.034 | GR_PRED |
| 1273 | CYBASC3 | SEQ ID NO. 739 | 0.199 | 0.218 | 1.094 | GR_CORT |
| 1274 | CYBASC3 | SEQ ID NO. 739 | 0.199 | 0.174 | 0.873 | GR_DEX |
| 1275 | CYBASC3 | SEQ ID NO. 739 | 0.199 | 0.193 | 0.968 | GR_PRED |
| 1276 | NCOA1 | SEQ ID NO. 740 | 0.366 | 0.396 | 1.08 | GR_CORT |
| 1277 | NCOA1 | SEQ ID NO. 740 | 0.366 | 0.314 | 0.858 | GR_DEX |
| 1278 | NCOA1 | SEQ ID NO. 740 | 0.366 | 0.318 | 0.869 | GR_PRED |
| 1279 | ERCC2 | SEQ ID NO. 741 | 0.204 | 0.193 | 0.945 | GR_CORT |
| 1280 | ERCC2 | SEQ ID NO. 741 | 0.204 | 0.164 | 0.802 | GR_DEX |
| 1281 | ERCC2 | SEQ ID NO. 741 | 0.204 | 0.201 | 0.985 | GR_PRED |
| 1282 | PMM2 | SEQ ID NO. 742 | 9.304 | 9.246 | 0.994 | GR_CORT |
| 1283 | PMM2 | SEQ ID NO. 742 | 9.304 | 6.239 | 0.671 | GR_DEX |
| 1284 | PMM2 | SEQ ID NO. 742 | 9.304 | 8.994 | 0.967 | GR_PRED |
| 1285 | FAM55A | SEQ ID NO. 743 | 0.05 | 0.059 | 1.16 | GR_CORT |
| 1286 | FAM55A | SEQ ID NO. 743 | 0.05 | 0.047 | 0.936 | GR_DEX |
| 1287 | FAM55A | SEQ ID NO. 743 | 0.05 | 0.064 | 1.275 | GR_PRED |
| 1288 | EMC1 | SEQ ID NO. 744 | 0.121 | 0.165 | 1.36 | GR_CORT |
| 1289 | EMC1 | SEQ ID NO. 744 | 0.121 | 0.125 | 1.036 | GR_DEX |
| 1290 | EMC1 | SEQ ID NO. 744 | 0.121 | 0.105 | 0.869 | GR_PRED |
| 1291 | NULL | SEQ ID NO. 745 | 0.107 | 0.118 | 1.101 | GR_CORT |
| 1292 | NULL | SEQ ID NO. 745 | 0.107 | 0.332 | 3.104 | GR_DEX |
| 1293 | NULL | SEQ ID NO. 745 | 0.107 | 0.095 | 0.885 | GR_PRED |
| 1294 | NULL | SEQ ID NO. 746 | 0.314 | 0.392 | 1.248 | GR_CORT |
| 1295 | NULL | SEQ ID NO. 746 | 0.314 | 0.526 | 1.676 | GR_DEX |
| 1296 | NULL | SEQ ID NO. 746 | 0.314 | 0.443 | 1.411 | GR_PRED |
| 1297 | NULL | SEQ ID NO. 747 | 0.222 | 0.242 | 1.091 | GR_CORT |
| 1298 | NULL | SEQ ID NO. 747 | 0.222 | 0.175 | 0.791 | GR_DEX |
| 1299 | NULL | SEQ ID NO. 747 | 0.222 | 0.171 | 0.771 | GR_PRED |

FIG. 1AN -- TABLE 1 TRANSCRIPTIONAL BIOMARKER FUNCTIONAL DATA
SECTION 8A

| LINE_ID | GENE_SYMBOL | SEQUENCE_ID_LISTING | PROM_ACTIVITY_N O_INDUCTION | PROM_ACTIVITY_WI TH_INDUCTION | INDUCTION _RATIO | INDUCTION_CONDITIONS* |
|---|---|---|---|---|---|---|
| 1300 | HPS4 | SEQ ID NO. 748 | 0.16 | 0.179 | 1.119 | GR_CORT |
| 1301 | HPS4 | SEQ ID NO. 748 | 0.16 | 0.138 | 0.862 | GR_DEX |
| 1302 | HPS4 | SEQ ID NO. 748 | 0.16 | 0.114 | 0.711 | GR_PRED |
| 1303 | NULL | SEQ ID NO. 749 | 0.025 | 0.045 | 1.774 | GR_CORT |
| 1304 | NULL | SEQ ID NO. 749 | 0.025 | 0.17 | 6.771 | GR_DEX |
| 1305 | NULL | SEQ ID NO. 749 | 0.025 | 0.057 | 2.271 | GR_PRED |
| 1306 | PPP2R2A | SEQ ID NO. 750 | 0.076 | 0.086 | 1.129 | GR_CORT |
| 1307 | PPP2R2A | SEQ ID NO. 750 | 0.076 | 0.09 | 1.176 | GR_DEX |
| 1308 | PPP2R2A | SEQ ID NO. 750 | 0.076 | 0.079 | 1.037 | GR_PRED |
| 1309 | NULL | SEQ ID NO. 751 | 0.055 | 0.075 | 1.347 | GR_CORT |
| 1310 | NULL | SEQ ID NO. 751 | 0.055 | 0.133 | 2.395 | GR_DEX |
| 1311 | NULL | SEQ ID NO. 751 | 0.055 | 0.077 | 1.386 | GR_PRED |
| 1312 | KRT6C | SEQ ID NO. 752 | 0.267 | 0.3 | 1.124 | GR_CORT |
| 1313 | KRT6C | SEQ ID NO. 752 | 0.267 | 0.166 | 0.622 | GR_DEX |
| 1314 | KRT6C | SEQ ID NO. 752 | 0.267 | 0.202 | 0.759 | GR_PRED |
| 1315 | C8orf46 | SEQ ID NO. 753 | 0.177 | 0.194 | 1.097 | GR_CORT |
| 1316 | C8orf46 | SEQ ID NO. 753 | 0.177 | 0.325 | 1.839 | GR_DEX |
| 1317 | C8orf46 | SEQ ID NO. 753 | 0.177 | 0.225 | 1.271 | GR_PRED |
| 1318 | SMYD4 | SEQ ID NO. 754 | 0.049 | 0.07 | 1.413 | GR_CORT |
| 1319 | SMYD4 | SEQ ID NO. 754 | 0.049 | 0.121 | 2.454 | GR_DEX |
| 1320 | SMYD4 | SEQ ID NO. 754 | 0.049 | 0.088 | 1.79 | GR_PRED |
| 1321 | MECP2 | SEQ ID NO. 755 | 0.196 | 0.211 | 1.075 | GR_CORT |
| 1322 | MECP2 | SEQ ID NO. 755 | 0.196 | 0.168 | 0.855 | GR_DEX |
| 1323 | MECP2 | SEQ ID NO. 755 | 0.196 | 0.186 | 0.945 | GR_PRED |
| 1324 | MICAL1 | SEQ ID NO. 756 | 0.045 | 0.066 | 1.475 | GR_CORT |
| 1325 | MICAL1 | SEQ ID NO. 756 | 0.045 | 0.085 | 1.893 | GR_DEX |
| 1326 | MICAL1 | SEQ ID NO. 756 | 0.045 | 0.083 | 1.855 | GR_PRED |
| 1327 | EWAM | SEQ ID NO. 757 | 0.04 | 0.047 | 1.171 | GR_CORT |
| 1328 | EWAM | SEQ ID NO. 757 | 0.04 | 0.049 | 1.236 | GR_DEX |
| 1329 | EWAM | SEQ ID NO. 757 | 0.04 | 0.052 | 1.304 | GR_PRED |
| 1330 | GH1 | SEQ ID NO. 758 | 0.101 | 0.12 | 1.185 | GR_CORT |
| 1331 | GH1 | SEQ ID NO. 758 | 0.101 | 0.115 | 1.141 | GR_DEX |
| 1332 | GH1 | SEQ ID NO. 758 | 0.101 | 0.086 | 0.852 | GR_PRED |
| 1333 | NULL | SEQ ID NO. 759 | 0.011 | 0.015 | 1.537 | GR_CORT |
| 1334 | NULL | SEQ ID NO. 759 | 0.011 | 0.012 | 1.056 | GR_DEX |
| 1335 | NULL | SEQ ID NO. 759 | 0.011 | 0.015 | 1.37 | GR_PRED |
| 1336 | GIMAP8 | SEQ ID NO. 760 | 0.903 | 0.955 | 1.058 | GR_CORT |
| 1337 | GIMAP8 | SEQ ID NO. 760 | 0.903 | 0.946 | 1.048 | GR_DEX |
| 1338 | GIMAP8 | SEQ ID NO. 760 | 0.903 | 0.997 | 1.105 | GR_PRED |
| 1339 | IL9R | SEQ ID NO. 761 | 0.046 | 0.049 | 1.062 | GR_CORT |
| 1340 | IL9R | SEQ ID NO. 761 | 0.046 | 0.038 | 0.818 | GR_DEX |
| 1341 | IL9R | SEQ ID NO. 761 | 0.046 | 0.047 | 1.012 | GR_PRED |
| 1342 | NULL | SEQ ID NO. 761 | 0.455 | 0.536 | 1.179 | GR_CORT |
| 1343 | NULL | SEQ ID NO. 761 | 0.455 | 0.34 | 0.747 | GR_DEX |
| 1344 | NULL | SEQ ID NO. 761 | 0.455 | 0.383 | 0.841 | GR_PRED |
| 1345 | SERINC3 | SEQ ID NO. 762 | 4 | 4.12 | 1.03 | GR_CORT |
| 1346 | SERINC3 | SEQ ID NO. 762 | 4 | 4.616 | 1.154 | GR_DEX |
| 1347 | SERINC3 | SEQ ID NO. 762 | 4 | 5.946 | 1.487 | GR_PRED |

FIG. 1AO -- TABLE 1 TRANSCRIPTIONAL BIOMARKER FUNCTIONAL DATA
SECTION 8A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS |
|---|---|---|---|---|---|---|
| 1348 | FNTA | SEQ ID NO. 763 | 0.485 | 0.449 | 0.925 | GR_CORT |
| 1349 | FNTA | SEQ ID NO. 763 | 0.485 | 0.409 | 0.843 | GR_DEX |
| 1350 | FNTA | SEQ ID NO. 763 | 0.485 | 0.475 | 0.98 | GR_PRED |
| 1351 | PFF2R2C | SEQ ID NO. 764 | 0.768 | 0.805 | 1.048 | GR_CORT |
| 1352 | PFF2R2C | SEQ ID NO. 764 | 0.768 | 0.507 | 0.659 | GR_DEX |
| 1353 | PFF2R2C | SEQ ID NO. 764 | 0.768 | 0.68 | 0.885 | GR_PRED |
| 1354 | BIRC6 | SEQ ID NO. 765 | 6.582 | 6.583 | 1 | GR_CORT |
| 1355 | BIRC6 | SEQ ID NO. 765 | 6.582 | 4.5 | 0.684 | GR_DEX |
| 1356 | BIRC6 | SEQ ID NO. 765 | 6.582 | 5.44 | 0.826 | GR_PRED |
| 1357 | FLJ44861 | SEQ ID NO. 766 | 0.095 | 0.097 | 1.027 | GR_CORT |
| 1358 | FLJ44861 | SEQ ID NO. 766 | 0.095 | 0.068 | 0.717 | GR_DEX |
| 1359 | FLJ44861 | SEQ ID NO. 766 | 0.095 | 0.093 | 0.981 | GR_PRED |
| 1360 | Null | SEQ ID NO. 767 | 0.184 | 0.233 | 1.26 | GR_CORT |
| 1361 | Null | SEQ ID NO. 767 | 0.184 | 0.328 | 1.78 | GR_DEX |
| 1362 | Null | SEQ ID NO. 767 | 0.184 | 0.337 | 1.826 | GR_PRED |
| 1363 | Null | SEQ ID NO. 768 | 0.027 | 0.03 | 1.097 | GR_CORT |
| 1364 | Null | SEQ ID NO. 768 | 0.027 | 0.023 | 0.842 | GR_DEX |
| 1365 | Null | SEQ ID NO. 768 | 0.027 | 0.035 | 1.291 | GR_PRED |
| 1366 | Null | SEQ ID NO. 768 | 0.104 | 0.124 | 1.201 | GR_CORT |
| 1367 | Null | SEQ ID NO. 768 | 0.104 | 0.103 | 0.993 | GR_DEX |
| 1368 | Null | SEQ ID NO. 768 | 0.104 | 0.097 | 0.94 | GR_PRED |
| 1369 | Null | SEQ ID NO. 769 | 0.152 | 0.228 | 1.502 | GR_CORT |
| 1370 | Null | SEQ ID NO. 769 | 0.152 | 0.706 | 4.649 | GR_DEX |
| 1371 | Null | SEQ ID NO. 769 | 0.152 | 0.332 | 2.186 | GR_PRED |
| 1372 | PHGDH | SEQ ID NO. 768 | 0.056 | 0.07 | 1.265 | GR_CORT |
| 1373 | PHGDH | SEQ ID NO. 768 | 0.056 | 0.136 | 2.44 | GR_DEX |
| 1374 | PHGDH | SEQ ID NO. 768 | 0.056 | 0.075 | 1.341 | GR_PRED |
| 1375 | YIPF5 | SEQ ID NO. 770 | 121.949 | 132.433 | 1.086 | GR_CORT |
| 1376 | YIPF5 | SEQ ID NO. 770 | 121.949 | 95.964 | 0.787 | GR_DEX |
| 1377 | YIPF5 | SEQ ID NO. 770 | 121.949 | 113.332 | 0.929 | GR_PRED |
| 1378 | CD160 | SEQ ID NO. 771 | 0.094 | 0.122 | 1.295 | GR_CORT |
| 1379 | CD160 | SEQ ID NO. 771 | 0.094 | 0.286 | 3.023 | GR_DEX |
| 1380 | CD160 | SEQ ID NO. 771 | 0.094 | 0.157 | 1.666 | GR_PRED |
| 1381 | DPEP1 | SEQ ID NO. 772 | 0.183 | 0.256 | 1.396 | GR_CORT |
| 1382 | DPEP1 | SEQ ID NO. 772 | 0.183 | 0.291 | 1.589 | GR_DEX |
| 1383 | DPEP1 | SEQ ID NO. 772 | 0.183 | 0.215 | 1.175 | GR_PRED |
| 1384 | MEST | SEQ ID NO. 773 | 2.184 | 2.201 | 1.008 | GR_CORT |
| 1385 | MEST | SEQ ID NO. 773 | 2.184 | 1.898 | 0.869 | GR_DEX |
| 1386 | MEST | SEQ ID NO. 773 | 2.184 | 2.101 | 0.962 | GR_PRED |
| 1387 | COMT | SEQ ID NO. 774 | 17.44 | 21.993 | 1.258 | GR_CORT |
| 1388 | COMT | SEQ ID NO. 774 | 17.44 | 15.625 | 0.896 | GR_DEX |
| 1389 | COMT | SEQ ID NO. 774 | 17.44 | 17.614 | 1.01 | GR_PRED |
| 1390 | B2M | SEQ ID NO. 775 | 0.041 | 0.042 | 1.006 | GR_CORT |
| 1391 | B2M | SEQ ID NO. 775 | 0.041 | 0.05 | 1.196 | GR_DEX |
| 1392 | B2M | SEQ ID NO. 775 | 0.041 | 0.044 | 1.067 | GR_PRED |
| 1393 | SEPX1 | SEQ ID NO. 776 | 1.433 | 1.488 | 1.039 | GR_CORT |
| 1394 | SEPX1 | SEQ ID NO. 776 | 1.433 | 1.331 | 0.922 | GR_DEX |
| 1395 | SEPX1 | SEQ ID NO. 776 | 1.433 | 1.242 | 0.867 | GR_PRED |

FIG. 1AP -- TABLE 1 TRANSCRIPTIONAL BIOMARKER FUNCTIONAL DATA
SECTION 8A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS* |
|---|---|---|---|---|---|---|
| 1396 | WNT5A | SEQ ID NO. 777 | 0.415 | 0.478 | 1.152 | GR_CORT |
| 1397 | WNT5A | SEQ ID NO. 777 | 0.415 | 0.328 | 0.789 | GR_DEX |
| 1398 | WNT5A | SEQ ID NO. 777 | 0.415 | 0.363 | 0.875 | GR_PRED |
| 1399 | B2M | SEQ ID NO. 778 | 89.956 | 88.069 | 0.979 | GR_CORT |
| 1400 | B2M | SEQ ID NO. 778 | 89.956 | 57.828 | 0.643 | GR_DEX |
| 1401 | B2M | SEQ ID NO. 778 | 89.956 | 69.351 | 0.771 | GR_PRED |
| 1402 | IDH1 | SEQ ID NO. 779 | 46.908 | 46.129 | 0.983 | GR_CORT |
| 1403 | IDH1 | SEQ ID NO. 779 | 46.908 | 43.078 | 0.918 | GR_DEX |
| 1404 | IDH1 | SEQ ID NO. 779 | 46.908 | 53.296 | 1.136 | GR_PRED |
| 1405 | HSP90AB1 | SEQ ID NO. 780 | 0.092 | 0.124 | 1.353 | GR_CORT |
| 1406 | HSP90AB1 | SEQ ID NO. 780 | 0.092 | 0.09 | 0.98 | GR_DEX |
| 1407 | HSP90AB1 | SEQ ID NO. 780 | 0.092 | 0.097 | 1.049 | GR_PRED |
| 1408 | C1R | SEQ ID NO. 781 | 0.439 | 0.489 | 1.115 | GR_CORT |
| 1409 | C1R | SEQ ID NO. 781 | 0.439 | 0.658 | 1.5 | GR_DEX |
| 1410 | C1R | SEQ ID NO. 781 | 0.439 | 0.582 | 1.325 | GR_PRED |
| 1411 | UGCG | SEQ ID NO. 782 | 4.116 | 4.945 | 1.201 | GR_CORT |
| 1412 | UGCG | SEQ ID NO. 782 | 4.116 | 3.367 | 0.818 | GR_DEX |
| 1413 | UGCG | SEQ ID NO. 782 | 4.116 | 4.488 | 1.09 | GR_PRED |
| 1414 | PFKL | SEQ ID NO. 783 | 5.06 | 5.031 | 0.994 | GR_CORT |
| 1415 | PFKL | SEQ ID NO. 783 | 5.06 | 4.941 | 0.976 | GR_DEX |
| 1416 | PFKL | SEQ ID NO. 783 | 5.06 | 5.394 | 1.066 | GR_PRED |
| 1417 | CPS1 | SEQ ID NO. 784 | 6.8 | 7.826 | 1.151 | GR_CORT |
| 1418 | CPS1 | SEQ ID NO. 784 | 6.8 | 5.931 | 0.872 | GR_DEX |
| 1419 | CPS1 | SEQ ID NO. 784 | 6.8 | 7.173 | 1.055 | GR_PRED |
| 1420 | B2M | SEQ ID NO. 785 | 0.082 | 0.095 | 1.15 | GR_CORT |
| 1421 | B2M | SEQ ID NO. 785 | 0.082 | 0.067 | 0.812 | GR_DEX |
| 1422 | B2M | SEQ ID NO. 785 | 0.082 | 0.08 | 0.968 | GR_PRED |
| 1423 | PSMA6 | SEQ ID NO. 786 | 31.273 | 37.772 | 1.208 | GR_CORT |
| 1424 | PSMA6 | SEQ ID NO. 786 | 31.273 | 25.214 | 0.806 | GR_DEX |
| 1425 | PSMA6 | SEQ ID NO. 786 | 31.273 | 26.71 | 0.854 | GR_PRED |
| 1426 | RNF11 | SEQ ID NO. 787 | 0.037 | 0.052 | 1.421 | GR_CORT |
| 1427 | RNF11 | SEQ ID NO. 787 | 0.037 | 0.038 | 1.029 | GR_DEX |
| 1428 | RNF11 | SEQ ID NO. 787 | 0.037 | 0.042 | 1.143 | GR_PRED |
| 1429 | SERPINA1 | SEQ ID NO. 788 | 1.01 | 1.074 | 1.064 | GR_CORT |
| 1430 | SERPINA1 | SEQ ID NO. 788 | 1.01 | 1.173 | 1.162 | GR_DEX |
| 1431 | SERPINA1 | SEQ ID NO. 788 | 1.01 | 1.152 | 1.141 | GR_PRED |
| 1432 | SMURF2 | SEQ ID NO. 789 | 0.053 | 0.069 | 1.31 | GR_CORT |
| 1433 | SMURF2 | SEQ ID NO. 789 | 0.053 | 0.049 | 0.941 | GR_DEX |
| 1434 | SMURF2 | SEQ ID NO. 789 | 0.053 | 0.053 | 1.002 | GR_PRED |
| 1435 | NULL | SEQ ID NO. 790 | 0.657 | 0.592 | 0.901 | GR_CORT |
| 1436 | NULL | SEQ ID NO. 790 | 0.657 | 0.485 | 0.738 | GR_DEX |
| 1437 | NULL | SEQ ID NO. 790 | 0.657 | 0.59 | 0.897 | GR_PRED |
| 1438 | GBF1 | SEQ ID NO. 791 | 0.076 | 0.091 | 1.204 | GR_CORT |
| 1439 | GBF1 | SEQ ID NO. 791 | 0.076 | 0.06 | 0.793 | GR_DEX |
| 1440 | GBF1 | SEQ ID NO. 791 | 0.076 | 0.085 | 1.121 | GR_PRED |
| 1441 | TTN | SEQ ID NO. 792 | 0.143 | 0.155 | 1.082 | GR_CORT |
| 1442 | TTN | SEQ ID NO. 792 | 0.143 | 0.137 | 0.956 | GR_DEX |
| 1443 | TTN | SEQ ID NO. 792 | 0.143 | 0.163 | 1.139 | GR_PRED |

FIG. 1AQ — TABLE 1 TRANSCRIPTIONAL BIOMARKER FUNCTIONAL DATA
SECTION 8A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS* |
|---|---|---|---|---|---|---|
| 1444 | SRPK2 | SEQ ID NO. 793 | 0.037 | 0.039 | 1.047 | GR_CORT |
| 1445 | SRPK2 | SEQ ID NO. 793 | 0.037 | 0.056 | 1.507 | GR_DEX |
| 1446 | SRPK2 | SEQ ID NO. 793 | 0.037 | 0.043 | 1.155 | GR_PRED |
| 1447 | MKNK2 | SEQ ID NO. 794 | 5.43 | 6.716 | 1.237 | GR_CORT |
| 1448 | MKNK2 | SEQ ID NO. 794 | 5.43 | 4.055 | 0.747 | GR_DEX |
| 1449 | MKNK2 | SEQ ID NO. 794 | 5.43 | 3.981 | 0.733 | GR_PRED |
| 1450 | ATP6AP1 | SEQ ID NO. 795 | 0.128 | 0.162 | 1.267 | GR_CORT |
| 1451 | ATP6AP1 | SEQ ID NO. 795 | 0.128 | 0.108 | 0.849 | GR_DEX |
| 1452 | ATP6AP1 | SEQ ID NO. 795 | 0.128 | 0.128 | 0.999 | GR_PRED |
| 1453 | GLUL | SEQ ID NO. 796 | 0.149 | 0.195 | 1.311 | GR_CORT |
| 1454 | GLUL | SEQ ID NO. 796 | 0.149 | 0.248 | 1.664 | GR_DEX |
| 1455 | GLUL | SEQ ID NO. 796 | 0.149 | 0.174 | 1.165 | GR_PRED |
| 1456 | IGFBP1 | SEQ ID NO. 797 | 0.078 | 0.094 | 1.202 | GR_CORT |
| 1457 | IGFBP1 | SEQ ID NO. 797 | 0.078 | 0.078 | 0.995 | GR_DEX |
| 1458 | IGFBP1 | SEQ ID NO. 797 | 0.078 | 0.078 | 0.997 | GR_PRED |
| 1459 | IGFBP1 | SEQ ID NO. 798 | 0.096 | 0.104 | 1.083 | GR_CORT |
| 1460 | IGFBP1 | SEQ ID NO. 798 | 0.096 | 0.074 | 0.775 | GR_DEX |
| 1461 | IGFBP1 | SEQ ID NO. 798 | 0.096 | 0.09 | 0.939 | GR_PRED |
| 1462 | TARP | SEQ ID NO. 799 | 8.139 | 6.322 | 0.777 | GR_CORT |
| 1463 | TARP | SEQ ID NO. 799 | 8.139 | 5.723 | 0.703 | GR_DEX |
| 1464 | TARP | SEQ ID NO. 799 | 8.139 | 6.028 | 0.741 | GR_PRED |
| 1465 | SLC37A3 | SEQ ID NO. 800 | 5.876 | 5.768 | 0.982 | GR_CORT |
| 1466 | SLC37A3 | SEQ ID NO. 800 | 5.876 | 5.746 | 0.978 | GR_DEX |
| 1467 | SLC37A3 | SEQ ID NO. 800 | 5.876 | 5.091 | 0.866 | GR_PRED |
| 1468 | MEST | SEQ ID NO. 801 | 0.266 | 0.287 | 1.078 | GR_CORT |
| 1469 | MEST | SEQ ID NO. 801 | 0.266 | 0.209 | 0.785 | GR_DEX |
| 1470 | MEST | SEQ ID NO. 801 | 0.266 | 0.274 | 1.032 | GR_PRED |
| 1471 | AKAP9 | SEQ ID NO. 801 | 0.51 | 0.614 | 1.203 | GR_CORT |
| 1472 | AKAP9 | SEQ ID NO. 801 | 0.51 | 0.479 | 0.939 | GR_DEX |
| 1473 | AKAP9 | SEQ ID NO. 801 | 0.51 | 0.564 | 1.105 | GR_PRED |
| 1474 | FAM3C | SEQ ID NO. 801 | 2.8 | 2.94 | 1.05 | GR_CORT |
| 1475 | FAM3C | SEQ ID NO. 801 | 2.8 | 2.913 | 1.04 | GR_DEX |
| 1476 | FAM3C | SEQ ID NO. 801 | 2.8 | 2.744 | 0.98 | GR_PRED |
| 1477 | PLOD3 | SEQ ID NO. 801 | 18.043 | 21.025 | 1.165 | GR_CORT |
| 1478 | PLOD3 | SEQ ID NO. 801 | 18.043 | 15.398 | 0.853 | GR_DEX |
| 1479 | PLOD3 | SEQ ID NO. 801 | 18.043 | 19.065 | 1.057 | GR_PRED |
| 1480 | MEST | SEQ ID NO. 801 | 37.011 | 38.569 | 1.042 | GR_CORT |
| 1481 | NUB1 | SEQ ID NO. 801 | 37.011 | 34.498 | 0.932 | GR_DEX |
| 1482 | NUB1 | SEQ ID NO. 801 | 37.011 | 33.451 | 0.904 | GR_PRED |
| 1483 | RAB11A | SEQ ID NO. 802 | 12.934 | 12.844 | 0.993 | GR_CORT |
| 1484 | RAB11A | SEQ ID NO. 802 | 12.934 | 8.248 | 0.638 | GR_DEX |
| 1485 | RAB11A | SEQ ID NO. 802 | 12.934 | 9.867 | 0.763 | GR_PRED |
| 1486 | MEST | SEQ ID NO. 803 | 1.822 | 2.051 | 1.126 | GR_CORT |
| 1487 | MEST | SEQ ID NO. 803 | 1.822 | 1.479 | 0.812 | GR_DEX |
| 1488 | MEST | SEQ ID NO. 803 | 1.822 | 1.718 | 0.943 | GR_PRED |
| 1489 | ADM | SEQ ID NO. 803 | 16.631 | 21.191 | 1.274 | GR_CORT |
| 1490 | ADM | SEQ ID NO. 803 | 16.631 | 22.419 | 1.348 | GR_DEX |
| 1491 | ADM | SEQ ID NO. 803 | 16.631 | 16.306 | 0.98 | GR_PRED |

FIG. 1AR -- TABLE 1 TRANSCRIPTIONAL BIOMARKER FUNCTIONAL DATA
SECTION 8A

| LINE_ID | GENE_SYMBOL | SEQUENCE_ID_LISTING | PROM_ACTIVITY_N O_INDUCTION | PROM_ACTIVITY_N TH_INDUCTION | PROM_ACTIVITY_WI INDUCTION | INDUCTION_RATIO | INDUCTION_CONDITIONS* |
|---|---|---|---|---|---|---|---|
| 1492 | CAT | SEQ ID NO. 803 | 6.31 | 5.971 | | 0.946 | GR_CORT |
| 1493 | CAT | SEQ ID NO. 803 | 6.31 | 5.411 | | 0.857 | GR_DEX |
| 1494 | CAT | SEQ ID NO. 803 | 6.31 | 4.716 | | 0.747 | GR_PRED |
| 1495 | TXN | SEQ ID NO. 804 | 2.481 | 2.461 | | 0.992 | GR_CORT |
| 1496 | TXN | SEQ ID NO. 804 | 2.481 | 1.839 | | 0.741 | GR_DEX |
| 1497 | TXN | SEQ ID NO. 804 | 2.481 | 2.479 | | 0.999 | GR_PRED |
| 1498 | HSP90AB1 | SEQ ID NO. 804 | 217.828 | 176.047 | | 0.808 | GR_CORT |
| 1499 | HSP90AB1 | SEQ ID NO. 804 | 217.828 | 159.396 | | 0.732 | GR_DEX |
| 1500 | HSP90AB1 | SEQ ID NO. 804 | 217.828 | 167.581 | | 0.769 | GR_PRED |
| 1501 | SRGN | SEQ ID NO. 805 | 0.108 | 0.22 | | 2.041 | GR_CORT |
| 1502 | SRGN | SEQ ID NO. 805 | 0.108 | 0.546 | | 5.059 | GR_DEX |
| 1503 | SRGN | SEQ ID NO. 805 | 0.108 | 0.284 | | 2.634 | GR_PRED |
| 1504 | AMPD3 | SEQ ID NO. 806 | 0.497 | 0.565 | | 1.137 | GR_CORT |
| 1505 | AMPD3 | SEQ ID NO. 806 | 0.497 | 0.388 | | 0.782 | GR_DEX |
| 1506 | AMPD3 | SEQ ID NO. 806 | 0.497 | 0.443 | | 0.893 | GR_PRED |
| 1507 | AMPD3 | SEQ ID NO. 807 | 0.35 | 0.382 | | 1.092 | GR_CORT |
| 1508 | AMPD3 | SEQ ID NO. 807 | 0.35 | 0.246 | | 0.702 | GR_DEX |
| 1509 | AMPD3 | SEQ ID NO. 807 | 0.35 | 0.299 | | 0.854 | GR_PRED |
| 1510 | ZFP36L1 | SEQ ID NO. 808 | 1.904 | 1.926 | | 1.012 | GR_CORT |
| 1511 | ZFP36L1 | SEQ ID NO. 808 | 1.904 | 1.588 | | 0.834 | GR_DEX |
| 1512 | ZFP36L1 | SEQ ID NO. 808 | 1.904 | 1.606 | | 0.843 | GR_PRED |
| 1513 | CCL2 | SEQ ID NO. 809 | 0.131 | 0.161 | | 1.23 | GR_CORT |
| 1514 | CCL2 | SEQ ID NO. 809 | 0.131 | 0.135 | | 1.031 | GR_DEX |
| 1515 | CCL2 | SEQ ID NO. 809 | 0.131 | 0.131 | | 1.001 | GR_PRED |
| 1516 | IDH1 | SEQ ID NO. 810 | 11.204 | 12.677 | | 1.132 | GR_CORT |
| 1517 | IDH1 | SEQ ID NO. 810 | 11.204 | 11.514 | | 1.028 | GR_DEX |
| 1518 | IDH1 | SEQ ID NO. 810 | 11.204 | 11.405 | | 1.018 | GR_PRED |
| 1519 | EDN1 | SEQ ID NO. 811 | 12.879 | 12.813 | | 0.995 | GR_CORT |
| 1520 | EDN1 | SEQ ID NO. 811 | 12.879 | 8.524 | | 0.662 | GR_DEX |
| 1521 | EDN1 | SEQ ID NO. 811 | 12.879 | 9.645 | | 0.749 | GR_PRED |
| 1522 | ANP32E | SEQ ID NO. 812 | 3.584 | 3.684 | | 1.028 | GR_CORT |
| 1523 | ANP32E | SEQ ID NO. 812 | 3.584 | 4.461 | | 1.245 | GR_DEX |
| 1524 | ANP32E | SEQ ID NO. 812 | 3.584 | 3.799 | | 1.06 | GR_PRED |
| 1525 | PER1 | SEQ ID NO. 813 | 30.546 | 45.625 | | 1.494 | GR_CORT |
| 1526 | PER1 | SEQ ID NO. 813 | 30.546 | 42.828 | | 1.402 | GR_DEX |
| 1527 | PER1 | SEQ ID NO. 813 | 30.546 | 43.416 | | 1.421 | GR_PRED |
| 1528 | SNTA1 | SEQ ID NO. 814 | 1.6 | 3.352 | | 2.095 | GR_CORT |
| 1529 | SNTA1 | SEQ ID NO. 814 | 1.6 | 12.478 | | 7.799 | GR_DEX |
| 1530 | SNTA1 | SEQ ID NO. 814 | 1.6 | 6.64 | | 4.151 | GR_PRED |

FIG. 1AS -- TABLE 1 TRANSCRIPTIONAL BIOMARKER FUNCTIONAL DATA
SECTION 8A

| LINE_ID | GENE_SYMBOL | SEQUENCE_ID_LISTING | PROM_ACTIVITY_N O_INDUCTION | PROM_ACTIVITY_WI TH_INDUCTION | INDUCTION _RATIO | INDUCTION_CONDITIONS* |
|---|---|---|---|---|---|---|
| 1531 | HBS1L | SEQ ID NO. 815 | 3.722 | 4.37 | 1.174 | GR_CORT |
| 1532 | HBS1L | SEQ ID NO. 815 | 3.722 | 4.854 | 1.304 | GR_DEX |
| 1533 | HBS1L | SEQ ID NO. 815 | 3.722 | 3.334 | 0.896 | GR_PRED |
| 1534 | TSC22D3 | SEQ ID NO. 816 | 45.72 | 88.919 | 1.945 | GR_CORT |
| 1535 | TSC22D3 | SEQ ID NO. 816 | 45.72 | 176.275 | 3.856 | GR_DEX |
| 1536 | TSC22D3 | SEQ ID NO. 816 | 45.72 | 157.522 | 3.445 | GR_PRED |
| 1537 | LCN2 | SEQ ID NO. 817 | 4.607 | 5.141 | 1.116 | GR_CORT |
| 1538 | LCN2 | SEQ ID NO. 817 | 4.607 | 5.276 | 1.145 | GR_DEX |
| 1539 | LCN2 | SEQ ID NO. 817 | 4.607 | 4.683 | 1.017 | GR_PRED |
| 1540 | PHLDA1 | SEQ ID NO. 818 | 12.071 | 14.094 | 1.168 | GR_CORT |
| 1541 | PHLDA1 | SEQ ID NO. 818 | 12.071 | 12.428 | 1.03 | GR_DEX |
| 1542 | PHLDA1 | SEQ ID NO. 818 | 12.071 | 13.01 | 1.078 | GR_PRED |
| 1543 | GLUL | SEQ ID NO. 819 | 4.203 | 4.937 | 1.175 | GR_CORT |
| 1544 | GLUL | SEQ ID NO. 819 | 4.203 | 9.002 | 2.142 | GR_DEX |
| 1545 | GLUL | SEQ ID NO. 819 | 4.203 | 6.136 | 1.46 | GR_PRED |

FIG. 1AT -- TABLE 1 TRANSCRIPTIONAL BIOMARKER FUNCTIONAL DATA SECTION 12A

| LINE_ID | GENE_SYMBOL | SEQUENCE_ID_LISTING | PROM_ACTIVITY_N O_INDUCTION | PROM_ACTIVITY_N TH_INDUCTION | PROM_ACTIVITY_WI _INDUCTION_RATIO | INDUCTION_CONDITIONS* |
|---|---|---|---|---|---|---|
| 1546 | CCT4 | SEQ ID NO. 820 | 171.564 | 170.67 | 0.995 | HSF |

FIG. 1AU – TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_N O_INDUCTION | PROM_ACTIVITY_WI TH_INDUCTION | INDUCTION RATIO | INDUCTION_CONDITIONS* |
|---|---|---|---|---|---|---|
| 1547 | MDM2 | SEQ ID NO. 821 | 19.241 | 41.842 | 2.175 | HYPOX_DFO_HCT116 |
| 1548 | MDM2 | SEQ ID NO. 821 | 1.73 | 6.593 | 3.81 | HYPOX_DFO_HT1080 |
| 1549 | MDM2 | SEQ ID NO. 821 | 19.241 | 37.48 | 1.948 | HYPOX_O2_HCT116 |
| 1550 | MDM2 | SEQ ID NO. 821 | 1.73 | 3.592 | 2.076 | HYPOX_O2_HT1080 |
| 1551 | SIRT1 | SEQ ID NO. 822 | 935.85 | 666.669 | 0.712 | HYPOX_DFO_HCT116 |
| 1552 | SIRT1 | SEQ ID NO. 822 | 45.456 | 31.794 | 0.699 | HYPOX_DFO_HT1080 |
| 1553 | SIRT1 | SEQ ID NO. 822 | 935.85 | 672.65 | 0.719 | HYPOX_O2_HCT116 |
| 1554 | SIRT1 | SEQ ID NO. 822 | 45.456 | 34.837 | 0.766 | HYPOX_O2_HT1080 |
| 1555 | PIK3R2 | SEQ ID NO. 823 | 280.698 | 296.522 | 1.056 | HYPOX_DFO_HCT116 |
| 1556 | PIK3R2 | SEQ ID NO. 823 | 78.619 | 37.773 | 0.48 | HYPOX_DFO_HT1080 |
| 1557 | PIK3R2 | SEQ ID NO. 823 | 280.698 | 266.444 | 0.949 | HYPOX_O2_HCT116 |
| 1558 | PIK3R2 | SEQ ID NO. 823 | 78.619 | 58.624 | 0.746 | HYPOX_O2_HT1080 |
| 1559 | PSPH | SEQ ID NO. 823 | 47.256 | 29.873 | 0.632 | HYPOX_DFO_HCT116 |
| 1560 | PSPH | SEQ ID NO. 823 | 3.349 | 3.274 | 0.978 | HYPOX_DFO_HT1080 |
| 1561 | PSPH | SEQ ID NO. 823 | 47.256 | 32.887 | 0.696 | HYPOX_O2_HCT116 |
| 1562 | PSPH | SEQ ID NO. 823 | 3.349 | 3.342 | 0.998 | HYPOX_O2_HT1080 |
| 1563 | AKAP9 | SEQ ID NO. 823 | 918.486 | 830.353 | 0.904 | HYPOX_DFO_HCT116 |
| 1564 | AKAP9 | SEQ ID NO. 823 | 58.754 | 58.321 | 0.993 | HYPOX_DFO_HT1080 |
| 1565 | AKAP9 | SEQ ID NO. 823 | 918.486 | 693.764 | 0.755 | HYPOX_O2_HCT116 |
| 1566 | AKAP9 | SEQ ID NO. 823 | 58.754 | 54.245 | 0.923 | HYPOX_O2_HT1080 |
| 1567 | FAM3C | SEQ ID NO. 823 | 236.58 | 316.511 | 1.338 | HYPOX_DFO_HCT116 |
| 1568 | FAM3C | SEQ ID NO. 823 | 53.976 | 34.704 | 0.643 | HYPOX_DFO_HT1080 |
| 1569 | FAM3C | SEQ ID NO. 823 | 236.58 | 184.946 | 0.782 | HYPOX_O2_HCT116 |
| 1570 | FAM3C | SEQ ID NO. 823 | 53.976 | 39.655 | 0.735 | HYPOX_O2_HT1080 |
| 1571 | ECOP | SEQ ID NO. 823 | 54.919 | 33.509 | 0.61 | HYPOX_DFO_HCT116 |
| 1572 | ECOP | SEQ ID NO. 823 | 1.411 | 1.225 | 0.869 | HYPOX_DFO_HT1080 |
| 1573 | ECOP | SEQ ID NO. 823 | 54.919 | 39.835 | 0.725 | HYPOX_O2_HCT116 |
| 1574 | ECOP | SEQ ID NO. 823 | 1.411 | 1.347 | 0.954 | HYPOX_O2_HT1080 |
| 1575 | NULL | SEQ ID NO. 823 | 813.098 | 1567.791 | 1.928 | HYPOX_DFO_HCT116 |
| 1576 | NULL | SEQ ID NO. 823 | 380.901 | 176.143 | 0.46 | HYPOX_DFO_HT1080 |
| 1577 | NULL | SEQ ID NO. 823 | 813.098 | 1927.397 | 2.37 | HYPOX_O2_HCT116 |
| 1578 | NULL | SEQ ID NO. 823 | 382.901 | 323.833 | 0.846 | HYPOX_O2_HT1080 |
| 1579 | NULL | SEQ ID NO. 823 | 42.408 | 24.454 | 0.577 | HYPOX_DFO_HCT116 |
| 1580 | NULL | SEQ ID NO. 823 | 8.803 | 7.059 | 0.832 | HYPOX_DFO_HT1080 |
| 1581 | NULL | SEQ ID NO. 823 | 42.408 | 36.017 | 0.849 | HYPOX_O2_HCT116 |
| 1582 | NULL | SEQ ID NO. 823 | 8.803 | 14.376 | 1.796 | HYPOX_O2_HT1080 |
| 1583 | PLOD3 | SEQ ID NO. 823 | 1450.669 | 2128.426 | 1.467 | HYPOX_DFO_HCT116 |
| 1584 | PLOD3 | SEQ ID NO. 823 | 385.429 | 457.356 | 1.187 | HYPOX_DFO_HT1080 |
| 1585 | PLOD3 | SEQ ID NO. 823 | 1450.669 | 1420.232 | 0.979 | HYPOX_O2_HCT116 |
| 1586 | PLOD3 | SEQ ID NO. 823 | 385.429 | 454.256 | 1.179 | HYPOX_O2_HT1080 |
| 1587 | NULL | SEQ ID NO. 823 | 1852.134 | 3090.784 | 1.669 | HYPOX_DFO_HCT116 |
| 1588 | NULL | SEQ ID NO. 823 | 380.068 | 689.303 | 1.814 | HYPOX_DFO_HT1080 |
| 1589 | NULL | SEQ ID NO. 823 | 1852.134 | 1989.401 | 1.074 | HYPOX_O2_HCT116 |
| 1590 | NULL | SEQ ID NO. 823 | 380.068 | 413.771 | 1.089 | HYPOX_O2_HT1080 |
| 1591 | NULL | SEQ ID NO. 823 | 289.399 | 492.718 | 1.703 | HYPOX_DFO_HCT116 |
| 1592 | NULL | SEQ ID NO. 823 | 123.585 | 123.857 | 1.003 | HYPOX_DFO_HT1080 |
| 1593 | NULL | SEQ ID NO. 823 | 289.389 | 373.559 | 1.291 | HYPOX_O2_HCT116 |
| 1594 | NULL | SEQ ID NO. 823 | 123.585 | 146.187 | 1.183 | HYPOX_O2_HT1080 |

FIG. 1AV -- TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS* |
|---|---|---|---|---|---|---|
| 1595 | HERPUD2 | SEQ ID NO. 823 | 65.85 | 280.535 | 4.26 | HYPOX_DFO_HCT116 |
| 1596 | HERPUD2 | SEQ ID NO. 823 | 15.033 | 32.272 | 2.147 | HYPOX_DFO_HT1080 |
| 1597 | HERPUD2 | SEQ ID NO. 823 | 65.85 | 233.09 | 3.54 | HYPOX_O2_HCT116 |
| 1598 | HERPUD2 | SEQ ID NO. 823 | 15.033 | 17.894 | 1.19 | HYPOX_O2_HT1080 |
| 1599 | NULL | SEQ ID NO. 823 | 237.435 | 68.845 | 0.29 | HYPOX_DFO_HCT116 |
| 1600 | NULL | SEQ ID NO. 823 | 11.763 | 16.241 | 1.381 | HYPOX_DFO_HT1080 |
| 1601 | NULL | SEQ ID NO. 823 | 237.435 | 215.267 | 0.907 | HYPOX_O2_HCT116 |
| 1602 | NULL | SEQ ID NO. 823 | 11.763 | 13.286 | 1.129 | HYPOX_O2_HT1080 |
| 1603 | NCAPG2 | SEQ ID NO. 823 | 1565.254 | 1411.219 | 0.902 | HYPOX_DFO_HCT116 |
| 1604 | NCAPG2 | SEQ ID NO. 823 | 351.867 | 432.444 | 1.229 | HYPOX_DFO_HT1080 |
| 1605 | NCAPG2 | SEQ ID NO. 823 | 1565.254 | 1327.53 | 0.848 | HYPOX_O2_HCT116 |
| 1606 | NCAPG2 | SEQ ID NO. 823 | 351.867 | 361.878 | 1.028 | HYPOX_O2_HT1080 |
| 1607 | NUB1 | SEQ ID NO. 823 | 2208.425 | 2560.601 | 1.161 | HYPOX_DFO_HCT116 |
| 1608 | NUB1 | SEQ ID NO. 823 | 813.604 | 704.671 | 0.866 | HYPOX_DFO_HT1080 |
| 1609 | NUB1 | SEQ ID NO. 823 | 2208.425 | 2134.148 | 0.967 | HYPOX_O2_HCT116 |
| 1610 | NUB1 | SEQ ID NO. 823 | 813.604 | 689.727 | 0.843 | HYPOX_O2_HT1080 |
| 1611 | NULL | SEQ ID NO. 823 | 164.85 | 158.087 | 0.959 | HYPOX_DFO_HCT116 |
| 1612 | NULL | SEQ ID NO. 823 | 64.062 | 47.144 | 0.736 | HYPOX_DFO_HT1080 |
| 1613 | NULL | SEQ ID NO. 823 | 164.85 | 152.986 | 0.928 | HYPOX_O2_HCT116 |
| 1614 | NULL | SEQ ID NO. 823 | 64.062 | 47.241 | 0.737 | HYPOX_O2_HT1080 |
| 1615 | SLC4A2 | SEQ ID NO. 823 | 155.628 | 76.014 | 0.488 | HYPOX_DFO_HCT116 |
| 1616 | SLC4A2 | SEQ ID NO. 823 | 30.47 | 22.692 | 0.745 | HYPOX_DFO_HT1080 |
| 1617 | SLC4A2 | SEQ ID NO. 823 | 155.628 | 115.79 | 0.744 | HYPOX_O2_HCT116 |
| 1618 | SLC4A2 | SEQ ID NO. 823 | 30.47 | 27.63 | 0.907 | HYPOX_O2_HT1080 |
| 1619 | NULL | SEQ ID NO. 823 | 298.181 | 236.16 | 0.792 | HYPOX_DFO_HCT116 |
| 1620 | NULL | SEQ ID NO. 823 | 22.201 | 25.678 | 1.157 | HYPOX_DFO_HT1080 |
| 1621 | NULL | SEQ ID NO. 823 | 298.181 | 367.313 | 1.232 | HYPOX_O2_HCT116 |
| 1622 | NULL | SEQ ID NO. 823 | 22.201 | 23.451 | 1.056 | HYPOX_O2_HT1080 |
| 1623 | REPIN1 | SEQ ID NO. 823 | 832.105 | 442.097 | 0.531 | HYPOX_DFO_HCT116 |
| 1624 | REPIN1 | SEQ ID NO. 823 | 65.147 | 60.309 | 0.926 | HYPOX_DFO_HT1080 |
| 1625 | REPIN1 | SEQ ID NO. 823 | 832.105 | 708.993 | 0.852 | HYPOX_O2_HCT116 |
| 1626 | REPIN1 | SEQ ID NO. 823 | 65.147 | 73.901 | 1.134 | HYPOX_O2_HT1080 |
| 1627 | MICALL2 | SEQ ID NO. 823 | 613.145 | 208.21 | 0.34 | HYPOX_DFO_HCT116 |
| 1628 | MICALL2 | SEQ ID NO. 823 | 43.822 | 26.052 | 0.594 | HYPOX_DFO_HT1080 |
| 1629 | MICALL2 | SEQ ID NO. 823 | 613.145 | 371.042 | 0.605 | HYPOX_O2_HCT116 |
| 1630 | MICALL2 | SEQ ID NO. 823 | 43.822 | 34.974 | 0.798 | HYPOX_O2_HT1080 |
| 1631 | AIF1 | SEQ ID NO. 824 | 2.744 | 0.914 | 0.333 | HYPOX_DFO_HCT116 |
| 1632 | AIF1 | SEQ ID NO. 824 | 0.158 | 0.247 | 1.560 | HYPOX_DFO_HT1080 |
| 1633 | AIF1 | SEQ ID NO. 824 | 2.744 | 1.924 | 0.701 | HYPOX_O2_HCT116 |
| 1634 | AIF1 | SEQ ID NO. 824 | 0.158 | 0.21 | 1.333 | HYPOX_O2_HT1080 |
| 1635 | ERBB2 | SEQ ID NO. 825 | 480.915 | 642.718 | 1.336 | HYPOX_DFO_HCT116 |
| 1636 | ERBB2 | SEQ ID NO. 825 | 57.873 | 57.256 | 0.989 | HYPOX_DFO_HT1080 |
| 1637 | ERBB2 | SEQ ID NO. 825 | 480.915 | 440.493 | 0.916 | HYPOX_O2_HCT116 |
| 1638 | ERBB2 | SEQ ID NO. 825 | 57.873 | 52.491 | 0.907 | HYPOX_O2_HT1080 |
| 1639 | TNF | SEQ ID NO. 825 | 628.959 | 405.271 | 0.644 | HYPOX_DFO_HCT116 |
| 1640 | TNF | SEQ ID NO. 825 | 78.78 | 61.898 | 0.786 | HYPOX_DFO_HT1080 |
| 1641 | TNF | SEQ ID NO. 825 | 628.959 | 433.388 | 0.689 | HYPOX_O2_HCT116 |
| 1642 | TNF | SEQ ID NO. 825 | 78.78 | 60.204 | 0.764 | HYPOX_O2_HT1080 |

FIG. 1AW – TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_N O_INDUCTION | PROM_ACTIVITY_W1 TH_INDUCTION | INDUCTION_RATIO | INDUCTION_CONDITIONS* |
|---|---|---|---|---|---|---|
| 1643 | ITGB2 | SEQ ID NO. 826 | 57.666 | 13.629 | 0.236 | HYPOX_DFO_HCT116 |
| 1644 | ITGB2 | SEQ ID NO. 826 | 3.185 | 2.581 | 0.81 | HYPOX_DFO_HT1080 |
| 1645 | ITGB2 | SEQ ID NO. 826 | 57.666 | 34.014 | 0.59 | HYPOX_O2_HCT116 |
| 1646 | ITGB2 | SEQ ID NO. 826 | 3.185 | 3.654 | 1.147 | HYPOX_O2_HT1080 |
| 1647 | APEX1 | SEQ ID NO. 827 | 90.341 | 66.773 | 0.739 | HYPOX_DFO_HCT116 |
| 1648 | APEX1 | SEQ ID NO. 827 | 60.917 | 39.42 | 0.647 | HYPOX_DFO_HT1080 |
| 1649 | APEX1 | SEQ ID NO. 827 | 90.341 | 58.24 | 0.645 | HYPOX_O2_HCT116 |
| 1650 | APEX1 | SEQ ID NO. 827 | 60.917 | 60.866 | 0.999 | HYPOX_O2_HT1080 |
| 1651 | CDC73 | SEQ ID NO. 828 | 356.236 | 694.414 | 1.949 | HYPOX_DFO_HCT116 |
| 1652 | CDC73 | SEQ ID NO. 828 | 78.962 | 88.442 | 1.12 | HYPOX_DFO_HT1080 |
| 1653 | CDC73 | SEQ ID NO. 828 | 356.236 | 583.857 | 1.639 | HYPOX_O2_HCT116 |
| 1654 | CDC73 | SEQ ID NO. 828 | 78.962 | 77.532 | 0.982 | HYPOX_O2_HT1080 |
| 1655 | TIAL1 | SEQ ID NO. 829 | 302.97 | 547.485 | 1.807 | HYPOX_DFO_HCT116 |
| 1656 | TIAL1 | SEQ ID NO. 829 | 82.226 | 113.05 | 1.375 | HYPOX_DFO_HT1080 |
| 1657 | TIAL1 | SEQ ID NO. 829 | 302.97 | 419.649 | 1.385 | HYPOX_O2_HCT116 |
| 1658 | TIAL1 | SEQ ID NO. 829 | 82.226 | 89.304 | 1.086 | HYPOX_O2_HT1080 |
| 1659 | UNC13B | SEQ ID NO. 830 | 0.149 | 0.221 | 1.481 | HYPOX_DFO_HCT116 |
| 1660 | UNC13B | SEQ ID NO. 830 | 0.178 | 0.169 | 0.95 | HYPOX_DFO_HT1080 |
| 1661 | UNC13B | SEQ ID NO. 830 | 0.149 | 0.312 | 2.094 | HYPOX_O2_HCT116 |
| 1662 | UNC13B | SEQ ID NO. 830 | 0.178 | 0.078 | 0.437 | HYPOX_O2_HT1080 |
| 1663 | MAL | SEQ ID NO. 831 | 144.366 | 31.118 | 0.216 | HYPOX_DFO_HCT116 |
| 1664 | MAL | SEQ ID NO. 831 | 9.189 | 2.883 | 0.314 | HYPOX_DFO_HT1080 |
| 1665 | MAL | SEQ ID NO. 831 | 144.366 | 78.614 | 0.545 | HYPOX_O2_HCT116 |
| 1666 | MAL | SEQ ID NO. 831 | 9.189 | 8.119 | 0.884 | HYPOX_O2_HT1080 |
| 1667 | PDCD5 | SEQ ID NO. 832 | 204.137 | 165.355 | 0.81 | HYPOX_DFO_HCT116 |
| 1668 | PDCD5 | SEQ ID NO. 832 | 27.557 | 29.042 | 1.054 | HYPOX_DFO_HT1080 |
| 1669 | PDCD5 | SEQ ID NO. 832 | 204.137 | 196.64 | 0.963 | HYPOX_O2_HCT116 |
| 1670 | PDCD5 | SEQ ID NO. 832 | 27.557 | 28.62 | 1.039 | HYPOX_O2_HT1080 |
| 1671 | TGFB1 | SEQ ID NO. 833 | 264.355 | 100.138 | 0.379 | HYPOX_DFO_HCT116 |
| 1672 | TGFB1 | SEQ ID NO. 833 | 14.715 | 9.42 | 0.64 | HYPOX_DFO_HT1080 |
| 1673 | TGFB1 | SEQ ID NO. 833 | 264.355 | 179.109 | 0.678 | HYPOX_O2_HCT116 |
| 1674 | TGFB1 | SEQ ID NO. 833 | 14.715 | 10.569 | 0.718 | HYPOX_O2_HT1080 |
| 1675 | TGFB3 | SEQ ID NO. 834 | 18.804 | 11.518 | 0.613 | HYPOX_DFO_HCT116 |
| 1676 | TGFB3 | SEQ ID NO. 834 | 1.248 | 1.873 | 1.501 | HYPOX_DFO_HT1080 |
| 1677 | TGFB3 | SEQ ID NO. 834 | 18.804 | 17.832 | 0.948 | HYPOX_O2_HCT116 |
| 1678 | TGFB3 | SEQ ID NO. 834 | 1.248 | 1.327 | 1.063 | HYPOX_O2_HT1080 |
| 1679 | AK3L1 | SEQ ID NO. 835 | 341.45 | 161.704 | 0.474 | HYPOX_DFO_HCT116 |
| 1680 | AK3L1 | SEQ ID NO. 835 | 7.854 | 7.284 | 0.927 | HYPOX_DFO_HT1080 |
| 1681 | AK3L1 | SEQ ID NO. 835 | 341.45 | 366.508 | 1.073 | HYPOX_O2_HCT116 |
| 1682 | AK3L1 | SEQ ID NO. 835 | 7.854 | 8.435 | 1.074 | HYPOX_O2_HT1080 |
| 1683 | IL6R | SEQ ID NO. 836 | 184.451 | 120.445 | 0.653 | HYPOX_DFO_HCT116 |
| 1684 | IL6R | SEQ ID NO. 836 | 10.877 | 15.267 | 1.404 | HYPOX_DFO_HT1080 |
| 1685 | IL6R | SEQ ID NO. 836 | 184.451 | 136.139 | 0.738 | HYPOX_O2_HCT116 |
| 1686 | IL6R | SEQ ID NO. 836 | 10.877 | 8.675 | 0.798 | HYPOX_O2_HT1080 |
| 1687 | FRAP1 | SEQ ID NO. 837 | 2039.937 | 1766.092 | 0.866 | HYPOX_DFO_HCT116 |
| 1688 | FRAP1 | SEQ ID NO. 837 | 624.997 | 494.315 | 0.791 | HYPOX_DFO_HT1080 |
| 1689 | FRAP1 | SEQ ID NO. 837 | 2039.937 | 1397.246 | 0.685 | HYPOX_O2_HCT116 |
| 1690 | FRAP1 | SEQ ID NO. 837 | 624.997 | 412.291 | 0.66 | HYPOX_O2_HT1080 |

FIG. 1AX — TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_N O_INDUCTION | PROM_ACTIVITY_N TH_INDUCTION | PROM_ACTIVITY_WI TH_INDUCTION | INDUCTION_RATIO | INDUCTION_CONDITIONS* |
|---|---|---|---|---|---|---|---|
| 1691 | CSF3R | SEQ ID NO. 838 | 13.778 | | 3.076 | 0.223 | HYPOX_DFO_HCT116 |
| 1692 | CSF3R | SEQ ID NO. 838 | 0.861 | | 0.584 | 0.679 | HYPOX_DFO_HT1080 |
| 1693 | CSF3R | SEQ ID NO. 838 | 13.778 | | 7.562 | 0.549 | HYPOX_O2_HCT116 |
| 1694 | CSF3R | SEQ ID NO. 838 | 0.861 | | 1.033 | 1.199 | HYPOX_O2_HT1080 |
| 1695 | MTF1 | SEQ ID NO. 839 | 613.654 | | 1507.51 | 2.457 | HYPOX_DFO_HCT116 |
| 1696 | MTF1 | SEQ ID NO. 839 | 464.87 | | 486.958 | 1.048 | HYPOX_DFO_HT1080 |
| 1697 | MTF1 | SEQ ID NO. 839 | 613.654 | | 1648.029 | 2.686 | HYPOX_O2_HCT116 |
| 1698 | MTF1 | SEQ ID NO. 839 | 464.87 | | 297.5 | 0.64 | HYPOX_O2_HT1080 |
| 1699 | SLC2A1 | SEQ ID NO. 840 | 1188.379 | | 570.049 | 0.479 | HYPOX_DFO_HCT116 |
| 1700 | SLC2A1 | SEQ ID NO. 840 | 34.668 | | 27.112 | 0.782 | HYPOX_DFO_HT1080 |
| 1701 | SLC2A1 | SEQ ID NO. 840 | 1188.379 | | 714.146 | 0.601 | HYPOX_O2_HCT116 |
| 1702 | SLC2A1 | SEQ ID NO. 840 | 34.668 | | 27.765 | 0.801 | HYPOX_O2_HT1080 |
| 1703 | JUN | SEQ ID NO. 840 | 3771.193 | | 8604.946 | 2.282 | HYPOX_DFO_HCT116 |
| 1704 | JUN | SEQ ID NO. 840 | 339.824 | | 379.78 | 1.118 | HYPOX_DFO_HT1080 |
| 1705 | JUN | SEQ ID NO. 840 | 3771.193 | | 4231.05 | 1.122 | HYPOX_O2_HCT116 |
| 1706 | JUN | SEQ ID NO. 840 | 339.824 | | 227.487 | 0.669 | HYPOX_O2_HT1080 |
| 1707 | F3 | SEQ ID NO. 841 | 392.08 | | 120.513 | 0.307 | HYPOX_DFO_HCT116 |
| 1708 | F3 | SEQ ID NO. 841 | 7.698 | | 5.646 | 0.733 | HYPOX_DFO_HT1080 |
| 1709 | F3 | SEQ ID NO. 841 | 392.08 | | 243.673 | 0.621 | HYPOX_O2_HCT116 |
| 1710 | F3 | SEQ ID NO. 841 | 7.698 | | 3.959 | 0.514 | HYPOX_O2_HT1080 |
| 1711 | ARNT | SEQ ID NO. 842 | 228.591 | | 242.747 | 1.062 | HYPOX_DFO_HCT116 |
| 1712 | ARNT | SEQ ID NO. 842 | 41.997 | | 29.643 | 0.706 | HYPOX_DFO_HT1080 |
| 1713 | ARNT | SEQ ID NO. 842 | 228.591 | | 185.127 | 0.81 | HYPOX_O2_HCT116 |
| 1714 | ARNT | SEQ ID NO. 842 | 41.997 | | 38.969 | 0.928 | HYPOX_O2_HT1080 |
| 1715 | PTGS2 | SEQ ID NO. 842 | 918.171 | | 399.683 | 0.435 | HYPOX_DFO_HCT116 |
| 1716 | PTGS2 | SEQ ID NO. 842 | 49.388 | | 66.054 | 1.337 | HYPOX_DFO_HT1080 |
| 1717 | PTGS2 | SEQ ID NO. 842 | 918.171 | | 626.35 | 0.682 | HYPOX_O2_HCT116 |
| 1718 | PTGS2 | SEQ ID NO. 842 | 49.388 | | 40.904 | 0.828 | HYPOX_O2_HT1080 |
| 1719 | AGT | SEQ ID NO. 842 | 45.81 | | 22.013 | 0.481 | HYPOX_DFO_HCT116 |
| 1720 | AGT | SEQ ID NO. 842 | 4.575 | | 4.833 | 1.067 | HYPOX_DFO_HT1080 |
| 1721 | AGT | SEQ ID NO. 842 | 45.81 | | 26.979 | 0.589 | HYPOX_O2_HCT116 |
| 1722 | AGT | SEQ ID NO. 842 | 4.575 | | 2.546 | 0.556 | HYPOX_O2_HT1080 |
| 1723 | HK1 | SEQ ID NO. 843 | 26.626 | | 99.91 | 3.752 | HYPOX_DFO_HCT116 |
| 1724 | HK1 | SEQ ID NO. 843 | 7.293 | | 14.512 | 1.99 | HYPOX_DFO_HT1080 |
| 1725 | HK1 | SEQ ID NO. 843 | 26.626 | | 53.462 | 2.008 | HYPOX_O2_HCT116 |
| 1726 | HK1 | SEQ ID NO. 843 | 7.293 | | 8.675 | 1.19 | HYPOX_O2_HT1080 |
| 1727 | PTEN | SEQ ID NO. 844 | 227.268 | | 117.348 | 0.516 | HYPOX_DFO_HCT116 |
| 1728 | PTEN | SEQ ID NO. 844 | 56.62 | | 46.917 | 0.829 | HYPOX_DFO_HT1080 |
| 1729 | PTEN | SEQ ID NO. 844 | 227.268 | | 190.362 | 0.838 | HYPOX_O2_HCT116 |
| 1730 | PTEN | SEQ ID NO. 844 | 56.62 | | 49.176 | 0.869 | HYPOX_O2_HT1080 |
| 1731 | HIF1AN | SEQ ID NO. 845 | 484.862 | | 421.98 | 0.87 | HYPOX_DFO_HCT116 |
| 1732 | HIF1AN | SEQ ID NO. 845 | 114.018 | | 115.981 | 1.017 | HYPOX_DFO_HT1080 |
| 1733 | HIF1AN | SEQ ID NO. 845 | 484.862 | | 520.217 | 1.073 | HYPOX_O2_HCT116 |
| 1734 | HIF1AN | SEQ ID NO. 845 | 114.018 | | 110.158 | 0.966 | HYPOX_O2_HT1080 |

FIG. 1AY -- TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_N O_INDUCTION | PROM_ACTIVITY_WI TH_INDUCTION | INDUCTION RATIO | INDUCTION_CONDITIONS* |
|---|---|---|---|---|---|---|
| 1735 | ADRA2A | SEQ ID NO. 846 | 435.353 | 143.577 | 0.33 | HYPOX_DFO_HCT116 |
| 1736 | ADRA2A | SEQ ID NO. 846 | 25.003 | 17.451 | 0.698 | HYPOX_DFO_HT1080 |
| 1737 | ADRA2A | SEQ ID NO. 846 | 435.353 | 349.18 | 0.802 | HYPOX_O2_HCT116 |
| 1738 | ADRA2A | SEQ ID NO. 846 | 25.003 | 17.27 | 0.691 | HYPOX_O2_HT1080 |
| 1739 | ADRB1 | SEQ ID NO. 846 | 132.53 | 148.251 | 1.119 | HYPOX_DFO_HCT116 |
| 1740 | ADRB1 | SEQ ID NO. 846 | 4.9 | 5.241 | 1.07 | HYPOX_DFO_HT1080 |
| 1741 | ADRB1 | SEQ ID NO. 846 | 132.53 | 122.723 | 0.926 | HYPOX_O2_HCT116 |
| 1742 | ADRB1 | SEQ ID NO. 846 | 4.9 | 3.483 | 0.711 | HYPOX_O2_HT1080 |
| 1743 | ECD | SEQ ID NO. 847 | 2755.225 | 5387.427 | 1.955 | HYPOX_DFO_HCT116 |
| 1744 | ECD | SEQ ID NO. 847 | 953.617 | 930.919 | 0.976 | HYPOX_DFO_HT1080 |
| 1745 | ECD | SEQ ID NO. 847 | 2755.225 | 3490.19 | 1.267 | HYPOX_O2_HCT116 |
| 1746 | ECD | SEQ ID NO. 847 | 953.617 | 711.025 | 0.746 | HYPOX_O2_HT1080 |
| 1747 | ADM | SEQ ID NO. 847 | 1632.623 | 1178.436 | 0.722 | HYPOX_DFO_HCT116 |
| 1748 | ADM | SEQ ID NO. 847 | 63.178 | 52.122 | 0.825 | HYPOX_DFO_HT1080 |
| 1749 | ADM | SEQ ID NO. 847 | 1632.623 | 1397.003 | 0.856 | HYPOX_O2_HCT116 |
| 1750 | ADM | SEQ ID NO. 847 | 63.178 | 64.636 | 1.023 | HYPOX_O2_HT1080 |
| 1751 | LDHA16A | SEQ ID NO. 848 | 81.23 | 83.849 | 1.032 | HYPOX_DFO_HCT116 |
| 1752 | LDHA16A | SEQ ID NO. 848 | 1.563 | 1.965 | 1.257 | HYPOX_DFO_HT1080 |
| 1753 | LDHA16A | SEQ ID NO. 848 | 81.23 | 122.508 | 1.509 | HYPOX_O2_HCT116 |
| 1754 | LDHA16A | SEQ ID NO. 848 | 1.563 | 1.409 | 0.901 | HYPOX_O2_HT1080 |
| 1755 | LDHC | SEQ ID NO. 849 | 402.533 | 359.038 | 0.892 | HYPOX_DFO_HCT116 |
| 1756 | LDHC | SEQ ID NO. 849 | 7.613 | 13.416 | 1.762 | HYPOX_DFO_HT1080 |
| 1757 | LDHC | SEQ ID NO. 849 | 402.533 | 361.346 | 0.898 | HYPOX_O2_HCT116 |
| 1758 | LDHC | SEQ ID NO. 849 | 7.613 | 8.29 | 1.089 | HYPOX_O2_HT1080 |
| 1759 | CAT | SEQ ID NO. 849 | 666.498 | 147.715 | 0.222 | HYPOX_DFO_HCT116 |
| 1760 | CAT | SEQ ID NO. 849 | 47.693 | 21.731 | 0.456 | HYPOX_DFO_HT1080 |
| 1761 | CAT | SEQ ID NO. 849 | 666.498 | 213.466 | 0.32 | HYPOX_O2_HCT116 |
| 1762 | CAT | SEQ ID NO. 849 | 47.693 | 36.612 | 0.768 | HYPOX_O2_HT1080 |
| 1763 | IGF2 | SEQ ID NO. 850 | 1713.64 | 720.854 | 0.421 | HYPOX_DFO_HCT116 |
| 1764 | IGF2 | SEQ ID NO. 850 | 65.375 | 34.835 | 0.533 | HYPOX_DFO_HT1080 |
| 1765 | IGF2 | SEQ ID NO. 850 | 1713.64 | 1488.754 | 0.869 | HYPOX_O2_HCT116 |
| 1766 | IGF2 | SEQ ID NO. 850 | 65.375 | 53.836 | 0.823 | HYPOX_O2_HT1080 |
| 1767 | KCNA4 | SEQ ID NO. 851 | 260.917 | 53.218 | 0.204 | HYPOX_DFO_HCT116 |
| 1768 | KCNA4 | SEQ ID NO. 851 | 1.778 | 1.718 | 0.966 | HYPOX_DFO_HT1080 |
| 1769 | KCNA4 | SEQ ID NO. 851 | 260.917 | 135.262 | 0.518 | HYPOX_O2_HCT116 |
| 1770 | KCNA4 | SEQ ID NO. 851 | 1.778 | 1.487 | 0.836 | HYPOX_O2_HT1080 |
| 1771 | CASP1 | SEQ ID NO. 852 | 19.627 | 24.107 | 1.228 | HYPOX_DFO_HCT116 |
| 1772 | CASP1 | SEQ ID NO. 852 | 7.681 | 4.248 | 0.553 | HYPOX_DFO_HT1080 |
| 1773 | CASP1 | SEQ ID NO. 852 | 19.627 | 13.113 | 0.668 | HYPOX_O2_HCT116 |
| 1774 | CASP1 | SEQ ID NO. 852 | 7.681 | 3.32 | 0.432 | HYPOX_O2_HT1080 |
| 1775 | IL18 | SEQ ID NO. 853 | 502.713 | 255.834 | 0.509 | HYPOX_DFO_HCT116 |
| 1776 | IL18 | SEQ ID NO. 853 | 36.472 | 20.052 | 0.55 | HYPOX_DFO_HT1080 |
| 1777 | IL18 | SEQ ID NO. 853 | 502.713 | 247.723 | 0.493 | HYPOX_O2_HCT116 |
| 1778 | IL18 | SEQ ID NO. 853 | 36.472 | 24.163 | 0.662 | HYPOX_O2_HT1080 |
| 1779 | GAPDH | SEQ ID NO. 854 | 7.087 | 4.752 | 0.671 | HYPOX_DFO_HCT116 |
| 1780 | GAPDH | SEQ ID NO. 854 | 1.161 | 0.696 | 0.6 | HYPOX_DFO_HT1080 |
| 1781 | GAPDH | SEQ ID NO. 854 | 7.087 | 5.908 | 0.834 | HYPOX_O2_HCT116 |
| 1782 | GAPDH | SEQ ID NO. 854 | 1.161 | 0.988 | 0.851 | HYPOX_O2_HT1080 |

FIG. 1AZ — TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS* |
|---|---|---|---|---|---|---|
| 1783 | PFKM | SEQ ID NO. 855 | 772.161 | 172.784 | 0.224 | HYPOX_DFO_HCT116 |
| 1784 | PFKM | SEQ ID NO. 855 | 28.707 | 15.655 | 0.545 | HYPOX_DFO_HT1080 |
| 1785 | PFKM | SEQ ID NO. 855 | 772.161 | 398.773 | 0.516 | HYPOX_O2_HCT116 |
| 1786 | PFKM | SEQ ID NO. 855 | 28.707 | 22.078 | 0.769 | HYPOX_O2_HT1080 |
| 1787 | PFKM | SEQ ID NO. 856 | 11.126 | 7.62 | 0.685 | HYPOX_DFO_HCT116 |
| 1788 | PFKM | SEQ ID NO. 856 | 0.603 | 0.512 | 0.849 | HYPOX_DFO_HT1080 |
| 1789 | PFKM | SEQ ID NO. 856 | 11.126 | 6.257 | 0.562 | HYPOX_O2_HCT116 |
| 1790 | PFKM | SEQ ID NO. 856 | 0.603 | 0.471 | 0.781 | HYPOX_O2_HT1080 |
| 1791 | MDM2 | SEQ ID NO. 857 | 2131.907 | 3407.374 | 1.598 | HYPOX_DFO_HCT116 |
| 1792 | MDM2 | SEQ ID NO. 857 | 592.113 | 688.121 | 1.162 | HYPOX_DFO_HT1080 |
| 1793 | MDM2 | SEQ ID NO. 857 | 2131.907 | 3600.856 | 1.689 | HYPOX_O2_HCT116 |
| 1794 | MDM2 | SEQ ID NO. 857 | 592.113 | 372.203 | 0.629 | HYPOX_O2_HT1080 |
| 1795 | APAF1 | SEQ ID NO. 858 | 879.918 | 784.022 | 0.891 | HYPOX_DFO_HCT116 |
| 1796 | APAF1 | SEQ ID NO. 858 | 47.699 | 88.002 | 1.845 | HYPOX_DFO_HT1080 |
| 1797 | APAF1 | SEQ ID NO. 858 | 879.918 | 817.92 | 0.93 | HYPOX_O2_HCT116 |
| 1798 | APAF1 | SEQ ID NO. 858 | 47.699 | 96.522 | 2.024 | HYPOX_O2_HT1080 |
| 1799 | TXNRD1 | SEQ ID NO. 859 | 1109.053 | 1167.674 | 1.053 | HYPOX_DFO_HCT116 |
| 1800 | TXNRD1 | SEQ ID NO. 859 | 558.644 | 658.863 | 1.179 | HYPOX_DFO_HT1080 |
| 1801 | TXNRD1 | SEQ ID NO. 859 | 1109.053 | 1020.445 | 0.92 | HYPOX_O2_HCT116 |
| 1802 | TXNRD1 | SEQ ID NO. 859 | 558.644 | 371.081 | 0.664 | HYPOX_O2_HT1080 |
| 1803 | TXNRD1 | SEQ ID NO. 860 | 75.051 | 35.003 | 0.467 | HYPOX_DFO_HCT116 |
| 1804 | TXNRD1 | SEQ ID NO. 860 | 5.445 | 3.441 | 0.632 | HYPOX_DFO_HT1080 |
| 1805 | TXNRD1 | SEQ ID NO. 860 | 75.051 | 59.927 | 0.798 | HYPOX_O2_HCT116 |
| 1806 | TXNRD1 | SEQ ID NO. 860 | 5.445 | 4.669 | 0.857 | HYPOX_O2_HT1080 |
| 1807 | LDHB | SEQ ID NO. 861 | 1720.178 | 480.211 | 0.279 | HYPOX_DFO_HCT116 |
| 1808 | LDHB | SEQ ID NO. 861 | 111.56 | 83.296 | 0.747 | HYPOX_DFO_HT1080 |
| 1809 | LDHB | SEQ ID NO. 861 | 1720.178 | 875.048 | 0.509 | HYPOX_O2_HCT116 |
| 1810 | LDHB | SEQ ID NO. 861 | 111.56 | 77.509 | 0.695 | HYPOX_O2_HT1080 |
| 1811 | IGF1 | SEQ ID NO. 862 | 2.208 | 3.899 | 1.766 | HYPOX_DFO_HCT116 |
| 1812 | IGF1 | SEQ ID NO. 862 | 0.373 | 1.058 | 2.838 | HYPOX_DFO_HT1080 |
| 1813 | IGF1 | SEQ ID NO. 862 | 2.208 | 2.499 | 1.132 | HYPOX_O2_HCT116 |
| 1814 | IGF1 | SEQ ID NO. 862 | 0.373 | 0.197 | 0.527 | HYPOX_O2_HT1080 |
| 1815 | NOS1 | SEQ ID NO. 863 | 15.183 | 12.093 | 0.797 | HYPOX_DFO_HCT116 |
| 1816 | NOS1 | SEQ ID NO. 863 | 1.224 | 1.569 | 1.282 | HYPOX_DFO_HT1080 |
| 1817 | NOS1 | SEQ ID NO. 863 | 15.183 | 9.493 | 0.625 | HYPOX_O2_HCT116 |
| 1818 | NOS1 | SEQ ID NO. 863 | 1.224 | 1.245 | 1.017 | HYPOX_O2_HT1080 |
| 1819 | FLT1 | SEQ ID NO. 864 | 919.31 | 551.334 | 0.6 | HYPOX_DFO_HCT116 |
| 1820 | FLT1 | SEQ ID NO. 864 | 32.821 | 18.859 | 0.575 | HYPOX_DFO_HT1080 |
| 1821 | FLT1 | SEQ ID NO. 864 | 919.31 | 1094.631 | 1.191 | HYPOX_O2_HCT116 |
| 1822 | FLT1 | SEQ ID NO. 864 | 32.821 | 19.479 | 0.593 | HYPOX_O2_HT1080 |
| 1823 | HIF1A | SEQ ID NO. 865 | 1305.846 | 485.707 | 0.372 | HYPOX_DFO_HCT116 |
| 1824 | HIF1A | SEQ ID NO. 865 | 34.823 | 20.206 | 0.58 | HYPOX_DFO_HT1080 |
| 1825 | HIF1A | SEQ ID NO. 865 | 1305.846 | 708.181 | 0.542 | HYPOX_O2_HCT116 |
| 1826 | HIF1A | SEQ ID NO. 865 | 34.823 | 21.603 | 0.62 | HYPOX_O2_HT1080 |
| 1827 | FOS | SEQ ID NO. 865 | 3592.943 | 14086.926 | 3.921 | HYPOX_DFO_HCT116 |
| 1828 | FOS | SEQ ID NO. 865 | 191.894 | 246.115 | 1.283 | HYPOX_DFO_HT1080 |
| 1829 | FOS | SEQ ID NO. 865 | 3592.943 | 4347.594 | 1.21 | HYPOX_O2_HCT116 |
| 1830 | FOS | SEQ ID NO. 865 | 191.894 | 118.594 | 0.618 | HYPOX_O2_HT1080 |

*FIG. 1BA* -- TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_NO_INDUCTION | PROM_ACTIVITY_WITH_INDUCTION | INDUCTION_RATIO | INDUCTION_CONDITIONS |
|---|---|---|---|---|---|---|
| 1831 | EGLN3 | SEQ ID NO. 866 | 2371.351 | 1716.901 | 0.724 | HYPOX_DFO_HCT116 |
| 1832 | EGLN3 | SEQ ID NO. 866 | 141.384 | 79.107 | 0.56 | HYPOX_DFO_HCT116 |
| 1833 | EGLN3 | SEQ ID NO. 866 | 2371.351 | 1827.831 | 0.771 | HYPOX_O2_HCT116 |
| 1834 | EGLN3 | SEQ ID NO. 866 | 141.384 | 74.335 | 0.526 | HYPOX_O2_HT1080 |
| 1835 | HSP90AA1 | SEQ ID NO. 867 | 2236.906 | 5999.511 | 2.682 | HYPOX_DFO_HCT116 |
| 1836 | HSP90AA1 | SEQ ID NO. 867 | 771.62 | 628.314 | 0.814 | HYPOX_DFO_HT1080 |
| 1837 | HSP90AA1 | SEQ ID NO. 867 | 2236.906 | 4040.41 | 1.806 | HYPOX_O2_HCT116 |
| 1838 | HSP90AA1 | SEQ ID NO. 867 | 771.62 | 656.018 | 0.85 | HYPOX_O2_HT1080 |
| 1839 | LDHAL6B | SEQ ID NO. 868 | 92.568 | 49.901 | 0.539 | HYPOX_DFO_HCT116 |
| 1840 | LDHAL6B | SEQ ID NO. 868 | 2.713 | 3.489 | 1.286 | HYPOX_DFO_HT1080 |
| 1841 | LDHAL6B | SEQ ID NO. 868 | 92.568 | 183.843 | 1.986 | HYPOX_O2_HCT116 |
| 1842 | LDHAL6B | SEQ ID NO. 868 | 2.713 | 2.467 | 0.909 | HYPOX_O2_HT1080 |
| 1843 | MAP2K1 | SEQ ID NO. 869 | 837.066 | 725.493 | 0.867 | HYPOX_DFO_HCT116 |
| 1844 | MAP2K1 | SEQ ID NO. 869 | 127.602 | 128.683 | 1.008 | HYPOX_DFO_HT1080 |
| 1845 | MAP2K1 | SEQ ID NO. 869 | 837.066 | 1148.865 | 1.372 | HYPOX_O2_HCT116 |
| 1846 | MAP2K1 | SEQ ID NO. 869 | 127.602 | 104.191 | 0.817 | HYPOX_O2_HT1080 |
| 1847 | ARPP-19 | SEQ ID NO. 870 | 29.714 | 71.32 | 2.4 | HYPOX_DFO_HCT116 |
| 1848 | ARPP-19 | SEQ ID NO. 870 | 9.104 | 13.958 | 1.533 | HYPOX_DFO_HT1080 |
| 1849 | ARPP-19 | SEQ ID NO. 870 | 29.714 | 33.075 | 1.113 | HYPOX_O2_HCT116 |
| 1850 | ARPP-19 | SEQ ID NO. 870 | 9.104 | 8.192 | 0.9 | HYPOX_O2_HT1080 |
| 1851 | ARPP-19 | SEQ ID NO. 871 | 7.745 | 3.595 | 0.464 | HYPOX_DFO_HCT116 |
| 1852 | ARPP-19 | SEQ ID NO. 871 | 0.636 | 0.516 | 0.812 | HYPOX_DFO_HT1080 |
| 1853 | ARPP-19 | SEQ ID NO. 871 | 7.745 | 3.033 | 0.392 | HYPOX_O2_HCT116 |
| 1854 | ARPP-19 | SEQ ID NO. 871 | 0.636 | 0.638 | 1.002 | HYPOX_O2_HT1080 |
| 1855 | PKM2 | SEQ ID NO. 872 | 2042.598 | 673.687 | 0.33 | HYPOX_DFO_HCT116 |
| 1856 | PKM2 | SEQ ID NO. 872 | 58.284 | 29.727 | 0.51 | HYPOX_DFO_HT1080 |
| 1857 | PKM2 | SEQ ID NO. 872 | 2042.598 | 928.572 | 0.455 | HYPOX_O2_HCT116 |
| 1858 | PKM2 | SEQ ID NO. 872 | 58.284 | 36.208 | 0.621 | HYPOX_O2_HT1080 |
| 1859 | SELS | SEQ ID NO. 873 | 370.915 | 407.612 | 1.099 | HYPOX_DFO_HCT116 |
| 1860 | SELS | SEQ ID NO. 873 | 57.614 | 39.27 | 0.682 | HYPOX_DFO_HT1080 |
| 1861 | SELS | SEQ ID NO. 873 | 370.915 | 565.222 | 1.524 | HYPOX_O2_HCT116 |
| 1862 | SELS | SEQ ID NO. 873 | 57.614 | 38.37 | 0.666 | HYPOX_O2_HT1080 |
| 1863 | ALDOA | SEQ ID NO. 874 | 153.604 | 79.53 | 0.518 | HYPOX_DFO_HCT116 |
| 1864 | ALDOA | SEQ ID NO. 874 | 12.131 | 9.209 | 0.759 | HYPOX_DFO_HT1080 |
| 1865 | ALDOA | SEQ ID NO. 874 | 153.604 | 126.043 | 0.821 | HYPOX_O2_HCT116 |
| 1866 | ALDOA | SEQ ID NO. 874 | 12.131 | 12.024 | 0.991 | HYPOX_O2_HT1080 |
| 1867 | CREBBP | SEQ ID NO. 875 | 1924.826 | 4591.522 | 2.385 | HYPOX_DFO_HCT116 |
| 1868 | CREBBP | SEQ ID NO. 875 | 473.698 | 495.058 | 1.045 | HYPOX_DFO_HT1080 |
| 1869 | CREBBP | SEQ ID NO. 875 | 1924.826 | 1964.278 | 1.02 | HYPOX_O2_HCT116 |
| 1870 | CREBBP | SEQ ID NO. 875 | 473.698 | 517.468 | 1.092 | HYPOX_O2_HT1080 |
| 1871 | CHMP1A | SEQ ID NO. 876 | 2056.979 | 2751.415 | 1.338 | HYPOX_DFO_HCT116 |
| 1872 | CHMP1A | SEQ ID NO. 876 | 670.388 | 614.216 | 0.916 | HYPOX_DFO_HT1080 |
| 1873 | CHMP1A | SEQ ID NO. 876 | 2056.979 | 2228.164 | 1.083 | HYPOX_O2_HCT116 |
| 1874 | CHMP1A | SEQ ID NO. 876 | 670.388 | 567.429 | 0.846 | HYPOX_O2_HT1080 |
| 1875 | CCL2 | SEQ ID NO. 877 | 12.524 | 9.749 | 0.778 | HYPOX_DFO_HCT116 |
| 1876 | CCL2 | SEQ ID NO. 877 | 2.016 | 2.581 | 1.28 | HYPOX_DFO_HT1080 |
| 1877 | CCL2 | SEQ ID NO. 877 | 12.524 | 9.657 | 0.771 | HYPOX_O2_HCT116 |
| 1878 | CCL2 | SEQ ID NO. 877 | 2.016 | 1.496 | 0.742 | HYPOX_O2_HT1080 |

*FIG. 1BB* – TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS* |
|---|---|---|---|---|---|---|
| 1879 | CCL4 | SEQ ID NO. 878 | 9.427 | 4.509 | 0.478 | HYPOX_DFO_HCT116 |
| 1880 | CCL4 | SEQ ID NO. 878 | 2.145 | 2.165 | 1.009 | HYPOX_DFO_HT1080 |
| 1881 | CCL4 | SEQ ID NO. 878 | 9.427 | 9.158 | 0.971 | HYPOX_O2_HCT116 |
| 1882 | CCL4 | SEQ ID NO. 878 | 2.145 | 2.158 | 1.006 | HYPOX_O2_HT1080 |
| 1883 | EPX | SEQ ID NO. 879 | 106.884 | 19.771 | 0.185 | HYPOX_DFO_HCT116 |
| 1884 | EPX | SEQ ID NO. 879 | 7.178 | 5.478 | 0.763 | HYPOX_DFO_HT1080 |
| 1885 | EPX | SEQ ID NO. 879 | 106.884 | 70.219 | 0.657 | HYPOX_O2_HCT116 |
| 1886 | EPX | SEQ ID NO. 879 | 7.178 | 5.515 | 0.768 | HYPOX_O2_HT1080 |
| 1887 | ACE | SEQ ID NO. 880 | 601.343 | 173.421 | 0.288 | HYPOX_DFO_HCT116 |
| 1888 | ACE | SEQ ID NO. 880 | 77.903 | 31.193 | 0.4 | HYPOX_DFO_HT1080 |
| 1889 | ACE | SEQ ID NO. 880 | 601.343 | 344.845 | 0.573 | HYPOX_O2_HCT116 |
| 1890 | ACE | SEQ ID NO. 880 | 77.903 | 72.479 | 0.93 | HYPOX_O2_HT1080 |
| 1891 | ACE | SEQ ID NO. 880 | 70.286 | 60.57 | 0.862 | HYPOX_DFO_HCT116 |
| 1892 | ACE | SEQ ID NO. 881 | 4.17 | 2.25 | 0.54 | HYPOX_DFO_HT1080 |
| 1893 | ACE | SEQ ID NO. 881 | 70.286 | 46.711 | 0.665 | HYPOX_O2_HCT116 |
| 1894 | ACE | SEQ ID NO. 881 | 4.17 | 3.239 | 0.777 | HYPOX_O2_HT1080 |
| 1895 | TP53 | SEQ ID NO. 881 | 506.523 | 336.607 | 0.665 | HYPOX_DFO_HCT116 |
| 1896 | TP53 | SEQ ID NO. 881 | 67.6 | 82.848 | 1.226 | HYPOX_DFO_HT1080 |
| 1897 | TP53 | SEQ ID NO. 881 | 506.523 | 341.333 | 0.674 | HYPOX_O2_HCT116 |
| 1898 | TP53 | SEQ ID NO. 881 | 67.6 | 56.559 | 0.837 | HYPOX_O2_HT1080 |
| 1899 | MDS2A | SEQ ID NO. 881 | 53.847 | 18.337 | 0.341 | HYPOX_DFO_HCT116 |
| 1900 | MDS2A | SEQ ID NO. 881 | 3.555 | 3.248 | 0.914 | HYPOX_DFO_HT1080 |
| 1901 | MDS2A | SEQ ID NO. 881 | 53.847 | 26.666 | 0.495 | HYPOX_O2_HCT116 |
| 1902 | MDS2A | SEQ ID NO. 881 | 3.555 | 2.105 | 0.615 | HYPOX_O2_HT1080 |
| 1903 | CCL3 | SEQ ID NO. 882 | 3.001 | 0.611 | 0.203 | HYPOX_DFO_HCT116 |
| 1904 | CCL3 | SEQ ID NO. 882 | 0.131 | 0.157 | 1.198 | HYPOX_DFO_HT1080 |
| 1905 | CCL3 | SEQ ID NO. 882 | 3.001 | 2.896 | 0.965 | HYPOX_O2_HCT116 |
| 1906 | CCL3 | SEQ ID NO. 882 | 0.131 | 0.133 | 1.012 | HYPOX_O2_HT1080 |
| 1907 | EGLN2 | SEQ ID NO. 883 | 493.198 | 81.116 | 0.164 | HYPOX_DFO_HCT116 |
| 1908 | EGLN2 | SEQ ID NO. 883 | 65.403 | 41.764 | 0.639 | HYPOX_DFO_HT1080 |
| 1909 | EGLN2 | SEQ ID NO. 883 | 493.198 | 168.733 | 0.342 | HYPOX_O2_HCT116 |
| 1910 | EGLN2 | SEQ ID NO. 883 | 65.403 | 42.998 | 0.657 | HYPOX_O2_HT1080 |
| 1911 | HIF3A | SEQ ID NO. 884 | 64.557 | 8.893 | 0.138 | HYPOX_DFO_HCT116 |
| 1912 | HIF3A | SEQ ID NO. 884 | 1.151 | 0.422 | 0.367 | HYPOX_DFO_HT1080 |
| 1913 | HIF3A | SEQ ID NO. 884 | 64.557 | 40.964 | 0.635 | HYPOX_O2_HCT116 |
| 1914 | HIF3A | SEQ ID NO. 884 | 1.151 | 0.89 | 0.773 | HYPOX_O2_HT1080 |
| 1915 | KEAP1 | SEQ ID NO. 885 | 201.071 | 103.907 | 0.517 | HYPOX_DFO_HCT116 |
| 1916 | KEAP1 | SEQ ID NO. 885 | 31.796 | 22.444 | 0.706 | HYPOX_DFO_HT1080 |
| 1917 | KEAP1 | SEQ ID NO. 885 | 201.071 | 216.675 | 1.078 | HYPOX_O2_HCT116 |
| 1918 | KEAP1 | SEQ ID NO. 885 | 31.796 | 20.904 | 0.657 | HYPOX_O2_HT1080 |
| 1919 | IL11 | SEQ ID NO. 886 | 54.54 | 29.727 | 0.545 | HYPOX_DFO_HCT116 |
| 1920 | IL11 | SEQ ID NO. 886 | 7.589 | 6.071 | 0.8 | HYPOX_DFO_HT1080 |
| 1921 | IL11 | SEQ ID NO. 886 | 54.54 | 54.864 | 1.002 | HYPOX_O2_HCT116 |
| 1922 | IL11 | SEQ ID NO. 886 | 7.589 | 7.129 | 0.939 | HYPOX_O2_HT1080 |

FIG. 1BC — TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS* |
|---|---|---|---|---|---|---|
| 1923 | EPAS1 | SEQ ID NO. 887 | 1211.669 | 324.132 | 0.268 | HYPOX_DFO_HCT116 |
| 1924 | EPAS1 | SEQ ID NO. 887 | 25.426 | 12.114 | 0.476 | HYPOX_DFO_HT1080 |
| 1925 | EPAS1 | SEQ ID NO. 887 | 1211.669 | 1252.773 | 1.034 | HYPOX_O2_HCT116 |
| 1926 | EPAS1 | SEQ ID NO. 887 | 25.426 | 23.849 | 0.938 | HYPOX_O2_HT1080 |
| 1927 | EPAS1 | SEQ ID NO. 888 | 2.533 | 1.159 | 0.458 | HYPOX_DFO_HCT116 |
| 1928 | EPAS1 | SEQ ID NO. 888 | 0.323 | 0.243 | 0.754 | HYPOX_DFO_HT1080 |
| 1929 | EPAS1 | SEQ ID NO. 888 | 2.533 | 1.811 | 0.715 | HYPOX_O2_HCT116 |
| 1930 | EPAS1 | SEQ ID NO. 888 | 0.323 | 0.257 | 0.798 | HYPOX_O2_HT1080 |
| 1931 | IL1R2 | SEQ ID NO. 888 | 84.014 | 22.929 | 0.273 | HYPOX_DFO_HCT116 |
| 1932 | IL1R2 | SEQ ID NO. 889 | 1.392 | 1.02 | 0.733 | HYPOX_DFO_HT1080 |
| 1933 | IL1R2 | SEQ ID NO. 889 | 84.014 | 65.739 | 0.782 | HYPOX_O2_HCT116 |
| 1934 | IL1R2 | SEQ ID NO. 889 | 1.392 | 1.076 | 0.773 | HYPOX_O2_HT1080 |
| 1935 | IL1RN | SEQ ID NO. 890 | 54.93 | 16.355 | 0.298 | HYPOX_DFO_HCT116 |
| 1936 | IL1RN | SEQ ID NO. 890 | 1.54 | 1.24 | 0.805 | HYPOX_DFO_HT1080 |
| 1937 | IL1RN | SEQ ID NO. 890 | 54.93 | 38.569 | 0.702 | HYPOX_O2_HCT116 |
| 1938 | IL1RN | SEQ ID NO. 890 | 1.54 | 1.332 | 0.865 | HYPOX_O2_HT1080 |
| 1939 | AGXT | SEQ ID NO. 891 | 246.948 | 222.317 | 0.9 | HYPOX_DFO_HCT116 |
| 1940 | AGXT | SEQ ID NO. 891 | 82.904 | 73.911 | 0.892 | HYPOX_DFO_HT1080 |
| 1941 | AGXT | SEQ ID NO. 891 | 246.948 | 207.785 | 0.841 | HYPOX_O2_HCT116 |
| 1942 | AGXT | SEQ ID NO. 891 | 82.904 | 69.639 | 0.84 | HYPOX_O2_HT1080 |
| 1943 | SOS1 | SEQ ID NO. 892 | 488.679 | 503.954 | 1.031 | HYPOX_DFO_HCT116 |
| 1944 | SOS1 | SEQ ID NO. 892 | 46.734 | 43.03 | 0.921 | HYPOX_DFO_HT1080 |
| 1945 | SOS1 | SEQ ID NO. 892 | 488.679 | 490.106 | 1.003 | HYPOX_O2_HCT116 |
| 1946 | SOS1 | SEQ ID NO. 892 | 46.734 | 29.6 | 0.633 | HYPOX_O2_HT1080 |
| 1947 | ADRA2B | SEQ ID NO. 893 | 32.047 | 15.35 | 0.479 | HYPOX_DFO_HCT116 |
| 1948 | ADRA2B | SEQ ID NO. 893 | 1.087 | 0.867 | 0.798 | HYPOX_DFO_HT1080 |
| 1949 | ADRA2B | SEQ ID NO. 893 | 32.047 | 27.966 | 0.873 | HYPOX_O2_HCT116 |
| 1950 | ADRA2B | SEQ ID NO. 893 | 1.087 | 1.072 | 0.987 | HYPOX_O2_HT1080 |
| 1951 | IL1A | SEQ ID NO. 894 | 5.975 | 2.803 | 0.469 | HYPOX_DFO_HCT116 |
| 1952 | IL1A | SEQ ID NO. 894 | 1.236 | 0.903 | 0.731 | HYPOX_DFO_HT1080 |
| 1953 | IL1A | SEQ ID NO. 894 | 5.975 | 4.939 | 0.827 | HYPOX_O2_HCT116 |
| 1954 | IL1A | SEQ ID NO. 894 | 1.236 | 0.876 | 0.709 | HYPOX_O2_HT1080 |
| 1955 | IL1B | SEQ ID NO. 895 | 56.914 | 44.189 | 0.776 | HYPOX_DFO_HCT116 |
| 1956 | IL1B | SEQ ID NO. 895 | 27.317 | 25.109 | 0.919 | HYPOX_DFO_HT1080 |
| 1957 | IL1B | SEQ ID NO. 895 | 56.914 | 43.952 | 0.772 | HYPOX_O2_HCT116 |
| 1958 | IL1B | SEQ ID NO. 895 | 27.317 | 19.532 | 0.715 | HYPOX_O2_HT1080 |
| 1959 | NFE2L2 | SEQ ID NO. 896 | 390.778 | 365.751 | 0.936 | HYPOX_DFO_HCT116 |
| 1960 | NFE2L2 | SEQ ID NO. 896 | 21.622 | 22.128 | 1.023 | HYPOX_DFO_HT1080 |
| 1961 | NFE2L2 | SEQ ID NO. 896 | 390.778 | 272.834 | 0.698 | HYPOX_O2_HCT116 |
| 1962 | NFE2L2 | SEQ ID NO. 896 | 21.622 | 17.088 | 0.79 | HYPOX_O2_HT1080 |
| 1963 | NFE2L2 | SEQ ID NO. 897 | 151.111 | 136.315 | 0.902 | HYPOX_DFO_HCT116 |
| 1964 | NFE2L2 | SEQ ID NO. 897 | 23.657 | 7.173 | 0.303 | HYPOX_DFO_HT1080 |
| 1965 | NFE2L2 | SEQ ID NO. 897 | 151.111 | 110.955 | 0.734 | HYPOX_O2_HCT116 |
| 1966 | NFE2L2 | SEQ ID NO. 897 | 23.657 | 10.752 | 0.455 | HYPOX_O2_HT1080 |
| 1967 | TOP1 | SEQ ID NO. 898 | 3158.131 | 3977.765 | 1.26 | HYPOX_DFO_HCT116 |
| 1968 | TOP1 | SEQ ID NO. 898 | 372.007 | 295.658 | 0.795 | HYPOX_DFO_HT1080 |
| 1969 | TOP1 | SEQ ID NO. 898 | 3158.131 | 4756.561 | 1.506 | HYPOX_O2_HCT116 |
| 1970 | TOP1 | SEQ ID NO. 898 | 372.007 | 252.12 | 0.678 | HYPOX_O2_HT1080 |

FIG. 1BD – TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS* |
|---|---|---|---|---|---|---|
| 1971 | MYT1 | SEQ ID NO. 899 | 144.343 | 55.154 | 0.382 | HYPOX_DFO_HCT116 |
| 1972 | MYT1 | SEQ ID NO. 899 | 20.297 | 13.031 | 0.642 | HYPOX_DFO_HT1080 |
| 1973 | MYT1 | SEQ ID NO. 899 | 144.343 | 87.224 | 0.604 | HYPOX_O2_HCT116 |
| 1974 | MYT1 | SEQ ID NO. 899 | 20.297 | 16.865 | 0.831 | HYPOX_O2_HT1080 |
| 1975 | SOD1 | SEQ ID NO. 900 | 67.701 | 41.525 | 0.613 | HYPOX_DFO_HCT116 |
| 1976 | SOD1 | SEQ ID NO. 900 | 4.692 | 3.217 | 0.686 | HYPOX_DFO_HT1080 |
| 1977 | SOD1 | SEQ ID NO. 900 | 67.701 | 49.223 | 0.727 | HYPOX_O2_HCT116 |
| 1978 | SOD1 | SEQ ID NO. 900 | 4.692 | 3.113 | 0.663 | HYPOX_O2_HT1080 |
| 1979 | HMOX1 | SEQ ID NO. 901 | 137.697 | 100.174 | 0.727 | HYPOX_DFO_HCT116 |
| 1980 | HMOX1 | SEQ ID NO. 901 | 10.081 | 5.451 | 0.541 | HYPOX_DFO_HT1080 |
| 1981 | HMOX1 | SEQ ID NO. 901 | 137.697 | 87.37 | 0.635 | HYPOX_O2_HCT116 |
| 1982 | HMOX1 | SEQ ID NO. 901 | 10.081 | 6.528 | 0.648 | HYPOX_O2_HT1080 |
| 1983 | EP300 | SEQ ID NO. 902 | 118.714 | 152.324 | 1.283 | HYPOX_DFO_HCT116 |
| 1984 | EP300 | SEQ ID NO. 902 | 9.659 | 8.007 | 0.829 | HYPOX_DFO_HT1080 |
| 1985 | EP300 | SEQ ID NO. 902 | 118.714 | 132.373 | 1.115 | HYPOX_O2_HCT116 |
| 1986 | EP300 | SEQ ID NO. 902 | 9.659 | 7.567 | 0.783 | HYPOX_O2_HT1080 |
| 1987 | EP300 | SEQ ID NO. 903 | 3699.178 | 11084.092 | 2.996 | HYPOX_DFO_HCT116 |
| 1988 | EP300 | SEQ ID NO. 903 | 860.188 | 1232.09 | 1.432 | HYPOX_DFO_HT1080 |
| 1989 | EP300 | SEQ ID NO. 903 | 3699.178 | 4326.228 | 1.17 | HYPOX_O2_HCT116 |
| 1990 | EP300 | SEQ ID NO. 903 | 860.188 | 691.373 | 0.804 | HYPOX_O2_HT1080 |
| 1991 | MAPK1 | SEQ ID NO. 904 | 83.669 | 57.398 | 0.686 | HYPOX_DFO_HCT116 |
| 1992 | MAPK1 | SEQ ID NO. 904 | 16.274 | 9.133 | 0.561 | HYPOX_DFO_HT1080 |
| 1993 | MAPK1 | SEQ ID NO. 904 | 83.669 | 42.677 | 0.51 | HYPOX_O2_HCT116 |
| 1994 | MAPK1 | SEQ ID NO. 904 | 16.274 | 15.258 | 0.938 | HYPOX_O2_HT1080 |
| 1995 | PDGFB | SEQ ID NO. 905 | 572.435 | 209.442 | 0.366 | HYPOX_DFO_HCT116 |
| 1996 | PDGFB | SEQ ID NO. 905 | 18.372 | 11.861 | 0.646 | HYPOX_DFO_HT1080 |
| 1997 | PDGFB | SEQ ID NO. 905 | 572.435 | 286.46 | 0.5 | HYPOX_O2_HCT116 |
| 1998 | PDGFB | SEQ ID NO. 905 | 18.372 | 15.748 | 0.857 | HYPOX_O2_HT1080 |
| 1999 | A4GALT | SEQ ID NO. 906 | 90.102 | 85.284 | 0.947 | HYPOX_DFO_HCT116 |
| 2000 | A4GALT | SEQ ID NO. 906 | 4.318 | 3.159 | 0.732 | HYPOX_DFO_HT1080 |
| 2001 | A4GALT | SEQ ID NO. 906 | 90.102 | 69.862 | 0.775 | HYPOX_O2_HCT116 |
| 2002 | A4GALT | SEQ ID NO. 906 | 4.318 | 4.11 | 0.952 | HYPOX_O2_HT1080 |
| 2003 | VHL | SEQ ID NO. 907 | 45.246 | 64.762 | 1.431 | HYPOX_DFO_HCT116 |
| 2004 | VHL | SEQ ID NO. 907 | 10.894 | 11.26 | 1.034 | HYPOX_DFO_HT1080 |
| 2005 | VHL | SEQ ID NO. 907 | 45.246 | 35.509 | 0.785 | HYPOX_O2_HCT116 |
| 2006 | VHL | SEQ ID NO. 907 | 10.894 | 7.78 | 0.714 | HYPOX_O2_HT1080 |
| 2007 | DAG1 | SEQ ID NO. 908 | 1103.867 | 1071.05 | 0.97 | HYPOX_DFO_HCT116 |
| 2008 | DAG1 | SEQ ID NO. 908 | 105.516 | 146.075 | 1.384 | HYPOX_DFO_HT1080 |
| 2009 | DAG1 | SEQ ID NO. 908 | 1103.867 | 1619.879 | 1.467 | HYPOX_O2_HCT116 |
| 2010 | DAG1 | SEQ ID NO. 908 | 105.516 | 176.494 | 1.673 | HYPOX_O2_HT1080 |
| 2011 | TF | SEQ ID NO. 909 | 12.857 | 4.896 | 0.381 | HYPOX_DFO_HCT116 |
| 2012 | TF | SEQ ID NO. 909 | 0.565 | 1.039 | 1.841 | HYPOX_DFO_HT1080 |
| 2013 | TF | SEQ ID NO. 909 | 12.857 | 9.696 | 0.754 | HYPOX_O2_HCT116 |
| 2014 | TF | SEQ ID NO. 909 | 0.565 | 0.479 | 0.848 | HYPOX_O2_HT1080 |
| 2015 | CP | SEQ ID NO. 910 | 12.644 | 3.653 | 0.289 | HYPOX_DFO_HCT116 |
| 2016 | CP | SEQ ID NO. 910 | 0.435 | 0.447 | 1.026 | HYPOX_DFO_HT1080 |
| 2017 | CP | SEQ ID NO. 910 | 12.644 | 5.398 | 0.427 | HYPOX_O2_HCT116 |
| 2018 | CP | SEQ ID NO. 910 | 0.435 | 0.404 | 0.929 | HYPOX_O2_HT1080 |

FIG. 1BE -- TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_N O_INDUCTION | PROM_ACTIVITY_W TH_INDUCTION | INDUCTION RATIO | INDUCTION_CONDITIONS* |
|---|---|---|---|---|---|---|
| 2019 | MFI2 | SEQ ID NO. 911 | 187.799 | 50.341 | 0.321 | HYPOX_DFO_HCT116 |
| 2020 | MFI2 | SEQ ID NO. 911 | 15.268 | 6.108 | 0.4 | HYPOX_DFO_HT1080 |
| 2021 | MFI2 | SEQ ID NO. 911 | 187.799 | 103.654 | 0.552 | HYPOX_O2_HCT116 |
| 2022 | MFI2 | SEQ ID NO. 911 | 15.268 | 13.543 | 0.887 | HYPOX_O2_HT1080 |
| 2023 | NULL | SEQ ID NO. 912 | 3.519 | 1.034 | 0.294 | HYPOX_DFO_HCT116 |
| 2024 | NULL | SEQ ID NO. 912 | 0.161 | 0.091 | 0.562 | HYPOX_DFO_HT1080 |
| 2025 | NULL | SEQ ID NO. 912 | 3.519 | 1.486 | 0.422 | HYPOX_O2_HCT116 |
| 2026 | NULL | SEQ ID NO. 912 | 0.161 | 0.144 | 0.894 | HYPOX_O2_HT1080 |
| 2027 | SOD3 | SEQ ID NO. 913 | 6.125 | 3.069 | 0.501 | HYPOX_DFO_HCT116 |
| 2028 | SOD3 | SEQ ID NO. 913 | 22.335 | 16.266 | 0.728 | HYPOX_DFO_HT1080 |
| 2029 | SOD3 | SEQ ID NO. 913 | 6.125 | 3.36 | 0.549 | HYPOX_O2_HCT116 |
| 2030 | SOD3 | SEQ ID NO. 913 | 22.335 | 16.352 | 0.732 | HYPOX_O2_HT1080 |
| 2031 | IL8 | SEQ ID NO. 913 | 110.548 | 142.199 | 1.286 | HYPOX_DFO_HCT116 |
| 2032 | IL8 | SEQ ID NO. 913 | 8.642 | 15.151 | 1.753 | HYPOX_DFO_HT1080 |
| 2033 | IL8 | SEQ ID NO. 913 | 110.548 | 109.946 | 0.995 | HYPOX_O2_HCT116 |
| 2034 | IL8 | SEQ ID NO. 913 | 8.642 | 3.381 | 0.97 | HYPOX_O2_HT1080 |
| 2035 | CXCL1 | SEQ ID NO. 914 | 440.033 | 207.228 | 0.471 | HYPOX_DFO_HCT116 |
| 2036 | CXCL1 | SEQ ID NO. 914 | 59.513 | 32.253 | 0.542 | HYPOX_DFO_HT1080 |
| 2037 | CXCL1 | SEQ ID NO. 914 | 440.033 | 449.403 | 1.021 | HYPOX_O2_HCT116 |
| 2038 | CXCL1 | SEQ ID NO. 914 | 59.513 | 48.276 | 0.811 | HYPOX_O2_HT1080 |
| 2039 | EGF | SEQ ID NO. 914 | 1159.131 | 656.494 | 0.566 | HYPOX_DFO_HCT116 |
| 2040 | EGF | SEQ ID NO. 914 | 151.775 | 99.097 | 0.653 | HYPOX_DFO_HT1080 |
| 2041 | EGF | SEQ ID NO. 914 | 1159.131 | 395.994 | 0.342 | HYPOX_O2_HCT116 |
| 2042 | EGF | SEQ ID NO. 914 | 151.775 | 103.962 | 0.685 | HYPOX_O2_HT1080 |
| 2043 | CXCL2 | SEQ ID NO. 915 | 79.761 | 39.072 | 0.49 | HYPOX_DFO_HCT116 |
| 2044 | CXCL2 | SEQ ID NO. 915 | 4.732 | 2.902 | 0.613 | HYPOX_DFO_HT1080 |
| 2045 | CXCL2 | SEQ ID NO. 915 | 79.761 | 56.271 | 0.705 | HYPOX_O2_HCT116 |
| 2046 | CXCL2 | SEQ ID NO. 915 | 4.732 | 4.912 | 1.038 | HYPOX_O2_HT1080 |
| 2047 | CASP3 | SEQ ID NO. 916 | 445.691 | 680.251 | 1.526 | HYPOX_DFO_HCT116 |
| 2048 | CASP3 | SEQ ID NO. 916 | 85.469 | 116.388 | 1.362 | HYPOX_DFO_HT1080 |
| 2049 | CASP3 | SEQ ID NO. 916 | 445.691 | 310.311 | 0.697 | HYPOX_O2_HCT116 |
| 2050 | CASP3 | SEQ ID NO. 916 | 85.469 | 61.132 | 0.715 | HYPOX_O2_HT1080 |
| 2051 | KIF2A | SEQ ID NO. 917 | 972.29 | 622.5 | 0.64 | HYPOX_DFO_HCT116 |
| 2052 | KIF2A | SEQ ID NO. 917 | 165.986 | 147.116 | 0.886 | HYPOX_DFO_HT1080 |
| 2053 | KIF2A | SEQ ID NO. 917 | 972.29 | 741.795 | 0.763 | HYPOX_O2_HCT116 |
| 2054 | KIF2A | SEQ ID NO. 917 | 165.986 | 134.728 | 0.812 | HYPOX_O2_HT1080 |
| 2055 | PIK3R1 | SEQ ID NO. 918 | 2.84 | 1.347 | 0.474 | HYPOX_DFO_HCT116 |
| 2056 | PIK3R1 | SEQ ID NO. 918 | 0.262 | 0.064 | 0.244 | HYPOX_DFO_HT1080 |
| 2057 | PIK3R1 | SEQ ID NO. 918 | 2.84 | 1.382 | 0.487 | HYPOX_O2_HCT116 |
| 2058 | PIK3R1 | SEQ ID NO. 918 | 0.262 | 0.102 | 0.391 | HYPOX_O2_HT1080 |
| 2059 | CSF2 | SEQ ID NO. 919 | 73.639 | 33.193 | 0.451 | HYPOX_DFO_HCT116 |
| 2060 | CSF2 | SEQ ID NO. 919 | 6.005 | 8.041 | 1.339 | HYPOX_DFO_HT1080 |
| 2061 | CSF2 | SEQ ID NO. 919 | 73.639 | 79.048 | 1.073 | HYPOX_O2_HCT116 |
| 2062 | CSF2 | SEQ ID NO. 919 | 6.005 | 4.209 | 0.701 | HYPOX_O2_HT1080 |
| 2063 | EGR1 | SEQ ID NO. 920 | 4033.967 | 25775.884 | 6.39 | HYPOX_DFO_HCT116 |
| 2064 | EGR1 | SEQ ID NO. 920 | 300.382 | 589.113 | 1.961 | HYPOX_DFO_HT1080 |
| 2065 | EGR1 | SEQ ID NO. 920 | 4033.967 | 11565.462 | 2.867 | HYPOX_O2_HCT116 |
| 2066 | EGR1 | SEQ ID NO. 920 | 300.382 | 232.933 | 0.775 | HYPOX_O2_HT1080 |

*FIG. 1BF* -- TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_N O_INDUCTION | PROM_ACTIVITY_WI TH_INDUCTION | INDUCTION RATIO | INDUCTION_CONDITIONS* |
|---|---|---|---|---|---|---|
| 2067 | LTA | SEQ ID NO. 921 | 14.645 | 7.859 | 0.537 | HYPOX_DFO_HCT116 |
| 2068 | LTA | SEQ ID NO. 921 | 2.049 | 1.208 | 0.589 | HYPOX_DFO_HT1080 |
| 2069 | LTA | SEQ ID NO. 921 | 14.645 | 9.559 | 0.653 | HYPOX_O2_HCT116 |
| 2070 | LTA | SEQ ID NO. 921 | 2.049 | 1.54 | 0.752 | HYPOX_O2_HT1080 |
| 2071 | HSPA1A | SEQ ID NO. 921 | 1424.991 | 736.189 | 0.516 | HYPOX_DFO_HCT116 |
| 2072 | HSPA1A | SEQ ID NO. 921 | 45.433 | 31.821 | 0.7 | HYPOX_DFO_HT1080 |
| 2073 | HSPA1A | SEQ ID NO. 921 | 1484.991 | 1036.842 | 0.698 | HYPOX_O2_HCT116 |
| 2074 | HSPA1A | SEQ ID NO. 921 | 45.433 | 45.535 | 1.002 | HYPOX_O2_HT1080 |
| 2075 | HSPA1B | SEQ ID NO. 922 | 2627.228 | 2635.127 | 1.003 | HYPOX_DFO_HCT116 |
| 2076 | HSPA1B | SEQ ID NO. 922 | 268.427 | 123.009 | 0.458 | HYPOX_DFO_HT1080 |
| 2077 | HSPA1B | SEQ ID NO. 922 | 2627.228 | 2308.871 | 0.879 | HYPOX_O2_HCT116 |
| 2078 | HSPA1B | SEQ ID NO. 922 | 268.427 | 196.846 | 0.733 | HYPOX_O2_HT1080 |
| 2079 | CDKN1A | SEQ ID NO. 923 | 1677.304 | 1124.466 | 0.67 | HYPOX_DFO_HCT116 |
| 2080 | CDKN1A | SEQ ID NO. 923 | 107.836 | 67.99 | 0.63 | HYPOX_DFO_HT1080 |
| 2081 | CDKN1A | SEQ ID NO. 923 | 1677.304 | 962.787 | 0.574 | HYPOX_O2_HCT116 |
| 2082 | CDKN1A | SEQ ID NO. 923 | 107.836 | 58.331 | 0.541 | HYPOX_O2_HT1080 |
| 2083 | LPAL2 | SEQ ID NO. 924 | 0.385 | 0.312 | 0.809 | HYPOX_DFO_HCT116 |
| 2084 | LPAL2 | SEQ ID NO. 924 | 0.142 | 0.063 | 0.444 | HYPOX_DFO_HT1080 |
| 2085 | LPAL2 | SEQ ID NO. 924 | 0.385 | 0.304 | 0.789 | HYPOX_O2_HCT116 |
| 2086 | LPAL2 | SEQ ID NO. 924 | 0.142 | 0.071 | 0.498 | HYPOX_O2_HT1080 |
| 2087 | IL6 | SEQ ID NO. 924 | 10.951 | 10.77 | 0.983 | HYPOX_DFO_HCT116 |
| 2088 | IL6 | SEQ ID NO. 924 | 8.365 | 5.603 | 0.67 | HYPOX_DFO_HT1080 |
| 2089 | IL6 | SEQ ID NO. 924 | 10.951 | 13.653 | 1.247 | HYPOX_O2_HCT116 |
| 2090 | IL6 | SEQ ID NO. 924 | 8.365 | 6.642 | 0.794 | HYPOX_O2_HT1080 |
| 2091 | SERPINE1 | SEQ ID NO. 924 | 972.805 | 694.912 | 0.714 | HYPOX_DFO_HCT116 |
| 2092 | SERPINE1 | SEQ ID NO. 924 | 117.951 | 310.616 | 2.633 | HYPOX_DFO_HT1080 |
| 2093 | SERPINE1 | SEQ ID NO. 924 | 972.805 | 1980.978 | 2.036 | HYPOX_O2_HCT116 |
| 2094 | SERPINE1 | SEQ ID NO. 924 | 117.951 | 169.078 | 1.433 | HYPOX_O2_HT1080 |
| 2095 | NOS3 | SEQ ID NO. 925 | 123.03 | 150.634 | 1.226 | HYPOX_DFO_HCT116 |
| 2096 | NOS3 | SEQ ID NO. 925 | 9.482 | 8.334 | 0.879 | HYPOX_DFO_HT1080 |
| 2097 | NOS3 | SEQ ID NO. 925 | 123.03 | 114.22 | 0.928 | HYPOX_O2_HCT116 |
| 2098 | NOS3 | SEQ ID NO. 925 | 9.482 | 8.756 | 0.923 | HYPOX_O2_HT1080 |
| 2099 | NOS3 | SEQ ID NO. 926 | 47.324 | 41.439 | 0.876 | HYPOX_DFO_HCT116 |
| 2100 | NOS3 | SEQ ID NO. 926 | 4.771 | 4.467 | 0.936 | HYPOX_DFO_HT1080 |
| 2101 | NOS3 | SEQ ID NO. 926 | 47.324 | 61.286 | 1.295 | HYPOX_O2_HCT116 |
| 2102 | NOS3 | SEQ ID NO. 926 | 4.771 | 3.794 | 0.795 | HYPOX_O2_HT1080 |
| 2103 | SHFM1 | SEQ ID NO. 927 | 777.395 | 1106.711 | 1.424 | HYPOX_DFO_HCT116 |
| 2104 | SHFM1 | SEQ ID NO. 927 | 259.741 | 263.363 | 1.014 | HYPOX_DFO_HT1080 |
| 2105 | SHFM1 | SEQ ID NO. 927 | 777.395 | 1030.25 | 1.325 | HYPOX_O2_HCT116 |
| 2106 | SHFM1 | SEQ ID NO. 927 | 259.741 | 208.286 | 0.802 | HYPOX_O2_HT1080 |
| 2107 | BNIP3L | SEQ ID NO. 928 | 123.081 | 22.696 | 0.184 | HYPOX_DFO_HCT116 |
| 2108 | BNIP3L | SEQ ID NO. 928 | 2.308 | 1.289 | 0.558 | HYPOX_DFO_HT1080 |
| 2109 | BNIP3L | SEQ ID NO. 928 | 123.081 | 49.437 | 0.402 | HYPOX_O2_HCT116 |
| 2110 | BNIP3L | SEQ ID NO. 928 | 2.308 | 1.613 | 0.699 | HYPOX_O2_HT1080 |
| 2111 | LOC440258 | SEQ ID NO. 929 | 375.175 | 355.124 | 0.947 | HYPOX_DFO_HCT116 |
| 2112 | LOC440258 | SEQ ID NO. 929 | 59.313 | 73.6 | 1.241 | HYPOX_DFO_HT1080 |
| 2113 | LOC440258 | SEQ ID NO. 929 | 375.175 | 418.479 | 1.115 | HYPOX_O2_HCT116 |
| 2114 | LOC440258 | SEQ ID NO. 929 | 59.313 | 55.316 | 0.933 | HYPOX_O2_HT1080 |

FIG. 1BG -- TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS |
|---|---|---|---|---|---|---|
| 2115 | NRG1 | SEQ ID NO. 930 | 245.498 | 53.655 | 0.219 | HYPOX_DFO_HCT116 |
| 2116 | NRG1 | SEQ ID NO. 930 | 2.866 | 1.997 | 0.697 | HYPOX_DFO_HT1080 |
| 2117 | NRG1 | SEQ ID NO. 930 | 245.498 | 112.327 | 0.458 | HYPOX_O2_HCT116 |
| 2118 | NRG1 | SEQ ID NO. 930 | 2.866 | 2.465 | 0.86 | HYPOX_O2_HT1080 |
| 2119 | NRG1 | SEQ ID NO. 931 | 15.622 | 8.357 | 0.535 | HYPOX_DFO_HCT116 |
| 2120 | NRG1 | SEQ ID NO. 931 | 1.251 | 0.92 | 0.735 | HYPOX_DFO_HT1080 |
| 2121 | NRG1 | SEQ ID NO. 931 | 15.622 | 9.983 | 0.639 | HYPOX_O2_HCT116 |
| 2122 | NRG1 | SEQ ID NO. 931 | 1.251 | 0.694 | 0.555 | HYPOX_O2_HT1080 |
| 2123 | IL11RA | SEQ ID NO. 932 | 62.69 | 30.907 | 0.493 | HYPOX_DFO_HCT116 |
| 2124 | IL11RA | SEQ ID NO. 932 | 3.789 | 1.657 | 0.437 | HYPOX_DFO_HT1080 |
| 2125 | IL11RA | SEQ ID NO. 932 | 62.69 | 40.078 | 0.639 | HYPOX_O2_HCT116 |
| 2126 | IL11RA | SEQ ID NO. 932 | 3.789 | 3.789 | 1 | HYPOX_O2_HT1080 |
| 2127 | TXN | SEQ ID NO. 932 | 33.501 | 45.98 | 1.373 | HYPOX_DFO_HCT116 |
| 2128 | TXN | SEQ ID NO. 932 | 5.73 | 5.049 | 0.881 | HYPOX_DFO_HT1080 |
| 2129 | TXN | SEQ ID NO. 932 | 33.501 | 39.463 | 1.178 | HYPOX_O2_HCT116 |
| 2130 | TXN | SEQ ID NO. 932 | 5.73 | 3.979 | 0.694 | HYPOX_O2_HT1080 |
| 2131 | AK1 | SEQ ID NO. 933 | 1269.183 | 279.686 | 0.22 | HYPOX_DFO_HCT116 |
| 2132 | AK1 | SEQ ID NO. 933 | 93.525 | 41.974 | 0.449 | HYPOX_DFO_HT1080 |
| 2133 | AK1 | SEQ ID NO. 933 | 1269.183 | 557.256 | 0.439 | HYPOX_O2_HCT116 |
| 2134 | AK1 | SEQ ID NO. 933 | 93.525 | 74.293 | 0.794 | HYPOX_O2_HT1080 |
| 2135 | TIMP1 | SEQ ID NO. 934 | 2609.472 | 3902.797 | 1.496 | HYPOX_DFO_HCT116 |
| 2136 | TIMP1 | SEQ ID NO. 934 | 531.326 | 571.479 | 1.075 | HYPOX_DFO_HT1080 |
| 2137 | TIMP1 | SEQ ID NO. 934 | 2609.472 | 3440.742 | 1.319 | HYPOX_O2_HCT116 |
| 2138 | TIMP1 | SEQ ID NO. 934 | 531.326 | 433.771 | 0.816 | HYPOX_O2_HT1080 |
| 2139 | PAK3 | SEQ ID NO. 935 | 120.752 | 49.15 | 0.407 | HYPOX_DFO_HCT116 |
| 2140 | PAK3 | SEQ ID NO. 935 | 10.892 | 6.818 | 0.626 | HYPOX_DFO_HT1080 |
| 2141 | PAK3 | SEQ ID NO. 935 | 120.752 | 70.442 | 0.583 | HYPOX_O2_HCT116 |
| 2142 | PAK3 | SEQ ID NO. 935 | 10.892 | 9.946 | 0.913 | HYPOX_O2_HT1080 |
| 2143 | IL13RA1 | SEQ ID NO. 936 | 256.049 | 182.744 | 0.714 | HYPOX_DFO_HCT116 |
| 2144 | IL13RA1 | SEQ ID NO. 936 | 13.473 | 7.1 | 0.527 | HYPOX_DFO_HT1080 |
| 2145 | IL13RA1 | SEQ ID NO. 936 | 256.049 | 159.439 | 0.623 | HYPOX_O2_HCT116 |
| 2146 | IL13RA1 | SEQ ID NO. 936 | 13.473 | 9.825 | 0.729 | HYPOX_O2_HT1080 |
| 2147 | IL13RA2 | SEQ ID NO. 937 | 48.576 | 15.781 | 0.325 | HYPOX_DFO_HCT116 |
| 2148 | IL13RA2 | SEQ ID NO. 937 | 46.621 | 29.935 | 0.491 | HYPOX_DFO_HT1080 |
| 2149 | IL13RA2 | SEQ ID NO. 937 | 48.576 | 23.83 | 0.785 | HYPOX_O2_HCT116 |
| 2150 | IL13RA2 | SEQ ID NO. 937 | 46.621 | 36.596 | 0.785 | HYPOX_O2_HT1080 |
| 2151 | AIFM1 | SEQ ID NO. 938 | 337.867 | 265.829 | 0.787 | HYPOX_DFO_HCT116 |
| 2152 | AIFM1 | SEQ ID NO. 938 | 76.435 | 77.608 | 1.015 | HYPOX_DFO_HT1080 |
| 2153 | AIFM1 | SEQ ID NO. 938 | 337.867 | 315.275 | 0.933 | HYPOX_O2_HCT116 |
| 2154 | AIFM1 | SEQ ID NO. 938 | 76.435 | 64.207 | 0.84 | HYPOX_O2_HT1080 |
| 2155 | IL9R | SEQ ID NO. 939 | 3.435 | 1.316 | 0.383 | HYPOX_DFO_HCT116 |
| 2156 | IL9R | SEQ ID NO. 939 | 0.253 | 0.23 | 0.907 | HYPOX_DFO_HT1080 |
| 2157 | IL9R | SEQ ID NO. 939 | 3.435 | 1.842 | 0.536 | HYPOX_O2_HCT116 |
| 2158 | IL9R | SEQ ID NO. 939 | 0.253 | 0.24 | 0.948 | HYPOX_O2_HT1080 |
| 2159 | PDK3 | SEQ ID NO. 940 | 190.752 | 183.604 | 0.959 | HYPOX_DFO_HCT116 |
| 2160 | PDK3 | SEQ ID NO. 940 | 4.569 | 17.824 | 3.901 | HYPOX_DFO_HT1080 |
| 2161 | PDK3 | SEQ ID NO. 940 | 190.752 | 400.535 | 2.1 | HYPOX_O2_HCT116 |
| 2162 | PDK3 | SEQ ID NO. 940 | 4.569 | 12.012 | 2.629 | HYPOX_O2_HT1080 |

FIG. 1BH -- TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_NO_INDUCTION | PROM_ACTIVITY_WITH_INDUCTION | INDUCTION_RATIO | INDUCTION_CONDITIONS |
|---|---|---|---|---|---|---|
| 2163 | PLAGL1 | SEQ ID NO. 941 | 740.752 | 616.643 | 0.832 | HYPOX_DFO_HCT116 |
| 2164 | PLAGL1 | SEQ ID NO. 941 | 126.479 | 82.911 | 0.656 | HYPOX_DFO_HT1080 |
| 2165 | PLAGL1 | SEQ ID NO. 941 | 740.752 | 1025.186 | 1.384 | HYPOX_O2_HCT116 |
| 2166 | PLAGL1 | SEQ ID NO. 941 | 126.479 | 80.895 | 0.64 | HYPOX_O2_HT1080 |
| 2167 | PFKP | SEQ ID NO. 942 | 260.069 | 174.895 | 0.672 | HYPOX_DFO_HCT116 |
| 2168 | PFKP | SEQ ID NO. 942 | 3.565 | 3.274 | 0.918 | HYPOX_DFO_HT1080 |
| 2169 | PFKP | SEQ ID NO. 942 | 260.069 | 242.583 | 0.933 | HYPOX_O2_HCT116 |
| 2170 | PFKP | SEQ ID NO. 942 | 3.565 | 5.098 | 1.43 | HYPOX_O2_HT1080 |
| 2171 | TXNDC4 | SEQ ID NO. 943 | 756.87 | 2014.832 | 2.662 | HYPOX_DFO_HCT116 |
| 2172 | TXNDC4 | SEQ ID NO. 943 | 473.512 | 484.332 | 1.023 | HYPOX_DFO_HT1080 |
| 2173 | TXNDC4 | SEQ ID NO. 943 | 756.87 | 999.715 | 1.321 | HYPOX_O2_HCT116 |
| 2174 | TXNDC4 | SEQ ID NO. 943 | 473.512 | 281.615 | 0.595 | HYPOX_O2_HT1080 |
| 2175 | C3 | SEQ ID NO. 944 | 14.033 | 13.116 | 0.935 | HYPOX_DFO_HCT116 |
| 2176 | C3 | SEQ ID NO. 944 | 2.056 | 2.165 | 1.053 | HYPOX_DFO_HT1080 |
| 2177 | C3 | SEQ ID NO. 944 | 14.033 | 15.573 | 1.11 | HYPOX_O2_HCT116 |
| 2178 | C3 | SEQ ID NO. 944 | 2.056 | 3.304 | 1.607 | HYPOX_O2_HT1080 |
| 2179 | NOTCH4 | SEQ ID NO. 945 | 23.892 | 16.251 | 0.68 | HYPOX_DFO_HCT116 |
| 2180 | NOTCH4 | SEQ ID NO. 945 | 8.312 | 9.076 | 1.092 | HYPOX_DFO_HT1080 |
| 2181 | NOTCH4 | SEQ ID NO. 945 | 23.892 | 11.841 | 0.496 | HYPOX_O2_HCT116 |
| 2182 | NOTCH4 | SEQ ID NO. 945 | 8.312 | 5.996 | 0.721 | HYPOX_O2_HT1080 |
| 2183 | HTATIP2 | SEQ ID NO. 946 | 40.952 | 15.022 | 0.367 | HYPOX_DFO_HCT116 |
| 2184 | HTATIP2 | SEQ ID NO. 946 | 1.928 | 0.935 | 0.485 | HYPOX_DFO_HT1080 |
| 2185 | HTATIP2 | SEQ ID NO. 946 | 40.952 | 27.073 | 0.661 | HYPOX_O2_HCT116 |
| 2186 | HTATIP2 | SEQ ID NO. 946 | 1.928 | 1.903 | 0.987 | HYPOX_O2_HT1080 |
| 2187 | TUBB2C | SEQ ID NO. 947 | 2689.959 | 2947.7 | 1.096 | HYPOX_DFO_HCT116 |
| 2188 | TUBB2C | SEQ ID NO. 947 | 573.291 | 456.258 | 0.796 | HYPOX_DFO_HT1080 |
| 2189 | TUBB2C | SEQ ID NO. 947 | 2689.959 | 4211.043 | 1.528 | HYPOX_O2_HCT116 |
| 2190 | TUBB2C | SEQ ID NO. 947 | 573.291 | 475.904 | 0.83 | HYPOX_O2_HT1080 |
| 2191 | ATRN | SEQ ID NO. 948 | 493.728 | 344.848 | 0.698 | HYPOX_DFO_HCT116 |
| 2192 | ATRN | SEQ ID NO. 948 | 94.384 | 81.681 | 0.865 | HYPOX_DFO_HT1080 |
| 2193 | ATRN | SEQ ID NO. 948 | 493.728 | 430.861 | 0.873 | HYPOX_O2_HCT116 |
| 2194 | ATRN | SEQ ID NO. 948 | 94.384 | 70.759 | 0.75 | HYPOX_O2_HT1080 |
| 2195 | TLR2 | SEQ ID NO. 949 | 195.243 | 69.127 | 0.354 | HYPOX_DFO_HCT116 |
| 2196 | TLR2 | SEQ ID NO. 949 | 12.2 | 5.825 | 0.477 | HYPOX_DFO_HT1080 |
| 2197 | TLR2 | SEQ ID NO. 949 | 195.243 | 154.272 | 0.79 | HYPOX_O2_HCT116 |
| 2198 | TLR2 | SEQ ID NO. 949 | 12.2 | 11.174 | 0.916 | HYPOX_O2_HT1080 |
| 2199 | PML | SEQ ID NO. 950 | 4.120 | 4.893 | 1.187 | HYPOX_DFO_HCT116 |
| 2200 | PML | SEQ ID NO. 950 | 0.374 | 0.436 | 1.139 | HYPOX_DFO_HT1080 |
| 2201 | PML | SEQ ID NO. 950 | 4.120 | 5.111 | 1.24 | HYPOX_O2_HCT116 |
| 2202 | PML | SEQ ID NO. 950 | 0.374 | 0.293 | 0.785 | HYPOX_O2_HT1080 |
| 2203 | CYCS | SEQ ID NO. 950 | 3115.944 | 9545.921 | 3.064 | HYPOX_DFO_HCT116 |
| 2204 | CYCS | SEQ ID NO. 950 | 1380.548 | 1803.352 | 1.306 | HYPOX_DFO_HT1080 |
| 2205 | CYCS | SEQ ID NO. 950 | 3115.944 | 4526.704 | 1.453 | HYPOX_O2_HCT116 |
| 2206 | CYCS | SEQ ID NO. 950 | 1380.548 | 1012.001 | 0.733 | HYPOX_O2_HT1080 |
| 2207 | TOLLIP | SEQ ID NO. 951 | 101.439 | 357.715 | 3.526 | HYPOX_DFO_HCT116 |
| 2208 | TOLLIP | SEQ ID NO. 951 | 72.687 | 82.365 | 1.133 | HYPOX_DFO_HT1080 |
| 2209 | TOLLIP | SEQ ID NO. 951 | 101.439 | 190.334 | 1.876 | HYPOX_O2_HCT116 |
| 2210 | TOLLIP | SEQ ID NO. 951 | 72.687 | 62.95 | 0.866 | HYPOX_O2_HT1080 |

*FIG. 1BI* - TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS |
|---|---|---|---|---|---|---|
| 2211 | CCL24 | SEQ ID NO. 952 | 1.969 | 0.9 | 0.457 | HYPOX_DFO_HCT116 |
| 2212 | CCL24 | SEQ ID NO. 952 | 0.163 | 0.123 | 0.759 | HYPOX_DFO_HT1080 |
| 2213 | CCL24 | SEQ ID NO. 952 | 1.969 | 1.337 | 0.679 | HYPOX_O2_HCT116 |
| 2214 | CCL24 | SEQ ID NO. 952 | 0.163 | 0.127 | 0.784 | HYPOX_O2_HT1080 |
| 2215 | NPPB | SEQ ID NO. 953 | 9.49 | 23.47 | 2.473 | HYPOX_DFO_HCT116 |
| 2216 | NPPB | SEQ ID NO. 953 | 1.412 | 1.724 | 1.221 | HYPOX_DFO_HT1080 |
| 2217 | NPPB | SEQ ID NO. 953 | 9.49 | 46.099 | 4.858 | HYPOX_O2_HCT116 |
| 2218 | NPPB | SEQ ID NO. 953 | 1.412 | 1.823 | 1.291 | HYPOX_O2_HT1080 |
| 2219 | CD74 | SEQ ID NO. 954 | 207.908 | 170.874 | 0.822 | HYPOX_DFO_HCT116 |
| 2220 | CD74 | SEQ ID NO. 954 | 40.72 | 34.92 | 0.858 | HYPOX_DFO_HT1080 |
| 2221 | CD74 | SEQ ID NO. 954 | 207.908 | 136.928 | 0.659 | HYPOX_O2_HCT116 |
| 2222 | CD74 | SEQ ID NO. 954 | 40.72 | 27.207 | 0.668 | HYPOX_O2_HT1080 |
| 2223 | MX1 | SEQ ID NO. 955 | 158.163 | 99.208 | 0.627 | HYPOX_DFO_HCT116 |
| 2224 | MX1 | SEQ ID NO. 955 | 488.93 | 115.584 | 0.236 | HYPOX_DFO_HT1080 |
| 2225 | MX1 | SEQ ID NO. 955 | 158.163 | 112.157 | 0.709 | HYPOX_O2_HCT116 |
| 2226 | MX1 | SEQ ID NO. 955 | 488.93 | 286.398 | 0.586 | HYPOX_O2_HT1080 |
| 2227 | IRF7 | SEQ ID NO. 956 | 1978.552 | 1206.342 | 0.61 | HYPOX_DFO_HCT116 |
| 2228 | IRF7 | SEQ ID NO. 956 | 281.833 | 164.402 | 0.583 | HYPOX_DFO_HT1080 |
| 2229 | IRF7 | SEQ ID NO. 956 | 1978.552 | 1908.424 | 0.965 | HYPOX_O2_HCT116 |
| 2230 | IRF7 | SEQ ID NO. 956 | 281.833 | 256.585 | 0.91 | HYPOX_O2_HT1080 |
| 2231 | GAB1 | SEQ ID NO. 957 | 177.986 | 74.141 | 0.417 | HYPOX_DFO_HCT116 |
| 2232 | GAB1 | SEQ ID NO. 957 | 20.751 | 23.777 | 1.146 | HYPOX_DFO_HT1080 |
| 2233 | GAB1 | SEQ ID NO. 957 | 177.986 | 268.133 | 1.506 | HYPOX_O2_HCT116 |
| 2234 | GAB1 | SEQ ID NO. 957 | 20.751 | 36.211 | 1.745 | HYPOX_O2_HT1080 |
| 2235 | IL17C | SEQ ID NO. 958 | 0.593 | 0.56 | 0.943 | HYPOX_DFO_HCT116 |
| 2236 | IL17C | SEQ ID NO. 958 | 0.148 | 0.452 | 3.058 | HYPOX_DFO_HT1080 |
| 2237 | IL17C | SEQ ID NO. 958 | 0.593 | 0.753 | 1.27 | HYPOX_O2_HCT116 |
| 2238 | IL17C | SEQ ID NO. 958 | 0.148 | 0.125 | 0.843 | HYPOX_O2_HT1080 |
| 2239 | ITGAL | SEQ ID NO. 959 | 5.768 | 3.926 | 0.681 | HYPOX_DFO_HCT116 |
| 2240 | ITGAL | SEQ ID NO. 959 | 1.27 | 0.54 | 0.425 | HYPOX_DFO_HT1080 |
| 2241 | ITGAL | SEQ ID NO. 959 | 5.768 | 3.027 | 0.525 | HYPOX_O2_HCT116 |
| 2242 | ITGAL | SEQ ID NO. 959 | 1.27 | 0.983 | 0.774 | HYPOX_O2_HT1080 |
| 2243 | DAPK3 | SEQ ID NO. 960 | 21.255 | 5.001 | 0.235 | HYPOX_DFO_HCT116 |
| 2244 | DAPK3 | SEQ ID NO. 960 | 0.801 | 0.46 | 0.574 | HYPOX_DFO_HT1080 |
| 2245 | DAPK3 | SEQ ID NO. 960 | 21.255 | 12.553 | 0.591 | HYPOX_O2_HCT116 |
| 2246 | DAPK3 | SEQ ID NO. 960 | 0.801 | 0.715 | 0.892 | HYPOX_O2_HT1080 |
| 2247 | PLAT | SEQ ID NO. 961 | 128.455 | 95.164 | 0.741 | HYPOX_DFO_HCT116 |
| 2248 | PLAT | SEQ ID NO. 961 | 27.74 | 11.469 | 0.413 | HYPOX_DFO_HT1080 |
| 2249 | PLAT | SEQ ID NO. 961 | 128.455 | 51.848 | 0.404 | HYPOX_O2_HCT116 |
| 2250 | PLAT | SEQ ID NO. 961 | 27.74 | 24.64 | 0.888 | HYPOX_O2_HT1080 |
| 2251 | C19orf10 | SEQ ID NO. 962 | 481.088 | 599.193 | 1.245 | HYPOX_DFO_HCT116 |
| 2252 | C19orf10 | SEQ ID NO. 962 | 46.235 | 44.589 | 0.964 | HYPOX_DFO_HT1080 |
| 2253 | C19orf10 | SEQ ID NO. 962 | 481.088 | 380.489 | 0.791 | HYPOX_O2_HCT116 |
| 2254 | C19orf10 | SEQ ID NO. 962 | 46.235 | 42.286 | 0.915 | HYPOX_O2_HT1080 |
| 2255 | PROK2 | SEQ ID NO. 963 | 62.276 | 37.375 | 0.6 | HYPOX_DFO_HCT116 |
| 2256 | PROK2 | SEQ ID NO. 963 | 7.803 | 5.616 | 0.739 | HYPOX_DFO_HT1080 |
| 2257 | PROK2 | SEQ ID NO. 963 | 62.276 | 71.83 | 1.153 | HYPOX_O2_HCT116 |
| 2258 | PROK2 | SEQ ID NO. 963 | 7.803 | 7.868 | 1.035 | HYPOX_O2_HT1080 |

FIG. 1BJ -- TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS* |
|---|---|---|---|---|---|---|
| 2259 | PPP2R1A | SEQ ID NO. 964 | 11.459 | 7.518 | 0.656 | HYPOX_DFO_HCT116 |
| 2260 | PPP2R1A | SEQ ID NO. 964 | 1.803 | 2.115 | 1.173 | HYPOX_DFO_HT1080 |
| 2261 | PPP2R1A | SEQ ID NO. 964 | 11.459 | 7.24 | 0.632 | HYPOX_O2_HCT116 |
| 2262 | PPP2R1A | SEQ ID NO. 964 | 1.803 | 1.785 | 0.99 | HYPOX_O2_HT1080 |
| 2263 | SIVA1 | SEQ ID NO. 965 | 690.043 | 322.396 | 0.467 | HYPOX_DFO_HCT116 |
| 2264 | SIVA1 | SEQ ID NO. 965 | 152.73 | 125.693 | 0.823 | HYPOX_DFO_HT1080 |
| 2265 | SIVA1 | SEQ ID NO. 965 | 690.043 | 565.214 | 0.819 | HYPOX_O2_HCT116 |
| 2266 | SIVA1 | SEQ ID NO. 965 | 152.73 | 143.954 | 0.943 | HYPOX_O2_HT1080 |
| 2267 | PGM1 | SEQ ID NO. 966 | 41.752 | 20.068 | 0.481 | HYPOX_DFO_HCT116 |
| 2268 | PGM1 | SEQ ID NO. 966 | 1.992 | 1.12 | 0.562 | HYPOX_DFO_HT1080 |
| 2269 | PGM1 | SEQ ID NO. 966 | 41.752 | 36.01 | 0.862 | HYPOX_O2_HCT116 |
| 2270 | PGM1 | SEQ ID NO. 966 | 1.992 | 1.545 | 0.775 | HYPOX_O2_HT1080 |
| 2271 | CCR4 | SEQ ID NO. 967 | 3.702 | 1.036 | 0.28 | HYPOX_DFO_HCT116 |
| 2272 | CCR4 | SEQ ID NO. 967 | 0.216 | 0.514 | 2.38 | HYPOX_DFO_HT1080 |
| 2273 | CCR4 | SEQ ID NO. 967 | 3.702 | 2.104 | 0.568 | HYPOX_O2_HCT116 |
| 2274 | CCR4 | SEQ ID NO. 967 | 0.216 | 0.137 | 0.634 | HYPOX_O2_HT1080 |
| 2275 | PPP2R1B | SEQ ID NO. 968 | 11.229 | 2.89 | 0.257 | HYPOX_DFO_HCT116 |
| 2276 | PPP2R1B | SEQ ID NO. 968 | 1.206 | 0.336 | 0.279 | HYPOX_DFO_HT1080 |
| 2277 | PPP2R1B | SEQ ID NO. 968 | 11.229 | 6.268 | 0.558 | HYPOX_O2_HCT116 |
| 2278 | PPP2R1B | SEQ ID NO. 968 | 1.206 | 1.169 | 0.969 | HYPOX_O2_HT1080 |
| 2279 | TKTL1 | SEQ ID NO. 969 | 1973.708 | 2957.633 | 1.499 | HYPOX_DFO_HCT116 |
| 2280 | TKTL1 | SEQ ID NO. 969 | 340.369 | 316.704 | 0.93 | HYPOX_DFO_HT1080 |
| 2281 | TKTL1 | SEQ ID NO. 969 | 1973.708 | 3812.302 | 1.932 | HYPOX_O2_HCT116 |
| 2282 | TKTL1 | SEQ ID NO. 969 | 340.369 | 408.179 | 1.199 | HYPOX_O2_HT1080 |
| 2283 | HPSE | SEQ ID NO. 970 | 42.717 | 19.894 | 0.466 | HYPOX_DFO_HCT116 |
| 2284 | HPSE | SEQ ID NO. 970 | 2.297 | 2.486 | 1.082 | HYPOX_DFO_HT1080 |
| 2285 | HPSE | SEQ ID NO. 970 | 42.717 | 25.838 | 0.605 | HYPOX_O2_HCT116 |
| 2286 | HPSE | SEQ ID NO. 970 | 2.297 | 1.819 | 0.792 | HYPOX_O2_HT1080 |
| 2287 | HDAC9 | SEQ ID NO. 971 | 4.959 | 2.494 | 0.503 | HYPOX_DFO_HCT116 |
| 2288 | HDAC9 | SEQ ID NO. 971 | 2.635 | 2.415 | 0.917 | HYPOX_DFO_HT1080 |
| 2289 | HDAC9 | SEQ ID NO. 971 | 4.959 | 2.878 | 0.58 | HYPOX_O2_HCT116 |
| 2290 | HDAC9 | SEQ ID NO. 971 | 2.635 | 1.642 | 0.623 | HYPOX_O2_HT1080 |
| 2291 | IFI16 | SEQ ID NO. 972 | 100.751 | 26.176 | 0.26 | HYPOX_DFO_HCT116 |
| 2292 | IFI16 | SEQ ID NO. 972 | 5.778 | 4.126 | 0.714 | HYPOX_DFO_HT1080 |
| 2293 | IFI16 | SEQ ID NO. 972 | 100.751 | 36.868 | 0.366 | HYPOX_O2_HCT116 |
| 2294 | IFI16 | SEQ ID NO. 972 | 5.778 | 3.625 | 0.627 | HYPOX_O2_HT1080 |
| 2295 | HSP90AB1 | SEQ ID NO. 972 | 2284.063 | 2192.217 | 0.96 | HYPOX_DFO_HCT116 |
| 2296 | HSP90AB1 | SEQ ID NO. 972 | 396.017 | 169.618 | 0.428 | HYPOX_DFO_HT1080 |
| 2297 | HSP90AB1 | SEQ ID NO. 972 | 2284.063 | 3129.546 | 1.37 | HYPOX_O2_HCT116 |
| 2298 | HSP90AB1 | SEQ ID NO. 972 | 396.017 | 415.678 | 1.05 | HYPOX_O2_HT1080 |
| 2299 | DIABLO | SEQ ID NO. 973 | 497.938 | 1043.388 | 2.095 | HYPOX_DFO_HCT116 |
| 2300 | DIABLO | SEQ ID NO. 973 | 96.065 | 104.711 | 1.09 | HYPOX_DFO_HT1080 |
| 2301 | DIABLO | SEQ ID NO. 973 | 497.938 | 1161.976 | 2.334 | HYPOX_O2_HCT116 |
| 2302 | DIABLO | SEQ ID NO. 973 | 96.065 | 51.336 | 0.534 | HYPOX_O2_HT1080 |
| 2303 | SGK2 | SEQ ID NO. 974 | 18.705 | 10.647 | 0.569 | HYPOX_DFO_HCT116 |
| 2304 | SGK2 | SEQ ID NO. 974 | 0.829 | 0.94 | 1.134 | HYPOX_DFO_HT1080 |
| 2305 | SGK2 | SEQ ID NO. 974 | 18.705 | 12.669 | 0.677 | HYPOX_O2_HCT116 |
| 2306 | SGK2 | SEQ ID NO. 974 | 0.829 | 0.59 | 0.712 | HYPOX_O2_HT1080 |

FIG. 1BK -- TABLE 1 TRANSCRIPTIONAL BIOMARKER FUNCTIONAL DATA
SECTION 1A

| LINE_ID | GENE_SYMBOL | SEQUENCE_ID_LISTING | FROM_ACTIVITY_N O_INDUCTION | FROM_ACTIVITY_WI TH_INDUCTION | INDUCTION_RATIO | INDUCTION_CONDITIONS |
|---|---|---|---|---|---|---|
| 2307 | F11R | SEQ ID NO. 975 | 230.603 | 63.638 | 0.276 | HYPOX_DFO_HCT116 |
| 2308 | F11R | SEQ ID NO. 975 | 4.271 | 3.436 | 0.804 | HYPOX_DFO_HT1080 |
| 2309 | F11R | SEQ ID NO. 975 | 230.603 | 116.725 | 0.506 | HYPOX_O2_HCT116 |
| 2310 | F11R | SEQ ID NO. 975 | 4.271 | 3.584 | 0.839 | HYPOX_O2_HT1080 |
| 2311 | STK17A | SEQ ID NO. 976 | 410.493 | 274.48 | 0.669 | HYPOX_DFO_HCT116 |
| 2312 | STK17A | SEQ ID NO. 976 | 34.699 | 34.983 | 1.008 | HYPOX_DFO_HT1080 |
| 2313 | STK17A | SEQ ID NO. 976 | 410.493 | 311.227 | 0.758 | HYPOX_O2_HCT116 |
| 2314 | STK17A | SEQ ID NO. 976 | 34.699 | 30.298 | 0.873 | HYPOX_O2_HT1080 |
| 2315 | AGGF1 | SEQ ID NO. 977 | 2011.599 | 3752.741 | 1.866 | HYPOX_DFO_HCT116 |
| 2316 | AGGF1 | SEQ ID NO. 977 | 402.968 | 607.93 | 1.509 | HYPOX_DFO_HT1080 |
| 2317 | AGGF1 | SEQ ID NO. 977 | 2011.599 | 2349.643 | 1.168 | HYPOX_O2_HCT116 |
| 2318 | AGGF1 | SEQ ID NO. 977 | 402.968 | 384.287 | 0.954 | HYPOX_O2_HT1080 |
| 2319 | LY75 | SEQ ID NO. 978 | 112.236 | 33.721 | 0.3 | HYPOX_DFO_HCT116 |
| 2320 | LY75 | SEQ ID NO. 978 | 3.794 | 2.56 | 0.675 | HYPOX_DFO_HT1080 |
| 2321 | LY75 | SEQ ID NO. 978 | 112.236 | 77.743 | 0.693 | HYPOX_O2_HCT116 |
| 2322 | LY75 | SEQ ID NO. 978 | 3.794 | 2.607 | 0.687 | HYPOX_O2_HT1080 |
| 2323 | IQCD | SEQ ID NO. 979 | 314.744 | 295.965 | 0.94 | HYPOX_DFO_HCT116 |
| 2324 | IQCD | SEQ ID NO. 979 | 17.53 | 19.643 | 1.121 | HYPOX_DFO_HT1080 |
| 2325 | IQCD | SEQ ID NO. 979 | 314.744 | 242.363 | 0.77 | HYPOX_O2_HCT116 |
| 2326 | IQCD | SEQ ID NO. 979 | 17.53 | 11.35 | 0.647 | HYPOX_O2_HT1080 |
| 2327 | BCL2L11 | SEQ ID NO. 980 | 51.477 | 33.142 | 0.644 | HYPOX_DFO_HCT116 |
| 2328 | BCL2L11 | SEQ ID NO. 980 | 1.1 | 0.921 | 0.837 | HYPOX_DFO_HT1080 |
| 2329 | BCL2L11 | SEQ ID NO. 980 | 51.477 | 41.703 | 0.81 | HYPOX_O2_HCT116 |
| 2330 | BCL2L11 | SEQ ID NO. 980 | 1.1 | 0.878 | 0.797 | HYPOX_O2_HT1080 |
| 2331 | ADORA1 | SEQ ID NO. 981 | 312.191 | 132.43 | 0.424 | HYPOX_DFO_HCT116 |
| 2332 | ADORA1 | SEQ ID NO. 981 | 24.322 | 15.183 | 0.624 | HYPOX_DFO_HT1080 |
| 2333 | ADORA1 | SEQ ID NO. 981 | 312.191 | 233.021 | 0.746 | HYPOX_O2_HCT116 |
| 2334 | ADORA1 | SEQ ID NO. 981 | 24.322 | 18.369 | 0.755 | HYPOX_O2_HT1080 |
| 2335 | MDH2 | SEQ ID NO. 982 | 280.437 | 216.379 | 0.773 | HYPOX_DFO_HCT116 |
| 2336 | MDH2 | SEQ ID NO. 982 | 153.778 | 135.28 | 0.38 | HYPOX_DFO_HT1080 |
| 2337 | MDH2 | SEQ ID NO. 982 | 280.437 | 212.517 | 0.758 | HYPOX_O2_HCT116 |
| 2338 | MDH2 | SEQ ID NO. 982 | 153.778 | 119.114 | 0.775 | HYPOX_O2_HT1080 |
| 2339 | GPI | SEQ ID NO. 983 | 1.092 | 0.877 | 0.803 | HYPOX_DFO_HCT116 |
| 2340 | GPI | SEQ ID NO. 983 | 0.36 | 0.464 | 1.289 | HYPOX_DFO_HT1080 |
| 2341 | GPI | SEQ ID NO. 983 | 1.092 | 1.256 | 1.15 | HYPOX_O2_HCT116 |
| 2342 | GPI | SEQ ID NO. 983 | 0.36 | 0.327 | 0.908 | HYPOX_O2_HT1080 |
| 2343 | OXA1L | SEQ ID NO. 984 | 53.16 | 72.692 | 1.367 | HYPOX_DFO_HCT116 |
| 2344 | OXA1L | SEQ ID NO. 984 | 21.393 | 35.533 | 1.661 | HYPOX_DFO_HT1080 |
| 2345 | OXA1L | SEQ ID NO. 984 | 53.16 | 47.376 | 0.891 | HYPOX_O2_HCT116 |
| 2346 | OXA1L | SEQ ID NO. 984 | 21.393 | 16.782 | 0.784 | HYPOX_O2_HT1080 |
| 2347 | NR3C1 | SEQ ID NO. 984 | 108.431 | 37.721 | 0.348 | HYPOX_DFO_HCT116 |
| 2348 | NR3C1 | SEQ ID NO. 984 | 15.596 | 11.263 | 0.722 | HYPOX_DFO_HT1080 |
| 2349 | NR3C1 | SEQ ID NO. 984 | 108.431 | 127.095 | 1.172 | HYPOX_O2_HCT116 |
| 2350 | NR3C1 | SEQ ID NO. 984 | 15.596 | 16.196 | 1.038 | HYPOX_O2_HT1080 |
| 2351 | VPS45 | SEQ ID NO. 985 | 120.074 | 165.847 | 1.381 | HYPOX_DFO_HCT116 |
| 2352 | VPS45 | SEQ ID NO. 985 | 39.406 | 21.411 | 0.543 | HYPOX_DFO_HT1080 |
| 2353 | VPS45 | SEQ ID NO. 985 | 120.074 | 127.813 | 1.064 | HYPOX_O2_HCT116 |
| 2354 | VPS45 | SEQ ID NO. 985 | 39.406 | 27.978 | 0.71 | HYPOX_O2_HT1080 |

FIG. 1BL -- TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_N_O_INDUCTION | PROM_ACTIVITY_WI_TH_INDUCTION | INDUCTION_RATIO | INDUCTION_CONDITIONS" |
|---|---|---|---|---|---|---|
| 2355 | TNFRSF10A | SEQ ID NO. 986 | 39.534 | 16.12 | 0.408 | HYPOX_DFO_HCT116 |
| 2356 | TNFRSF10A | SEQ ID NO. 986 | 1.547 | 1.254 | 0.811 | HYPOX_DFO_HT1080 |
| 2357 | TNFRSF10A | SEQ ID NO. 986 | 39.534 | 30.823 | 0.78 | HYPOX_O2_HCT116 |
| 2358 | TNFRSF10A | SEQ ID NO. 986 | 1.547 | 1.683 | 1.088 | HYPOX_O2_HT1080 |
| 2359 | PLG | SEQ ID NO. 987 | 4.511 | 1.579 | 0.35 | HYPOX_DFO_HCT116 |
| 2360 | PLG | SEQ ID NO. 987 | 0.164 | 0.216 | 1.317 | HYPOX_DFO_HT1080 |
| 2361 | PLG | SEQ ID NO. 987 | 4.511 | 3.324 | 0.737 | HYPOX_O2_HCT116 |
| 2362 | PLG | SEQ ID NO. 987 | 0.164 | 0.13 | 0.792 | HYPOX_O2_HT1080 |
| 2363 | SLC2A10 | SEQ ID NO. 988 | 18.59 | 8.131 | 0.437 | HYPOX_DFO_HCT116 |
| 2364 | SLC2A10 | SEQ ID NO. 988 | 1.281 | 0.245 | 0.191 | HYPOX_DFO_HT1080 |
| 2365 | SLC2A10 | SEQ ID NO. 988 | 18.59 | 16.337 | 0.906 | HYPOX_O2_HCT116 |
| 2366 | SLC2A10 | SEQ ID NO. 988 | 1.281 | 0.313 | 0.245 | HYPOX_O2_HT1080 |
| 2367 | CIDEC | SEQ ID NO. 989 | 1756.651 | 3151.249 | 1.794 | HYPOX_DFO_HCT116 |
| 2368 | CIDEC | SEQ ID NO. 989 | 500.154 | 598.284 | 1.196 | HYPOX_DFO_HT1080 |
| 2369 | CIDEC | SEQ ID NO. 989 | 1756.651 | 1546.694 | 0.88 | HYPOX_O2_HCT116 |
| 2370 | CIDEC | SEQ ID NO. 989 | 500.154 | 390.721 | 0.781 | HYPOX_O2_HT1080 |
| 2371 | TP73 | SEQ ID NO. 990 | 497.671 | 435.832 | 0.876 | HYPOX_DFO_HCT116 |
| 2372 | TP73 | SEQ ID NO. 990 | 9.613 | 5.858 | 0.609 | HYPOX_DFO_HT1080 |
| 2373 | TP73 | SEQ ID NO. 990 | 497.671 | 308.639 | 0.62 | HYPOX_O2_HCT116 |
| 2374 | TP73 | SEQ ID NO. 990 | 9.613 | 5.977 | 0.622 | HYPOX_O2_HT1080 |
| 2375 | RHOB | SEQ ID NO. 991 | 112.562 | 236.471 | 2.1 | HYPOX_DFO_HCT116 |
| 2376 | RHOB | SEQ ID NO. 991 | 30.352 | 15.955 | 0.526 | HYPOX_DFO_HT1080 |
| 2377 | RHOB | SEQ ID NO. 991 | 112.562 | 160.714 | 1.428 | HYPOX_O2_HCT116 |
| 2378 | RHOB | SEQ ID NO. 991 | 30.352 | 24.845 | 0.819 | HYPOX_O2_HT1080 |
| 2379 | NDUFA13 | SEQ ID NO. 992 | 194.725 | 290.239 | 1.491 | HYPOX_DFO_HCT116 |
| 2380 | NDUFA13 | SEQ ID NO. 992 | 29.014 | 40.48 | 1.395 | HYPOX_DFO_HT1080 |
| 2381 | NDUFA13 | SEQ ID NO. 992 | 194.725 | 198.455 | 1.019 | HYPOX_O2_HCT116 |
| 2382 | NDUFA13 | SEQ ID NO. 992 | 29.014 | 27.314 | 0.941 | HYPOX_O2_HT1080 |
| 2383 | DDAH1 | SEQ ID NO. 993 | 5.759 | 5.419 | 0.941 | HYPOX_DFO_HCT116 |
| 2384 | DDAH1 | SEQ ID NO. 993 | 0.61 | 1.826 | 2.992 | HYPOX_DFO_HT1080 |
| 2385 | DDAH1 | SEQ ID NO. 993 | 5.759 | 11.959 | 2.077 | HYPOX_O2_HCT116 |
| 2386 | DDAH1 | SEQ ID NO. 993 | 0.61 | 0.554 | 0.908 | HYPOX_O2_HT1080 |
| 2387 | CCL26 | SEQ ID NO. 994 | 74.445 | 42.711 | 0.574 | HYPOX_DFO_HCT116 |
| 2388 | CCL26 | SEQ ID NO. 994 | 8.597 | 3.956 | 0.46 | HYPOX_DFO_HT1080 |
| 2389 | CCL26 | SEQ ID NO. 994 | 74.445 | 54.145 | 0.727 | HYPOX_O2_HCT116 |
| 2390 | CCL26 | SEQ ID NO. 994 | 8.597 | 5.888 | 0.685 | HYPOX_O2_HT1080 |
| 2391 | PLG | SEQ ID NO. 995 | 0.437 | 0.527 | 1.207 | HYPOX_DFO_HCT116 |
| 2392 | PLG | SEQ ID NO. 995 | 0.097 | 0.126 | 1.298 | HYPOX_DFO_HT1080 |
| 2393 | PLG | SEQ ID NO. 995 | 0.437 | 0.648 | 1.483 | HYPOX_O2_HCT116 |
| 2394 | PLG | SEQ ID NO. 995 | 0.097 | 0.068 | 0.7 | HYPOX_O2_HT1080 |
| 2395 | CUL4A | SEQ ID NO. 996 | 6.257 | 2.264 | 0.362 | HYPOX_DFO_HCT116 |
| 2396 | CUL4A | SEQ ID NO. 996 | 0.679 | 0.416 | 0.612 | HYPOX_DFO_HT1080 |
| 2397 | CUL4A | SEQ ID NO. 996 | 6.257 | 6.148 | 0.982 | HYPOX_O2_HCT116 |
| 2398 | CUL4A | SEQ ID NO. 996 | 0.679 | 0.806 | 1.187 | HYPOX_O2_HT1080 |
| 2399 | DAPK1 | SEQ ID NO. 997 | 39.169 | 31.776 | 0.811 | HYPOX_DFO_HCT116 |
| 2400 | DAPK1 | SEQ ID NO. 997 | 3.671 | 2.815 | 0.767 | HYPOX_DFO_HT1080 |
| 2401 | DAPK1 | SEQ ID NO. 997 | 39.169 | 46.028 | 1.175 | HYPOX_O2_HCT116 |
| 2402 | DAPK1 | SEQ ID NO. 997 | 3.671 | 3.195 | 0.87 | HYPOX_O2_HT1080 |

FIG. 1BM -- TABLE 1 TRANSCRIPTIONAL BIOMARKER FUNCTIONAL DATA
SECTION 1A

| LINE_ID | GENE_SYMBOL | SEQUENCE_ID_LISTING | FROM_ACTIVITY_N O_INDUCTION | FROM_ACTIVITY_WI TH_INDUCTION | INDUCTION_RATIO | INDUCTION_CONDITIONS" |
|---|---|---|---|---|---|---|
| 2403 | FOXO3 | SEQ ID NO. 998 | 139.28 | 67.597 | 0.485 | HYPOX_DFO_HCT116 |
| 2404 | FOXO3 | SEQ ID NO. 998 | 5.192 | 6.834 | 1.316 | HYPOX_DFO_HT1080 |
| 2405 | FOXO3 | SEQ ID NO. 998 | 139.28 | 258.327 | 1.855 | HYPOX_O2_HCT116 |
| 2406 | FOXO3 | SEQ ID NO. 998 | 5.192 | 7.234 | 1.393 | HYPOX_O2_HT1080 |
| 2407 | FPR2 | SEQ ID NO. 999 | 16.955 | 10.511 | 0.62 | HYPOX_DFO_HCT116 |
| 2408 | FPR2 | SEQ ID NO. 999 | 0.748 | 0.589 | 0.787 | HYPOX_DFO_HT1080 |
| 2409 | FPR2 | SEQ ID NO. 999 | 16.955 | 9.434 | 0.556 | HYPOX_O2_HCT116 |
| 2410 | FPR2 | SEQ ID NO. 999 | 0.748 | 0.608 | 0.812 | HYPOX_O2_HT1080 |
| 2411 | PPP2R1A | SEQ ID NO. 1000 | 35.067 | 87.396 | 2.492 | HYPOX_DFO_HCT116 |
| 2412 | PPP2R1A | SEQ ID NO. 1000 | 8.148 | 10.139 | 1.244 | HYPOX_DFO_HT1080 |
| 2413 | PPP2R1A | SEQ ID NO. 1000 | 35.067 | 47.852 | 1.365 | HYPOX_O2_HCT116 |
| 2414 | PPP2R1A | SEQ ID NO. 1000 | 8.148 | 7.849 | 0.963 | HYPOX_O2_HT1080 |
| 2415 | ALOX15B | SEQ ID NO. 1001 | 167.08 | 100.843 | 0.604 | HYPOX_DFO_HCT116 |
| 2416 | ALOX15B | SEQ ID NO. 1001 | 2.093 | 2.056 | 0.982 | HYPOX_DFO_HT1080 |
| 2417 | ALOX15B | SEQ ID NO. 1001 | 167.08 | 119.923 | 0.718 | HYPOX_O2_HCT116 |
| 2418 | ALOX15B | SEQ ID NO. 1001 | 2.093 | 3.571 | 1.706 | HYPOX_O2_HT1080 |
| 2419 | STK25 | SEQ ID NO. 1002 | 210.179 | 113.483 | 0.54 | HYPOX_DFO_HCT116 |
| 2420 | STK25 | SEQ ID NO. 1002 | 55.128 | 51.48 | 0.934 | HYPOX_DFO_HT1080 |
| 2421 | STK25 | SEQ ID NO. 1002 | 210.179 | 221.396 | 1.053 | HYPOX_O2_HCT116 |
| 2422 | STK25 | SEQ ID NO. 1002 | 55.128 | 49.625 | 0.9 | HYPOX_O2_HT1080 |
| 2423 | PLA2G2E | SEQ ID NO. 1003 | 35.822 | 16.997 | 0.475 | HYPOX_DFO_HCT116 |
| 2424 | PLA2G2E | SEQ ID NO. 1003 | 2.769 | 1.386 | 0.501 | HYPOX_DFO_HT1080 |
| 2425 | PLA2G2E | SEQ ID NO. 1003 | 35.822 | 16.966 | 0.474 | HYPOX_O2_HCT116 |
| 2426 | PLA2G2E | SEQ ID NO. 1003 | 2.769 | 2.224 | 0.803 | HYPOX_O2_HT1080 |
| 2427 | DHX8 | SEQ ID NO. 1004 | 651.463 | 726.317 | 1.115 | HYPOX_DFO_HCT116 |
| 2428 | DHX8 | SEQ ID NO. 1004 | 274.142 | 203.463 | 0.742 | HYPOX_DFO_HT1080 |
| 2429 | DHX8 | SEQ ID NO. 1004 | 651.463 | 919.922 | 1.412 | HYPOX_O2_HCT116 |
| 2430 | DHX8 | SEQ ID NO. 1004 | 274.142 | 202.58 | 0.739 | HYPOX_O2_HT1080 |
| 2431 | PDLIM1 | SEQ ID NO. 1005 | 223.939 | 281.103 | 1.255 | HYPOX_DFO_HCT116 |
| 2432 | PDLIM1 | SEQ ID NO. 1005 | 8.83 | 4.796 | 0.543 | HYPOX_DFO_HT1080 |
| 2433 | PDLIM1 | SEQ ID NO. 1005 | 223.939 | 187.446 | 0.837 | HYPOX_O2_HCT116 |
| 2434 | PDLIM1 | SEQ ID NO. 1005 | 8.83 | 7.798 | 0.883 | HYPOX_O2_HT1080 |
| 2435 | FASN | SEQ ID NO. 1006 | 93.235 | 32.029 | 0.344 | HYPOX_DFO_HCT116 |
| 2436 | FASN | SEQ ID NO. 1006 | 2.999 | 2.513 | 0.838 | HYPOX_DFO_HT1080 |
| 2437 | FASN | SEQ ID NO. 1006 | 93.235 | 104.791 | 1.124 | HYPOX_O2_HCT116 |
| 2438 | FASN | SEQ ID NO. 1006 | 2.999 | 4.098 | 1.366 | HYPOX_O2_HT1080 |
| 2439 | PKLR | SEQ ID NO. 1007 | 0.608 | 0.583 | 0.958 | HYPOX_DFO_HCT116 |
| 2440 | PKLR | SEQ ID NO. 1007 | 0.152 | 0.175 | 1.155 | HYPOX_DFO_HT1080 |
| 2441 | PKLR | SEQ ID NO. 1007 | 0.608 | 0.661 | 1.087 | HYPOX_O2_HCT116 |
| 2442 | PKLR | SEQ ID NO. 1007 | 0.152 | 0.108 | 0.714 | HYPOX_O2_HT1080 |
| 2443 | TGFB2 | SEQ ID NO. 1008 | 39.559 | 26.232 | 0.663 | HYPOX_DFO_HCT116 |
| 2444 | TGFB2 | SEQ ID NO. 1008 | 2.232 | 1.715 | 0.768 | HYPOX_DFO_HT1080 |
| 2445 | TGFB2 | SEQ ID NO. 1008 | 39.559 | 39.818 | 1.007 | HYPOX_O2_HCT116 |
| 2446 | TGFB2 | SEQ ID NO. 1008 | 2.232 | 1.858 | 0.833 | HYPOX_O2_HT1080 |
| 2447 | MPR1 | SEQ ID NO. 1009 | 46.271 | 16.599 | 0.359 | HYPOX_DFO_HCT116 |
| 2448 | MPR1 | SEQ ID NO. 1009 | 2.265 | 1.257 | 0.555 | HYPOX_DFO_HT1080 |
| 2449 | MPR1 | SEQ ID NO. 1009 | 46.271 | 39.042 | 0.844 | HYPOX_O2_HCT116 |
| 2450 | MPR1 | SEQ ID NO. 1009 | 2.265 | 1.665 | 0.735 | HYPOX_O2_HT1080 |

FIG. 1BN -- TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_N O_INDUCTION | PROM_ACTIVITY_WI TH_INDUCTION | INDUCTION RATIO | INDUCTION_CONDITIONS* |
|---|---|---|---|---|---|---|
| 2451 | NLRP1C | SEQ ID NO. 1010 | 24.315 | 18.439 | 0.76 | HYPOX_DFO_HCT116 |
| 2452 | NLRP1C | SEQ ID NO. 1010 | 6.577 | 5.197 | 0.79 | HYPOX_DFO_HT1080 |
| 2453 | NLRP1C | SEQ ID NO. 1010 | 24.315 | 18.204 | 0.749 | HYPOX_O2_HCT116 |
| 2454 | NLRP1C | SEQ ID NO. 1010 | 6.577 | 5.727 | 0.871 | HYPOX_O2_HT1080 |
| 2455 | IGF1R | SEQ ID NO. 1011 | 2.378 | 1.389 | 0.584 | HYPOX_DFO_HCT116 |
| 2456 | IGF1R | SEQ ID NO. 1011 | 0.346 | 0.246 | 0.71 | HYPOX_DFO_HT1080 |
| 2457 | IGF1R | SEQ ID NO. 1011 | 2.378 | 2.244 | 0.943 | HYPOX_O2_HCT116 |
| 2458 | IGF1R | SEQ ID NO. 1011 | 0.346 | 0.303 | 0.876 | HYPOX_O2_HT1080 |
| 2459 | BCL6 | SEQ ID NO. 1011 | 1621.383 | 2201.977 | 1.358 | HYPOX_DFO_HCT116 |
| 2460 | BCL6 | SEQ ID NO. 1011 | 176.256 | 150.542 | 0.854 | HYPOX_DFO_HT1080 |
| 2461 | BCL6 | SEQ ID NO. 1011 | 1621.383 | 1052.873 | 0.649 | HYPOX_O2_HCT116 |
| 2462 | BCL6 | SEQ ID NO. 1011 | 176.256 | 110.391 | 0.626 | HYPOX_O2_HT1080 |
| 2463 | MDH1 | SEQ ID NO. 1012 | 32.534 | 46.447 | 1.428 | HYPOX_DFO_HCT116 |
| 2464 | MDH1 | SEQ ID NO. 1012 | 6.372 | 2.554 | 0.401 | HYPOX_DFO_HT1080 |
| 2465 | MDH1 | SEQ ID NO. 1012 | 32.534 | 25.442 | 0.782 | HYPOX_O2_HCT116 |
| 2466 | MDH1 | SEQ ID NO. 1012 | 6.372 | 5.286 | 0.83 | HYPOX_O2_HT1080 |
| 2467 | SERPINF1 | SEQ ID NO. 1013 | 46.451 | 8.163 | 0.176 | HYPOX_DFO_HCT116 |
| 2468 | SERPINF1 | SEQ ID NO. 1013 | 1.015 | 0.783 | 0.771 | HYPOX_DFO_HT1080 |
| 2469 | SERPINF1 | SEQ ID NO. 1013 | 46.451 | 22.969 | 0.494 | HYPOX_O2_HCT116 |
| 2470 | SERPINF1 | SEQ ID NO. 1013 | 1.015 | 0.884 | 0.871 | HYPOX_O2_HT1080 |
| 2471 | CEBPG | SEQ ID NO. 1014 | 1093.287 | 644.593 | 0.59 | HYPOX_DFO_HCT116 |
| 2472 | CEBPG | SEQ ID NO. 1014 | 162.988 | 107.872 | 0.662 | HYPOX_DFO_HT1080 |
| 2473 | CEBPG | SEQ ID NO. 1014 | 1093.287 | 768.736 | 0.703 | HYPOX_O2_HCT116 |
| 2474 | CEBPG | SEQ ID NO. 1014 | 162.988 | 128.91 | 0.791 | HYPOX_O2_HT1080 |
| 2475 | BAX | SEQ ID NO. 1015 | 64.445 | 55.469 | 0.861 | HYPOX_DFO_HCT116 |
| 2476 | BAX | SEQ ID NO. 1015 | 9.265 | 5.575 | 0.602 | HYPOX_DFO_HT1080 |
| 2477 | BAX | SEQ ID NO. 1015 | 64.445 | 37.126 | 0.576 | HYPOX_O2_HCT116 |
| 2478 | BAX | SEQ ID NO. 1015 | 9.265 | 8.852 | 0.955 | HYPOX_O2_HT1080 |
| 2479 | CFLAR | SEQ ID NO. 1016 | 1.744 | 1.446 | 0.83 | HYPOX_DFO_HCT116 |
| 2480 | CFLAR | SEQ ID NO. 1016 | 0.418 | 0.626 | 1.498 | HYPOX_DFO_HT1080 |
| 2481 | CFLAR | SEQ ID NO. 1016 | 1.744 | 0.963 | 0.552 | HYPOX_O2_HCT116 |
| 2482 | CFLAR | SEQ ID NO. 1016 | 0.418 | 0.339 | 0.812 | HYPOX_O2_HT1080 |
| 2483 | GPR68 | SEQ ID NO. 1017 | 54.797 | 44.399 | 0.81 | HYPOX_DFO_HCT116 |
| 2484 | GPR68 | SEQ ID NO. 1017 | 20.421 | 14.963 | 0.733 | HYPOX_DFO_HT1080 |
| 2485 | GPR68 | SEQ ID NO. 1017 | 54.797 | 48.495 | 0.885 | HYPOX_O2_HCT116 |
| 2486 | GPR68 | SEQ ID NO. 1017 | 20.421 | 16.894 | 0.827 | HYPOX_O2_HT1080 |
| 2487 | DDAH1 | SEQ ID NO. 1018 | 52.822 | 52.897 | 1.001 | HYPOX_DFO_HCT116 |
| 2488 | DDAH1 | SEQ ID NO. 1018 | 9.653 | 3.783 | 0.392 | HYPOX_DFO_HT1080 |
| 2489 | DDAH1 | SEQ ID NO. 1018 | 52.822 | 39.614 | 0.75 | HYPOX_O2_HCT116 |
| 2490 | DDAH1 | SEQ ID NO. 1018 | 9.653 | 7.613 | 0.789 | HYPOX_O2_HT1080 |
| 2491 | FASN | SEQ ID NO. 1018 | 1153.199 | 3135.6 | 2.719 | HYPOX_DFO_HCT116 |
| 2492 | FASN | SEQ ID NO. 1018 | 176.167 | 156.259 | 0.887 | HYPOX_DFO_HT1080 |
| 2493 | FASN | SEQ ID NO. 1018 | 1153.199 | 1539.71 | 1.335 | HYPOX_O2_HCT116 |
| 2494 | FASN | SEQ ID NO. 1018 | 176.167 | 126.926 | 0.721 | HYPOX_O2_HT1080 |
| 2495 | MAP3K10 | SEQ ID NO. 1019 | 41.376 | 19.045 | 0.46 | HYPOX_DFO_HCT116 |
| 2496 | MAP3K10 | SEQ ID NO. 1019 | 9.731 | 8.833 | 0.908 | HYPOX_DFO_HT1080 |
| 2497 | MAP3K10 | SEQ ID NO. 1019 | 41.376 | 48.228 | 1.166 | HYPOX_O2_HCT116 |
| 2498 | MAP3K10 | SEQ ID NO. 1019 | 9.731 | 9.023 | 0.927 | HYPOX_O2_HT1080 |

FIG. 1BO -- TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS* |
|---|---|---|---|---|---|---|
| 2499 | NOTCH4 | SEQ ID NO. 1020 | 76.892 | 66.393 | 0.864 | HYPOX_DFO_HCT116 |
| 2500 | NOTCH4 | SEQ ID NO. 1020 | 8.833 | 12.79 | 1.448 | HYPOX_DFO_HT1080 |
| 2501 | NOTCH4 | SEQ ID NO. 1020 | 76.892 | 53.187 | 0.693 | HYPOX_O2_HCT116 |
| 2502 | NOTCH4 | SEQ ID NO. 1020 | 8.833 | 7.474 | 0.846 | HYPOX_O2_HT1080 |
| 2503 | PFKP | SEQ ID NO. 1021 | 8.794 | 10.795 | 1.228 | HYPOX_DFO_HCT116 |
| 2504 | PFKP | SEQ ID NO. 1021 | 0.506 | 0.475 | 0.94 | HYPOX_DFO_HT1080 |
| 2505 | PFKP | SEQ ID NO. 1021 | 8.794 | 5.947 | 0.676 | HYPOX_O2_HCT116 |
| 2506 | PFKP | SEQ ID NO. 1021 | 0.506 | 0.406 | 0.803 | HYPOX_O2_HT1080 |
| 2507 | CXCL5 | SEQ ID NO. 1022 | 5.448 | 2.959 | 0.543 | HYPOX_DFO_HCT116 |
| 2508 | CXCL5 | SEQ ID NO. 1022 | 0.963 | 0.868 | 0.902 | HYPOX_DFO_HT1080 |
| 2509 | CXCL5 | SEQ ID NO. 1022 | 5.448 | 4.8 | 0.881 | HYPOX_O2_HCT116 |
| 2510 | CXCL5 | SEQ ID NO. 1022 | 0.963 | 0.852 | 0.885 | HYPOX_O2_HT1080 |
| 2511 | COL4A3 | SEQ ID NO. 1023 | 255.429 | 134.053 | 0.525 | HYPOX_DFO_HCT116 |
| 2512 | COL4A3 | SEQ ID NO. 1023 | 4.222 | 3.272 | 0.775 | HYPOX_DFO_HT1080 |
| 2513 | COL4A3 | SEQ ID NO. 1023 | 255.429 | 212.595 | 0.832 | HYPOX_O2_HCT116 |
| 2514 | COL4A3 | SEQ ID NO. 1023 | 4.222 | 4.103 | 0.972 | HYPOX_O2_HT1080 |
| 2515 | PRKCA | SEQ ID NO. 1024 | 22.657 | 10.644 | 0.47 | HYPOX_DFO_HCT116 |
| 2516 | PRKCA | SEQ ID NO. 1024 | 1.964 | 2.226 | 1.133 | HYPOX_DFO_HT1080 |
| 2517 | PRKCA | SEQ ID NO. 1024 | 22.657 | 17.417 | 0.768 | HYPOX_O2_HCT116 |
| 2518 | PRKCA | SEQ ID NO. 1024 | 1.964 | 1.841 | 0.937 | HYPOX_O2_HT1080 |
| 2519 | AOX1 | SEQ ID NO. 1025 | 121.067 | 18.487 | 0.153 | HYPOX_DFO_HCT116 |
| 2520 | AOX1 | SEQ ID NO. 1025 | 5.948 | 5.159 | 0.867 | HYPOX_DFO_HT1080 |
| 2521 | AOX1 | SEQ ID NO. 1025 | 121.067 | 76.856 | 0.635 | HYPOX_O2_HCT116 |
| 2522 | AOX1 | SEQ ID NO. 1025 | 5.948 | 6.098 | 1.025 | HYPOX_O2_HT1080 |
| 2523 | ADORA2A | SEQ ID NO. 1026 | 270.891 | 67.387 | 0.249 | HYPOX_DFO_HCT116 |
| 2524 | ADORA2A | SEQ ID NO. 1026 | 8.382 | 4.056 | 0.464 | HYPOX_DFO_HT1080 |
| 2525 | ADORA2A | SEQ ID NO. 1026 | 270.891 | 133.812 | 0.494 | HYPOX_O2_HCT116 |
| 2526 | ADORA2A | SEQ ID NO. 1026 | 8.382 | 6.551 | 0.782 | HYPOX_O2_HT1080 |
| 2527 | ERCC2 | SEQ ID NO. 1027 | 32.062 | 5.486 | 0.171 | HYPOX_DFO_HCT116 |
| 2528 | ERCC2 | SEQ ID NO. 1027 | 4.252 | 1.256 | 0.295 | HYPOX_DFO_HT1080 |
| 2529 | ERCC2 | SEQ ID NO. 1027 | 32.062 | 25.222 | 0.787 | HYPOX_O2_HCT116 |
| 2530 | ERCC2 | SEQ ID NO. 1027 | 4.252 | 2.68 | 0.63 | HYPOX_O2_HT1080 |
| 2531 | ACO2 | SEQ ID NO. 1028 | 877.213 | 1441.842 | 1.644 | HYPOX_DFO_HCT116 |
| 2532 | ACO2 | SEQ ID NO. 1028 | 179.326 | 239.539 | 1.336 | HYPOX_DFO_HT1080 |
| 2533 | ACO2 | SEQ ID NO. 1028 | 877.213 | 1356.833 | 1.547 | HYPOX_O2_HCT116 |
| 2534 | ACO2 | SEQ ID NO. 1028 | 179.326 | 159.142 | 0.887 | HYPOX_O2_HT1080 |
| 2535 | NFX1 | SEQ ID NO. 1029 | 7.968 | 39.898 | 5.007 | HYPOX_DFO_HCT116 |
| 2536 | NFX1 | SEQ ID NO. 1029 | 2.868 | 1.438 | 0.501 | HYPOX_DFO_HT1080 |
| 2537 | NFX1 | SEQ ID NO. 1029 | 7.968 | 10.375 | 1.302 | HYPOX_O2_HCT116 |
| 2538 | NFX1 | SEQ ID NO. 1029 | 2.868 | 1.757 | 0.613 | HYPOX_O2_HT1080 |
| 2539 | MMP25 | SEQ ID NO. 1030 | 20.573 | 8.032 | 0.39 | HYPOX_DFO_HCT116 |
| 2540 | MMP25 | SEQ ID NO. 1030 | 0.537 | 0.439 | 0.818 | HYPOX_DFO_HT1080 |
| 2541 | MMP25 | SEQ ID NO. 1030 | 20.573 | 20.308 | 0.987 | HYPOX_O2_HCT116 |
| 2542 | MMP25 | SEQ ID NO. 1030 | 0.537 | 0.591 | 1.101 | HYPOX_O2_HT1080 |
| 2543 | PFKP | SEQ ID NO. 1031 | 42.451 | 25.825 | 0.608 | HYPOX_DFO_HCT116 |
| 2544 | PFKP | SEQ ID NO. 1031 | 1.598 | 1.419 | 0.888 | HYPOX_DFO_HT1080 |
| 2545 | PFKP | SEQ ID NO. 1031 | 42.451 | 40.756 | 0.96 | HYPOX_O2_HCT116 |
| 2546 | PFKP | SEQ ID NO. 1031 | 1.598 | 1.36 | 0.851 | HYPOX_O2_HT1080 |

FIG. 1BP -- TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_N O_INDUCTION | PROM_ACTIVITY_WI TH_INDUCTION | INDUCTION RATIO | INDUCTION_CONDITIONS |
|---|---|---|---|---|---|---|
| 2547 | CCL1 | SEQ ID NO. 1032 | 4.268 | 3.084 | 0.722 | HYPOX_DFO_HCT116 |
| 2548 | CCL1 | SEQ ID NO. 1032 | 1.107 | 1.132 | 1.023 | HYPOX_DFO_HT1080 |
| 2549 | CCL1 | SEQ ID NO. 1032 | 4.268 | 2.78 | 0.651 | HYPOX_O2_HCT116 |
| 2550 | CCL1 | SEQ ID NO. 1032 | 1.107 | 0.946 | 0.854 | HYPOX_O2_HT1080 |
| 2551 | RHOB | SEQ ID NO. 1033 | 2.183 | 1.802 | 0.826 | HYPOX_DFO_HCT116 |
| 2552 | RHOB | SEQ ID NO. 1033 | 0.371 | 0.357 | 0.961 | HYPOX_DFO_HT1080 |
| 2553 | RHOB | SEQ ID NO. 1033 | 2.183 | 2.682 | 1.229 | HYPOX_O2_HCT116 |
| 2554 | RHOB | SEQ ID NO. 1033 | 0.371 | 0.343 | 0.924 | HYPOX_O2_HT1080 |
| 2555 | MKL1 | SEQ ID NO. 1034 | 2718.578 | 4252.232 | 1.566 | HYPOX_DFO_HCT116 |
| 2556 | MKL1 | SEQ ID NO. 1034 | 452.664 | 487.595 | 1.077 | HYPOX_DFO_HT1080 |
| 2557 | MKL1 | SEQ ID NO. 1034 | 2718.578 | 4578.464 | 1.684 | HYPOX_O2_HCT116 |
| 2558 | MKL1 | SEQ ID NO. 1034 | 452.664 | 308.096 | 0.681 | HYPOX_O2_HT1080 |
| 2559 | BCLAF1 | SEQ ID NO. 1035 | 1244.099 | 2911.732 | 2.341 | HYPOX_DFO_HCT116 |
| 2560 | BCLAF1 | SEQ ID NO. 1035 | 385.203 | 511.648 | 1.328 | HYPOX_DFO_HT1080 |
| 2561 | BCLAF1 | SEQ ID NO. 1035 | 1244.099 | 2803.369 | 2.253 | HYPOX_O2_HCT116 |
| 2562 | BCLAF1 | SEQ ID NO. 1035 | 385.203 | 267.484 | 0.694 | HYPOX_O2_HT1080 |
| 2563 | IRS1 | SEQ ID NO. 1036 | 96.078 | 24.202 | 0.252 | HYPOX_DFO_HCT116 |
| 2564 | IRS1 | SEQ ID NO. 1036 | 8.168 | 2.286 | 0.28 | HYPOX_DFO_HT1080 |
| 2565 | IRS1 | SEQ ID NO. 1036 | 96.078 | 73.861 | 0.769 | HYPOX_O2_HCT116 |
| 2566 | IRS1 | SEQ ID NO. 1036 | 8.168 | 4.567 | 0.559 | HYPOX_O2_HT1080 |
| 2567 | H6PD | SEQ ID NO. 1037 | 2.977 | 1.752 | 0.589 | HYPOX_DFO_HCT116 |
| 2568 | H6PD | SEQ ID NO. 1037 | 0.582 | 0.947 | 1.626 | HYPOX_DFO_HT1080 |
| 2569 | H6PD | SEQ ID NO. 1037 | 2.977 | 3.355 | 1.127 | HYPOX_O2_HCT116 |
| 2570 | H6PD | SEQ ID NO. 1037 | 0.582 | 0.652 | 1.12 | HYPOX_O2_HT1080 |
| 2571 | GPX3 | SEQ ID NO. 1038 | 401.538 | 97.528 | 0.243 | HYPOX_DFO_HCT116 |
| 2572 | GPX3 | SEQ ID NO. 1038 | 8.662 | 4.277 | 0.494 | HYPOX_DFO_HT1080 |
| 2573 | GPX3 | SEQ ID NO. 1038 | 401.538 | 251.526 | 0.626 | HYPOX_O2_HCT116 |
| 2574 | GPX3 | SEQ ID NO. 1038 | 8.662 | 6.361 | 0.734 | HYPOX_O2_HT1080 |
| 2575 | PTX3 | SEQ ID NO. 1039 | 35.233 | 13.421 | 0.381 | HYPOX_DFO_HCT116 |
| 2576 | PTX3 | SEQ ID NO. 1039 | 2.866 | 1.621 | 0.566 | HYPOX_DFO_HT1080 |
| 2577 | PTX3 | SEQ ID NO. 1039 | 35.233 | 17.209 | 0.488 | HYPOX_O2_HCT116 |
| 2578 | PTX3 | SEQ ID NO. 1039 | 2.866 | 1.66 | 0.579 | HYPOX_O2_HT1080 |
| 2579 | TGDS | SEQ ID NO. 1040 | 264.296 | 234.316 | 0.887 | HYPOX_DFO_HCT116 |
| 2580 | TGDS | SEQ ID NO. 1040 | 49.534 | 25.642 | 0.518 | HYPOX_DFO_HT1080 |
| 2581 | TGDS | SEQ ID NO. 1040 | 264.296 | 205.797 | 0.779 | HYPOX_O2_HCT116 |
| 2582 | TGDS | SEQ ID NO. 1040 | 49.534 | 36.055 | 0.728 | HYPOX_O2_HT1080 |
| 2583 | ARG2 | SEQ ID NO. 1040 | 293.479 | 565.43 | 1.927 | HYPOX_DFO_HCT116 |
| 2584 | ARG2 | SEQ ID NO. 1040 | 9.546 | 14.614 | 1.531 | HYPOX_DFO_HT1080 |
| 2585 | ARG2 | SEQ ID NO. 1040 | 293.479 | 420.218 | 1.432 | HYPOX_O2_HCT116 |
| 2586 | ARG2 | SEQ ID NO. 1040 | 9.546 | 7.205 | 0.755 | HYPOX_O2_HT1080 |
| 2587 | TPST1 | SEQ ID NO. 1041 | 50.245 | 38.713 | 0.77 | HYPOX_DFO_HCT116 |
| 2588 | TPST1 | SEQ ID NO. 1041 | 6.454 | 3.139 | 0.486 | HYPOX_DFO_HT1080 |
| 2589 | TPST1 | SEQ ID NO. 1041 | 50.245 | 28.196 | 0.561 | HYPOX_O2_HCT116 |
| 2590 | TPST1 | SEQ ID NO. 1041 | 6.454 | 3.264 | 0.506 | HYPOX_O2_HT1080 |
| 2591 | AHSG | SEQ ID NO. 1042 | 0.691 | 0.693 | 1.003 | HYPOX_DFO_HCT116 |
| 2592 | AHSG | SEQ ID NO. 1042 | 0.733 | 0.612 | 0.834 | HYPOX_DFO_HT1080 |
| 2593 | AHSG | SEQ ID NO. 1042 | 0.691 | 1.129 | 1.633 | HYPOX_O2_HCT116 |
| 2594 | AHSG | SEQ ID NO. 1042 | 0.733 | 0.614 | 0.837 | HYPOX_O2_HT1080 |

FIG. 1BQ -- TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS |
|---|---|---|---|---|---|---|
| 2595 | TP63 | SEQ ID NO. 1043 | 23.381 | 3.883 | 0.166 | HYPOX_DFO_HCT116 |
| 2596 | TP63 | SEQ ID NO. 1043 | 0.313 | 0.151 | 0.484 | HYPOX_DFO_HT1080 |
| 2597 | TP63 | SEQ ID NO. 1043 | 23.381 | 9.537 | 0.408 | HYPOX_O2_HCT116 |
| 2598 | TP63 | SEQ ID NO. 1043 | 0.313 | 0.416 | 1.33 | HYPOX_O2_HT1080 |
| 2599 | UGCGL2 | SEQ ID NO. 1044 | 493.37 | 276.419 | 0.56 | HYPOX_DFO_HCT116 |
| 2600 | UGCGL2 | SEQ ID NO. 1044 | 56.411 | 46.338 | 0.821 | HYPOX_DFO_HT1080 |
| 2601 | UGCGL2 | SEQ ID NO. 1044 | 493.37 | 334.624 | 0.678 | HYPOX_O2_HCT116 |
| 2602 | UGCGL2 | SEQ ID NO. 1044 | 56.411 | 48.837 | 0.866 | HYPOX_O2_HT1080 |
| 2603 | ICEBERG | SEQ ID NO. 1045 | 7.934 | 5.367 | 0.676 | HYPOX_DFO_HCT116 |
| 2604 | ICEBERG | SEQ ID NO. 1045 | 0.489 | 0.563 | 1.153 | HYPOX_DFO_HT1080 |
| 2605 | ICEBERG | SEQ ID NO. 1045 | 7.934 | 3.6 | 0.454 | HYPOX_O2_HCT116 |
| 2606 | ICEBERG | SEQ ID NO. 1045 | 0.489 | 0.729 | 1.492 | HYPOX_O2_HT1080 |
| 2607 | LARP5 | SEQ ID NO. 1046 | 3899.605 | 8215.554 | 2.107 | HYPOX_DFO_HCT116 |
| 2608 | LARP5 | SEQ ID NO. 1046 | 1190.004 | 1700.684 | 1.429 | HYPOX_DFO_HT1080 |
| 2609 | LARP5 | SEQ ID NO. 1046 | 3899.605 | 7596.145 | 1.948 | HYPOX_O2_HCT116 |
| 2610 | LARP5 | SEQ ID NO. 1046 | 1190.004 | 1054.265 | 0.886 | HYPOX_O2_HT1080 |
| 2611 | CMOT2 | SEQ ID NO. 1047 | 855.969 | 683.157 | 0.798 | HYPOX_DFO_HCT116 |
| 2612 | CMOT2 | SEQ ID NO. 1047 | 333.067 | 450.456 | 1.352 | HYPOX_DFO_HT1080 |
| 2613 | CMOT2 | SEQ ID NO. 1047 | 855.969 | 514.825 | 0.601 | HYPOX_O2_HCT116 |
| 2614 | CMOT2 | SEQ ID NO. 1047 | 333.067 | 330.242 | 0.992 | HYPOX_O2_HT1080 |
| 2615 | IDS | SEQ ID NO. 1048 | 302.605 | 323.091 | 1.068 | HYPOX_DFO_HCT116 |
| 2616 | IDS | SEQ ID NO. 1048 | 51.982 | 67.217 | 1.293 | HYPOX_DFO_HT1080 |
| 2617 | IDS | SEQ ID NO. 1048 | 302.605 | 217.469 | 0.719 | HYPOX_O2_HCT116 |
| 2618 | IDS | SEQ ID NO. 1048 | 51.982 | 58.305 | 1.122 | HYPOX_O2_HT1080 |
| 2619 | SFRS4 | SEQ ID NO. 1049 | 310.824 | 264.469 | 0.851 | HYPOX_DFO_HCT116 |
| 2620 | SFRS4 | SEQ ID NO. 1049 | 85.432 | 78.388 | 0.918 | HYPOX_DFO_HT1080 |
| 2621 | SFRS4 | SEQ ID NO. 1049 | 310.824 | 269.435 | 0.867 | HYPOX_O2_HCT116 |
| 2622 | SFRS4 | SEQ ID NO. 1049 | 85.432 | 72.077 | 0.844 | HYPOX_O2_HT1080 |
| 2623 | UBE3C | SEQ ID NO. 1050 | 208.597 | 240.703 | 1.154 | HYPOX_DFO_HCT116 |
| 2624 | UBE3C | SEQ ID NO. 1050 | 102.483 | 147.006 | 1.434 | HYPOX_DFO_HT1080 |
| 2625 | UBE3C | SEQ ID NO. 1050 | 208.597 | 240.510 | 1.153 | HYPOX_O2_HCT116 |
| 2626 | UBE3C | SEQ ID NO. 1050 | 102.483 | 97.49 | 0.951 | HYPOX_O2_HT1080 |
| 2627 | SAMD11 | SEQ ID NO. 1051 | 681.827 | 437.396 | 0.642 | HYPOX_DFO_HCT116 |
| 2628 | SAMD11 | SEQ ID NO. 1051 | 31.485 | 20.571 | 0.652 | HYPOX_DFO_HT1080 |
| 2629 | SAMD11 | SEQ ID NO. 1051 | 681.827 | 413.517 | 0.605 | HYPOX_O2_HCT116 |
| 2630 | SAMD11 | SEQ ID NO. 1051 | 31.485 | 33.202 | 1.055 | HYPOX_O2_HT1080 |
| 2631 | CHIC2 | SEQ ID NO. 1052 | 131.827 | 62.821 | 0.477 | HYPOX_DFO_HCT116 |
| 2632 | CHIC2 | SEQ ID NO. 1052 | 27.959 | 18.018 | 0.644 | HYPOX_DFO_HT1080 |
| 2633 | CHIC2 | SEQ ID NO. 1052 | 131.827 | 94.698 | 0.718 | HYPOX_O2_HCT116 |
| 2634 | CHIC2 | SEQ ID NO. 1052 | 27.959 | 24.19 | 0.865 | HYPOX_O2_HT1080 |
| 2635 | ZBTB25 | SEQ ID NO. 1053 | 788.34 | 588.095 | 0.746 | HYPOX_DFO_HCT116 |
| 2636 | ZBTB25 | SEQ ID NO. 1053 | 87.766 | 118.403 | 1.349 | HYPOX_DFO_HT1080 |
| 2637 | ZBTB25 | SEQ ID NO. 1053 | 788.34 | 993.089 | 1.26 | HYPOX_O2_HCT116 |
| 2638 | ZBTB25 | SEQ ID NO. 1053 | 87.766 | 192.443 | 2.193 | HYPOX_O2_HT1080 |
| 2639 | NULL | SEQ ID NO. 1054 | 239.257 | 155.069 | 0.648 | HYPOX_DFO_HCT116 |
| 2640 | NULL | SEQ ID NO. 1054 | 38.991 | 25.945 | 0.665 | HYPOX_DFO_HT1080 |
| 2641 | NULL | SEQ ID NO. 1054 | 239.257 | 129.54 | 0.541 | HYPOX_O2_HCT116 |
| 2642 | NULL | SEQ ID NO. 1054 | 38.991 | 28.851 | 0.74 | HYPOX_O2_HT1080 |

FIG. 1BR -- TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS* |
|---|---|---|---|---|---|---|
| 2643 | BEX2 | SEQ ID NO. 1055 | 111.152 | 113.159 | 1.018 | HYPOX_DFO_HCT116 |
| 2644 | BEX2 | SEQ ID NO. 1055 | 4.361 | 3.521 | 0.807 | HYPOX_DFO_HT1080 |
| 2645 | BEX2 | SEQ ID NO. 1055 | 111.152 | 65.483 | 0.589 | HYPOX_O2_HCT116 |
| 2646 | BEX2 | SEQ ID NO. 1055 | 4.361 | 2.558 | 0.587 | HYPOX_O2_HT1080 |
| 2647 | CDT1 | SEQ ID NO. 1056 | 183.164 | 143.798 | 0.785 | HYPOX_DFO_HCT116 |
| 2648 | CDT1 | SEQ ID NO. 1056 | 44.047 | 36.126 | 0.82 | HYPOX_DFO_HT1080 |
| 2649 | CDT1 | SEQ ID NO. 1056 | 183.164 | 173.154 | 0.945 | HYPOX_O2_HCT116 |
| 2650 | CDT1 | SEQ ID NO. 1056 | 44.047 | 54.317 | 1.233 | HYPOX_O2_HT1080 |
| 2651 | TTYH2 | SEQ ID NO. 1057 | 203.631 | 84.003 | 0.413 | HYPOX_DFO_HCT116 |
| 2652 | TTYH2 | SEQ ID NO. 1057 | 14.386 | 7.058 | 0.491 | HYPOX_DFO_HT1080 |
| 2653 | TTYH2 | SEQ ID NO. 1057 | 203.631 | 120.014 | 0.589 | HYPOX_O2_HCT116 |
| 2654 | TTYH2 | SEQ ID NO. 1057 | 14.386 | 9.835 | 0.683 | HYPOX_O2_HT1080 |
| 2655 | LAMCL3 | SEQ ID NO. 1058 | 268.137 | 125.007 | 0.466 | HYPOX_DFO_HCT116 |
| 2656 | LAMCL3 | SEQ ID NO. 1058 | 3.835 | 2.771 | 0.723 | HYPOX_DFO_HT1080 |
| 2657 | LAMCL3 | SEQ ID NO. 1058 | 268.137 | 133.19 | 0.497 | HYPOX_O2_HCT116 |
| 2658 | LAMCL3 | SEQ ID NO. 1058 | 3.835 | 2.447 | 0.638 | HYPOX_O2_HT1080 |
| 2659 | ZNF141 | SEQ ID NO. 1059 | 562.008 | 405.123 | 0.721 | HYPOX_DFO_HCT116 |
| 2660 | ZNF141 | SEQ ID NO. 1059 | 155.247 | 85.662 | 0.552 | HYPOX_DFO_HT1080 |
| 2661 | ZNF141 | SEQ ID NO. 1059 | 562.008 | 464.815 | 0.827 | HYPOX_O2_HCT116 |
| 2662 | ZNF141 | SEQ ID NO. 1059 | 155.247 | 119.409 | 0.769 | HYPOX_O2_HT1080 |
| 2663 | UBE2Z | SEQ ID NO. 1060 | 120.314 | 105.083 | 0.873 | HYPOX_DFO_HCT116 |
| 2664 | UBE2Z | SEQ ID NO. 1060 | 34.315 | 40.286 | 1.174 | HYPOX_DFO_HT1080 |
| 2665 | UBE2Z | SEQ ID NO. 1060 | 120.314 | 107.571 | 0.894 | HYPOX_O2_HCT116 |
| 2666 | UBE2Z | SEQ ID NO. 1060 | 34.315 | 38.864 | 1.133 | HYPOX_O2_HT1080 |
| 2667 | PANK1 | SEQ ID NO. 1061 | 289.532 | 124.191 | 0.429 | HYPOX_DFO_HCT116 |
| 2668 | PANK1 | SEQ ID NO. 1061 | 2.021 | 4.63 | 2.291 | HYPOX_DFO_HT1080 |
| 2669 | PANK1 | SEQ ID NO. 1061 | 289.532 | 134.172 | 0.463 | HYPOX_O2_HCT116 |
| 2670 | PANK1 | SEQ ID NO. 1061 | 2.021 | 2.484 | 1.229 | HYPOX_O2_HT1080 |
| 2671 | ZNF770 | SEQ ID NO. 1062 | 1617.893 | 4107.965 | 2.539 | HYPOX_DFO_HCT116 |
| 2672 | ZNF770 | SEQ ID NO. 1062 | 575.422 | 955.614 | 1.661 | HYPOX_DFO_HT1080 |
| 2673 | ZNF770 | SEQ ID NO. 1062 | 1617.893 | 3327.145 | 2.058 | HYPOX_O2_HCT116 |
| 2674 | ZNF770 | SEQ ID NO. 1062 | 575.422 | 650.026 | 1.13 | HYPOX_O2_HT1080 |
| 2675 | SERP2 | SEQ ID NO. 1063 | 66.617 | 47.778 | 0.717 | HYPOX_DFO_HCT116 |
| 2676 | SERP2 | SEQ ID NO. 1063 | 6.291 | 6.514 | 1.035 | HYPOX_DFO_HT1080 |
| 2677 | SERP2 | SEQ ID NO. 1063 | 66.617 | 89.297 | 1.34 | HYPOX_O2_HCT116 |
| 2678 | SERP2 | SEQ ID NO. 1063 | 6.291 | 7.714 | 1.226 | HYPOX_O2_HT1080 |
| 2679 | OTUD7A | SEQ ID NO. 1064 | 232.291 | 301.244 | 1.297 | HYPOX_DFO_HCT116 |
| 2680 | OTUD7A | SEQ ID NO. 1064 | 9.735 | 6.377 | 0.655 | HYPOX_DFO_HT1080 |
| 2681 | OTUD7A | SEQ ID NO. 1064 | 232.291 | 444.763 | 1.915 | HYPOX_O2_HCT116 |
| 2682 | OTUD7A | SEQ ID NO. 1064 | 9.735 | 6.594 | 0.677 | HYPOX_O2_HT1080 |
| 2683 | ZNF146 | SEQ ID NO. 1065 | 1963.442 | 3455.817 | 1.76 | HYPOX_DFO_HCT116 |
| 2684 | ZNF146 | SEQ ID NO. 1065 | 643.241 | 1037.934 | 1.616 | HYPOX_DFO_HT1080 |
| 2685 | ZNF146 | SEQ ID NO. 1065 | 1963.442 | 2166.459 | 1.103 | HYPOX_O2_HCT116 |
| 2686 | ZNF146 | SEQ ID NO. 1065 | 643.241 | 666.212 | 1.037 | HYPOX_O2_HT1080 |
| 2687 | ZNF565 | SEQ ID NO. 1066 | 1784.678 | 3693.728 | 2.07 | HYPOX_DFO_HCT116 |
| 2688 | ZNF565 | SEQ ID NO. 1066 | 252.65 | 352.432 | 1.395 | HYPOX_DFO_HT1080 |
| 2689 | ZNF565 | SEQ ID NO. 1066 | 1784.678 | 1978.935 | 1.109 | HYPOX_O2_HCT116 |
| 2690 | ZNF565 | SEQ ID NO. 1066 | 252.65 | 241.866 | 0.957 | HYPOX_O2_HT1080 |

FIG. 1BS -- TABLE 1 TRANSCRIPTIONAL BIOMARKER FUNCTIONAL DATA
SECTION 1A

| LINE_ID | GENE_SYMBOL | SEQUENCE_ID_LISTING | FROM_ACTIVITY_N O_INDUCTION | FROM_ACTIVITY_WI TH_INDUCTION | INDUCTION_RATIO | INDUCTION_CONDITIONS* |
|---|---|---|---|---|---|---|
| 2691 | NULL | SEQ ID NO. 1067 | 43.14 | 47.667 | 1.105 | HYPOX_DFO_HCT116 |
| 2692 | NULL | SEQ ID NO. 1067 | 2.992 | 3.11 | 1.039 | HYPOX_DFO_HT1080 |
| 2693 | NULL | SEQ ID NO. 1067 | 43.14 | 48.896 | 1.087 | HYPOX_O2_HCT116 |
| 2694 | NULL | SEQ ID NO. 1067 | 2.992 | 3.558 | 1.189 | HYPOX_O2_HT1080 |
| 2695 | HFE | SEQ ID NO. 1068 | 10.06 | 3.091 | 0.307 | HYPOX_DFO_HCT116 |
| 2696 | HFE | SEQ ID NO. 1068 | 1.133 | 1.017 | 0.898 | HYPOX_DFO_HT1080 |
| 2697 | HFE | SEQ ID NO. 1068 | 10.06 | 5.994 | 0.596 | HYPOX_O2_HCT116 |
| 2698 | HFE | SEQ ID NO. 1068 | 1.133 | 1.184 | 1.045 | HYPOX_O2_HT1080 |
| 2699 | DCBLD1 | SEQ ID NO. 1069 | 213.494 | 198.719 | 0.931 | HYPOX_DFO_HCT116 |
| 2700 | DCBLD1 | SEQ ID NO. 1069 | 6.756 | 6.226 | 0.921 | HYPOX_DFO_HT1080 |
| 2701 | DCBLD1 | SEQ ID NO. 1069 | 213.494 | 244.618 | 1.146 | HYPOX_O2_HCT116 |
| 2702 | DCBLD1 | SEQ ID NO. 1069 | 6.756 | 7.703 | 1.14 | HYPOX_O2_HT1080 |
| 2703 | IPPK | SEQ ID NO. 1070 | 20.383 | 64.317 | 3.155 | HYPOX_DFO_HCT116 |
| 2704 | IPPK | SEQ ID NO. 1070 | 6.977 | 8.872 | 1.272 | HYPOX_DFO_HT1080 |
| 2705 | IPPK | SEQ ID NO. 1070 | 20.383 | 42.433 | 2.082 | HYPOX_O2_HCT116 |
| 2706 | IPPK | SEQ ID NO. 1070 | 6.977 | 7.182 | 1.028 | HYPOX_O2_HT1080 |
| 2707 | NULL | SEQ ID NO. 1071 | 2411.409 | 6641.096 | 2.754 | HYPOX_DFO_HCT116 |
| 2708 | NULL | SEQ ID NO. 1071 | 262.672 | 440.755 | 1.678 | HYPOX_DFO_HT1080 |
| 2709 | NULL | SEQ ID NO. 1071 | 2411.409 | 3586.297 | 1.487 | HYPOX_O2_HCT116 |
| 2710 | NULL | SEQ ID NO. 1071 | 262.672 | 247.492 | 0.942 | HYPOX_O2_HT1080 |
| 2711 | NULL | SEQ ID NO. 1072 | 182.353 | 168.267 | 0.926 | HYPOX_DFO_HCT116 |
| 2712 | NULL | SEQ ID NO. 1072 | 3.164 | 3.429 | 1.155 | HYPOX_DFO_HT1080 |
| 2713 | NULL | SEQ ID NO. 1072 | 182.353 | 181.855 | 0.995 | HYPOX_O2_HCT116 |
| 2714 | NULL | SEQ ID NO. 1072 | 8.164 | 6.848 | 0.839 | HYPOX_O2_HT1080 |
| 2715 | 9-Sep | SEQ ID NO. 1073 | 197.835 | 82.069 | 0.415 | HYPOX_DFO_HCT116 |
| 2716 | 9-Sep | SEQ ID NO. 1073 | 5.486 | 2.823 | 0.515 | HYPOX_DFO_HT1080 |
| 2717 | 9-Sep | SEQ ID NO. 1073 | 197.835 | 153.293 | 0.776 | HYPOX_O2_HCT116 |
| 2718 | 9-Sep | SEQ ID NO. 1073 | 5.486 | 4.955 | 0.903 | HYPOX_O2_HT1080 |
| 2719 | POLI | SEQ ID NO. 1074 | 391.129 | 400.174 | 1.023 | HYPOX_DFO_HCT116 |
| 2720 | POLI | SEQ ID NO. 1074 | 33.926 | 40.255 | 1.187 | HYPOX_DFO_HT1080 |
| 2721 | POLI | SEQ ID NO. 1074 | 391.129 | 181.256 | 0.463 | HYPOX_O2_HCT116 |
| 2722 | POLI | SEQ ID NO. 1074 | 33.926 | 45.168 | 1.331 | HYPOX_O2_HT1080 |
| 2723 | GPBP1 | SEQ ID NO. 1075 | 1451.778 | 2992.651 | 2.061 | HYPOX_DFO_HCT116 |
| 2724 | GPBP1 | SEQ ID NO. 1075 | 423.764 | 670.902 | 1.583 | HYPOX_DFO_HT1080 |
| 2725 | GPBP1 | SEQ ID NO. 1075 | 1451.778 | 2858 | 1.969 | HYPOX_O2_HCT116 |
| 2726 | GPBP1 | SEQ ID NO. 1075 | 423.764 | 385.731 | 0.91 | HYPOX_O2_HT1080 |
| 2727 | NULL | SEQ ID NO. 1076 | 226.476 | 247.792 | 1.094 | HYPOX_DFO_HCT116 |
| 2728 | NULL | SEQ ID NO. 1076 | 60.072 | 88.194 | 1.468 | HYPOX_DFO_HT1080 |
| 2729 | NULL | SEQ ID NO. 1076 | 226.476 | 497.821 | 2.198 | HYPOX_O2_HCT116 |
| 2730 | NULL | SEQ ID NO. 1076 | 60.072 | 73.694 | 1.227 | HYPOX_O2_HT1080 |
| 2731 | WDR54 | SEQ ID NO. 1077 | 425.921 | 531.656 | 1.248 | HYPOX_DFO_HCT116 |
| 2732 | WDR54 | SEQ ID NO. 1077 | 73.843 | 237.614 | 3.218 | HYPOX_DFO_HT1080 |
| 2733 | WDR54 | SEQ ID NO. 1077 | 425.921 | 1090.953 | 2.561 | HYPOX_O2_HCT116 |
| 2734 | WDR54 | SEQ ID NO. 1077 | 73.843 | 203.266 | 1.309 | HYPOX_O2_HT1080 |
| 2735 | TCF15 | SEQ ID NO. 1078 | 294.885 | 203.536 | 0.69 | HYPOX_DFO_HCT116 |
| 2736 | TCF15 | SEQ ID NO. 1078 | 7.345 | 16.037 | 2.18 | HYPOX_DFO_HT1080 |
| 2737 | TCF15 | SEQ ID NO. 1078 | 294.885 | 393.375 | 1.334 | HYPOX_O2_HCT116 |
| 2738 | TCF15 | SEQ ID NO. 1078 | 7.345 | 17.967 | 2.446 | HYPOX_O2_HT1080 |

FIG. 1BT – TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS |
|---|---|---|---|---|---|---|
| 2739 | CYB5R4 | SEQ ID NO. 1079 | 298.644 | 266.361 | 0.892 | HYPOX_DFO_HCT116 |
| 2740 | CYB5R4 | SEQ ID NO. 1079 | 27.363 | 30.095 | 1.1 | HYPOX_DFO_HT1080 |
| 2741 | CYB5R4 | SEQ ID NO. 1079 | 298.644 | 452.321 | 1.515 | HYPOX_O2_HCT116 |
| 2742 | CYB5R4 | SEQ ID NO. 1079 | 27.363 | 24.269 | 0.888 | HYPOX_O2_HT1080 |
| 2743 | C3orf1 | SEQ ID NO. 1080 | 149.45 | 533.6 | 3.57 | HYPOX_DFO_HCT116 |
| 2744 | C3orf1 | SEQ ID NO. 1080 | 25.811 | 34.675 | 1.343 | HYPOX_DFO_HT1080 |
| 2745 | C3orf1 | SEQ ID NO. 1080 | 149.45 | 209.589 | 1.402 | HYPOX_O2_HCT116 |
| 2746 | C3orf1 | SEQ ID NO. 1080 | 25.811 | 21.105 | 0.818 | HYPOX_O2_HT1080 |
| 2747 | ASB13 | SEQ ID NO. 1081 | 165.715 | 154.809 | 0.935 | HYPOX_DFO_HCT116 |
| 2748 | ASB13 | SEQ ID NO. 1081 | 10.723 | 9.564 | 0.892 | HYPOX_DFO_HT1080 |
| 2749 | ASB13 | SEQ ID NO. 1081 | 165.715 | 130.163 | 0.785 | HYPOX_O2_HCT116 |
| 2750 | ASB13 | SEQ ID NO. 1081 | 10.723 | 6.895 | 0.643 | HYPOX_O2_HT1080 |
| 2751 | FLJ25715 | SEQ ID NO. 1082 | 2418.929 | 4677.742 | 1.934 | HYPOX_DFO_HCT116 |
| 2752 | FLJ25715 | SEQ ID NO. 1082 | 293.894 | 681.378 | 2.318 | HYPOX_DFO_HT1080 |
| 2753 | FLJ25715 | SEQ ID NO. 1082 | 2418.929 | 4143.174 | 1.713 | HYPOX_O2_HCT116 |
| 2754 | FLJ25715 | SEQ ID NO. 1082 | 293.894 | 380.925 | 1.296 | HYPOX_O2_HT1080 |
| 2755 | CTDP1 | SEQ ID NO. 1083 | 1442.882 | 4699.858 | 3.396 | HYPOX_DFO_HCT116 |
| 2756 | CTDP1 | SEQ ID NO. 1083 | 625.981 | 1127.823 | 1.802 | HYPOX_DFO_HT1080 |
| 2757 | CTDP1 | SEQ ID NO. 1083 | 1442.882 | 3919.671 | 2.717 | HYPOX_O2_HCT116 |
| 2758 | CTDP1 | SEQ ID NO. 1083 | 625.981 | 553.652 | 0.884 | HYPOX_O2_HT1080 |
| 2759 | NULL | SEQ ID NO. 1084 | 194.949 | 217.718 | 1.117 | HYPOX_DFO_HCT116 |
| 2760 | NULL | SEQ ID NO. 1084 | 25.399 | 37.744 | 1.486 | HYPOX_DFO_HT1080 |
| 2761 | NULL | SEQ ID NO. 1084 | 194.949 | 364.833 | 1.871 | HYPOX_O2_HCT116 |
| 2762 | NULL | SEQ ID NO. 1084 | 25.399 | 33.623 | 1.324 | HYPOX_O2_HT1080 |
| 2763 | SNIP | SEQ ID NO. 1085 | 55.776 | 28.071 | 0.503 | HYPOX_DFO_HCT116 |
| 2764 | SNIP | SEQ ID NO. 1085 | 1.96 | 1.351 | 0.689 | HYPOX_DFO_HT1080 |
| 2765 | SNIP | SEQ ID NO. 1085 | 55.776 | 57.016 | 1.022 | HYPOX_O2_HCT116 |
| 2766 | SNIP | SEQ ID NO. 1085 | 1.96 | 1.645 | 0.839 | HYPOX_O2_HT1080 |
| 2767 | GLS2 | SEQ ID NO. 1086 | 94.73 | 49.512 | 0.523 | HYPOX_DFO_HCT116 |
| 2768 | GLS2 | SEQ ID NO. 1086 | 2.728 | 4.373 | 1.603 | HYPOX_DFO_HT1080 |
| 2769 | GLS2 | SEQ ID NO. 1086 | 94.73 | 50.82 | 0.536 | HYPOX_O2_HCT116 |
| 2770 | GLS2 | SEQ ID NO. 1086 | 2.728 | 3.183 | 1.167 | HYPOX_O2_HT1080 |
| 2771 | TYMP | SEQ ID NO. 1087 | 129.755 | 59.123 | 0.456 | HYPOX_DFO_HCT116 |
| 2772 | TYMP | SEQ ID NO. 1087 | 20.283 | 17.221 | 0.849 | HYPOX_DFO_HT1080 |
| 2773 | TYMP | SEQ ID NO. 1087 | 129.755 | 96.108 | 0.741 | HYPOX_O2_HCT116 |
| 2774 | TYMP | SEQ ID NO. 1087 | 20.283 | 15.463 | 0.763 | HYPOX_O2_HT1080 |
| 2775 | NULL | SEQ ID NO. 1088 | 20.767 | 22.188 | 1.068 | HYPOX_DFO_HCT116 |
| 2776 | NULL | SEQ ID NO. 1088 | 2.549 | 2.795 | 1.096 | HYPOX_DFO_HT1080 |
| 2777 | NULL | SEQ ID NO. 1088 | 20.767 | 37.43 | 1.802 | HYPOX_O2_HCT116 |
| 2778 | NULL | SEQ ID NO. 1088 | 2.549 | 2.197 | 0.862 | HYPOX_O2_HT1080 |
| 2779 | KIAA1143 | SEQ ID NO. 1089 | 675.35 | 1381.697 | 2.046 | HYPOX_DFO_HCT116 |
| 2780 | KIAA1143 | SEQ ID NO. 1089 | 207.99 | 279.429 | 1.343 | HYPOX_DFO_HT1080 |
| 2781 | KIAA1143 | SEQ ID NO. 1089 | 675.35 | 732.568 | 1.085 | HYPOX_O2_HCT116 |
| 2782 | KIAA1143 | SEQ ID NO. 1089 | 207.99 | 230.351 | 1.108 | HYPOX_O2_HT1080 |
| 2783 | PDXK | SEQ ID NO. 1090 | 1354.902 | 1972.628 | 1.456 | HYPOX_DFO_HCT116 |
| 2784 | PDXK | SEQ ID NO. 1090 | 244.714 | 457.194 | 1.868 | HYPOX_DFO_HT1080 |
| 2785 | PDXK | SEQ ID NO. 1090 | 1354.902 | 1637.905 | 1.209 | HYPOX_O2_HCT116 |
| 2786 | PDXK | SEQ ID NO. 1090 | 244.714 | 308.47 | 1.261 | HYPOX_O2_HT1080 |

FIG. 1BU — TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_N O_INDUCTION | PROM_ACTIVITY_WI TH_INDUCTION | INDUCTION RATIO | INDUCTION_CONDITIONS* |
|---|---|---|---|---|---|---|
| 2787 | PRIM2 | SEQ ID NO. 1091 | 1881.581 | 2723.308 | 1.45 | HYPOX_DFO_HCT116 |
| 2788 | PRIM2 | SEQ ID NO. 1091 | 360.337 | 317.274 | 0.88 | HYPOX_DFO_HT1080 |
| 2789 | PRIM2 | SEQ ID NO. 1091 | 1881.581 | 2071.491 | 1.101 | HYPOX_O2_HCT116 |
| 2790 | PRIM2 | SEQ ID NO. 1091 | 360.337 | 241.624 | 0.671 | HYPOX_O2_HT1080 |
| 2791 | SRPK1 | SEQ ID NO. 1092 | 21.81 | 6.854 | 0.314 | HYPOX_DFO_HCT116 |
| 2792 | SRPK1 | SEQ ID NO. 1092 | 1.668 | 1.583 | 0.949 | HYPOX_DFO_HT1080 |
| 2793 | SRPK1 | SEQ ID NO. 1092 | 21.81 | 10.244 | 0.47 | HYPOX_O2_HCT116 |
| 2794 | SRPK1 | SEQ ID NO. 1092 | 1.668 | 2.028 | 1.216 | HYPOX_O2_HT1080 |
| 2795 | ATP4B | SEQ ID NO. 1093 | 13.398 | 4.531 | 0.338 | HYPOX_DFO_HCT116 |
| 2796 | ATP4B | SEQ ID NO. 1093 | 1.698 | 0.699 | 0.411 | HYPOX_DFO_HT1080 |
| 2797 | ATP4B | SEQ ID NO. 1093 | 13.398 | 13.395 | 1 | HYPOX_O2_HCT116 |
| 2798 | ATP4B | SEQ ID NO. 1093 | 1.698 | 1.437 | 0.846 | HYPOX_O2_HT1080 |
| 2799 | PHPT1 | SEQ ID NO. 1094 | 824.438 | 598.639 | 0.726 | HYPOX_DFO_HCT116 |
| 2800 | PHPT1 | SEQ ID NO. 1094 | 147.928 | 122.253 | 0.826 | HYPOX_DFO_HT1080 |
| 2801 | PHPT1 | SEQ ID NO. 1094 | 824.438 | 826.759 | 1.003 | HYPOX_O2_HCT116 |
| 2802 | PHPT1 | SEQ ID NO. 1094 | 147.928 | 124.645 | 0.843 | HYPOX_O2_HT1080 |
| 2803 | LAP3 | SEQ ID NO. 1095 | 100.93 | 137.248 | 1.36 | HYPOX_DFO_HCT116 |
| 2804 | LAP3 | SEQ ID NO. 1095 | 22.133 | 22.873 | 1.033 | HYPOX_DFO_HT1080 |
| 2805 | LAP3 | SEQ ID NO. 1095 | 100.93 | 117.613 | 1.167 | HYPOX_O2_HCT116 |
| 2806 | LAP3 | SEQ ID NO. 1095 | 22.133 | 19.387 | 0.876 | HYPOX_O2_HT1080 |
| 2807 | NCOR1 | SEQ ID NO. 1096 | 387.739 | 569.853 | 1.47 | HYPOX_DFO_HCT116 |
| 2808 | NCOR1 | SEQ ID NO. 1096 | 126.745 | 112.368 | 0.867 | HYPOX_DFO_HT1080 |
| 2809 | NCOR1 | SEQ ID NO. 1096 | 387.739 | 510.488 | 1.317 | HYPOX_O2_HCT116 |
| 2810 | NCOR1 | SEQ ID NO. 1096 | 126.745 | 92.541 | 0.73 | HYPOX_O2_HT1080 |
| 2811 | C7orf42 | SEQ ID NO. 1097 | 288.202 | 636.238 | 2.208 | HYPOX_DFO_HCT116 |
| 2812 | C7orf42 | SEQ ID NO. 1097 | 59.895 | 103.332 | 1.725 | HYPOX_DFO_HT1080 |
| 2813 | C7orf42 | SEQ ID NO. 1097 | 288.202 | 407.374 | 1.413 | HYPOX_O2_HCT116 |
| 2814 | C7orf42 | SEQ ID NO. 1097 | 59.895 | 74.214 | 1.239 | HYPOX_O2_HT1080 |
| 2815 | NULL | SEQ ID NO. 1098 | 1.855 | 0.747 | 0.402 | HYPOX_DFO_HCT116 |
| 2816 | NULL | SEQ ID NO. 1098 | 0.163 | 0.137 | 0.845 | HYPOX_DFO_HT1080 |
| 2817 | NULL | SEQ ID NO. 1098 | 1.855 | 1.192 | 0.642 | HYPOX_O2_HCT116 |
| 2818 | NULL | SEQ ID NO. 1098 | 0.163 | 0.096 | 0.589 | HYPOX_O2_HT1080 |
| 2819 | INSM2 | SEQ ID NO. 1099 | 304.406 | 295.238 | 0.97 | HYPOX_DFO_HCT116 |
| 2820 | INSM2 | SEQ ID NO. 1099 | 6.601 | 5.569 | 0.844 | HYPOX_DFO_HT1080 |
| 2821 | INSM2 | SEQ ID NO. 1099 | 304.406 | 221.869 | 0.729 | HYPOX_O2_HCT116 |
| 2822 | INSM2 | SEQ ID NO. 1099 | 6.601 | 5.935 | 0.899 | HYPOX_O2_HT1080 |
| 2823 | VAV2 | SEQ ID NO. 1100 | 162.438 | 101.883 | 0.627 | HYPOX_DFO_HCT116 |
| 2824 | VAV2 | SEQ ID NO. 1100 | 39.299 | 34.038 | 0.866 | HYPOX_DFO_HT1080 |
| 2825 | VAV2 | SEQ ID NO. 1100 | 162.438 | 194.623 | 1.198 | HYPOX_O2_HCT116 |
| 2826 | VAV2 | SEQ ID NO. 1100 | 39.299 | 40.143 | 1.021 | HYPOX_O2_HT1080 |
| 2827 | NULL | SEQ ID NO. 1101 | 1669.422 | 3723.206 | 2.23 | HYPOX_DFO_HCT116 |
| 2828 | NULL | SEQ ID NO. 1101 | 519.428 | 435.218 | 0.838 | HYPOX_DFO_HT1080 |
| 2829 | NULL | SEQ ID NO. 1101 | 1669.422 | 2871.16 | 1.72 | HYPOX_O2_HCT116 |
| 2830 | NULL | SEQ ID NO. 1101 | 519.428 | 420.543 | 0.81 | HYPOX_O2_HT1080 |
| 2831 | PLXDC1 | SEQ ID NO. 1102 | 108.693 | 73.822 | 0.679 | HYPOX_DFO_HCT116 |
| 2832 | PLXDC1 | SEQ ID NO. 1102 | 5.387 | 5.168 | 0.959 | HYPOX_DFO_HT1080 |
| 2833 | PLXDC1 | SEQ ID NO. 1102 | 108.693 | 98.38 | 0.905 | HYPOX_O2_HCT116 |
| 2834 | PLXDC1 | SEQ ID NO. 1102 | 5.387 | 4.65 | 0.863 | HYPOX_O2_HT1080 |

FIG. 1BV — TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS |
|---|---|---|---|---|---|---|
| 2835 | C12orf45 | SEQ ID NO. 1103 | 472.976 | 285.246 | 0.603 | HYPOX_DFO_HCT116 |
| 2836 | C12orf45 | SEQ ID NO. 1103 | 94.096 | 143.089 | 1.52 | HYPOX_DFO_HT1080 |
| 2837 | C12orf45 | SEQ ID NO. 1103 | 472.976 | 254.565 | 0.538 | HYPOX_O2_HCT116 |
| 2838 | C12orf45 | SEQ ID NO. 1103 | 94.096 | 99.268 | 1.055 | HYPOX_O2_HT1080 |
| 2839 | IMA | SEQ ID NO. 1104 | 231.592 | 117.806 | 0.509 | HYPOX_DFO_HCT116 |
| 2840 | IMA | SEQ ID NO. 1104 | 10.524 | 9.784 | 0.93 | HYPOX_DFO_HT1080 |
| 2841 | IMA | SEQ ID NO. 1104 | 231.592 | 170.271 | 0.735 | HYPOX_O2_HCT116 |
| 2842 | IMA | SEQ ID NO. 1104 | 10.524 | 10.297 | 0.979 | HYPOX_O2_HT1080 |
| 2843 | VAPA | SEQ ID NO. 1105 | 1244.997 | 917.092 | 0.737 | HYPOX_DFO_HCT116 |
| 2844 | VAPA | SEQ ID NO. 1105 | 407.734 | 494.577 | 1.213 | HYPOX_DFO_HT1080 |
| 2845 | VAPA | SEQ ID NO. 1105 | 1244.997 | 988.443 | 0.794 | HYPOX_O2_HCT116 |
| 2846 | VAPA | SEQ ID NO. 1105 | 407.734 | 327.697 | 0.804 | HYPOX_O2_HT1080 |
| 2847 | KIF15 | SEQ ID NO. 1106 | 83.514 | 84.71 | 1.014 | HYPOX_DFO_HCT116 |
| 2848 | KIF15 | SEQ ID NO. 1106 | 11.71 | 11.988 | 1.024 | HYPOX_DFO_HT1080 |
| 2849 | KIF15 | SEQ ID NO. 1106 | 83.514 | 46.495 | 0.557 | HYPOX_O2_HCT116 |
| 2850 | KIF15 | SEQ ID NO. 1106 | 11.71 | 14.674 | 1.253 | HYPOX_O2_HT1080 |
| 2851 | TBRG4 | SEQ ID NO. 1107 | 2104.353 | 6899.746 | 3.279 | HYPOX_DFO_HCT116 |
| 2852 | TBRG4 | SEQ ID NO. 1107 | 246.24 | 505.45 | 2.053 | HYPOX_DFO_HT1080 |
| 2853 | TBRG4 | SEQ ID NO. 1107 | 2104.353 | 2994.478 | 1.423 | HYPOX_O2_HCT116 |
| 2854 | TBRG4 | SEQ ID NO. 1107 | 246.24 | 268.537 | 1.091 | HYPOX_O2_HT1080 |
| 2855 | AP3M2 | SEQ ID NO. 1108 | 108.847 | 167.579 | 1.54 | HYPOX_DFO_HCT116 |
| 2856 | AP3M2 | SEQ ID NO. 1108 | 15.712 | 10.633 | 0.677 | HYPOX_DFO_HT1080 |
| 2857 | AP3M2 | SEQ ID NO. 1108 | 108.847 | 101.389 | 0.931 | HYPOX_O2_HCT116 |
| 2858 | AP3M2 | SEQ ID NO. 1108 | 15.712 | 10.086 | 0.642 | HYPOX_O2_HT1080 |
| 2859 | ANAPC2 | SEQ ID NO. 1109 | 630.063 | 1072.577 | 1.702 | HYPOX_DFO_HCT116 |
| 2860 | ANAPC2 | SEQ ID NO. 1109 | 163.306 | 168.089 | 1.029 | HYPOX_DFO_HT1080 |
| 2861 | ANAPC2 | SEQ ID NO. 1109 | 630.063 | 988.001 | 1.568 | HYPOX_O2_HCT116 |
| 2862 | ANAPC2 | SEQ ID NO. 1109 | 163.306 | 134.825 | 0.826 | HYPOX_O2_HT1080 |
| 2863 | NULL | SEQ ID NO. 1110 | 5.117 | 1.983 | 0.388 | HYPOX_DFO_HCT116 |
| 2864 | NULL | SEQ ID NO. 1110 | 0.949 | 1.796 | 1.892 | HYPOX_DFO_HT1080 |
| 2865 | NULL | SEQ ID NO. 1110 | 5.117 | 4.492 | 0.878 | HYPOX_O2_HCT116 |
| 2866 | NULL | SEQ ID NO. 1110 | 0.949 | 1.308 | 1.378 | HYPOX_O2_HT1080 |
| 2867 | PDZD11 | SEQ ID NO. 1111 | 1445.058 | 1699.085 | 1.176 | HYPOX_DFO_HCT116 |
| 2868 | PDZD11 | SEQ ID NO. 1111 | 481.755 | 413.481 | 0.858 | HYPOX_DFO_HT1080 |
| 2869 | PDZD11 | SEQ ID NO. 1111 | 1445.058 | 1567.971 | 1.085 | HYPOX_O2_HCT116 |
| 2870 | PDZD11 | SEQ ID NO. 1111 | 481.755 | 324.456 | 0.673 | HYPOX_O2_HT1080 |
| 2871 | PC | SEQ ID NO. 1111 | 233.302 | 236.092 | 1.012 | HYPOX_DFO_HCT116 |
| 2872 | PC | SEQ ID NO. 1111 | 20.68 | 22.183 | 1.073 | HYPOX_DFO_HT1080 |
| 2873 | PC | SEQ ID NO. 1111 | 233.302 | 314.101 | 1.346 | HYPOX_O2_HCT116 |
| 2874 | PC | SEQ ID NO. 1111 | 20.68 | 15.439 | 0.747 | HYPOX_O2_HT1080 |
| 2875 | CHD9 | SEQ ID NO. 1112 | 127.734 | 111.581 | 0.874 | HYPOX_DFO_HCT116 |
| 2876 | CHD9 | SEQ ID NO. 1112 | 16.794 | 11.343 | 0.675 | HYPOX_DFO_HT1080 |
| 2877 | CHD9 | SEQ ID NO. 1112 | 127.734 | 102.077 | 0.799 | HYPOX_O2_HCT116 |
| 2878 | CHD9 | SEQ ID NO. 1112 | 16.794 | 9.731 | 0.579 | HYPOX_O2_HT1080 |

FIG. 1BW -- TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_N O_INDUCTION | PROM_ACTIVITY_W ITH_INDUCTION | INDUCTION_RATIO | INDUCTION_CONDITIONS |
|---|---|---|---|---|---|---|
| 2879 | CYB561 | SEQ ID NO. 1113 | 185.999 | 108.019 | 0.581 | HYPOX_DFO_HCT116 |
| 2880 | CYB561 | SEQ ID NO. 1113 | 8.146 | 5.401 | 0.663 | HYPOX_DFO_HT1080 |
| 2881 | CYB561 | SEQ ID NO. 1113 | 185.999 | 184.314 | 0.991 | HYPOX_O2_HCT116 |
| 2882 | CYB561 | SEQ ID NO. 1113 | 8.146 | 6.956 | 0.854 | HYPOX_O2_HT1080 |
| 2883 | COL5A1 | SEQ ID NO. 1114 | 850.282 | 470.701 | 0.554 | HYPOX_DFO_HCT116 |
| 2884 | COL5A1 | SEQ ID NO. 1114 | 56.104 | 37.105 | 0.661 | HYPOX_DFO_HT1080 |
| 2885 | COL5A1 | SEQ ID NO. 1114 | 850.282 | 672.772 | 0.791 | HYPOX_O2_HCT116 |
| 2886 | COL5A1 | SEQ ID NO. 1114 | 56.104 | 60.442 | 1.077 | HYPOX_O2_HT1080 |
| 2887 | NFIX | SEQ ID NO. 1115 | 68.751 | 65.533 | 0.953 | HYPOX_DFO_HCT116 |
| 2888 | NFIX | SEQ ID NO. 1115 | 4.008 | 9.405 | 2.346 | HYPOX_DFO_HT1080 |
| 2889 | NFIX | SEQ ID NO. 1115 | 68.751 | 79.18 | 1.152 | HYPOX_O2_HCT116 |
| 2890 | NFIX | SEQ ID NO. 1115 | 4.008 | 8.17 | 2.038 | HYPOX_O2_HT1080 |
| 2891 | NULL | SEQ ID NO. 1116 | 4019.52 | 2652.756 | 0.66 | HYPOX_DFO_HCT116 |
| 2892 | NULL | SEQ ID NO. 1116 | 1622.326 | 1172.313 | 0.723 | HYPOX_DFO_HT1080 |
| 2893 | NULL | SEQ ID NO. 1116 | 4019.52 | 5181.82 | 1.289 | HYPOX_O2_HCT116 |
| 2894 | NULL | SEQ ID NO. 1116 | 1622.326 | 1204.6 | 0.743 | HYPOX_O2_HT1080 |
| 2895 | IRF9 | SEQ ID NO. 1117 | 0.203 | 0.352 | 1.73 | HYPOX_DFO_HCT116 |
| 2896 | IRF9 | SEQ ID NO. 1117 | 0.077 | 0.115 | 1.499 | HYPOX_DFO_HT1080 |
| 2897 | IRF9 | SEQ ID NO. 1117 | 0.203 | 0.568 | 2.792 | HYPOX_O2_HCT116 |
| 2898 | IRF9 | SEQ ID NO. 1117 | 0.077 | 0.571 | 7.423 | HYPOX_O2_HT1080 |
| 2899 | COL8A2 | SEQ ID NO. 1118 | 27.781 | 7.244 | 0.261 | HYPOX_DFO_HCT116 |
| 2900 | COL8A2 | SEQ ID NO. 1118 | 1.184 | 1.337 | 1.129 | HYPOX_DFO_HT1080 |
| 2901 | COL8A2 | SEQ ID NO. 1118 | 27.781 | 17.752 | 0.639 | HYPOX_O2_HCT116 |
| 2902 | COL8A2 | SEQ ID NO. 1118 | 1.184 | 1.14 | 0.962 | HYPOX_O2_HT1080 |
| 2903 | RGMB | SEQ ID NO. 1119 | 225.195 | 122.023 | 0.542 | HYPOX_DFO_HCT116 |
| 2904 | RGMB | SEQ ID NO. 1119 | 37.482 | 21.035 | 0.561 | HYPOX_DFO_HT1080 |
| 2905 | RGMB | SEQ ID NO. 1119 | 225.195 | 180.103 | 0.8 | HYPOX_O2_HCT116 |
| 2906 | RGMB | SEQ ID NO. 1119 | 37.482 | 22.524 | 0.601 | HYPOX_O2_HT1080 |
| 2907 | MZF1 | SEQ ID NO. 1120 | 898.437 | 1144.64 | 1.274 | HYPOX_DFO_HCT116 |
| 2908 | MZF1 | SEQ ID NO. 1120 | 259.175 | 511.137 | 1.972 | HYPOX_DFO_HT1080 |
| 2909 | MZF1 | SEQ ID NO. 1120 | 898.437 | 1650.623 | 1.837 | HYPOX_O2_HCT116 |
| 2910 | MZF1 | SEQ ID NO. 1120 | 259.175 | 295.531 | 1.14 | HYPOX_O2_HT1080 |
| 2911 | CSGALNACT2 | SEQ ID NO. 1121 | 319.7 | 235.41 | 0.736 | HYPOX_DFO_HCT116 |
| 2912 | CSGALNACT2 | SEQ ID NO. 1121 | 37.217 | 45.961 | 1.235 | HYPOX_DFO_HT1080 |
| 2913 | CSGALNACT2 | SEQ ID NO. 1121 | 319.7 | 571.559 | 1.788 | HYPOX_O2_HCT116 |
| 2914 | CSGALNACT2 | SEQ ID NO. 1121 | 37.217 | 41.782 | 1.123 | HYPOX_O2_HT1080 |
| 2915 | PGD | SEQ ID NO. 1121 | 1078.115 | 495.957 | 0.46 | HYPOX_DFO_HCT116 |
| 2916 | PGD | SEQ ID NO. 1121 | 58.103 | 34.036 | 0.586 | HYPOX_DFO_HT1080 |
| 2917 | PGD | SEQ ID NO. 1121 | 1078.115 | 831.598 | 0.771 | HYPOX_O2_HCT116 |
| 2918 | PGD | SEQ ID NO. 1121 | 58.103 | 40.498 | 0.697 | HYPOX_O2_HT1080 |
| 2919 | VCAM1 | SEQ ID NO. 1121 | 63.318 | 21.12 | 0.334 | HYPOX_DFO_HCT116 |
| 2920 | VCAM1 | SEQ ID NO. 1121 | 2.879 | 1.376 | 0.478 | HYPOX_DFO_HT1080 |
| 2921 | VCAM1 | SEQ ID NO. 1121 | 63.318 | 35.856 | 0.566 | HYPOX_O2_HCT116 |
| 2922 | VCAM1 | SEQ ID NO. 1121 | 2.879 | 2.007 | 0.697 | HYPOX_O2_HT1080 |

FIG. 1BX — TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS |
|---|---|---|---|---|---|---|
| 2923 | MXI1 | SEQ ID NO. 1122 | 117.161 | 76.35 | 0.652 | HYPOX_DFO_HCT116 |
| 2924 | MXI1 | SEQ ID NO. 1122 | 11.146 | 10.291 | 0.923 | HYPOX_DFO_HT1080 |
| 2925 | MXI1 | SEQ ID NO. 1122 | 117.161 | 84.411 | 0.72 | HYPOX_O2_HCT116 |
| 2926 | MXI1 | SEQ ID NO. 1122 | 11.146 | 6.241 | 0.56 | HYPOX_O2_HT1080 |
| 2927 | MXI1 | SEQ ID NO. 1123 | 249.768 | 143.25 | 0.574 | HYPOX_DFO_HCT116 |
| 2928 | MXI1 | SEQ ID NO. 1123 | 2.504 | 1.715 | 0.685 | HYPOX_DFO_HT1080 |
| 2929 | MXI1 | SEQ ID NO. 1123 | 249.768 | 127.591 | 0.511 | HYPOX_O2_HCT116 |
| 2930 | MXI1 | SEQ ID NO. 1123 | 2.504 | 1.766 | 0.705 | HYPOX_O2_HT1080 |
| 2931 | CDH15 | SEQ ID NO. 1124 | 233.161 | 214.473 | 0.92 | HYPOX_DFO_HCT116 |
| 2932 | CDH15 | SEQ ID NO. 1124 | 9.087 | 37.122 | 4.085 | HYPOX_DFO_HT1080 |
| 2933 | CDH15 | SEQ ID NO. 1124 | 233.161 | 212 | 0.909 | HYPOX_O2_HCT116 |
| 2934 | CDH15 | SEQ ID NO. 1124 | 9.087 | 19.252 | 2.119 | HYPOX_O2_HT1080 |
| 2935 | FDXR | SEQ ID NO. 1125 | 451.511 | 589.691 | 1.307 | HYPOX_DFO_HCT116 |
| 2936 | FDXR | SEQ ID NO. 1125 | 127.31 | 162.734 | 1.278 | HYPOX_DFO_HT1080 |
| 2937 | FDXR | SEQ ID NO. 1125 | 451.511 | 447.571 | 0.991 | HYPOX_O2_HCT116 |
| 2938 | FDXR | SEQ ID NO. 1125 | 127.31 | 87.618 | 0.688 | HYPOX_O2_HT1080 |
| 2939 | COX7A2L | SEQ ID NO. 1126 | 1616.084 | 2467.961 | 1.527 | HYPOX_DFO_HCT116 |
| 2940 | COX7A2L | SEQ ID NO. 1126 | 538.856 | 469.048 | 0.87 | HYPOX_DFO_HT1080 |
| 2941 | COX7A2L | SEQ ID NO. 1126 | 1616.084 | 2917.884 | 1.806 | HYPOX_O2_HCT116 |
| 2942 | COX7A2L | SEQ ID NO. 1126 | 538.856 | 343.284 | 0.637 | HYPOX_O2_HT1080 |
| 2943 | APOBEC3C | SEQ ID NO. 1127 | 226.438 | 69.388 | 0.306 | HYPOX_DFO_HCT116 |
| 2944 | APOBEC3C | SEQ ID NO. 1127 | 12.139 | 6.125 | 0.505 | HYPOX_DFO_HT1080 |
| 2945 | APOBEC3C | SEQ ID NO. 1127 | 226.438 | 149.428 | 0.66 | HYPOX_O2_HCT116 |
| 2946 | APOBEC3C | SEQ ID NO. 1127 | 12.139 | 9.684 | 0.799 | HYPOX_O2_HT1080 |
| 2947 | SEC62 | SEQ ID NO. 1128 | 244.948 | 98.272 | 0.401 | HYPOX_DFO_HCT116 |
| 2948 | SEC62 | SEQ ID NO. 1128 | 109.85 | 61.217 | 0.557 | HYPOX_DFO_HT1080 |
| 2949 | SEC62 | SEQ ID NO. 1128 | 244.948 | 167.911 | 0.685 | HYPOX_O2_HCT116 |
| 2950 | SEC62 | SEQ ID NO. 1128 | 109.85 | 100.495 | 0.915 | HYPOX_O2_HT1080 |
| 2951 | SEC62 | SEQ ID NO. 1129 | 32.43 | 9.335 | 0.288 | HYPOX_DFO_HCT116 |
| 2952 | SEC62 | SEQ ID NO. 1129 | 0.883 | 1.269 | 1.437 | HYPOX_DFO_HT1080 |
| 2953 | SEC62 | SEQ ID NO. 1129 | 32.43 | 13.575 | 0.419 | HYPOX_O2_HCT116 |
| 2954 | SEC62 | SEQ ID NO. 1129 | 0.883 | 0.549 | 0.622 | HYPOX_O2_HT1080 |
| 2955 | SEC62 | SEQ ID NO. 1130 | 2.535 | 1.7 | 0.671 | HYPOX_DFO_HCT116 |
| 2956 | SEC62 | SEQ ID NO. 1130 | 0.456 | 0.478 | 1.048 | HYPOX_DFO_HT1080 |
| 2957 | SEC62 | SEQ ID NO. 1130 | 2.535 | 1.836 | 0.724 | HYPOX_O2_HCT116 |
| 2958 | SEC62 | SEQ ID NO. 1130 | 0.456 | 0.381 | 0.835 | HYPOX_O2_HT1080 |
| 2959 | MAPK10 | SEQ ID NO. 1131 | 32.522 | 11.68 | 0.359 | HYPOX_DFO_HCT116 |
| 2960 | MAPK10 | SEQ ID NO. 1131 | 11.962 | 7.743 | 0.647 | HYPOX_DFO_HT1080 |
| 2961 | MAPK10 | SEQ ID NO. 1131 | 32.522 | 10.692 | 0.328 | HYPOX_O2_HCT116 |
| 2962 | MAPK10 | SEQ ID NO. 1131 | 11.962 | 8.437 | 0.705 | HYPOX_O2_HT1080 |
| 2963 | MAPK10 | SEQ ID NO. 1132 | 3.778 | 1.549 | 0.41 | HYPOX_DFO_HCT116 |
| 2964 | MAPK10 | SEQ ID NO. 1132 | 0.276 | 0.186 | 0.674 | HYPOX_DFO_HT1080 |
| 2965 | MAPK10 | SEQ ID NO. 1132 | 3.778 | 3.258 | 0.862 | HYPOX_O2_HCT116 |
| 2966 | MAPK10 | SEQ ID NO. 1132 | 0.276 | 0.179 | 0.649 | HYPOX_O2_HT1080 |
| 2967 | GCLC | SEQ ID NO. 1133 | 427.273 | 326.084 | 0.763 | HYPOX_DFO_HCT116 |
| 2968 | GCLC | SEQ ID NO. 1133 | 26.311 | 23.387 | 0.889 | HYPOX_DFO_HT1080 |
| 2969 | GCLC | SEQ ID NO. 1133 | 427.273 | 213.827 | 0.501 | HYPOX_O2_HCT116 |
| 2970 | GCLC | SEQ ID NO. 1133 | 26.311 | 16.074 | 0.619 | HYPOX_O2_HT1080 |

FIG. 1BY -- TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_M O_INDUCTION | PROM_ACTIVITY_WI TH_INDUCTION | INDUCTION _RATIO | INDUCTION_CONDITIONS" |
|---|---|---|---|---|---|---|
| 2971 | RHOBTB2 | SEQ ID NO. 1134 | 88.457 | 38.304 | 0.433 | HYPOX_DFO_HCT116 |
| 2972 | RHOBTB2 | SEQ ID NO. 1134 | 17.727 | 14.451 | 0.815 | HYPOX_DFO_HT1080 |
| 2973 | RHOBTB2 | SEQ ID NO. 1134 | 88.457 | 76.841 | 0.869 | HYPOX_O2_HCT116 |
| 2974 | RHOBTB2 | SEQ ID NO. 1134 | 17.727 | 13.943 | 0.787 | HYPOX_O2_HT1080 |
| 2975 | MDRG1 | SEQ ID NO. 1135 | 2939.745 | 4068.42 | 1.384 | HYPOX_DFO_HCT116 |
| 2976 | MDRG1 | SEQ ID NO. 1135 | 256.435 | 372.719 | 1.453 | HYPOX_DFO_HT1080 |
| 2977 | MDRG1 | SEQ ID NO. 1135 | 2939.745 | 5016.674 | 1.706 | HYPOX_O2_HCT116 |
| 2978 | MDRG1 | SEQ ID NO. 1135 | 256.435 | 252.658 | 0.985 | HYPOX_O2_HT1080 |
| 2979 | PAPPA | SEQ ID NO. 1136 | 2.441 | 3.112 | 1.275 | HYPOX_DFO_HCT116 |
| 2980 | PAPPA | SEQ ID NO. 1136 | 1.21 | 1.817 | 1.503 | HYPOX_DFO_HT1080 |
| 2981 | PAPPA | SEQ ID NO. 1136 | 2.441 | 2.165 | 0.887 | HYPOX_O2_HCT116 |
| 2982 | PAPPA | SEQ ID NO. 1136 | 1.21 | 0.771 | 0.637 | HYPOX_O2_HT1080 |
| 2983 | PAPPA | SEQ ID NO. 1137 | 71.409 | 29.141 | 0.408 | HYPOX_DFO_HCT116 |
| 2984 | PAPPA | SEQ ID NO. 1137 | 1.068 | 0.726 | 0.68 | HYPOX_DFO_HT1080 |
| 2985 | PAPPA | SEQ ID NO. 1137 | 71.409 | 29.608 | 0.415 | HYPOX_O2_HCT116 |
| 2986 | PAPPA | SEQ ID NO. 1137 | 1.068 | 0.811 | 0.76 | HYPOX_O2_HT1080 |
| 2987 | PTGES | SEQ ID NO. 1138 | 10.928 | 18.356 | 1.68 | HYPOX_DFO_HCT116 |
| 2988 | PTGES | SEQ ID NO. 1138 | 1.589 | 1.667 | 1.049 | HYPOX_DFO_HT1080 |
| 2989 | PTGES | SEQ ID NO. 1138 | 10.928 | 10.799 | 0.988 | HYPOX_O2_HCT116 |
| 2990 | PTGES | SEQ ID NO. 1138 | 1.589 | 3.935 | 2.477 | HYPOX_O2_HT1080 |
| 2991 | HOOK1 | SEQ ID NO. 1139 | 8.206 | 4.065 | 0.495 | HYPOX_DFO_HCT116 |
| 2992 | HOOK1 | SEQ ID NO. 1139 | 0.311 | 0.155 | 0.5 | HYPOX_DFO_HT1080 |
| 2993 | HOOK1 | SEQ ID NO. 1139 | 8.206 | 5.33 | 0.65 | HYPOX_O2_HCT116 |
| 2994 | HOOK1 | SEQ ID NO. 1139 | 0.311 | 0.226 | 0.727 | HYPOX_O2_HT1080 |
| 2995 | APOA2 | SEQ ID NO. 1139 | 6.296 | 8.93 | 1.418 | HYPOX_DFO_HCT116 |
| 2996 | APOA2 | SEQ ID NO. 1139 | 0.293 | 0.335 | 1.146 | HYPOX_DFO_HT1080 |
| 2997 | APOA2 | SEQ ID NO. 1139 | 6.296 | 3.677 | 0.584 | HYPOX_O2_HCT116 |
| 2998 | APOA2 | SEQ ID NO. 1139 | 0.293 | 0.822 | 2.808 | HYPOX_O2_HT1080 |
| 2999 | HSP90AA1 | SEQ ID NO. 1140 | 231.185 | 301.027 | 1.302 | HYPOX_DFO_HCT116 |
| 3000 | HSP90AA1 | SEQ ID NO. 1140 | 56.298 | 76.957 | 1.367 | HYPOX_DFO_HT1080 |
| 3001 | HSP90AA1 | SEQ ID NO. 1140 | 231.185 | 263.914 | 1.142 | HYPOX_O2_HCT116 |
| 3002 | HSP90AA1 | SEQ ID NO. 1140 | 56.298 | 77.38 | 1.374 | HYPOX_O2_HT1080 |
| 3003 | MT3 | SEQ ID NO. 1141 | 32.633 | 56.563 | 1.733 | HYPOX_DFO_HCT116 |
| 3004 | MT3 | SEQ ID NO. 1141 | 1.124 | 2.204 | 1.96 | HYPOX_DFO_HT1080 |
| 3005 | MT3 | SEQ ID NO. 1141 | 32.633 | 75.536 | 2.315 | HYPOX_O2_HCT116 |
| 3006 | MT3 | SEQ ID NO. 1141 | 1.124 | 2.135 | 1.898 | HYPOX_O2_HT1080 |
| 3007 | NOS2A | SEQ ID NO. 1142 | 240.793 | 136.88 | 0.568 | HYPOX_DFO_HCT116 |
| 3008 | NOS2A | SEQ ID NO. 1142 | 36.486 | 38.019 | 1.042 | HYPOX_DFO_HT1080 |
| 3009 | NOS2A | SEQ ID NO. 1142 | 240.793 | 137.713 | 0.572 | HYPOX_O2_HCT116 |
| 3010 | NOS2A | SEQ ID NO. 1142 | 36.486 | 27.474 | 0.753 | HYPOX_O2_HT1080 |
| 3011 | IL1R2 | SEQ ID NO. 1143 | 53.825 | 37.34 | 0.694 | HYPOX_DFO_HCT116 |
| 3012 | IL1R2 | SEQ ID NO. 1143 | 4.362 | 4.348 | 0.997 | HYPOX_DFO_HT1080 |
| 3013 | IL1R2 | SEQ ID NO. 1143 | 53.825 | 37.555 | 0.698 | HYPOX_O2_HCT116 |
| 3014 | IL1R2 | SEQ ID NO. 1143 | 4.362 | 2.974 | 0.682 | HYPOX_O2_HT1080 |
| 3015 | IL1R1 | SEQ ID NO. 1144 | 91.2 | 53.659 | 0.588 | HYPOX_DFO_HCT116 |
| 3016 | IL1R1 | SEQ ID NO. 1144 | 2.335 | 2.384 | 1.021 | HYPOX_DFO_HT1080 |
| 3017 | IL1R1 | SEQ ID NO. 1144 | 91.2 | 106.45 | 1.167 | HYPOX_O2_HCT116 |
| 3018 | IL1R1 | SEQ ID NO. 1144 | 2.335 | 2.126 | 0.911 | HYPOX_O2_HT1080 |

FIG. 1BZ — TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_M O_INDUCTION | PROM_ACTIVITY_WI TH_INDUCTION | INDUCTION_RATIO | INDUCTION_CONDITIONS* |
|---|---|---|---|---|---|---|
| 3019 | TXNRD2 | SEQ ID NO. 1145 | 9.209 | 5.261 | 0.571 | HYPOX_DFO_HCT116 |
| 3020 | TXNRD2 | SEQ ID NO. 1145 | 1.254 | 1.404 | 1.119 | HYPOX_DFO_HT1080 |
| 3021 | TXNRD2 | SEQ ID NO. 1145 | 9.209 | 5.378 | 0.584 | HYPOX_O2_HCT116 |
| 3022 | TXNRD2 | SEQ ID NO. 1145 | 1.254 | 1.457 | 1.162 | HYPOX_O2_HT1080 |
| 3023 | GPX1 | SEQ ID NO. 1145 | 292.703 | 333.944 | 1.141 | HYPOX_DFO_HCT116 |
| 3024 | GPX1 | SEQ ID NO. 1145 | 75.309 | 95.871 | 1.273 | HYPOX_DFO_HT1080 |
| 3025 | GPX1 | SEQ ID NO. 1145 | 292.708 | 227.491 | 0.777 | HYPOX_O2_HCT116 |
| 3026 | GPX1 | SEQ ID NO. 1145 | 75.309 | 74.135 | 0.984 | HYPOX_O2_HT1080 |
| 3027 | TFRC | SEQ ID NO. 1146 | 11.089 | 3.389 | 0.306 | HYPOX_DFO_HCT116 |
| 3028 | TFRC | SEQ ID NO. 1146 | 0.877 | 0.716 | 0.817 | HYPOX_DFO_HT1080 |
| 3029 | TFRC | SEQ ID NO. 1146 | 11.089 | 2.86 | 0.258 | HYPOX_O2_HCT116 |
| 3030 | TFRC | SEQ ID NO. 1146 | 0.377 | 0.382 | 1.006 | HYPOX_O2_HT1080 |
| 3031 | VEGFA | SEQ ID NO. 1147 | 719.472 | 252.636 | 0.351 | HYPOX_DFO_HCT116 |
| 3032 | VEGFA | SEQ ID NO. 1147 | 26.895 | 21.278 | 0.791 | HYPOX_DFO_HT1080 |
| 3033 | VEGFA | SEQ ID NO. 1147 | 719.472 | 634.547 | 0.882 | HYPOX_O2_HCT116 |
| 3034 | VEGFA | SEQ ID NO. 1147 | 26.895 | 30.382 | 1.13 | HYPOX_O2_HT1080 |
| 3035 | AK3 | SEQ ID NO. 1148 | 2.735 | 2.634 | 0.963 | HYPOX_DFO_HCT116 |
| 3036 | AK3 | SEQ ID NO. 1148 | 0.735 | 2.72 | 3.7 | HYPOX_DFO_HT1080 |
| 3037 | AK3 | SEQ ID NO. 1148 | 2.735 | 6.965 | 2.546 | HYPOX_O2_HCT116 |
| 3038 | AK3 | SEQ ID NO. 1148 | 0.735 | 1.692 | 2.302 | HYPOX_O2_HT1080 |
| 3039 | APOA2 | SEQ ID NO. 1149 | 8.311 | 6.751 | 0.812 | HYPOX_DFO_HCT116 |
| 3040 | APOA2 | SEQ ID NO. 1149 | 0.695 | 0.637 | 0.916 | HYPOX_DFO_HT1080 |
| 3041 | APOA2 | SEQ ID NO. 1149 | 8.311 | 6.996 | 0.842 | HYPOX_O2_HCT116 |
| 3042 | APOA2 | SEQ ID NO. 1149 | 0.695 | 0.498 | 0.718 | HYPOX_O2_HT1080 |
| 3043 | APAF1 | SEQ ID NO. 1150 | 2.902 | 1.073 | 0.37 | HYPOX_DFO_HCT116 |
| 3044 | APAF1 | SEQ ID NO. 1150 | 0.284 | 0.192 | 0.676 | HYPOX_DFO_HT1080 |
| 3045 | APAF1 | SEQ ID NO. 1150 | 2.902 | 1.387 | 0.478 | HYPOX_O2_HCT116 |
| 3046 | APAF1 | SEQ ID NO. 1150 | 0.284 | 0.178 | 0.625 | HYPOX_O2_HT1080 |
| 3047 | ARNT2 | SEQ ID NO. 1151 | 2.823 | 1.761 | 0.624 | HYPOX_DFO_HCT116 |
| 3048 | ARNT2 | SEQ ID NO. 1151 | 0.443 | 0.603 | 1.361 | HYPOX_DFO_HT1080 |
| 3049 | ARNT2 | SEQ ID NO. 1151 | 2.823 | 2.351 | 0.833 | HYPOX_O2_HCT116 |
| 3050 | ARNT2 | SEQ ID NO. 1151 | 0.443 | 0.31 | 0.699 | HYPOX_O2_HT1080 |
| 3051 | CCL5 | SEQ ID NO. 1151 | 53.656 | 51.604 | 0.963 | HYPOX_DFO_HCT116 |
| 3052 | CCL5 | SEQ ID NO. 1151 | 10.392 | 8.019 | 0.772 | HYPOX_DFO_HT1080 |
| 3053 | CCL5 | SEQ ID NO. 1151 | 53.656 | 46.585 | 0.868 | HYPOX_O2_HCT116 |
| 3054 | CCL5 | SEQ ID NO. 1151 | 10.392 | 8.145 | 0.784 | HYPOX_O2_HT1080 |
| 3055 | IL1R1 | SEQ ID NO. 1152 | 138.918 | 31.906 | 0.23 | HYPOX_DFO_HCT116 |
| 3056 | IL1R1 | SEQ ID NO. 1152 | 8.055 | 4.872 | 0.605 | HYPOX_DFO_HT1080 |
| 3057 | IL1R1 | SEQ ID NO. 1152 | 138.918 | 60.312 | 0.434 | HYPOX_O2_HCT116 |
| 3058 | IL1R1 | SEQ ID NO. 1152 | 8.055 | 4.386 | 0.544 | HYPOX_O2_HT1080 |
| 3059 | IL18R1 | SEQ ID NO. 1153 | 2.83 | 2.859 | 1.011 | HYPOX_DFO_HCT116 |
| 3060 | IL18R1 | SEQ ID NO. 1153 | 0.14 | 1.116 | 7.957 | HYPOX_DFO_HT1080 |
| 3061 | IL18R1 | SEQ ID NO. 1153 | 2.83 | 1.33 | 0.47 | HYPOX_O2_HCT116 |
| 3062 | IL18R1 | SEQ ID NO. 1153 | 0.14 | 0.315 | 2.245 | HYPOX_O2_HT1080 |
| 3063 | IL13 | SEQ ID NO. 1154 | 7.749 | 3.068 | 0.396 | HYPOX_DFO_HCT116 |
| 3064 | IL13 | SEQ ID NO. 1154 | 1.195 | 0.967 | 0.809 | HYPOX_DFO_HT1080 |
| 3065 | IL13 | SEQ ID NO. 1154 | 7.749 | 3.259 | 0.421 | HYPOX_O2_HCT116 |
| 3066 | IL13 | SEQ ID NO. 1154 | 1.195 | 1.214 | 1.016 | HYPOX_O2_HT1080 |

*FIG. 1CA* -- TABLE 1 TRANSCRIPTIONAL BIOMARKER FUNCTIONAL DATA
SECTION 1A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS* |
|---|---|---|---|---|---|---|
| 3067 | PRKAA1 | SEQ ID NO. 1155 | 275.175 | 272.407 | 0.99 | HYPOX_DFO_HCT116 |
| 3068 | PRKAA1 | SEQ ID NO. 1155 | 107.763 | 88.086 | 0.817 | HYPOX_DFO_HT1080 |
| 3069 | PRKAA1 | SEQ ID NO. 1155 | 275.175 | 391.182 | 1.422 | HYPOX_O2_HCT116 |
| 3070 | PRKAA1 | SEQ ID NO. 1155 | 107.763 | 82.24 | 0.763 | HYPOX_O2_HT1080 |
| 3071 | EDN1 | SEQ ID NO. 1156 | 318.531 | 259.461 | 0.815 | HYPOX_DFO_HCT116 |
| 3072 | EDN1 | SEQ ID NO. 1156 | 79.058 | 71.137 | 0.9 | HYPOX_DFO_HT1080 |
| 3073 | EDN1 | SEQ ID NO. 1156 | 318.531 | 257.6 | 0.809 | HYPOX_O2_HCT116 |
| 3074 | EDN1 | SEQ ID NO. 1156 | 79.058 | 61.91 | 0.783 | HYPOX_O2_HT1080 |
| 3075 | IL1RN | SEQ ID NO. 1157 | 146.842 | 69.106 | 0.471 | HYPOX_DFO_HCT116 |
| 3076 | IL1RN | SEQ ID NO. 1157 | 12.826 | 7.35 | 0.573 | HYPOX_DFO_HT1080 |
| 3077 | IL1RN | SEQ ID NO. 1157 | 146.842 | 70.045 | 0.477 | HYPOX_O2_HCT116 |
| 3078 | IL1RN | SEQ ID NO. 1157 | 12.826 | 10.516 | 0.82 | HYPOX_O2_HT1080 |
| 3079 | TF | SEQ ID NO. 1158 | 24.907 | 14.833 | 0.596 | HYPOX_DFO_HCT116 |
| 3080 | TF | SEQ ID NO. 1158 | 2.218 | 1.553 | 0.7 | HYPOX_DFO_HT1080 |
| 3081 | TF | SEQ ID NO. 1158 | 24.907 | 19.689 | 0.791 | HYPOX_O2_HCT116 |
| 3082 | TF | SEQ ID NO. 1158 | 2.218 | 1.87 | 0.843 | HYPOX_O2_HT1080 |
| 3083 | ZBTB1 | SEQ ID NO. 1159 | 328.433 | 313.236 | 0.954 | HYPOX_DFO_HCT116 |
| 3084 | ZBTB1 | SEQ ID NO. 1159 | 43.19 | 44.614 | 1.033 | HYPOX_DFO_HT1080 |
| 3085 | ZBTB1 | SEQ ID NO. 1159 | 328.433 | 540.552 | 1.646 | HYPOX_O2_HCT116 |
| 3086 | ZBTB1 | SEQ ID NO. 1159 | 43.19 | 40.664 | 0.942 | HYPOX_O2_HT1080 |

FIG. 1CB — TABLE 1 TRANSCRIPTIONAL BIOMARKER FUNCTIONAL DATA
SECTION 11A

| LINE_ID | GENE_SYMBOL | SEQUENCE_ID_LISTING | PROM_ACTIVITY_NO_INDUCTION | PROM_ACTIVITY_WITH_INDUCTION | INDUCTION_RATIO | INDUCTION_CONDITIONS |
|---|---|---|---|---|---|---|
| 3087 | COMT | SEQ ID NO. 1158 | 0.606 | 0.578 | 0.954 | NFkB |
| 3088 | NELL | SEQ ID NO. 1159 | 0.042 | 0.086 | 2.032 | NFkB |
| 3089 | NR4A2 | SEQ ID NO. 1160 | 7.855 | 9.788 | 1.246 | NFkB |
| 3090 | RNASE2 | SEQ ID NO. 1160 | 0.27 | 0.31 | 1.151 | NFkB |
| 3091 | CCL15 | SEQ ID NO. 1161 | 0.212 | 0.271 | 1.281 | NFkB |
| 3092 | SCNN1A | SEQ ID NO. 1161 | 0.059 | 0.125 | 2.106 | NFkB |
| 3093 | SLC2A5 | SEQ ID NO. 1162 | 0.321 | 0.304 | 0.947 | NFkB |
| 3094 | BCL2 | SEQ ID NO. 1162 | 0.07 | 0.13 | 1.848 | NFkB |
| 3095 | TFPI2 | SEQ ID NO. 1163 | 2.172 | 4.916 | 2.263 | NFkB |
| 3096 | MEST | SEQ ID NO. 1163 | 0.958 | 0.924 | 0.965 | NFkB |
| 3097 | IL2 | SEQ ID NO. 1164 | 0.076 | 0.114 | 1.505 | NFkB |
| 3098 | IFNB1 | SEQ ID NO. 1165 | 23.527 | 24.962 | 1.061 | NFkB |
| 3099 | IL2RA | SEQ ID NO. 1166 | 0.401 | 0.475 | 1.185 | NFkB |
| 3100 | IER3 | SEQ ID NO. 1167 | 18.433 | 51.529 | 2.795 | NFkB |
| 3101 | CD36 | SEQ ID NO. 1167 | 0.331 | 0.201 | 0.607 | NFkB |
| 3102 | CCND1 | SEQ ID NO. 1168 | 3.92 | 2.9 | 0.74 | NFkB |
| 3103 | LTB | SEQ ID NO. 1169 | 1.365 | 1.165 | 0.854 | NFkB |
| 3104 | BCL2L1 | SEQ ID NO. 1170 | 1.903 | 2.002 | 1.052 | NFkB |
| 3105 | ADM | SEQ ID NO. 1170 | 18.475 | 17.251 | 0.888 | NFkB |
| 3106 | CCL2 | SEQ ID NO. 1170 | 20.678 | 13.789 | 0.667 | NFkB |
| 3107 | MOSC2A | SEQ ID NO. 1170 | 0.964 | 0.923 | 0.958 | NFkB |
| 3108 | IL1B | SEQ ID NO. 1170 | 7.952 | 10.816 | 1.36 | NFkB |
| 3109 | LTA | SEQ ID NO. 1170 | 1.339 | 1.817 | 1.357 | NFkB |
| 3110 | IL6 | SEQ ID NO. 1170 | 0.076 | 0.115 | 1.512 | NFkB |
| 3111 | IRF7 | SEQ ID NO. 1170 | 10.126 | 10.589 | 1.047 | NFkB |
| 3112 | CXCL5 | SEQ ID NO. 1170 | 0.844 | 1.978 | 2.343 | NFkB |
| 3113 | VEGFA | SEQ ID NO. 1170 | 0.168 | 0.25 | 1.49 | NFkB |
| 3114 | IL13 | SEQ ID NO. 1170 | 0.459 | 0.65 | 1.416 | NFkB |
| 3115 | SDPR | SEQ ID NO. 1170 | 1.849 | 1.829 | 0.989 | NFkB |
| 3116 | IL15 | SEQ ID NO. 1171 | 0.055 | 0.124 | 2.28 | NFkB |
| 3117 | SEPP1 | SEQ ID NO. 1172 | 0.068 | 0.087 | 1.268 | NFkB |
| 3118 | SEPP1 | SEQ ID NO. 1173 | 4.914 | 3.85 | 0.783 | NFkB |
| 3119 | SELP | SEQ ID NO. 1174 | 5.567 | 5.29 | 0.95 | NFkB |
| 3120 | IL1A | SEQ ID NO. 1175 | 0.039 | 0.064 | 1.659 | NFkB |
| 3121 | BDKRB1 | SEQ ID NO. 1176 | 8.428 | 22.715 | 2.695 | NFkB |
| 3122 | PTX3 | SEQ ID NO. 1177 | 0.542 | 2.433 | 4.491 | NFkB |
| 3123 | SEPP1 | SEQ ID NO. 1178 | 0.04 | 0.062 | 1.58 | NFkB |
| 3124 | BCL2 | SEQ ID NO. 1179 | 0.389 | 0.236 | 0.619 | NFkB |
| 3125 | DEFB104A | SEQ ID NO. 1180 | 0.057 | 0.059 | 1.041 | NFkB |
| 3126 | IL1RN | SEQ ID NO. 1181 | 0.109 | 0.137 | 1.255 | NFkB |
| 3127 | CCL11 | SEQ ID NO. 1182 | 0.045 | 0.063 | 1.381 | NFkB |
| 3128 | CSRP1 | SEQ ID NO. 1183 | 0.902 | 0.662 | 0.734 | NFkB |
| 3129 | CNTN1 | SEQ ID NO. 1184 | 0.641 | 0.412 | 0.643 | NFkB |
| 3130 | CXCR5 | SEQ ID NO. 1185 | 0.418 | 0.539 | 1.288 | NFkB |
| 3131 | TAP1 | SEQ ID NO. 1186 | 0.045 | 0.062 | 1.367 | NFkB |
| 3132 | CD209 | SEQ ID NO. 1187 | 1.736 | 1.494 | 0.861 | NFkB |
| 3133 | ELF3 | SEQ ID NO. 1188 | 0.027 | 0.047 | 1.728 | NFkB |
| 3134 | IRF2 | SEQ ID NO. 1189 | 0.141 | 0.185 | 1.307 | NFkB |

FIG. 1CC -- TABLE 1 TRANSCRIPTIONAL BIOMARKER FUNCTIONAL DATA
SECTION 11A

| LINE_ID | GENE_SYMBOL | SEQUENCE_ID_LISTING | PROM_ACTIVITY_N_O_INDUCTION | PROM_ACTIVITY_WI_TH_INDUCTION | INDUCTION_RATIO | INDUCTION_CONDITIONS* |
|---|---|---|---|---|---|---|
| 3135 | SCMN1A | SEQ ID NO. 1190 | 0.121 | 0.152 | 1.261 | NFkB |
| 3136 | CD74 | SEQ ID NO. 1191 | 1.729 | 7.298 | 4.221 | NFkB |
| 3137 | OPRM1 | SEQ ID NO. 1192 | 0.038 | 0.036 | 0.955 | NFkB |
| 3138 | IL1RN | SEQ ID NO. 1193 | 5.36 | 16.203 | 3.023 | NFkB |
| 3139 | VEGFA | SEQ ID NO. 1194 | 0.107 | 0.154 | 1.439 | NFkB |
| 3140 | TGM2 | SEQ ID NO. 1195 | 0.317 | 0.322 | 1.016 | NFkB |
| 3141 | MMP9 | SEQ ID NO. 1196 | 0.557 | 2.334 | 4.188 | NFkB |
| 3142 | IL15RA | SEQ ID NO. 1197 | 0.096 | 0.089 | 0.923 | NFkB |
| 3143 | HMOX1 | SEQ ID NO. 1198 | 1.188 | 0.897 | 0.755 | NFkB |
| 3144 | IRF4 | SEQ ID NO. 1199 | 0.287 | 0.178 | 0.619 | NFkB |
| 3145 | AGER | SEQ ID NO. 1200 | 2.225 | 2.456 | 1.104 | NFkB |
| 3146 | CD83 | SEQ ID NO. 1201 | 0.314 | 1.386 | 4.411 | NFkB |
| 3147 | PSMA2 | SEQ ID NO. 1202 | 15.596 | 13.998 | 0.898 | NFkB |
| 3148 | NOD2 | SEQ ID NO. 1203 | 0.543 | 2.678 | 4.931 | NFkB |
| 3149 | PTGS2 | SEQ ID NO. 1203 | 0.584 | 0.533 | 0.913 | NFkB |
| 3150 | TNC | SEQ ID NO. 1204 | 2.225 | 2.175 | 0.978 | NFkB |
| 3151 | CSRP1 | SEQ ID NO. 1205 | 6.03 | 8.169 | 1.355 | NFkB |
| 3152 | MYC | SEQ ID NO. 1206 | 3.09 | 2.91 | 0.942 | NFkB |
| 3153 | CSF1 | SEQ ID NO. 1207 | 0.509 | 0.343 | 0.674 | NFkB |
| 3154 | CSF3 | SEQ ID NO. 1208 | 0.116 | 0.295 | 2.554 | NFkB |
| 3155 | IL15 | SEQ ID NO. 1209 | 3.574 | 11.885 | 3.325 | NFkB |
| 3156 | MYC | SEQ ID NO. 1210 | 0.082 | 0.085 | 1.044 | NFkB |
| 3157 | CD44 | SEQ ID NO. 1211 | 1.456 | 1.321 | 0.907 | NFkB |
| 3158 | PITX3 | SEQ ID NO. 1212 | 0.24 | 0.246 | 1.026 | NFkB |
| 3159 | ENG | SEQ ID NO. 1213 | 7.391 | 7.475 | 1.011 | NFkB |
| 3160 | NOL3 | SEQ ID NO. 1214 | 77.312 | 83.453 | 1.079 | NFkB |
| 3161 | PDGFB | SEQ ID NO. 1215 | 0.624 | 0.575 | 0.922 | NFkB |
| 3162 | PLCD1 | SEQ ID NO. 1216 | 1.783 | 1.082 | 0.607 | NFkB |
| 3163 | SOD2 | SEQ ID NO. 1217 | 30.694 | 30.468 | 0.993 | NFkB |
| 3164 | IRF4 | SEQ ID NO. 1218 | 2.495 | 2.518 | 1.009 | NFkB |
| 3165 | IL11 | SEQ ID NO. 1219 | 6.139 | 3.504 | 0.571 | NFkB |
| 3166 | SEPP1 | SEQ ID NO. 1220 | 0.101 | 0.127 | 1.267 | NFkB |
| 3167 | SOD2 | SEQ ID NO. 1221 | 0.118 | 0.13 | 1.101 | NFkB |
| 3168 | CD69 | SEQ ID NO. 1222 | 0.257 | 1.957 | 7.62 | NFkB |
| 3169 | IL9 | SEQ ID NO. 1223 | 1.156 | 1.247 | 1.079 | NFkB |

FIG. 1CD -- TABLE 1 TRANSCRIPTIONAL BIOMARKER FUNCTIONAL DATA
SECTION 11A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS* |
|---|---|---|---|---|---|---|
| 3170 | CRP | SEQ ID NO. 1224 | 0.111 | 0.1 | 0.897 | NFkB |
| 3171 | CCL15 | SEQ ID NO. 1225 | 0.148 | 0.139 | 0.944 | NFkB |
| 3172 | NOS2A | SEQ ID NO. 1226 | 16.271 | 8.751 | 0.538 | NFkB |
| 3173 | F3 | SEQ ID NO. 1227 | 0.103 | 0.236 | 2.289 | NFkB |
| 3174 | DEFB4 | SEQ ID NO. 1228 | 0.191 | 0.289 | 1.512 | NFkB |
| 3175 | TGM2 | SEQ ID NO. 1229 | 0.094 | 0.091 | 0.963 | NFkB |
| 3176 | ELF3 | SEQ ID NO. 1230 | 1.385 | 2.337 | 1.688 | NFkB |
| 3177 | TPM1 | SEQ ID NO. 1231 | 12.025 | 12.06 | 1.003 | NFkB |
| 3178 | IL6 | SEQ ID NO. 1232 | 0.22 | 0.23 | 1.045 | NFkB |
| 3179 | TGM2 | SEQ ID NO. 1233 | 0.585 | 1.173 | 2.005 | NFkB |
| 3180 | PTAFR | SEQ ID NO. 1234 | 0.169 | 0.197 | 1.166 | NFkB |
| 3181 | TNNC1 | SEQ ID NO. 1235 | 2.425 | 2.396 | 0.988 | NFkB |
| 3182 | ELF3 | SEQ ID NO. 1236 | 0.068 | 0.167 | 2.45 | NFkB |
| 3183 | NR4A2 | SEQ ID NO. 1237 | 0.186 | 0.13 | 0.7 | NFkB |
| 3184 | PSMB9 | SEQ ID NO. 1238 | 0.654 | 6.828 | 10.435 | NFkB |
| 3185 | PER1 | SEQ ID NO. 1238 | 15.89 | 8.45 | 0.532 | NFkB |
| 3186 | SNTA1 | SEQ ID NO. 1238 | 13.936 | 11.658 | 0.837 | NFkB |

FIG. 1CE -- TABLE 1 TRANSCRIPTIONAL BIOMARKER FUNCTIONAL DATA
SECTION 4A

| LINE_ID | GENE_SYMBOL | SEQUENCE_ID_LISTING | PROM_ACTIVITY_N 0_INDUCTION | PROM_ACTIVITY_WI TH_INDUCTION | INDUCTION_RATIO | INDUCTION_CONDITIONS |
|---|---|---|---|---|---|---|
| 3187 | GLRX2 | SEQ ID NO. 1238 | 1.114 | 0.943 | 0.847 | p53 |
| 3188 | NULL | SEQ ID NO. 1239 | 0.561 | 1.82 | 3.243 | p53 |
| 3189 | GLRX2 | SEQ ID NO. 1239 | 0.577 | 0.815 | 1.411 | p53 |
| 3190 | RAB14 | SEQ ID NO. 1240 | 0.484 | 0.506 | 1.045 | p53 |
| 3191 | NEDD9 | SEQ ID NO. 1240 | 2.467 | 1.902 | 0.771 | p53 |
| 3192 | IHPK2 | SEQ ID NO. 1241 | 0.248 | 0.323 | 1.3 | p53 |
| 3193 | TAX1BP1 | SEQ ID NO. 1242 | 0.08 | 0.075 | 0.935 | p53 |
| 3194 | NULL | SEQ ID NO. 1243 | 0.596 | 1.369 | 2.299 | p53 |
| 3195 | NULL | SEQ ID NO. 1244 | 2.067 | 2.025 | 0.979 | p53 |
| 3196 | PNPLA8 | SEQ ID NO. 1245 | 52.658 | 52.968 | 1.006 | p53 |
| 3197 | DNAH11 | SEQ ID NO. 1246 | 13.357 | 11.099 | 0.831 | p53 |
| 3198 | NULL | SEQ ID NO. 1247 | 0.154 | 0.385 | 2.508 | p53 |
| 3199 | REM33 | SEQ ID NO. 1248 | 1.822 | 2.491 | 1.367 | p53 |
| 3200 | TARP | SEQ ID NO. 1249 | 0.046 | 0.039 | 1.193 | p53 |
| 3201 | RAC1 | SEQ ID NO. 1250 | 0.21 | 0.511 | 2.43 | p53 |
| 3202 | NULL | SEQ ID NO. 1251 | 25.297 | 8.524 | 0.337 | p53 |
| 3203 | TAS2R4 | SEQ ID NO. 1252 | 0.201 | 0.281 | 1.397 | p53 |
| 3204 | NULL | SEQ ID NO. 1253 | 0.138 | 0.303 | 2.192 | p53 |
| 3205 | NULL | SEQ ID NO. 1254 | 0.277 | 0.717 | 2.593 | p53 |
| 3206 | NULL | SEQ ID NO. 1255 | 0.196 | 0.311 | 1.589 | p53 |
| 3207 | NULL | SEQ ID NO. 1256 | 0.262 | 0.312 | 1.192 | p53 |
| 3208 | EEPD1 | SEQ ID NO. 1257 | 0.213 | 0.301 | 1.414 | p53 |
| 3209 | RSPH10B | SEQ ID NO. 1258 | 0.85 | 1.109 | 1.305 | p53 |
| 3210 | CPA4 | SEQ ID NO. 1259 | 387.071 | 321.88 | 0.832 | p53 |
| 3211 | NULL | SEQ ID NO. 1260 | 10.49 | 29.57 | 2.819 | p53 |
| 3212 | NULL | SEQ ID NO. 1261 | 0.226 | 0.523 | 2.314 | p53 |
| 3213 | NULL | SEQ ID NO. 1262 | 1.896 | 1.098 | 0.579 | p53 |
| 3214 | PRSS2 | SEQ ID NO. 1263 | 0.147 | 0.215 | 1.461 | p53 |
| 3215 | LAMB1 | SEQ ID NO. 1264 | 0.087 | 0.172 | 1.976 | p53 |
| 3216 | EVX1 | SEQ ID NO. 1265 | 0.18 | 0.563 | 3.122 | p53 |
| 3217 | CALD1 | SEQ ID NO. 1266 | 0.588 | 0.691 | 1.175 | p53 |
| 3218 | WIPI2 | SEQ ID NO. 1267 | 0.648 | 0.92 | 1.42 | p53 |
| 3219 | NULL | SEQ ID NO. 1268 | 0.947 | 1.516 | 1.6 | p53 |
| 3220 | ATXN7L1 | SEQ ID NO. 1269 | 0.138 | 0.168 | 1.222 | p53 |
| 3221 | NULL | SEQ ID NO. 1270 | 1.997 | 2.889 | 1.447 | p53 |
| 3222 | TARP | SEQ ID NO. 1271 | 0.036 | 0.046 | 1.274 | p53 |
| 3223 | CPA3 | SEQ ID NO. 1272 | 12.233 | 5.197 | 0.425 | p53 |
| 3224 | tcag7.1177 | SEQ ID NO. 1273 | 9.953 | 10.519 | 1.057 | p53 |
| 3225 | NULL | SEQ ID NO. 1274 | 0.147 | 0.184 | 1.247 | p53 |
| 3226 | TMEM209 | SEQ ID NO. 1275 | 656.53 | 363.552 | 0.554 | p53 |
| 3227 | NULL | SEQ ID NO. 1276 | 0.139 | 0.392 | 2.814 | p53 |
| 3228 | ZNSCAN1 | SEQ ID NO. 1277 | 1.107 | 1.666 | 1.506 | p53 |
| 3229 | LRCH4 | SEQ ID NO. 1278 | 0.083 | 0.144 | 1.725 | p53 |
| 3230 | NULL | SEQ ID NO. 1279 | 1.082 | 1 | 0.924 | p53 |
| 3231 | NULL | SEQ ID NO. 1280 | 11.641 | 13.087 | 1.124 | p53 |
| 3232 | MRPL30 | SEQ ID NO. 1281 | 6.719 | 6.878 | 1.024 | p53 |

FIG. 1CF - TABLE 1 TRANSCRIPTIONAL BIOMARKER FUNCTIONAL DATA
SECTION 4A

| LINE_ID | GENE_SYMBOL | SEQUENCE_ID_LISTING | PROM_ACTIVITY_NO_INDUCTION | PROM_ACTIVITY_WI TH_INDUCTION | INDUCTION_RATIO | INDUCTION_CONDITIONS |
|---|---|---|---|---|---|---|
| 3233 | CALU | SEQ ID NO. 1282 | 13.329 | 14.714 | 1.104 | p53 |
| 3234 | CNPY4 | SEQ ID NO. 1283 | 1.53 | 1.874 | 1.224 | p53 |
| 3235 | GNA12 | SEQ ID NO. 1284 | 0.187 | 0.102 | 0.547 | p53 |
| 3236 | SRCRB4D | SEQ ID NO. 1285 | 4.325 | 2.489 | 0.575 | p53 |
| 3237 | C7orf60 | SEQ ID NO. 1286 | 139.996 | 165.029 | 1.179 | p53 |
| 3238 | NULL | SEQ ID NO. 1287 | 0.357 | 0.321 | 0.9 | p53 |
| 3239 | CALM1 | SEQ ID NO. 1288 | 0.596 | 1.08 | 1.812 | p53 |
| 3240 | TAF6 | SEQ ID NO. 1289 | 7.044 | 9.372 | 1.33 | p53 |
| 3241 | PSPH | SEQ ID NO. 1289 | 0.54 | 0.871 | 1.611 | p53 |
| 3242 | PSMA2 | SEQ ID NO. 1290 | 0.928 | 1.419 | 1.53 | p53 |
| 3243 | NULL | SEQ ID NO. 1291 | 0.348 | 0.43 | 1.237 | p53 |
| 3244 | AKAP8 | SEQ ID NO. 1291 | 4.542 | 5.428 | 1.195 | p53 |
| 3245 | FAM3C | SEQ ID NO. 1291 | 2.446 | 2.545 | 1.04 | p53 |
| 3246 | CCT6A | SEQ ID NO. 1292 | 19.278 | 22.722 | 1.179 | p53 |
| 3247 | NULL | SEQ ID NO. 1293 | 30.788 | 26.841 | 0.872 | p53 |
| 3248 | ECOP | SEQ ID NO. 1293 | 2.936 | 3.049 | 1.038 | p53 |
| 3249 | MYO1G | SEQ ID NO. 1294 | 0.324 | 0.538 | 1.662 | p53 |
| 3250 | MYO1G | SEQ ID NO. 1295 | 0.484 | 0.538 | 1.113 | p53 |
| 3251 | NULL | SEQ ID NO. 1296 | 0.249 | 0.376 | 1.512 | p53 |
| 3252 | ZCWPW1 | SEQ ID NO. 1297 | 18.967 | 12.441 | 0.656 | p53 |
| 3253 | GRM8 | SEQ ID NO. 1298 | 0.2 | 0.238 | 1.192 | p53 |
| 3254 | NULL | SEQ ID NO. 1298 | 35.408 | 14.135 | 0.399 | p53 |
| 3255 | MEPCE | SEQ ID NO. 1299 | 7.09 | 7.992 | 1.127 | p53 |
| 3256 | NULL | SEQ ID NO. 1299 | 3.017 | 1.08 | 0.535 | p53 |
| 3257 | HDAPV | SEQ ID NO. 1300 | 5.65 | 2.543 | 0.45 | p53 |
| 3258 | SNX8 | SEQ ID NO. 1301 | 1.6 | 1.802 | 1.128 | p53 |
| 3259 | GMEB2 | SEQ ID NO. 1302 | 0.574 | 0.57 | 0.992 | p53 |
| 3260 | ZCWPW1 | SEQ ID NO. 1303 | 1.108 | 1.107 | 0.999 | p53 |
| 3261 | CENTA1 | SEQ ID NO. 1304 | 0.358 | 0.406 | 1.134 | p53 |
| 3262 | PLOD3 | SEQ ID NO. 1304 | 23.238 | 31.698 | 1.364 | p53 |
| 3263 | TRIM74 | SEQ ID NO. 1305 | 0.432 | 0.919 | 2.128 | p53 |
| 3264 | NULL | SEQ ID NO. 1305 | 29.506 | 19.815 | 0.672 | p53 |
| 3265 | NULL | SEQ ID NO. 1305 | 5.941 | 6.129 | 1.032 | p53 |
| 3266 | TRIM74 | SEQ ID NO. 1306 | 0.216 | 0.537 | 2.487 | p53 |
| 3267 | MEPCE | SEQ ID NO. 1306 | 7.958 | 7.144 | 0.898 | p53 |
| 3268 | HERPUD2 | SEQ ID NO. 1307 | 1.679 | 2.111 | 1.258 | p53 |
| 3269 | FKBP5 | SEQ ID NO. 1308 | 0.289 | 0.67 | 2.317 | p53 |
| 3270 | NULL | SEQ ID NO. 1308 | 1.298 | 1.033 | 0.796 | p53 |
| 3271 | MCAPG2 | SEQ ID NO. 1308 | 34.013 | 7.626 | 0.224 | p53 |
| 3272 | NULL | SEQ ID NO. 1309 | 19.69 | 28.614 | 1.453 | p53 |
| 3273 | NULL | SEQ ID NO. 1310 | 0.317 | 0.513 | 1.618 | p53 |
| 3274 | MUB1 | SEQ ID NO. 1310 | 91.834 | 107.805 | 1.174 | p53 |
| 3275 | NULL | SEQ ID NO. 1310 | 3.656 | 11.242 | 3.075 | p53 |
| 3276 | SLC44A2 | SEQ ID NO. 1310 | 1.452 | 1.472 | 1.014 | p53 |
| 3277 | NULL | SEQ ID NO. 1311 | 0.204 | 0.25 | 1.224 | p53 |
| 3278 | NULL | SEQ ID NO. 1311 | 1.226 | 0.843 | 0.688 | p53 |
| 3279 | PSPH | SEQ ID NO. 1312 | 4.182 | 5.887 | 1.408 | p53 |
| 3280 | ZNF786 | SEQ ID NO. 1313 | 0.401 | 0.551 | 1.374 | p53 |

FIG. 1CG -- TABLE 1 TRANSCRIPTIONAL BIOMARKER FUNCTIONAL DATA
SECTION 4A

| LINE_ID | GENE_SYMBOL | SEQUENCE_ID_LISTING | PROM_ACTIVITY_N O_INDUCTION | PROM_ACTIVITY_N TH_INDUCTION | PROM_ACTIVITY_WI INDUCTION_RATIO | INDUCTION_CONDITIONS* |
|---|---|---|---|---|---|---|
| 3281 | REPIN1 | SEQ ID NO. 1313 | 3.631 | 4.983 | 1.372 | p53 |
| 3282 | ACTB | SEQ ID NO. 1314 | 77.803 | 88.987 | 1.143 | p53 |
| 3283 | MICALL2 | SEQ ID NO. 1314 | 1.714 | 1.412 | 0.824 | p53 |
| 3284 | POLK | SEQ ID NO. 1315 | 0.519 | 0.417 | 0.804 | p53 |
| 3285 | NOTCH2 | SEQ ID NO. 1316 | 0.249 | 0.293 | 1.175 | p53 |
| 3286 | USP16 | SEQ ID NO. 1317 | 0.076 | 0.062 | 0.811 | p53 |
| 3287 | LIG4 | SEQ ID NO. 1318 | 0.288 | 2.667 | 9.255 | p53 |
| 3288 | MCL1 | SEQ ID NO. 1319 | 0.182 | 0.19 | 1.043 | p53 |
| 3289 | NCKAP1 | SEQ ID NO. 1320 | 0.093 | 0.506 | 5.46 | p53 |
| 3290 | TIA1 | SEQ ID NO. 1321 | 0.079 | 0.156 | 1.972 | p53 |
| 3291 | RAB10 | SEQ ID NO. 1322 | 0.244 | 0.282 | 1.152 | p53 |
| 3292 | ALB | SEQ ID NO. 1323 | 1.722 | 0.728 | 0.423 | p53 |
| 3293 | PRG4 | SEQ ID NO. 1324 | 1.554 | 1.009 | 0.649 | p53 |
| 3294 | CDC42 | SEQ ID NO. 1325 | 0.028 | 0.036 | 1.27 | p53 |
| 3295 | GAS2 | SEQ ID NO. 1326 | 0.227 | 0.409 | 1.799 | p53 |
| 3296 | CD86 | SEQ ID NO. 1327 | 0.222 | 0.39 | 1.755 | p53 |
| 3297 | RBM5 | SEQ ID NO. 1328 | 0.215 | 0.159 | 0.741 | p53 |
| 3298 | TP63 | SEQ ID NO. 1329 | 0.26 | 0.282 | 1.085 | p53 |
| 3299 | APP | SEQ ID NO. 1330 | 0.558 | 0.924 | 1.656 | p53 |
| 3300 | EIF2AK2 | SEQ ID NO. 1331 | 0.2 | 0.197 | 0.985 | p53 |
| 3301 | PBOV1 | SEQ ID NO. 1332 | 0.73 | 0.657 | 0.9 | p53 |
| 3302 | BAG1 | SEQ ID NO. 1333 | 0.191 | 0.141 | 0.738 | p53 |
| 3303 | CTNNBL1 | SEQ ID NO. 1334 | 0.085 | 0.097 | 1.143 | p53 |
| 3304 | 1-Dec | SEQ ID NO. 1335 | 0.544 | 0.585 | 1.076 | p53 |
| 3305 | NIPBL | SEQ ID NO. 1336 | 0.121 | 0.176 | 1.455 | p53 |
| 3306 | USP16 | SEQ ID NO. 1337 | 1.246 | 1.619 | 1.299 | p53 |
| 3307 | GEM1 | SEQ ID NO. 1338 | 0.132 | 0.203 | 1.533 | p53 |
| 3308 | BACA | SEQ ID NO. 1339 | 0.417 | 0.432 | 1.036 | p53 |
| 3309 | IL17A | SEQ ID NO. 1340 | 0.489 | 1.084 | 2.219 | p53 |
| 3310 | RFFL | SEQ ID NO. 1341 | 29.862 | 20.644 | 0.681 | p53 |
| 3311 | MAP2K6 | SEQ ID NO. 1342 | 3.268 | 1.438 | 0.44 | p53 |
| 3312 | ST5 | SEQ ID NO. 1343 | 0.302 | 0.34 | 1.127 | p53 |
| 3313 | RAB7L1 | SEQ ID NO. 1344 | 3.057 | 3.322 | 1.087 | p53 |
| 3314 | SYCP1 | SEQ ID NO. 1345 | 0.411 | 0.28 | 0.681 | p53 |
| 3315 | IFNW1 | SEQ ID NO. 1346 | 0.213 | 0.258 | 1.213 | p53 |
| 3316 | RBM5 | SEQ ID NO. 1347 | 0.263 | 0.221 | 0.841 | p53 |
| 3317 | CD5L | SEQ ID NO. 1348 | 0.25 | 0.279 | 1.115 | p53 |
| 3318 | FILIP1L | SEQ ID NO. 1349 | 0.307 | 0.675 | 2.201 | p53 |
| 3319 | POLD3 | SEQ ID NO. 1350 | 10.228 | 3.168 | 0.31 | p53 |
| 3320 | CIDEC | SEQ ID NO. 1351 | 0.178 | 0.183 | 1.025 | p53 |
| 3321 | CCNG1 | SEQ ID NO. 1352 | 6.609 | 8.855 | 1.34 | p53 |
| 3322 | MONO | SEQ ID NO. 1353 | 0.268 | 0.227 | 0.846 | p53 |
| 3323 | XRCC6 | SEQ ID NO. 1354 | 0.675 | 0.658 | 0.975 | p53 |
| 3324 | CASC3 | SEQ ID NO. 1355 | 0.322 | 0.412 | 1.28 | p53 |
| 3325 | CD86 | SEQ ID NO. 1356 | 0.891 | 0.678 | 0.76 | p53 |
| 3326 | BRMS1L | SEQ ID NO. 1357 | 1.728 | 2.293 | 1.327 | p53 |
| 3327 | TERF1 | SEQ ID NO. 1358 | 0.071 | 0.157 | 2.201 | p53 |
| 3328 | CIDEC | SEQ ID NO. 1359 | 0.105 | 0.179 | 1.7 | p53 |

FIG. 1CH – TABLE 1 TRANSCRIPTIONAL BIOMARKER FUNCTIONAL DATA
SECTION 4A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS* |
|---|---|---|---|---|---|---|
| 3329 | RAB27B | SEQ ID NO. 1360 | 3.152 | 5.205 | 1.651 | p53 |
| 3330 | DNASE1L3 | SEQ ID NO. 1361 | 0.412 | 0.585 | 1.42 | p53 |
| 3331 | POLE | SEQ ID NO. 1362 | 0.041 | 0.054 | 1.328 | p53 |
| 3332 | FOXN3 | SEQ ID NO. 1363 | 0.814 | 1.233 | 1.515 | p53 |
| 3333 | MAPRE2 | SEQ ID NO. 1364 | 8.672 | 13.299 | 1.533 | p53 |
| 3334 | CIDEC | SEQ ID NO. 1365 | 0.205 | 0.343 | 1.672 | p53 |
| 3335 | CIDEC | SEQ ID NO. 1366 | 0.439 | 0.629 | 1.433 | p53 |
| 3336 | CD38 | SEQ ID NO. 1367 | 0.114 | 0.129 | 1.13 | p53 |
| 3337 | ERCC3 | SEQ ID NO. 1368 | 17.899 | 14.026 | 0.784 | p53 |
| 3338 | XPC | SEQ ID NO. 1369 | 314.268 | 736.905 | 2.345 | p53 |
| 3339 | RIPK3 | SEQ ID NO. 1370 | 0.865 | 0.808 | 0.934 | p53 |
| 3340 | CIT | SEQ ID NO. 1371 | 0.985 | 0.632 | 0.642 | p53 |
| 3341 | MTSS1 | SEQ ID NO. 1372 | 0.597 | 0.636 | 1.065 | p53 |
| 3342 | GFI1B | SEQ ID NO. 1373 | 0.563 | 0.558 | 0.991 | p53 |
| 3343 | NHLRC2 | SEQ ID NO. 1374 | 14.872 | 11.939 | 0.803 | p53 |
| 3344 | PTTG1IP | SEQ ID NO. 1375 | 0.206 | 0.158 | 0.766 | p53 |
| 3345 | PINX1 | SEQ ID NO. 1376 | 115.527 | 107.223 | 0.928 | p53 |
| 3346 | TOP2A | SEQ ID NO. 1377 | 12.808 | 5.484 | 0.428 | p53 |
| 3347 | MRPS11 | SEQ ID NO. 1378 | 5.102 | 6.931 | 1.359 | p53 |
| 3348 | GTF2H4 | SEQ ID NO. 1379 | 203.133 | 205.13 | 1.01 | p53 |
| 3349 | GDNF | SEQ ID NO. 1380 | 0.823 | 0.814 | 0.989 | p53 |
| 3350 | IER3 | SEQ ID NO. 1381 | 4.978 | 19.089 | 3.834 | p53 |
| 3351 | SPHK1 | SEQ ID NO. 1382 | 0.089 | 0.122 | 1.757 | p53 |
| 3352 | RUVBL2 | SEQ ID NO. 1383 | 0.824 | 0.628 | 0.625 | p53 |
| 3353 | NOD2 | SEQ ID NO. 1384 | 0.225 | 0.33 | 1.467 | p53 |
| 3354 | IL2RA | SEQ ID NO. 1385 | 0.128 | 0.342 | 2.675 | p53 |
| 3355 | POLG2 | SEQ ID NO. 1386 | 1.508 | 1.381 | 0.916 | p53 |
| 3356 | TRAF1 | SEQ ID NO. 1387 | 1.243 | 3.327 | 2.678 | p53 |
| 3357 | SULT1A3 | SEQ ID NO. 1388 | 1.198 | 1.37 | 1.144 | p53 |
| 3358 | PPM1F | SEQ ID NO. 1389 | 64.594 | 26.375 | 0.408 | p53 |
| 3359 | GLCCI1 | SEQ ID NO. 1390 | 1.299 | 1.151 | 0.886 | p53 |
| 3360 | GATC | SEQ ID NO. 1391 | 0.562 | 0.629 | 1.119 | p53 |
| 3361 | RAB7L1 | SEQ ID NO. 1392 | 0.396 | 0.465 | 1.174 | p53 |
| 3362 | CLK1 | SEQ ID NO. 1393 | 10.726 | 21.485 | 2.003 | p53 |
| 3363 | SON | SEQ ID NO. 1394 | 0.416 | 0.33 | 0.793 | p53 |
| 3364 | OPA1 | SEQ ID NO. 1395 | 95.118 | 105.705 | 1.111 | p53 |
| 3365 | SILV | SEQ ID NO. 1396 | 0.178 | 0.186 | 1.046 | p53 |
| 3366 | CARD14 | SEQ ID NO. 1397 | 9.477 | 9.482 | 1.001 | p53 |
| 3367 | PARC | SEQ ID NO. 1398 | 1.065 | 0.65 | 0.61 | p53 |
| 3368 | MRPL46 | SEQ ID NO. 1399 | 0.853 | 1.207 | 1.415 | p53 |
| 3369 | RPA3 | SEQ ID NO. 1400 | 1.225 | 3.862 | 3.154 | p53 |
| 3370 | TNFRSF10B | SEQ ID NO. 1401 | 1.181 | 0.739 | 0.626 | p53 |
| 3371 | IGHMBP2 | SEQ ID NO. 1402 | 0.758 | 1.115 | 1.47 | p53 |
| 3372 | TOX4 | SEQ ID NO. 1403 | 95.223 | 109.497 | 1.15 | p53 |
| 3373 | ITGB2 | SEQ ID NO. 1404 | 0.432 | 1.602 | 3.713 | p53 |
| 3374 | GART | SEQ ID NO. 1405 | 7.855 | 12.378 | 1.576 | p53 |
| 3375 | LCAT | SEQ ID NO. 1406 | 41.177 | 30.935 | 0.751 | p53 |
| 3376 | CCNY | SEQ ID NO. 1407 | 0.795 | 0.543 | 0.682 | p53 |

FIG. 1CI – TABLE 1 TRANSCRIPTIONAL BIOMARKER FUNCTIONAL DATA
SECTION 4A

| LINE_ID | GENE_SYMBOL | SEQUENCE_ID_LISTING | PROM_ACTIVITY_N O_INDUCTION | PROM_ACTIVITY_W TH_INDUCTION | PROM_ACTIVITY_WI _RATIO | INDUCTION INDUCTION_CONDITIONS* |
|---|---|---|---|---|---|---|
| 3377 | FGF1 | SEQ ID NO. 1407 | 0.293 | 1.49 | 5.084 | p53 |
| 3378 | PTTG1IP | SEQ ID NO. 1408 | 1.173 | 0.972 | 0.829 | p53 |
| 3379 | BSG3 | SEQ ID NO. 1409 | 2.676 | 3.947 | 1.475 | p53 |
| 3380 | HSPA5 | SEQ ID NO. 1410 | 2226.016 | 2223.837 | 0.999 | p53 |
| 3381 | SILV | SEQ ID NO. 1411 | 0.043 | 0.071 | 1.633 | p53 |
| 3382 | SPN | SEQ ID NO. 1412 | 2.032 | 2.092 | 1.029 | p53 |
| 3383 | SKN | SEQ ID NO. 1413 | 6.772 | 10.342 | 1.527 | p53 |
| 3384 | ATP13A4 | SEQ ID NO. 1414 | 0.654 | 0.541 | 0.828 | p53 |
| 3385 | RPA3 | SEQ ID NO. 1415 | 4.215 | 2.604 | 0.618 | p53 |
| 3386 | PRKCZ | SEQ ID NO. 1416 | 0.76 | 0.824 | 1.084 | p53 |
| 3387 | STAG3 | SEQ ID NO. 1417 | 1.681 | 1.642 | 0.977 | p53 |
| 3388 | TAF3 | SEQ ID NO. 1418 | 8.929 | 6.077 | 0.681 | p53 |
| 3389 | EPM2AIP1 | SEQ ID NO. 1419 | 2.608 | 1.354 | 0.519 | p53 |
| 3390 | MLH1 | SEQ ID NO. 1420 | 88.367 | 120.426 | 1.36 | p53 |
| 3391 | RAB33B | SEQ ID NO. 1421 | 1.087 | 1.543 | 1.42 | p53 |
| 3392 | MYO18A | SEQ ID NO. 1422 | 0.724 | 2.453 | 3.391 | p53 |
| 3393 | APC2 | SEQ ID NO. 1423 | 1.805 | 1.765 | 0.978 | p53 |
| 3394 | TRIAP1 | SEQ ID NO. 1424 | 13.722 | 16.686 | 1.216 | p53 |
| 3395 | NLRP1 | SEQ ID NO. 1425 | 0.236 | 0.498 | 2.112 | p53 |
| 3396 | CCT7 | SEQ ID NO. 1426 | 0.291 | 0.215 | 0.741 | p53 |
| 3397 | MCM8 | SEQ ID NO. 1427 | 1.956 | 1.296 | 0.663 | p53 |
| 3398 | IHPK3 | SEQ ID NO. 1428 | 0.94 | 3.261 | 3.468 | p53 |
| 3399 | KATNB1 | SEQ ID NO. 1429 | 0.899 | 1.128 | 1.255 | p53 |
| 3400 | DDB2 | SEQ ID NO. 1430 | 52.554 | 65.637 | 1.249 | p53 |
| 3401 | PTP4A1 | SEQ ID NO. 1431 | 121.74 | 143.231 | 1.177 | p53 |
| 3402 | GART | SEQ ID NO. 1432 | 18.03 | 21.07 | 1.169 | p53 |
| 3403 | S100A6 | SEQ ID NO. 1433 | 3.492 | 4.375 | 1.253 | p53 |
| 3404 | RAB2B | SEQ ID NO. 1434 | 11.2 | 14.536 | 1.298 | p53 |
| 3405 | APEB1 | SEQ ID NO. 1435 | 0.147 | 0.166 | 1.126 | p53 |
| 3406 | MCC | SEQ ID NO. 1436 | 0.605 | 0.71 | 1.173 | p53 |
| 3407 | HPS5 | SEQ ID NO. 1437 | 3.308 | 4.962 | 1.5 | p53 |
| 3408 | RAB38 | SEQ ID NO. 1438 | 0.463 | 0.661 | 1.427 | p53 |
| 3409 | LSM3 | SEQ ID NO. 1439 | 3.187 | 1.641 | 0.515 | p53 |
| 3410 | FGFR1OP2 | SEQ ID NO. 1440 | 68.89 | 96.993 | 1.408 | p53 |
| 3411 | SOCS2 | SEQ ID NO. 1441 | 0.242 | 0.188 | 0.777 | p53 |
| 3412 | DDX41 | SEQ ID NO. 1442 | 37.563 | 17.286 | 0.46 | p53 |
| 3413 | PPP1R13L | SEQ ID NO. 1443 | 0.493 | 0.741 | 1.505 | p53 |
| 3414 | E2F7 | SEQ ID NO. 1444 | 0.528 | 1.322 | 2.503 | p53 |
| 3415 | ANAPC4 | SEQ ID NO. 1445 | 1.182 | 0.953 | 0.806 | p53 |
| 3416 | DDT | SEQ ID NO. 1446 | 4.535 | 2.638 | 0.582 | p53 |
| 3417 | GSTP1 | SEQ ID NO. 1447 | 0.11 | 0.23 | 2.083 | p53 |
| 3418 | RAD23A | SEQ ID NO. 1448 | 2.413 | 2.645 | 1.096 | p53 |
| 3419 | MBD6 | SEQ ID NO. 1449 | 3.526 | 6.626 | 0.777 | p53 |
| 3420 | DUSP6 | SEQ ID NO. 1450 | 0.49 | 0.783 | 1.597 | p53 |
| 3421 | PITPNM1 | SEQ ID NO. 1451 | 0.28 | 0.406 | 1.453 | p53 |
| 3422 | RAP2B | SEQ ID NO. 1452 | 3.805 | 5.179 | 1.361 | p53 |
| 3423 | MLL | SEQ ID NO. 1453 | 9.351 | 4.017 | 0.494 | p53 |
| 3424 | MRPS26 | SEQ ID NO. 1454 | 0.769 | 0.451 | 0.586 | p53 |

FIG. 1CJ -- TABLE 1 TRANSCRIPTIONAL BIOMARKER FUNCTIONAL DATA
SECTION 4A

| LINE_ID | GENE_SYMBOL | SEQUENCE_ID_LISTING | PROM_ACTIVITY_N O_INDUCTION | PROM_ACTIVITY_WI TH_INDUCTION | INDUCTION RATIO | INDUCTION_CONDITIONS |
|---|---|---|---|---|---|---|
| 3425 | C10orf11 | SEQ ID NO. 1453 | 79.355 | 85.1 | 1.072 | p53 |
| 3426 | MOAP1 | SEQ ID NO. 1454 | 3.217 | 4.613 | 1.434 | p53 |
| 3427 | STAG3 | SEQ ID NO. 1455 | 8.916 | 1.891 | 0.212 | p53 |
| 3428 | MAFK | SEQ ID NO. 1456 | 1.418 | 1.992 | 1.405 | p53 |
| 3429 | APC2 | SEQ ID NO. 1457 | 0.4 | 0.43 | 1.075 | p53 |
| 3430 | RAD1 | SEQ ID NO. 1458 | 0.188 | 0.209 | 1.112 | p53 |
| 3431 | MRPL21 | SEQ ID NO. 1459 | 0.794 | 1.162 | 1.463 | p53 |
| 3432 | DAPK2 | SEQ ID NO. 1460 | 0.274 | 0.221 | 0.808 | p53 |
| 3433 | NULL | SEQ ID NO. 1461 | 1.897 | 2.573 | 1.356 | p53 |
| 3434 | KIAA0562 | SEQ ID NO. 1462 | 6.076 | 9.883 | 1.626 | p53 |
| 3435 | CDKN1B | SEQ ID NO. 1463 | 46.625 | 27.06 | 0.58 | p53 |
| 3436 | FGF4 | SEQ ID NO. 1464 | 0.661 | 0.881 | 1.332 | p53 |
| 3437 | RAN | SEQ ID NO. 1465 | 53.687 | 43.127 | 0.803 | p53 |
| 3438 | ACVR1C | SEQ ID NO. 1466 | 0.643 | 0.754 | 1.174 | p53 |
| 3439 | RAB33B | SEQ ID NO. 1467 | 1.324 | 1.445 | 1.092 | p53 |
| 3440 | APC2 | SEQ ID NO. 1468 | 7.454 | 5.89 | 0.79 | p53 |
| 3441 | CDKN1A | SEQ ID NO. 1469 | 0.975 | 0.133 | 1.775 | p53 |
| 3442 | RAP2B | SEQ ID NO. 1470 | 0.777 | 0.777 | 1.001 | p53 |
| 3443 | TRAF4 | SEQ ID NO. 1471 | 5.074 | 11.761 | 2.318 | p53 |
| 3444 | LIG1 | SEQ ID NO. 1472 | 37.313 | 37.011 | 0.992 | p53 |
| 3445 | ARHGEF6 | SEQ ID NO. 1473 | 0.586 | 0.666 | 1.177 | p53 |
| 3446 | PLK3 | SEQ ID NO. 1474 | 2.582 | 5.455 | 2.112 | p53 |
| 3447 | IKIP | SEQ ID NO. 1475 | 6.37 | 32.701 | 5.133 | p53 |
| 3448 | HSPE1 | SEQ ID NO. 1476 | 5.518 | 4.127 | 0.748 | p53 |
| 3449 | ITGAE | SEQ ID NO. 1477 | 2.005 | 3.078 | 1.536 | p53 |
| 3450 | PRELID1 | SEQ ID NO. 1478 | 279.554 | 231.028 | 0.826 | p53 |
| 3451 | LTB4R | SEQ ID NO. 1479 | 2.245 | 1.716 | 0.764 | p53 |
| 3452 | JAK2 | SEQ ID NO. 1480 | 8.756 | 6.751 | 0.771 | p53 |
| 3453 | NULL | SEQ ID NO. 1481 | 77.819 | 47.292 | 0.608 | p53 |
| 3454 | LTBP2 | SEQ ID NO. 1482 | 0.457 | 0.285 | 0.623 | p53 |
| 3455 | PRKCE | SEQ ID NO. 1483 | 0.612 | 0.756 | 1.236 | p53 |
| 3456 | UBR7 | SEQ ID NO. 1484 | 6.156 | 9.662 | 1.57 | p53 |
| 3457 | NULL | SEQ ID NO. 1485 | 3.253 | 2.533 | 0.779 | p53 |
| 3458 | LOC112236 | SEQ ID NO. 1486 | 0.14 | 0.525 | 3.755 | p53 |
| 3459 | CDK5R1 | SEQ ID NO. 1487 | 0.81 | 0.894 | 1.104 | p53 |
| 3460 | C20orf177 | SEQ ID NO. 1488 | 0.688 | 0.4 | 0.582 | p53 |
| 3461 | SOCS3 | SEQ ID NO. 1489 | 1.155 | 1.276 | 1.105 | p53 |
| 3462 | RAB40C | SEQ ID NO. 1490 | 7.146 | 9.35 | 1.308 | p53 |
| 3463 | YWHAH | SEQ ID NO. 1491 | 7.289 | 2.31 | 0.317 | p53 |
| 3464 | TP53I13 | SEQ ID NO. 1492 | 0.653 | 0.72 | 1.102 | p53 |
| 3465 | PIK3R5 | SEQ ID NO. 1493 | 0.254 | 0.506 | 1.995 | p53 |
| 3466 | RTEL1 | SEQ ID NO. 1494 | 16.562 | 21.216 | 1.281 | p53 |
| 3467 | NULL | SEQ ID NO. 1495 | 21.745 | 9.44 | 0.434 | p53 |
| 3468 | CGCT | SEQ ID NO. 1496 | 202.068 | 105.979 | 0.524 | p53 |
| 3469 | FAMCF | SEQ ID NO. 1497 | 5.616 | 4.687 | 0.835 | p53 |
| 3470 | PTP4A1 | SEQ ID NO. 1498 | 0.257 | 0.405 | 1.576 | p53 |
| 3471 | RAN | SEQ ID NO. 1499 | 1.207 | 0.447 | 0.371 | p53 |
| 3472 | BAG3 | SEQ ID NO. 1499 | 0.078 | 0.077 | 0.976 | p53 |

FIG. 1CK -- TABLE 1 TRANSCRIPTIONAL BIOMARKER FUNCTIONAL DATA
SECTION 4A

| LINE_ID | GENE_SYMBOL | SEQUENCE_ID_LISTING | PROM_ACTIVITY_NO_INDUCTION | PROM_ACTIVITY_WITH_INDUCTION | PROM_ACTIVITY_WI_INDUCTION_RATIO | INDUCTION_CONDITIONS* |
|---|---|---|---|---|---|---|
| 3473 | APTX | SEQ ID NO. 1500 | 0.709 | 0.464 | 0.655 | p53 |
| 3474 | RAGE | SEQ ID NO. 1501 | 1.781 | 3.482 | 1.955 | p53 |
| 3475 | USMG5 | SEQ ID NO. 1502 | 984.112 | 695.876 | 0.707 | p53 |
| 3476 | NULL | SEQ ID NO. 1503 | 1.071 | 1.863 | 1.74 | p53 |
| 3477 | TPD52L1 | SEQ ID NO. 1504 | 0.163 | 0.302 | 1.854 | p53 |
| 3478 | TRMT6 | SEQ ID NO. 1505 | 0.627 | 1.308 | 2.085 | p53 |
| 3479 | REV3L | SEQ ID NO. 1506 | 14.86 | 25.552 | 1.72 | p53 |
| 3480 | PDGFB | SEQ ID NO. 1507 | 1.485 | 0.918 | 0.618 | p53 |
| 3481 | GSG2 | SEQ ID NO. 1508 | 2.486 | 0.801 | 0.322 | p53 |
| 3482 | CARD10 | SEQ ID NO. 1509 | 0.885 | 0.909 | 1.028 | p53 |
| 3483 | REV3L | SEQ ID NO. 1510 | 0.349 | 1.372 | 3.928 | p53 |
| 3484 | MGAM | SEQ ID NO. 1511 | 0.062 | 0.04 | 0.651 | p53 |
| 3485 | RAD21 | SEQ ID NO. 1512 | 1.325 | 1.168 | 0.882 | p53 |
| 3486 | MAPK1 | SEQ ID NO. 1513 | 0.122 | 0.168 | 1.378 | p53 |
| 3487 | DNASE1 | SEQ ID NO. 1514 | 0.962 | 0.81 | 0.842 | p53 |
| 3488 | ACTA2 | SEQ ID NO. 1514 | 11.921 | 17.825 | 1.495 | p53 |
| 3489 | CASP8AP2 | SEQ ID NO. 1515 | 9.196 | 2.638 | 0.287 | p53 |
| 3490 | CDK5R1 | SEQ ID NO. 1516 | 1.781 | 1.44 | 0.808 | p53 |
| 3491 | CIDEB | SEQ ID NO. 1517 | 1.032 | 0.888 | 0.861 | p53 |

FIG. 1CL -- TABLE 1 TRANSCRIPTIONAL BIOMARKER FUNCTIONAL DATA
SECTION 4A

| LINE_ID | GENE_SYMBOL | SEQUENCE_ID_LISTING | PROM_ACTIVITY_N O_INDUCTION | PROM_ACTIVITY_N TH_INDUCTION | PROM_ACTIVITY_WI INDUCTION | INDUCTION_RATIO | INDUCTION_CONDITIONS |
|---|---|---|---|---|---|---|---|
| 3492 | MTL5 | SEQ ID NO. 1518 | 0.446 | | 0.185 | 0.415 | p53 |
| 3493 | SLC2A1 | SEQ ID NO. 1518 | 1.271 | | 1.088 | 0.855 | p53 |
| 3494 | ARNT | SEQ ID NO. 1518 | 1.238 | | 1.498 | 1.209 | p53 |
| 3495 | HK1 | SEQ ID NO. 1518 | 0.213 | | 0.339 | 1.59 | p53 |
| 3496 | PTEN | SEQ ID NO. 1518 | 2.736 | | 6.078 | 2.221 | p53 |
| 3497 | CASP1 | SEQ ID NO. 1518 | 0.166 | | 0.812 | 4.889 | p53 |
| 3498 | MDM2 | SEQ ID NO. 1518 | 126.801 | | 349.008 | 2.752 | p53 |
| 3499 | APAF1 | SEQ ID NO. 1518 | 6.33 | | 35.549 | 5.616 | p53 |
| 3500 | HSP90AA1 | SEQ ID NO. 1518 | 21.599 | | 18.935 | 0.877 | p53 |
| 3501 | ARPP-19 | SEQ ID NO. 1518 | 0.114 | | 0.312 | 2.725 | p53 |
| 3502 | PKM2 | SEQ ID NO. 1518 | 1.633 | | 0.851 | 0.521 | p53 |
| 3503 | SELS | SEQ ID NO. 1518 | 9.371 | | 7.781 | 0.83 | p53 |
| 3504 | ACE | SEQ ID NO. 1518 | 3.011 | | 4.026 | 1.337 | p53 |
| 3505 | NLR2 | SEQ ID NO. 1518 | 0.205 | | 0.261 | 1.275 | p53 |
| 3506 | HMOX1 | SEQ ID NO. 1518 | 0.455 | | 0.413 | 0.91 | p53 |
| 3507 | EGF | SEQ ID NO. 1518 | 6.369 | | 6.201 | 0.974 | p53 |
| 3508 | CDKN1A | SEQ ID NO. 1518 | 10.868 | | 6.887 | 0.634 | p53 |
| 3509 | TXN | SEQ ID NO. 1518 | 1.494 | | 1.465 | 0.981 | p53 |
| 3510 | CYCS | SEQ ID NO. 1518 | 19.71 | | 21.775 | 1.105 | p53 |
| 3511 | MX1 | SEQ ID NO. 1518 | 9.999 | | 10.481 | 1.048 | p53 |
| 3512 | DAPK3 | SEQ ID NO. 1518 | 0.258 | | 0.628 | 2.437 | p53 |
| 3513 | F11R | SEQ ID NO. 1518 | 0.227 | | 0.214 | 0.942 | p53 |
| 3514 | TNFRSF10A | SEQ ID NO. 1518 | 0.134 | | 0.163 | 1.22 | p53 |
| 3515 | NPR1 | SEQ ID NO. 1518 | 0.143 | | 0.074 | 0.515 | p53 |
| 3516 | MDH1 | SEQ ID NO. 1518 | 1.809 | | 1.285 | 0.711 | p53 |
| 3517 | BAX | SEQ ID NO. 1518 | 2.252 | | 1.162 | 0.516 | p53 |
| 3518 | ACO2 | SEQ ID NO. 1518 | 5.754 | | 8.319 | 1.446 | p53 |
| 3519 | MIF | SEQ ID NO. 1518 | 0.866 | | 3.401 | 3.928 | p53 |
| 3520 | RHOB | SEQ ID NO. 1518 | 0.051 | | 0.035 | 0.682 | p53 |
| 3521 | H6PD | SEQ ID NO. 1518 | 0.074 | | 0.349 | 4.703 | p53 |
| 3522 | AHSG | SEQ ID NO. 1518 | 0.366 | | 0.539 | 1.471 | p53 |
| 3523 | PANK1 | SEQ ID NO. 1518 | 2.372 | | 4.926 | 2.077 | p53 |
| 3524 | DCBLD1 | SEQ ID NO. 1518 | 0.267 | | 0.252 | 0.945 | p53 |
| 3525 | NULL | SEQ ID NO. 1518 | 8.756 | | 9.633 | 1.1 | p53 |
| 3526 | NULL | SEQ ID NO. 1518 | 28.848 | | 38.343 | 1.329 | p53 |
| 3527 | GLS2 | SEQ ID NO. 1518 | 0.203 | | 0.872 | 4.3 | p53 |
| 3528 | C12orf45 | SEQ ID NO. 1518 | 5.495 | | 11.184 | 2.035 | p53 |
| 3529 | MZF1 | SEQ ID NO. 1518 | 4.44 | | 6.7 | 1.509 | p53 |
| 3530 | MXI1 | SEQ ID NO. 1518 | 3.138 | | 1.848 | 0.589 | p53 |
| 3531 | APOBEC3C | SEQ ID NO. 1518 | 0.4 | | 0.596 | 1.491 | p53 |
| 3532 | GCLC | SEQ ID NO. 1518 | 0.606 | | 0.844 | 1.393 | p53 |
| 3533 | MT3 | SEQ ID NO. 1518 | 0.564 | | 0.782 | 1.386 | p53 |
| 3534 | TXNRD2 | SEQ ID NO. 1518 | 0.385 | | 0.553 | 1.435 | p53 |

*FIG. 1CM* -- TABLE 1 TRANSCRIPTIONAL BIOMARKER FUNCTIONAL DATA
SECTION 9A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS* |
|---|---|---|---|---|---|---|
| 3535 | RBKS | SEQ ID NO. 1519 | 0.079 | 0.081 | 1.022 | PPAR_alpha |
| 3536 | RBKS | SEQ ID NO. 1519 | 0.029 | 0.02 | 0.677 | PPAR_delta |
| 3537 | RBKS | SEQ ID NO. 1519 | 0.041 | 0.066 | 1.635 | PPAR_gamma |
| 3538 | NULL | SEQ ID NO. 1520 | 0.054 | 0.051 | 0.951 | PPAR_alpha |
| 3539 | NULL | SEQ ID NO. 1520 | 0.009 | 0.009 | 0.978 | PPAR_delta |
| 3540 | NULL | SEQ ID NO. 1520 | 0.029 | 0.064 | 2.238 | PPAR_gamma |
| 3541 | GLRX2 | SEQ ID NO. 1520 | 0.025 | 0.024 | 0.95 | PPAR_alpha |
| 3542 | GLRX2 | SEQ ID NO. 1520 | 0.007 | 0.007 | 0.935 | PPAR_delta |
| 3543 | GLRX2 | SEQ ID NO. 1520 | 0.014 | 0.017 | 1.208 | PPAR_gamma |
| 3544 | SLC7A5 | SEQ ID NO. 1521 | 0.025 | 0.037 | 1.498 | PPAR_alpha |
| 3545 | SLC7A5 | SEQ ID NO. 1521 | 0.007 | 0.008 | 1.091 | PPAR_delta |
| 3546 | SLC7A5 | SEQ ID NO. 1521 | 0.017 | 0.024 | 1.435 | PPAR_gamma |
| 3547 | CDK3 | SEQ ID NO. 1522 | 0.021 | 0.023 | 1.146 | PPAR_alpha |
| 3548 | CDK3 | SEQ ID NO. 1522 | 0.009 | 0.013 | 1.54 | PPAR_delta |
| 3549 | CDK3 | SEQ ID NO. 1522 | 0.011 | 0.014 | 1.318 | PPAR_gamma |
| 3550 | N4BP2L1 | SEQ ID NO. 1523 | 0.106 | 0.186 | 1.759 | PPAR_alpha |
| 3551 | N4BP2L1 | SEQ ID NO. 1523 | 0.046 | 0.073 | 1.589 | PPAR_delta |
| 3552 | N4BP2L1 | SEQ ID NO. 1523 | 0.113 | 0.147 | 1.304 | PPAR_gamma |
| 3553 | PARP12 | SEQ ID NO. 1524 | 0.107 | 0.136 | 1.263 | PPAR_alpha |
| 3554 | PARP12 | SEQ ID NO. 1524 | 0.009 | 0.014 | 1.669 | PPAR_delta |
| 3555 | PARP12 | SEQ ID NO. 1524 | 0.032 | 0.056 | 1.752 | PPAR_gamma |
| 3556 | AKAP9 | SEQ ID NO. 1524 | 1.002 | 1.107 | 1.105 | PPAR_alpha |
| 3557 | AKAP9 | SEQ ID NO. 1524 | 0.195 | 0.13 | 0.666 | PPAR_delta |
| 3558 | AKAP9 | SEQ ID NO. 1524 | 0.664 | 0.536 | 0.806 | PPAR_gamma |
| 3559 | NULL | SEQ ID NO. 1524 | 0.112 | 0.065 | 0.579 | PPAR_alpha |
| 3560 | NULL | SEQ ID NO. 1524 | 0.033 | 0.056 | 1.686 | PPAR_delta |
| 3561 | NULL | SEQ ID NO. 1524 | 0.044 | 0.049 | 1.097 | PPAR_gamma |
| 3562 | NUB1 | SEQ ID NO. 1524 | 2.404 | 1.71 | 0.711 | PPAR_alpha |
| 3563 | NUB1 | SEQ ID NO. 1524 | 0.754 | 1.157 | 1.533 | PPAR_delta |
| 3564 | NUB1 | SEQ ID NO. 1524 | 1.788 | 1.594 | 0.891 | PPAR_gamma |
| 3565 | REPIN1 | SEQ ID NO. 1524 | 0.405 | 0.277 | 0.686 | PPAR_alpha |
| 3566 | REPIN1 | SEQ ID NO. 1524 | 0.074 | 0.068 | 0.922 | PPAR_delta |
| 3567 | REPIN1 | SEQ ID NO. 1524 | 0.209 | 0.289 | 1.382 | PPAR_gamma |

*FIG. 1CN* -- TABLE 1 TRANSCRIPTIONAL BIOMARKER FUNCTIONAL DATA
SECTION 10A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS* |
|---|---|---|---|---|---|---|
| 3568 | SCD | SEQ ID NO. 1525 | 0.007 | 0.009 | 1.265 | RAR_alpha |
| 3569 | SCD | SEQ ID NO. 1525 | 0.017 | 0.027 | 1.567 | RAR_beta |
| 3570 | SCD | SEQ ID NO. 1525 | 0.03 | 0.017 | 0.543 | RAR_gamma |
| 3571 | ABCA1 | SEQ ID NO. 1525 | 0.209 | 0.32 | 1.532 | RAR_alpha |
| 3572 | ABCA1 | SEQ ID NO. 1525 | 0.226 | 0.446 | 1.98 | RAR_gamma |
| 3573 | NEDD9 | SEQ ID NO. 1525 | 0.17 | 0.09 | 0.532 | RAR_alpha |
| 3574 | NEDD9 | SEQ ID NO. 1525 | 0.278 | 0.206 | 0.743 | RAR_beta |
| 3575 | NEDD9 | SEQ ID NO. 1525 | 0.203 | 0.161 | 0.793 | RAR_gamma |
| 3576 | ABCC6 | SEQ ID NO. 1526 | 0.039 | 0.042 | 1.083 | RAR_alpha |
| 3577 | ABCC6 | SEQ ID NO. 1526 | 0.073 | 0.061 | 0.83 | RAR_beta |
| 3578 | ABCC6 | SEQ ID NO. 1526 | 0.063 | 0.043 | 0.686 | RAR_gamma |
| 3579 | CYP26A1 | SEQ ID NO. 1527 | 0.014 | 0.024 | 1.729 | RAR_alpha |
| 3580 | CYP26A1 | SEQ ID NO. 1527 | 0.032 | 0.032 | 1.012 | RAR_beta |
| 3581 | CYP26A1 | SEQ ID NO. 1527 | 0.024 | 0.024 | 1.003 | RAR_gamma |
| 3582 | AKAP9 | SEQ ID NO. 1527 | 0.336 | 0.184 | 0.549 | RAR_alpha |
| 3583 | AKAP9 | SEQ ID NO. 1527 | 0.383 | 0.252 | 0.657 | RAR_beta |
| 3584 | AKAP9 | SEQ ID NO. 1527 | 0.158 | 0.188 | 1.187 | RAR_gamma |
| 3585 | NULL | SEQ ID NO. 1527 | 0.049 | 0.046 | 0.929 | RAR_alpha |
| 3586 | NULL | SEQ ID NO. 1527 | 0.039 | 0.046 | 1.192 | RAR_beta |
| 3587 | NULL | SEQ ID NO. 1527 | 0.075 | 0.041 | 0.544 | RAR_gamma |
| 3588 | HOXA1 | SEQ ID NO. 1527 | 0.062 | 0.056 | 0.903 | RAR_alpha |
| 3589 | HOXA1 | SEQ ID NO. 1527 | 0.108 | 0.105 | 0.973 | RAR_gamma |
| 3590 | NUB1 | SEQ ID NO. 1527 | 0.816 | 0.915 | 1.122 | RAR_alpha |
| 3591 | NUB1 | SEQ ID NO. 1527 | 0.667 | 0.748 | 1.121 | RAR_gamma |
| 3592 | REPIN1 | SEQ ID NO. 1527 | 0.13 | 0.107 | 0.824 | RAR_beta |
| 3593 | REPIN1 | SEQ ID NO. 1527 | 0.117 | 0.111 | 0.942 | RAR_beta |
| 3594 | REPIN1 | SEQ ID NO. 1527 | 0.117 | 0.096 | 0.815 | RAR_gamma |
| 3595 | NEDD9 | SEQ ID NO. 1528 | 0.012 | 0.009 | 0.791 | RAR_alpha |
| 3596 | NEDD9 | SEQ ID NO. 1528 | 0.019 | 0.013 | 0.67 | RAR_beta |
| 3597 | NEDD9 | SEQ ID NO. 1528 | 0.009 | 0.015 | 1.551 | RAR_gamma |
| 3598 | PKD1 | SEQ ID NO. 1528 | 0.035 | 0.012 | 0.334 | RAR_alpha |
| 3599 | PKD1 | SEQ ID NO. 1528 | 0.016 | 0.019 | 1.197 | RAR_gamma |
| 3600 | PKD1 | SEQ ID NO. 1529 | 0.049 | 0.037 | 0.773 | RAR_alpha |
| 3601 | PKD1 | SEQ ID NO. 1529 | 0.08 | 0.055 | 0.69 | RAR_beta |
| 3602 | PKD1 | SEQ ID NO. 1529 | 0.126 | 0.033 | 0.265 | RAR_gamma |
| 3603 | NEDD9 | SEQ ID NO. 1529 | 0.035 | 0.018 | 0.495 | RAR_alpha |
| 3604 | NEDD9 | SEQ ID NO. 1529 | 0.058 | 0.042 | 0.727 | RAR_beta |
| 3605 | NEDD9 | SEQ ID NO. 1529 | 0.037 | 0.023 | 0.624 | RAR_gamma |
| 3606 | CXCR5 | SEQ ID NO. 1529 | 0.013 | 0.022 | 1.617 | RAR_alpha |
| 3607 | CXCR5 | SEQ ID NO. 1529 | 0.034 | 0.031 | 0.935 | RAR_beta |
| 3608 | CXCR5 | SEQ ID NO. 1529 | 0.027 | 0.022 | 0.8 | RAR_gamma |

FIG. 1CO -- TABLE 1 TRANSCRIPTIONAL BIOMARKER FUNCTIONAL DATA
SECTION 10A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS* |
|---|---|---|---|---|---|---|
| 3609 | PCK2 | SEQ ID NO. 1530 | 0.229 | 0.194 | 0.849 | RAR_alpha |
| 3610 | PCK2 | SEQ ID NO. 1530 | 0.269 | 0.174 | 0.646 | RAR_beta |
| 3611 | PCK2 | SEQ ID NO. 1530 | 0.423 | 0.177 | 0.418 | RAR_gamma |
| 3612 | HOXB1 | SEQ ID NO. 1531 | 0.005 | 0.007 | 1.208 | RAR_alpha |
| 3613 | HOXB1 | SEQ ID NO. 1531 | 0.004 | 0.003 | 0.783 | RAR_beta |
| 3614 | HOXB1 | SEQ ID NO. 1531 | 0.007 | 0.006 | 0.842 | RAR_gamma |
| 3615 | SCD | SEQ ID NO. 1532 | 0.005 | 0.005 | 1.044 | RAR_alpha |
| 3616 | SCD | SEQ ID NO. 1532 | 0.006 | 0.014 | 2.089 | RAR_beta |
| 3617 | SCD | SEQ ID NO. 1532 | 0.009 | 0.01 | 1.091 | RAR_gamma |
| 3618 | FOXA1 | SEQ ID NO. 1533 | 0.009 | 0.007 | 0.837 | RAR_alpha |
| 3619 | FOXA1 | SEQ ID NO. 1533 | 0.009 | 0.01 | 1.167 | RAR_beta |
| 3620 | FOXA1 | SEQ ID NO. 1533 | 0.011 | 0.012 | 1.068 | RAR_gamma |
| 3621 | RAI14 | SEQ ID NO. 1534 | 0.004 | 0.004 | 1.22 | RAR_alpha |
| 3622 | RAI14 | SEQ ID NO. 1534 | 0.005 | 0.004 | 0.76 | RAR_beta |
| 3623 | RAI14 | SEQ ID NO. 1534 | 0.006 | 0.006 | 0.907 | RAR_gamma |

*FIG. 1CP* -- TABLE 1 TRANSCRIPTIONAL BIOMARKER FUNCTIONAL DATA
SECTION 5A

| LINE_ID | GENE_SYMBOL | SEQUENCE_ID_LISTING | PROM_ACTIVITY_N O_INDUCTION | PROM_ACTIVITY_WI TH_INDUCTION | INDUCTION _RATIO | INDUCTION_CONDITIONS* |
|---|---|---|---|---|---|---|
| 3624 | LZTFL1 | SEQ ID NO. 1535 | 0.545 | 0.846 | 1.552 | SREBP_lov |
| 3625 | LZTFL1 | SEQ ID NO. 1535 | 0.545 | 0.42 | 0.772 | SREBP_synth |
| 3626 | LZTFL1 | SEQ ID NO. 1535 | 0.545 | 0.663 | 1.217 | SREBP_U186664 |
| 3627 | SCD | SEQ ID NO. 1535 | 0.435 | 2.051 | 4.721 | SREBP_lov |
| 3628 | SCD | SEQ ID NO. 1535 | 0.435 | 0.13 | 0.3 | SREBP_synth |
| 3629 | SCD | SEQ ID NO. 1535 | 0.435 | 1.668 | 3.838 | SREBP_U186664 |
| 3630 | TIPARP | SEQ ID NO. 1535 | 14.099 | 14.145 | 1.003 | SREBP_lov |
| 3631 | TIPARP | SEQ ID NO. 1535 | 14.099 | 16.856 | 1.196 | SREBP_synth |
| 3632 | TIPARP | SEQ ID NO. 1535 | 14.099 | 21.59 | 1.531 | SREBP_U186664 |
| 3633 | ACSL1 | SEQ ID NO. 1536 | 0.054 | 0.212 | 3.96 | SREBP_lov |
| 3634 | ACSL1 | SEQ ID NO. 1536 | 0.054 | 0.024 | 0.454 | SREBP_synth |
| 3635 | ACSL1 | SEQ ID NO. 1536 | 0.054 | 0.075 | 1.39 | SREBP_U186664 |
| 3636 | ACSL1 | SEQ ID NO. 1537 | 0.484 | 0.42 | 0.868 | SREBP_lov |
| 3637 | ACSL1 | SEQ ID NO. 1537 | 0.484 | 0.54 | 1.117 | SREBP_synth |
| 3638 | ACSL1 | SEQ ID NO. 1537 | 0.484 | 0.373 | 0.771 | SREBP_U186664 |
| 3639 | ACSL5 | SEQ ID NO. 1538 | 0.319 | 0.458 | 1.436 | SREBP_lov |
| 3640 | ACSL5 | SEQ ID NO. 1538 | 0.319 | 0.305 | 0.957 | SREBP_synth |
| 3641 | ACSL5 | SEQ ID NO. 1538 | 0.319 | 0.443 | 1.387 | SREBP_U186664 |
| 3642 | ACSL4 | SEQ ID NO. 1539 | 3.094 | 10.125 | 3.273 | SREBP_lov |
| 3643 | ACSL4 | SEQ ID NO. 1539 | 3.094 | 2.01 | 0.65 | SREBP_synth |
| 3644 | ACSL4 | SEQ ID NO. 1539 | 3.094 | 6.926 | 2.239 | SREBP_U186664 |
| 3645 | ACSL5 | SEQ ID NO. 1540 | 0.874 | 0.884 | 1.012 | SREBP_lov |
| 3646 | ACSL5 | SEQ ID NO. 1540 | 0.874 | 0.876 | 1.002 | SREBP_synth |
| 3647 | ACSL5 | SEQ ID NO. 1540 | 0.874 | 0.869 | 0.995 | SREBP_U186664 |
| 3648 | ACOT8 | SEQ ID NO. 1541 | 14.572 | 15.857 | 1.088 | SREBP_lov |
| 3649 | ACOT8 | SEQ ID NO. 1541 | 14.572 | 15.23 | 1.045 | SREBP_synth |
| 3650 | ACOT8 | SEQ ID NO. 1541 | 14.572 | 18.298 | 1.256 | SREBP_U186664 |
| 3651 | LIMS3 | SEQ ID NO. 1542 | 1.066 | 1.131 | 1.061 | SREBP_lov |
| 3652 | LIMS3 | SEQ ID NO. 1542 | 1.066 | 1.571 | 1.473 | SREBP_synth |
| 3653 | LIMS3 | SEQ ID NO. 1542 | 1.066 | 1.125 | 1.055 | SREBP_U186664 |
| 3654 | ATP6AP1 | SEQ ID NO. 1542 | 0.528 | 0.51 | 0.966 | SREBP_lov |
| 3655 | ATP6AP1 | SEQ ID NO. 1542 | 0.528 | 0.459 | 0.868 | SREBP_synth |
| 3656 | ATP6AP1 | SEQ ID NO. 1542 | 0.528 | 0.45 | 0.852 | SREBP_U186664 |
| 3657 | AKAP9 | SEQ ID NO. 1542 | 15.144 | 15.112 | 0.998 | SREBP_lov |
| 3658 | AKAP9 | SEQ ID NO. 1542 | 15.144 | 16.672 | 1.101 | SREBP_synth |
| 3659 | AKAP9 | SEQ ID NO. 1542 | 15.144 | 18.881 | 1.247 | SREBP_U186664 |

*FIG. 1CQ* — TABLE 1 TRANSCRIPTIONAL BIOMARKER FUNCTIONAL DATA
SECTION 5A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_ RATIO | INDUCTION_CONDITIONS* |
|---|---|---|---|---|---|---|
| 3660 | CYP51A1 | SEQ ID NO. 1543 | 0.113 | 0.376 | 3.337 | SREBP_low |
| 3661 | CYP51A1 | SEQ ID NO. 1543 | 0.113 | 0.095 | 0.84 | SREBP_synth |
| 3662 | CYP51A1 | SEQ ID NO. 1543 | 0.113 | 0.254 | 2.250 | SREBP_U18666A |
| 3663 | SNX8 | SEQ ID NO. 1543 | 5.099 | 6.656 | 1.305 | SREBP_low |
| 3664 | SNX8 | SEQ ID NO. 1543 | 5.099 | 6.406 | 1.256 | SREBP_synth |
| 3665 | SNX8 | SEQ ID NO. 1543 | 5.099 | 5.562 | 1.091 | SREBP_U18666A |
| 3666 | NULL | SEQ ID NO. 1543 | 51.527 | 48.051 | 0.933 | SREBP_low |
| 3667 | NULL | SEQ ID NO. 1543 | 51.527 | 46.693 | 0.906 | SREBP_synth |
| 3668 | NULL | SEQ ID NO. 1543 | 51.527 | 52.694 | 1.023 | SREBP_U18666A |
| 3669 | NULL | SEQ ID NO. 1543 | 13.355 | 12.508 | 0.937 | SREBP_low |
| 3670 | NULL | SEQ ID NO. 1543 | 13.355 | 12.069 | 0.904 | SREBP_synth |
| 3671 | NULL | SEQ ID NO. 1543 | 13.355 | 11.209 | 0.839 | SREBP_U18666A |
| 3672 | HERPUD2 | SEQ ID NO. 1543 | 11.269 | 9.929 | 0.881 | SREBP_low |
| 3673 | HERPUD2 | SEQ ID NO. 1543 | 11.269 | 9.617 | 0.853 | SREBP_synth |
| 3674 | HERPUD2 | SEQ ID NO. 1543 | 11.269 | 11.612 | 1.03 | SREBP_U18666A |
| 3675 | NULL | SEQ ID NO. 1543 | 1.806 | 1.747 | 0.968 | SREBP_low |
| 3676 | NULL | SEQ ID NO. 1543 | 1.806 | 1.66 | 0.919 | SREBP_synth |
| 3677 | NULL | SEQ ID NO. 1543 | 1.806 | 1.998 | 1.106 | SREBP_U18666A |
| 3678 | SCRN2 | SEQ ID NO. 1544 | 2.776 | 2.831 | 1.02 | SREBP_low |
| 3679 | SCRN1 | SEQ ID NO. 1544 | 2.776 | 2.831 | 1.02 | SREBP_synth |
| 3680 | SCRN1 | SEQ ID NO. 1544 | 2.776 | 2.187 | 0.788 | SREBP_U18666A |
| 3681 | NCAPG2 | SEQ ID NO. 1544 | 11.552 | 8.964 | 0.776 | SREBP_low |
| 3682 | NCAPG2 | SEQ ID NO. 1544 | 11.552 | 10.683 | 0.925 | SREBP_synth |
| 3683 | NCAPG2 | SEQ ID NO. 1544 | 11.552 | 7.687 | 0.665 | SREBP_U18666A |
| 3684 | NUB1 | SEQ ID NO. 1544 | 45.288 | 53.521 | 1.182 | SREBP_low |
| 3685 | NUB1 | SEQ ID NO. 1544 | 45.288 | 55.779 | 1.232 | SREBP_synth |
| 3686 | NUB1 | SEQ ID NO. 1544 | 45.288 | 53.21 | 1.175 | SREBP_U18666A |
| 3687 | SLC4A2 | SEQ ID NO. 1544 | 0.388 | 0.322 | 0.83 | SREBP_low |
| 3688 | SLC4A2 | SEQ ID NO. 1544 | 0.388 | 0.21 | 0.543 | SREBP_synth |
| 3689 | SLC4A2 | SEQ ID NO. 1544 | 0.388 | 0.256 | 0.661 | SREBP_U18666A |
| 3690 | NULL | SEQ ID NO. 1544 | 0.92 | 1.015 | 1.103 | SREBP_low |
| 3691 | NULL | SEQ ID NO. 1544 | 0.92 | 0.826 | 0.897 | SREBP_synth |
| 3692 | NULL | SEQ ID NO. 1544 | 0.92 | 1.778 | 1.932 | SREBP_U18666A |
| 3693 | REPIN1 | SEQ ID NO. 1544 | 11.036 | 12.84 | 1.163 | SREBP_low |
| 3694 | REPIN1 | SEQ ID NO. 1544 | 11.036 | 9.452 | 0.856 | SREBP_synth |
| 3695 | REPIN1 | SEQ ID NO. 1544 | 11.036 | 10.889 | 0.987 | SREBP_U18666A |
| 3696 | MICALL2 | SEQ ID NO. 1544 | 2.401 | 2.14 | 0.891 | SREBP_low |
| 3697 | MICALL2 | SEQ ID NO. 1544 | 2.401 | 2.573 | 1.072 | SREBP_synth |
| 3698 | MICALL2 | SEQ ID NO. 1544 | 2.401 | 2.321 | 0.967 | SREBP_U18666A |
| 3699 | CCAR1 | SEQ ID NO. 1545 | 17.85 | 18.283 | 1.025 | SREBP_low |
| 3700 | CCAR1 | SEQ ID NO. 1545 | 17.85 | 26.692 | 1.495 | SREBP_synth |
| 3701 | CCAR1 | SEQ ID NO. 1545 | 17.85 | 21.699 | 1.216 | SREBP_U18666A |
| 3702 | FLCN | SEQ ID NO. 1546 | 4 | 3.28 | 0.82 | SREBP_low |
| 3703 | FLCN | SEQ ID NO. 1546 | 4 | 6.528 | 1.632 | SREBP_synth |
| 3704 | FLCN | SEQ ID NO. 1546 | 4 | 6.86 | 1.715 | SREBP_U18666A |

FIG. 1CR -- TABLE 1 TRANSCRIPTIONAL BIOMARKER FUNCTIONAL DATA
SECTION 5A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS |
|---|---|---|---|---|---|---|
| 3705 | PIM2 | SEQ ID NO. 1547 | 4.809 | 9.348 | 1.944 | SREBP_low |
| 3706 | PIM2 | SEQ ID NO. 1547 | 4.809 | 4.309 | 0.896 | SREBP_synth |
| 3707 | PIM2 | SEQ ID NO. 1547 | 4.809 | 9.36 | 1.947 | SREBP_U18666A |
| 3708 | CCMC | SEQ ID NO. 1548 | 90.653 | 100.57 | 1.109 | SREBP_low |
| 3709 | CCMC | SEQ ID NO. 1548 | 90.653 | 120.893 | 1.334 | SREBP_synth |
| 3710 | CCMC | SEQ ID NO. 1548 | 90.653 | 111.557 | 1.231 | SREBP_U18666A |
| 3711 | GTF2H1 | SEQ ID NO. 1548 | 14.288 | 12.009 | 0.84 | SREBP_low |
| 3712 | GTF2H1 | SEQ ID NO. 1548 | 14.288 | 17.84 | 1.249 | SREBP_synth |
| 3713 | GTF2H1 | SEQ ID NO. 1548 | 14.288 | 12.442 | 0.871 | SREBP_U18666A |
| 3714 | APEX1 | SEQ ID NO. 1548 | 14.125 | 11.96 | 0.847 | SREBP_low |
| 3715 | APEX1 | SEQ ID NO. 1548 | 14.125 | 16.29 | 1.153 | SREBP_synth |
| 3716 | APEX1 | SEQ ID NO. 1548 | 14.125 | 11.452 | 0.811 | SREBP_U18666A |
| 3717 | MAPK3 | SEQ ID NO. 1549 | 0.397 | 0.438 | 1.102 | SREBP_low |
| 3718 | MAPK3 | SEQ ID NO. 1549 | 0.397 | 0.477 | 1.203 | SREBP_synth |
| 3719 | MAPK3 | SEQ ID NO. 1549 | 0.397 | 0.41 | 1.033 | SREBP_U18666A |
| 3720 | UBE4B | SEQ ID NO. 1550 | 53.835 | 54.445 | 1.011 | SREBP_low |
| 3721 | UBE4B | SEQ ID NO. 1550 | 53.835 | 61.92 | 1.15 | SREBP_synth |
| 3722 | UBE4B | SEQ ID NO. 1550 | 53.835 | 54.081 | 1.005 | SREBP_U18666A |
| 3723 | HPS5 | SEQ ID NO. 1550 | 14.051 | 12.142 | 0.864 | SREBP_low |
| 3724 | HPS5 | SEQ ID NO. 1550 | 14.051 | 18.379 | 1.308 | SREBP_synth |
| 3725 | HPS5 | SEQ ID NO. 1550 | 14.051 | 22.351 | 1.591 | SREBP_U18666A |
| 3726 | MOSPD2 | SEQ ID NO. 1551 | 9.724 | 13.783 | 1.417 | SREBP_low |
| 3727 | MOSPD2 | SEQ ID NO. 1551 | 9.724 | 10.647 | 1.095 | SREBP_synth |
| 3728 | MOSPD2 | SEQ ID NO. 1551 | 9.724 | 14.187 | 1.459 | SREBP_U18666A |
| 3729 | USP1 | SEQ ID NO. 1552 | 4.107 | 3.606 | 0.878 | SREBP_low |
| 3730 | USP1 | SEQ ID NO. 1552 | 4.107 | 5.465 | 1.331 | SREBP_synth |
| 3731 | USP1 | SEQ ID NO. 1552 | 4.107 | 3.711 | 0.904 | SREBP_U18666A |
| 3732 | DUSP1 | SEQ ID NO. 1552 | 52.44 | 60.878 | 1.161 | SREBP_low |
| 3733 | DUSP1 | SEQ ID NO. 1552 | 52.44 | 93.735 | 1.787 | SREBP_synth |
| 3734 | DUSP1 | SEQ ID NO. 1552 | 52.44 | 62.143 | 1.185 | SREBP_U18666A |
| 3735 | UBE4B | SEQ ID NO. 1553 | 20.528 | 23.551 | 1.147 | SREBP_low |
| 3736 | UBE4B | SEQ ID NO. 1553 | 20.528 | 25.972 | 1.265 | SREBP_synth |
| 3737 | UBE4B | SEQ ID NO. 1553 | 20.528 | 25.703 | 1.252 | SREBP_U18666A |
| 3738 | LZTS2 | SEQ ID NO. 1554 | 3.022 | 2.715 | 0.898 | SREBP_low |
| 3739 | LZTS2 | SEQ ID NO. 1554 | 3.022 | 3.658 | 1.21 | SREBP_synth |
| 3740 | LZTS2 | SEQ ID NO. 1554 | 3.022 | 2.515 | 0.832 | SREBP_U18666A |
| 3741 | HDAC5 | SEQ ID NO. 1555 | 4.696 | 6.434 | 1.37 | SREBP_low |
| 3742 | HDAC5 | SEQ ID NO. 1555 | 4.696 | 5.841 | 1.244 | SREBP_synth |
| 3743 | HDAC5 | SEQ ID NO. 1555 | 4.696 | 5.711 | 1.216 | SREBP_U18666A |
| 3744 | NTHL1 | SEQ ID NO. 1556 | 6.147 | 5.149 | 0.838 | SREBP_low |
| 3745 | NTHL1 | SEQ ID NO. 1556 | 6.147 | 6.195 | 1.008 | SREBP_synth |
| 3746 | NTHL1 | SEQ ID NO. 1556 | 6.147 | 4.652 | 0.757 | SREBP_U18666A |
| 3747 | TSC2 | SEQ ID NO. 1557 | 1.251 | 1.411 | 1.128 | SREBP_low |
| 3748 | TSC2 | SEQ ID NO. 1557 | 1.251 | 1.72 | 1.375 | SREBP_synth |
| 3749 | TSC2 | SEQ ID NO. 1557 | 1.251 | 1.286 | 1.028 | SREBP_U18666A |

FIG. 1CS – TABLE 1 TRANSCRIPTIONAL BIOMARKER FUNCTIONAL DATA
SECTION 5A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS |
|---|---|---|---|---|---|---|
| 3750 | RAD9A | SEQ ID NO. 1558 | 4.92 | 6.511 | 1.323 | SREBP_lov |
| 3751 | RAD9A | SEQ ID NO. 1558 | 4.92 | 5.116 | 1.04 | SREBP_synth |
| 3752 | RAD9A | SEQ ID NO. 1558 | 4.92 | 6.507 | 1.323 | SREBP_U18666A |
| 3753 | HDAC5 | SEQ ID NO. 1559 | 7.129 | 9.037 | 1.268 | SREBP_lov |
| 3754 | HDAC5 | SEQ ID NO. 1559 | 7.129 | 8.649 | 1.213 | SREBP_synth |
| 3755 | HDAC5 | SEQ ID NO. 1559 | 7.129 | 9.589 | 1.345 | SREBP_U18666A |
| 3756 | TSC2 | SEQ ID NO. 1560 | 6.224 | 5.85 | 0.94 | SREBP_lov |
| 3757 | TSC2 | SEQ ID NO. 1560 | 6.224 | 7.304 | 1.174 | SREBP_synth |
| 3758 | TSC2 | SEQ ID NO. 1560 | 6.224 | 5.85 | 0.94 | SREBP_U18666A |
| 3759 | SIRT1 | SEQ ID NO. 1561 | 1.301 | 1.256 | 0.965 | SREBP_lov |
| 3760 | SIRT1 | SEQ ID NO. 1561 | 1.301 | 1.614 | 1.241 | SREBP_synth |
| 3761 | SIRT1 | SEQ ID NO. 1561 | 1.301 | 1.082 | 0.832 | SREBP_U18666A |
| 3762 | G6PD | SEQ ID NO. 1562 | 19.863 | 22.318 | 1.124 | SREBP_lov |
| 3763 | G6PD | SEQ ID NO. 1562 | 19.863 | 20.708 | 1.043 | SREBP_synth |
| 3764 | G6PD | SEQ ID NO. 1562 | 19.863 | 21.953 | 1.105 | SREBP_U18666A |
| 3765 | TDG | SEQ ID NO. 1563 | 75.61 | 81.383 | 1.076 | SREBP_lov |
| 3766 | TDG | SEQ ID NO. 1563 | 75.61 | 92.965 | 1.23 | SREBP_synth |
| 3767 | TDG | SEQ ID NO. 1563 | 75.61 | 68.006 | 0.899 | SREBP_U18666A |
| 3768 | NULL | SEQ ID NO. 1564 | 14.323 | 15.655 | 1.093 | SREBP_lov |
| 3769 | NULL | SEQ ID NO. 1564 | 14.323 | 18.585 | 1.298 | SREBP_synth |
| 3770 | NULL | SEQ ID NO. 1564 | 14.323 | 20.513 | 1.432 | SREBP_U18666A |
| 3771 | ESPL1 | SEQ ID NO. 1565 | 1.634 | 1.754 | 1.074 | SREBP_lov |
| 3772 | ESPL1 | SEQ ID NO. 1565 | 1.634 | 1.646 | 1.007 | SREBP_synth |
| 3773 | ESPL1 | SEQ ID NO. 1565 | 1.634 | 1.35 | 0.826 | SREBP_U18666A |
| 3774 | OSGEP | SEQ ID NO. 1566 | 4.079 | 4.181 | 1.025 | SREBP_lov |
| 3775 | OSGEP | SEQ ID NO. 1566 | 4.079 | 3.566 | 0.874 | SREBP_synth |
| 3776 | OSGEP | SEQ ID NO. 1566 | 4.079 | 4.148 | 1.017 | SREBP_U18666A |
| 3777 | CDKL3 | SEQ ID NO. 1567 | 29.327 | 31.578 | 1.077 | SREBP_lov |
| 3778 | CDKL3 | SEQ ID NO. 1567 | 29.327 | 30.559 | 1.042 | SREBP_synth |
| 3779 | CDKL3 | SEQ ID NO. 1567 | 29.327 | 29.589 | 1.009 | SREBP_U18666A |
| 3780 | BAX | SEQ ID NO. 1567 | 0.89 | 0.872 | 0.98 | SREBP_lov |
| 3781 | BAX | SEQ ID NO. 1567 | 0.89 | 0.976 | 1.096 | SREBP_synth |
| 3782 | BAX | SEQ ID NO. 1567 | 0.89 | 0.814 | 0.914 | SREBP_U18666A |
| 3783 | PMVK | SEQ ID NO. 1567 | 2.027 | 1.759 | 0.868 | SREBP_lov |
| 3784 | PMVK | SEQ ID NO. 1567 | 2.027 | 2.072 | 1.022 | SREBP_synth |
| 3785 | PMVK | SEQ ID NO. 1567 | 2.027 | 2.204 | 1.087 | SREBP_U18666A |
| 3786 | SUPV3L1 | SEQ ID NO. 1568 | 10.547 | 11.118 | 1.054 | SREBP_lov |
| 3787 | SUPV3L1 | SEQ ID NO. 1568 | 10.547 | 11.792 | 1.118 | SREBP_synth |
| 3788 | SUPV3L1 | SEQ ID NO. 1568 | 10.547 | 12.999 | 1.232 | SREBP_U18666A |
| 3789 | ID1 | SEQ ID NO. 1568 | 10.5 | 8.855 | 0.843 | SREBP_lov |
| 3790 | ID1 | SEQ ID NO. 1568 | 10.5 | 10.055 | 0.958 | SREBP_synth |
| 3791 | ID1 | SEQ ID NO. 1568 | 10.5 | 9.843 | 0.937 | SREBP_U18666A |
| 3792 | PWP1 | SEQ ID NO. 1568 | 123.443 | 121.06 | 0.981 | SREBP_lov |
| 3793 | PWP1 | SEQ ID NO. 1568 | 123.443 | 140.448 | 1.138 | SREBP_synth |
| 3794 | PWP1 | SEQ ID NO. 1568 | 123.443 | 131.261 | 1.063 | SREBP_U18666A |
| 3795 | TIMM13 | SEQ ID NO. 1568 | 12.481 | 12.228 | 0.98 | SREBP_lov |
| 3796 | TIMM13 | SEQ ID NO. 1568 | 12.481 | 15.464 | 1.239 | SREBP_synth |
| 3797 | TIMM13 | SEQ ID NO. 1568 | 12.481 | 16.918 | 1.355 | SREBP_U18666A |

FIG. 1CT -- TABLE 1 TRANSCRIPTIONAL BIOMARKER FUNCTIONAL DATA
SECTION 5A

| LINE_ID | GENE_SYMBOL | SEQUENCE_ID_LISTING | PROM_ACTIVITY_N O_INDUCTION | PROM_ACTIVITY_N TH_INDUCTION | PROM_ACTIVITY_WI INDUCTION | INDUCTION_RATIO | INDUCTION_CONDITIONS* |
|---|---|---|---|---|---|---|---|
| 3798 | MAP1LC3B | SEQ ID NO. 1569 | 64.441 | | 68.853 | 1.068 | SREBP_lov |
| 3799 | MAP1LC3B | SEQ ID NO. 1569 | 64.441 | | 94.544 | 1.467 | SREBP_synth |
| 3800 | MAP1LC3B | SEQ ID NO. 1569 | 64.441 | | 117.332 | 1.821 | SREBP_U18666A |
| 3801 | ACACA | SEQ ID NO. 1570 | 3.186 | | 3.657 | 1.148 | SREBP_lov |
| 3802 | ACACA | SEQ ID NO. 1570 | 3.186 | | 4.424 | 1.389 | SREBP_synth |
| 3803 | ACACA | SEQ ID NO. 1570 | 3.186 | | 3.599 | 1.13 | SREBP_U18666A |
| 3804 | CYP51A1 | SEQ ID NO. 1571 | 0.258 | | 0.493 | 1.911 | SREBP_lov |
| 3805 | CYP51A1 | SEQ ID NO. 1571 | 0.258 | | 0.176 | 0.684 | SREBP_synth |
| 3806 | CYP51A1 | SEQ ID NO. 1571 | 0.258 | | 0.356 | 1.38 | SREBP_U18666A |
| 3807 | ACACA | SEQ ID NO. 1572 | 1.733 | | 4.278 | 2.469 | SREBP_lov |
| 3808 | ACACA | SEQ ID NO. 1572 | 1.733 | | 1.707 | 0.985 | SREBP_synth |
| 3809 | ACACA | SEQ ID NO. 1572 | 1.733 | | 3.582 | 2.067 | SREBP_U18666A |
| 3810 | ACSL1 | SEQ ID NO. 1573 | 0.109 | | 0.165 | 1.512 | SREBP_lov |
| 3811 | ACSL1 | SEQ ID NO. 1573 | 0.109 | | 0.096 | 0.875 | SREBP_synth |
| 3812 | ACSL1 | SEQ ID NO. 1573 | 0.109 | | 0.12 | 1.098 | SREBP_U18666A |
| 3813 | ELOVL6 | SEQ ID NO. 1574 | 0.683 | | 0.836 | 1.225 | SREBP_lov |
| 3814 | ELOVL6 | SEQ ID NO. 1574 | 0.683 | | 0.728 | 1.067 | SREBP_synth |
| 3815 | ELOVL6 | SEQ ID NO. 1574 | 0.683 | | 0.908 | 1.331 | SREBP_U18666A |
| 3816 | SCD | SEQ ID NO. 1574 | 0.034 | | 0.066 | 1.952 | SREBP_lov |
| 3817 | SCD | SEQ ID NO. 1574 | 0.034 | | 0.034 | 0.994 | SREBP_synth |
| 3818 | SCD | SEQ ID NO. 1574 | 0.034 | | 0.053 | 1.548 | SREBP_U18666A |
| 3819 | GGPS1 | SEQ ID NO. 1575 | 9.524 | | 8.738 | 0.917 | SREBP_lov |
| 3820 | GGPS1 | SEQ ID NO. 1575 | 9.524 | | 10.481 | 1.1 | SREBP_synth |
| 3821 | GGPS1 | SEQ ID NO. 1575 | 9.524 | | 11.436 | 1.201 | SREBP_U18666A |
| 3822 | PHGDH | SEQ ID NO. 1576 | 0.389 | | 0.339 | 0.87 | SREBP_lov |
| 3823 | PHGDH | SEQ ID NO. 1576 | 0.389 | | 0.382 | 0.98 | SREBP_synth |
| 3824 | PHGDH | SEQ ID NO. 1576 | 0.389 | | 0.389 | 0.999 | SREBP_U18666A |
| 3825 | SC5DL | SEQ ID NO. 1577 | 9.002 | | 29.708 | 3.3 | SREBP_lov |
| 3826 | SC5DL | SEQ ID NO. 1577 | 9.002 | | 7.443 | 0.827 | SREBP_synth |
| 3827 | SC5DL | SEQ ID NO. 1577 | 9.002 | | 25.694 | 2.854 | SREBP_U18666A |
| 3828 | GPAM | SEQ ID NO. 1578 | 31.195 | | 25.684 | 0.823 | SREBP_lov |
| 3829 | GPAM | SEQ ID NO. 1578 | 31.195 | | 38.092 | 1.221 | SREBP_synth |
| 3830 | GPAM | SEQ ID NO. 1578 | 31.195 | | 35.088 | 1.125 | SREBP_U18666A |
| 3831 | C19orf47 | SEQ ID NO. 1578 | 0.061 | | 0.075 | 1.222 | SREBP_lov |
| 3832 | C19orf47 | SEQ ID NO. 1578 | 0.061 | | 0.071 | 1.166 | SREBP_synth |
| 3833 | C19orf47 | SEQ ID NO. 1578 | 0.061 | | 0.078 | 1.269 | SREBP_U18666A |

FIG. 1CU -- TABLE 1 TRANSCRIPTIONAL BIOMARKER FUNCTIONAL DATA
SECTION 13A

| LINE_ID | GENE_SYMBOL | SEQUENCE_ID_LISTING | PROM_ACTIVITY_N O_INDUCTION | PROM_ACTIVITY_WI TH_INDUCTION | PROM_ACTIVITY_WI INDUCTION _RATIO | INDUCTION_CONDITIONS* |
|---|---|---|---|---|---|---|
| 3834 | EEF1B2 | SEQ ID NO. 1579 | 0.232 | 13.143 | 1.596 | SRF |
| 3835 | CPVL | SEQ ID NO. 1580 | 2.617 | 3.279 | 1.253 | SRF |
| 3836 | AKAP9 | SEQ ID NO. 1580 | 1.632 | 1.168 | 0.716 | SRF |
| 3837 | NULL | SEQ ID NO. 1580 | 1.956 | 2.11 | 1.078 | SRF |
| 3838 | NUB1 | SEQ ID NO. 1580 | 102.449 | 79.9 | 0.78 | SRF |
| 3839 | REPIN1 | SEQ ID NO. 1580 | 2.771 | 3.165 | 1.142 | SRF |
| 3840 | GADD45G | SEQ ID NO. 1580 | 1.783 | 2.079 | 1.166 | SRF |

*FIG. 1CV* — TABLE 1 TRANSCRIPTIONAL BIOMARKER FUNCTIONAL DATA
SECTION 6A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS |
|---|---|---|---|---|---|---|
| 3841 | LPP | SEQ ID NO. 1581 | 42.698 | 59.848 | 1.402 | STAT_IFNa |
| 3842 | LPP | SEQ ID NO. 1581 | 42.698 | 55.781 | 1.306 | STAT_IFNg |
| 3843 | NULL | SEQ ID NO. 1581 | 1.19 | 0.968 | 0.813 | STAT_IFNa |
| 3844 | NULL | SEQ ID NO. 1581 | 1.19 | 1.07 | 0.899 | STAT_IFNg |
| 3845 | HECW1 | SEQ ID NO. 1582 | 0.239 | 0.486 | 2.035 | STAT_IFNa |
| 3846 | HECW1 | SEQ ID NO. 1582 | 0.239 | 2.562 | 10.734 | STAT_IFNg |
| 3847 | CPA2 | SEQ ID NO. 1583 | 0.488 | 0.568 | 1.165 | STAT_IFNa |
| 3848 | CPA2 | SEQ ID NO. 1583 | 0.488 | 3.271 | 6.705 | STAT_IFNg |
| 3849 | AKAP9 | SEQ ID NO. 1583 | 69.535 | 62.343 | 0.897 | STAT_IFNa |
| 3850 | AKAP9 | SEQ ID NO. 1583 | 69.535 | 43.046 | 0.619 | STAT_IFNg |
| 3851 | RFC2 | SEQ ID NO. 1584 | 22.47 | 25.211 | 1.122 | STAT_IFNa |
| 3852 | RFC2 | SEQ ID NO. 1584 | 22.47 | 29.637 | 1.319 | STAT_IFNg |
| 3853 | NULL | SEQ ID NO. 1584 | 285.842 | 307.122 | 1.074 | STAT_IFNa |
| 3854 | NULL | SEQ ID NO. 1584 | 285.842 | 379.79 | 1.329 | STAT_IFNg |
| 3855 | NULL | SEQ ID NO. 1584 | 47.246 | 48.031 | 1.017 | STAT_IFNa |
| 3856 | NULL | SEQ ID NO. 1584 | 47.246 | 53.016 | 1.122 | STAT_IFNg |
| 3857 | HERPUD2 | SEQ ID NO. 1584 | 26.04 | 28.169 | 1.082 | STAT_IFNa |
| 3858 | HERPUD2 | SEQ ID NO. 1584 | 26.04 | 31.782 | 1.221 | STAT_IFNg |
| 3859 | NULL | SEQ ID NO. 1584 | 5.309 | 4.752 | 0.895 | STAT_IFNa |
| 3860 | NULL | SEQ ID NO. 1584 | 5.309 | 4.653 | 0.876 | STAT_IFNg |
| 3861 | POR | SEQ ID NO. 1584 | 203.813 | 254.43 | 1.248 | STAT_IFNa |
| 3862 | POR | SEQ ID NO. 1584 | 203.813 | 193.497 | 0.949 | STAT_IFNg |
| 3863 | NCAPG2 | SEQ ID NO. 1584 | 393.419 | 363.65 | 0.924 | STAT_IFNa |
| 3864 | NCAPG2 | SEQ ID NO. 1584 | 393.419 | 377.54 | 0.96 | STAT_IFNg |
| 3865 | NUB1 | SEQ ID NO. 1584 | 460.495 | 519.14 | 1.127 | STAT_IFNa |
| 3866 | NUB1 | SEQ ID NO. 1584 | 460.495 | 457.424 | 0.993 | STAT_IFNg |
| 3867 | SLC4A2 | SEQ ID NO. 1584 | 6.117 | 6.847 | 1.119 | STAT_IFNa |
| 3868 | SLC4A2 | SEQ ID NO. 1584 | 6.117 | 5.512 | 0.901 | STAT_IFNg |
| 3869 | NULL | SEQ ID NO. 1584 | 10.756 | 10.988 | 1.022 | STAT_IFNa |
| 3870 | NULL | SEQ ID NO. 1584 | 10.756 | 8.276 | 0.769 | STAT_IFNg |
| 3871 | PSPH | SEQ ID NO. 1584 | 51.492 | 54.541 | 1.059 | STAT_IFNa |
| 3872 | PSPH | SEQ ID NO. 1584 | 51.492 | 49.004 | 0.952 | STAT_IFNg |
| 3873 | REPIN1 | SEQ ID NO. 1584 | 11.709 | 9.696 | 0.828 | STAT_IFNa |
| 3874 | REPIN1 | SEQ ID NO. 1584 | 11.709 | 10.314 | 0.881 | STAT_IFNg |
| 3875 | MICALL2 | SEQ ID NO. 1584 | 13.814 | 11.783 | 0.853 | STAT_IFNa |
| 3876 | MICALL2 | SEQ ID NO. 1584 | 13.814 | 11.791 | 0.853 | STAT_IFNg |
| 3877 | PRKG2 | SEQ ID NO. 1585 | 0.403 | 0.74 | 1.834 | STAT_IFNa |
| 3878 | PRKG2 | SEQ ID NO. 1585 | 0.403 | 0.916 | 2.271 | STAT_IFNg |
| 3879 | ERG | SEQ ID NO. 1586 | 0.272 | 0.27 | 0.994 | STAT_IFNa |
| 3880 | ERG | SEQ ID NO. 1586 | 0.272 | 0.41 | 1.507 | STAT_IFNg |
| 3881 | TIMP3 | SEQ ID NO. 1587 | 0.361 | 1.084 | 3.005 | STAT_IFNa |
| 3882 | TIMP3 | SEQ ID NO. 1587 | 0.361 | 1.093 | 3.03 | STAT_IFNg |
| 3883 | CTNNBL1 | SEQ ID NO. 1588 | 271.107 | 349.239 | 1.288 | STAT_IFNa |
| 3884 | CTNNBL1 | SEQ ID NO. 1588 | 271.107 | 319.525 | 1.179 | STAT_IFNg |
| 3885 | DCLRE1C | SEQ ID NO. 1589 | 27.358 | 42.369 | 1.549 | STAT_IFNa |
| 3886 | DCLRE1C | SEQ ID NO. 1589 | 27.358 | 27.737 | 1.014 | STAT_IFNg |

FIG. 1CW -- TABLE 1 TRANSCRIPTIONAL BIOMARKER FUNCTIONAL DATA
SECTION 6A

| LINE_ID | GENE_SYMBOL | SEQUENCE_ID_LISTING | PROM_ACTIVITY_N O_INDUCTION | PROM_ACTIVITY_WI TH_INDUCTION | INDUCTION RATIO | INDUCTION_CONDITIONS* |
|---|---|---|---|---|---|---|
| 3887 | TP53BP1 | SEQ ID NO. 1590 | 11.752 | 13.904 | 1.183 | STAT_IFNa |
| 3888 | TP53BP1 | SEQ ID NO. 1590 | 11.752 | 24.782 | 2.107 | STAT_IFNg |
| 3889 | CASP7 | SEQ ID NO. 1591 | 4.489 | 7.319 | 1.631 | STAT_IFNa |
| 3890 | CASP7 | SEQ ID NO. 1591 | 4.489 | 5.323 | 1.186 | STAT_IFNg |
| 3891 | RAB7L1 | SEQ ID NO. 1591 | 1.522 | 2.71 | 1.78 | STAT_IFNa |
| 3892 | RAB7L1 | SEQ ID NO. 1591 | 1.522 | 2.365 | 1.554 | STAT_IFNg |
| 3893 | PYCARD | SEQ ID NO. 1592 | 0.976 | 2.623 | 2.687 | STAT_IFNa |
| 3894 | PYCARD | SEQ ID NO. 1592 | 0.976 | 1.595 | 1.634 | STAT_IFNg |
| 3895 | PPP1CA | SEQ ID NO. 1593 | 184.624 | 172.575 | 0.935 | STAT_IFNa |
| 3896 | PPP1CA | SEQ ID NO. 1593 | 184.624 | 165.72 | 0.898 | STAT_IFNg |
| 3897 | NOL3 | SEQ ID NO. 1594 | 2.102 | 1.669 | 0.794 | STAT_IFNa |
| 3898 | NOL3 | SEQ ID NO. 1594 | 2.102 | 1.559 | 0.742 | STAT_IFNg |
| 3899 | STAT1 | SEQ ID NO. 1595 | 191.128 | 474.353 | 2.482 | STAT_IFNa |
| 3900 | STAT1 | SEQ ID NO. 1595 | 191.128 | 182.175 | 0.953 | STAT_IFNg |
| 3901 | C1QTNF6 | SEQ ID NO. 1596 | 0.494 | 0.781 | 1.581 | STAT_IFNa |
| 3902 | C1QTNF6 | SEQ ID NO. 1596 | 0.494 | 0.981 | 1.985 | STAT_IFNg |
| 3903 | CCND1 | SEQ ID NO. 1596 | 8.38 | 8.499 | 1.014 | STAT_IFNa |
| 3904 | CCND1 | SEQ ID NO. 1596 | 8.38 | 7.946 | 0.948 | STAT_IFNg |
| 3905 | OSM | SEQ ID NO. 1597 | 1.566 | 1.874 | 1.196 | STAT_IFNa |
| 3906 | OSM | SEQ ID NO. 1597 | 1.566 | 1.937 | 1.237 | STAT_IFNg |
| 3907 | MIS12 | SEQ ID NO. 1598 | 89.558 | 77.6 | 0.866 | STAT_IFNa |
| 3908 | MIS12 | SEQ ID NO. 1598 | 89.558 | 74.879 | 0.836 | STAT_IFNg |
| 3909 | MCL1 | SEQ ID NO. 1599 | 32.124 | 25.69 | 0.8 | STAT_IFNa |
| 3910 | MCL1 | SEQ ID NO. 1599 | 32.124 | 25.087 | 0.781 | STAT_IFNg |
| 3911 | DERL2 | SEQ ID NO. 1600 | 29.781 | 46.502 | 1.561 | STAT_IFNa |
| 3912 | DERL2 | SEQ ID NO. 1600 | 29.781 | 38.818 | 1.303 | STAT_IFNg |
| 3913 | RAB20 | SEQ ID NO. 1601 | 2.643 | 4.377 | 1.656 | STAT_IFNa |
| 3914 | RAB20 | SEQ ID NO. 1601 | 2.643 | 3.643 | 1.379 | STAT_IFNg |
| 3915 | HSPB1 | SEQ ID NO. 1602 | 3.534 | 2.092 | 0.592 | STAT_IFNa |
| 3916 | HSPB1 | SEQ ID NO. 1602 | 3.534 | 1.803 | 0.51 | STAT_IFNg |
| 3917 | BAG1 | SEQ ID NO. 1603 | 102.529 | 193.903 | 1.891 | STAT_IFNa |
| 3918 | BAG1 | SEQ ID NO. 1603 | 102.529 | 122.107 | 1.191 | STAT_IFNg |
| 3919 | MIS12 | SEQ ID NO. 1604 | 114.698 | 142.803 | 1.245 | STAT_IFNa |
| 3920 | MIS12 | SEQ ID NO. 1604 | 114.698 | 143.808 | 1.254 | STAT_IFNg |
| 3921 | UFC1 | SEQ ID NO. 1605 | 21.056 | 21.376 | 1.015 | STAT_IFNa |
| 3922 | UFC1 | SEQ ID NO. 1605 | 21.056 | 16.09 | 0.764 | STAT_IFNg |
| 3923 | IRF1 | SEQ ID NO. 1605 | 0.379 | 12.998 | 34.335 | STAT_IFNa |
| 3924 | IRF1 | SEQ ID NO. 1605 | 0.379 | 1.44 | 3.805 | STAT_IFNg |
| 3925 | C19orf12 | SEQ ID NO. 1606 | 54.240 | 59.458 | 1.096 | STAT_IFNa |
| 3926 | C19orf12 | SEQ ID NO. 1606 | 54.240 | 79.133 | 1.459 | STAT_IFNg |
| 3927 | PARD3B | SEQ ID NO. 1607 | 6.672 | 8.272 | 1.24 | STAT_IFNa |
| 3928 | PARD3B | SEQ ID NO. 1607 | 6.672 | 6.016 | 0.902 | STAT_IFNg |
| 3929 | CDKN1C | SEQ ID NO. 1608 | 73.915 | 86.368 | 1.168 | STAT_IFNa |
| 3930 | CDKN1C | SEQ ID NO. 1608 | 73.915 | 116.247 | 1.573 | STAT_IFNg |
| 3931 | C7orf64 | SEQ ID NO. 1609 | 0.333 | 0.774 | 2.323 | STAT_IFNa |
| 3932 | C7orf64 | SEQ ID NO. 1609 | 0.333 | 1.128 | 3.387 | STAT_IFNg |
| 3933 | C7orf49 | SEQ ID NO. 1610 | 0.233 | 0.386 | 1.662 | STAT_IFNa |
| 3934 | C7orf49 | SEQ ID NO. 1610 | 0.233 | 0.7 | 2.998 | STAT_IFNg |

FIG. 1CX – TABLE 1 TRANSCRIPTIONAL BIOMARKER FUNCTIONAL DATA
SECTION 6A

| LINE_ID | GENE_SYMBOL | SEQUENCE_ID_LISTING | PROM_ACTIVITY_N O_INDUCTION | PROM_ACTIVITY_WI TH_INDUCTION | INDUCTION_RATIO | INDUCTION_CONDITIONS |
|---|---|---|---|---|---|---|
| 3935 | NULL | SEQ ID NO. 1611 | 103.22 | 103.988 | 1.007 | STAT_IFNa |
| 3936 | NULL | SEQ ID NO. 1611 | 108.22 | 116.144 | 1.073 | STAT_IFNg |
| 3937 | NLRP3 | SEQ ID NO. 1612 | 11.138 | 27.112 | 2.434 | STAT_IFNa |
| 3938 | NLRP3 | SEQ ID NO. 1612 | 11.138 | 14.401 | 1.293 | STAT_IFNg |
| 3939 | BIRC5 | SEQ ID NO. 1613 | 27.11 | 26.928 | 0.993 | STAT_IFNa |
| 3940 | BIRC5 | SEQ ID NO. 1613 | 27.11 | 22.908 | 0.845 | STAT_IFNg |
| 3941 | MAP3K11 | SEQ ID NO. 1614 | 1.963 | 2.403 | 1.224 | STAT_IFNa |
| 3942 | MAP3K11 | SEQ ID NO. 1614 | 1.963 | 1.913 | 0.975 | STAT_IFNg |
| 3943 | SGOL2 | SEQ ID NO. 1615 | 92.537 | 97.813 | 1.057 | STAT_IFNa |
| 3944 | SGOL2 | SEQ ID NO. 1615 | 92.537 | 78.898 | 0.853 | STAT_IFNg |
| 3945 | A2M | SEQ ID NO. 1616 | 2.128 | 2.335 | 1.097 | STAT_IFNa |
| 3946 | A2M | SEQ ID NO. 1616 | 2.128 | 18.147 | 8.528 | STAT_IFNg |
| 3947 | CASC4 | SEQ ID NO. 1617 | 11.467 | 13.129 | 1.145 | STAT_IFNa |
| 3948 | CASC4 | SEQ ID NO. 1617 | 11.467 | 8.78 | 0.766 | STAT_IFNg |
| 3949 | FOSB | SEQ ID NO. 1617 | 16.953 | 20.023 | 1.181 | STAT_IFNa |
| 3950 | FOSB | SEQ ID NO. 1617 | 16.953 | 27.679 | 1.633 | STAT_IFNg |
| 3951 | CCL2 | SEQ ID NO. 1617 | 0.864 | 0.997 | 1.154 | STAT_IFNa |
| 3952 | CCL2 | SEQ ID NO. 1617 | 0.864 | 1.054 | 1.22 | STAT_IFNg |
| 3953 | KIF2A | SEQ ID NO. 1617 | 185.168 | 170.879 | 0.923 | STAT_IFNa |
| 3954 | KIF2A | SEQ ID NO. 1617 | 185.168 | 486.4 | 2.627 | STAT_IFNg |
| 3955 | CDKN1A | SEQ ID NO. 1617 | 59.575 | 51.054 | 0.857 | STAT_IFNa |
| 3956 | CDKN1A | SEQ ID NO. 1617 | 59.575 | 55.446 | 0.931 | STAT_IFNg |
| 3957 | PAK3 | SEQ ID NO. 1617 | 5.133 | 5.697 | 1.11 | STAT_IFNa |
| 3958 | PAK3 | SEQ ID NO. 1617 | 5.133 | 5.403 | 1.053 | STAT_IFNg |
| 3959 | IFI16 | SEQ ID NO. 1617 | 3.288 | 3.023 | 0.92 | STAT_IFNa |
| 3960 | IFI16 | SEQ ID NO. 1617 | 3.288 | 3.568 | 1.085 | STAT_IFNg |
| 3961 | NR3C1 | SEQ ID NO. 1617 | 16 | 11.943 | 0.746 | STAT_IFNa |
| 3962 | NR3C1 | SEQ ID NO. 1617 | 16 | 13.622 | 0.851 | STAT_IFNg |
| 3963 | IRF9 | SEQ ID NO. 1617 | 2.862 | 2.679 | 0.936 | STAT_IFNa |
| 3964 | IRF9 | SEQ ID NO. 1617 | 2.862 | 2.839 | 0.992 | STAT_IFNg |
| 3965 | SEPP1 | SEQ ID NO. 1617 | 0.381 | 0.269 | 0.706 | STAT_IFNa |
| 3966 | SEPP1 | SEQ ID NO. 1617 | 0.381 | 0.466 | 1.222 | STAT_IFNg |
| 3967 | CSF1 | SEQ ID NO. 1617 | 2.387 | 25.943 | 10.868 | STAT_IFNa |
| 3968 | CSF1 | SEQ ID NO. 1617 | 2.387 | 96.942 | 40.61 | STAT_IFNg |
| 3969 | TAP1 | SEQ ID NO. 1617 | 71.874 | 114.576 | 1.594 | STAT_IFNa |
| 3970 | TAP1 | SEQ ID NO. 1617 | 71.874 | 142.121 | 1.977 | STAT_IFNg |
| 3971 | PSMB9 | SEQ ID NO. 1617 | 1.685 | 27.734 | 16.462 | STAT_IFNa |
| 3972 | PSMB9 | SEQ ID NO. 1617 | 1.685 | 115.419 | 68.511 | STAT_IFNg |
| 3973 | FASN | SEQ ID NO. 1617 | 764.113 | 734.447 | 0.961 | STAT_IFNa |
| 3974 | FASN | SEQ ID NO. 1617 | 764.113 | 772.704 | 1.011 | STAT_IFNg |
| 3975 | MYC | SEQ ID NO. 1618 | 4.439 | 3.229 | 0.727 | STAT_IFNa |
| 3976 | MYC | SEQ ID NO. 1618 | 4.439 | 3.489 | 0.786 | STAT_IFNg |
| 3977 | BCL2L1 | SEQ ID NO. 1619 | 5.597 | 4.771 | 0.852 | STAT_IFNa |
| 3978 | BCL2L1 | SEQ ID NO. 1619 | 5.597 | 7.567 | 1.352 | STAT_IFNg |

TRANSCRIPTION BIOMARKERS OF BIOLOGICAL RESPONSES AND METHODS OF USE

REFERENCE TO RELATED APPLICATIONS

This application is a divisional of U.S. patent application Ser. No. 14/329,984, filed on Jul. 13, 2014, now U.S. Pat. No. 9,663,823, which is a divisional of U.S. patent application Ser. No. 12/586,131, filed Sep. 16, 2009, now U.S. Pat. No. 8,815,779, the contents of which are incorporated herein by reference in their entirety.

SEQUENCE LISTING

A .txt file containing a Sequence Listing is filed with this application in lieu of a paper copy. The .txt file serves both as the Sequence Listing and as the Computer Readable Form. The .txt file has the following properties:
File Name: 1003-004-DIV-SL
File Size: 2.5 MB
Created: 2014 Jul. 13
Other Information: ASCII text file generated by script execution in Darwin Kernel of Unix (Mac OS 10.4.2); DOS compatible new-line characters (ASCII\015\012) interpreted correctly in MS-DOS, MS-Windows, Unix and Mac.

BACKGROUND OF THE INVENTION

Reporter constructs including an expression control sequence operably linked with a reporter sequence are widely used in biology to test for the activity of the expression control sequence under selected conditions. Typically, such constructs are used to test for the expression of the gene normally under transcriptional control of the control sequence. Such constructs have many uses. They can be used, for example, to monitor gene expression during cellular responses to signaling cascades. They also are useful in drug development assays. In drug development, the induction or suppression of expression of a gene by a drug candidate may be a desired or undesired event. In such assays, a cell that contains an expression construct comprising a control sequence for the gene of interest is contacted with a drug candidate and the expression of the reporter is monitored. Compositions that elicit an undesirable result may be eliminated from further testing. Alternatively, compositions that elicit a desired result may be subject to further testing.

In this age of systems biology, investigators may wish to study the activity of many genes in a biological response or pathway, or to identify compositions that modulate the activity of a biological response. Biological responses are characterized by the induction or suppression of many genes. Biological responses of interest include, for example, (1) the hypoxia response, (2) the response to estrogens; (3) the response to androgens; (4) the response mediated by the p53 protein; (5) the response to inhibitors or activators of cholesterol biosynthesis; (6) the interferon-mediated response; (7) the CREB-mediated response; (8) the response to glucocorticoids; (9) the PPAR-mediated response; (10) the RAR-mediated response; (11) the inflammation response induced by TNFa; (12) the heat shock response; and (13) the serum response.

Trinklein et al. have described a library that contains transcription regulatory sequences for thousands of genes in the genome and that are associated with various pathways. See, e.g., U.S. patent publications 2007-0161031 and 2009-0018031.

SUMMARY OF THE INVENTION

In one aspect this invention provides an expression construct comprising a transcriptional regulatory sequence operatively linked with a heterologous sequence encoding a reporter, wherein the transcription regulatory sequence is one of a gene of Table 1. In one aspect this invention provides a collection comprising a plurality of expression constructs, each expression construct comprising a transcriptional regulatory sequence operatively linked with a heterologous sequence encoding a reporter, wherein at least 20% of the expression constructs in the collection each comprise a transcription regulatory sequence of a different gene of Table 1. In certain embodiments, the transcription regulatory sequences include at least a fragment of a sequence selected from SEQ ID NO: 1 to SEQ ID NO. 174. In other embodiments, the transcription regulatory sequences include at least a fragment of a sequence selected from SEQ ID NO: 175 to SEQ ID NO. 1619. In one embodiment at least 20% of the expression constructs comprise transcription regulatory sequences differently selected from the group consisting of: (i) any of SEQ ID NO:1 to SEQ ID NO: 174; (ii) a sequence of at least 50 nucleotides having at least 90% sequence identity to a sequence of (i); and (iii) a fragment of a sequence of (i). In another embodiment the transcription regulatory sequences of the different genes of Table 1 are biomarkers of the same biological response. In another embodiment the transcription regulatory sequences of the different genes of Table 1 comprise biomarkers of different biological responses. For example, the plurality of different biological response could be 2, at least 2, 3, at least 3, no more than 3, 4, at least 4, no more than 4, 5, at least 5, no more than 5, 6, at least 6, no more than 6, 7, at least 7, no more than 7, 8, at least 8, no more than 8, 9, at least 9, no more than 9, 10, at least 10, no more than 10, 11, at least 11, no more than 11, 12, at least 12 no more than 12, or 13 different biological responses selected from (1) the hypoxia response, (2) the response to estrogens; (3) the response to androgens; (4) the response mediated by the p53 protein; (5) the response to inhibitors or activators of cholesterol biosynthesis; (6) the interferon-mediated response; (7) the CREB-mediated response; (8) the response to glucocorticoids; (9) the PPAR-mediated response; (10) the RAR-mediated response; (11) the inflammation response induced by TNFa; (12) the heat shock response; and (13) the serum response In another embodiment the transcription regulatory sequences of the different genes of Table 1 comprise at least three biomarkers of each of a plurality different biological responses. In another embodiment the expression construct is comprised in a plasmid, a virus, or a transposon vector. In another embodiment the expression construct is integrated into a chromosome in a cell or maintained as a stable episomal vector. In another embodiment the reporter is a light-emitting reporter, a fluorescent reporter or a colorimetric reporter. In another embodiment the heterologous sequence encoding the reporter comprises a luciferase gene. In another embodiment the collection comprises at least 10 and no more than 1000 different expression constructs. In another embodiment the collection comprises at least 10 and no more than 100 different expression constructs. In another embodiment the collection comprises at least 10 and no more than 50 different expression constructs. In another embodiment the collection comprises at least 50 and no more than 100 different expression constructs. In another embodiment each expression construct is comprised in a different molecule. In another embodiment each recombinant nucleic acid molecule is comprised in different well of at least one microtiter plate. In another embodiment the transcription regulatory sequences of the collection consist of or consist essentially of transcription regulatory sequences of genes of Table 1, or those comprising all or part of the sequences in the sequence listing, including those in Part I and/or Part II.

In one aspect this invention provides a cell comprising an expression construct comprising a transcriptional regulatory sequence operatively linked with a heterologous sequence encoding a reporter, wherein the transcription regulatory sequence is one of a gene of Table 1. In another aspect this invention provides a collection of a plurality of cells comprising expression constructs, each expression construct comprising a transcriptional regulatory sequence operatively linked with a heterologous sequence encoding a reporter, wherein at least 20% of the expression constructs each comprise a transcription regulatory sequence of a different gene of Table 1. In one embodiment each cell is comprised in different well of at least one microtiter plate. In another embodiment the cells are human cells. In another embodiment the cells are mammalian cells. In another embodiment at least one expression construct is stably integrated into a chromosome wherein the expression construct comprises a transcriptional regulatory sequence operatively linked with a heterologous sequence encoding a reporter, wherein the expression construct comprises a transcription regulatory sequence of a gene of Table 1. In another embodiment the cells comprise a plurality of different expression constructs, each comprising a transcription regulatory sequence of a different gene of Table 1. In another embodiment each different expression construct is comprised in a different cell of the cell line. In another embodiment the transcription regulatory sequences of the collection consist of or consist essentially of transcription regulatory sequences of genes of Table 1, or those comprising all or part of the sequences in the sequence listing, including those in Part I and/or Part II.

In another aspect this invention provides a multicellular organism that contains at least one expression construct comprising a transcriptional regulatory sequence operatively linked with a heterologous sequence encoding a reporter, wherein the expression construct comprises a transcription regulatory sequence of a gene of Table 1. In one embodiment the multicellular organism is selected from a plant, a vertebrate and an invertebrate.

In another aspect this invention provides a device comprising a plurality of receptacles, wherein each receptacle comprises an expression construct comprising a transcriptional regulatory sequence operatively linked with a heterologous sequence encoding a reporter, wherein at least 20% of the expression constructs each comprise a transcription regulatory sequence of a different gene of Table 1. In one embodiment the device comprises at least one microtiter plate.

In another aspect this invention provides a device comprising a plurality of receptacles, wherein each receptacle contains at least one cell comprising an expression construct, each expression construct comprising a transcriptional regulatory sequence operatively linked with a heterologous sequence encoding a reporter, wherein at least 20% of the expression constructs each comprise a transcription regulatory sequence of a different gene of Table 1. In one embodiment the device comprises at least one microtiter plate.

In another aspect this invention provides a method comprising: a) exposing at least one cell to a test condition, wherein the at least one cell comprises at least one expression construct comprising a transcriptional regulatory sequence operatively linked with a heterologous sequence encoding a reporter, wherein the transcription regulatory sequence is a transcription regulatory sequence of a gene of Table 1; b) measuring expression of the reporter; and c) correlating the measurement with a biological response for which the transcription regulatory sequence is a biomarker. In one embodiment the method further comprises i) measuring the activity of the reporter in the absence of the test condition; ii) measuring the activity of the reporter in the presence of the test condition; iii) measuring the difference or ratio of reporter activity between the cells exposed to the test condition and cells that were not; and iv) correlating the difference or ratio between treated and untreated measurements with a biological response. In one embodiment the transcription regulatory sequence comprises a sequence selected from the group consisting of: (i) any of SEQ ID NO:1 to SEQ ID NO: 174; (ii) a sequence of at least 50 nucleotides having at least 95% sequence identity to a sequence of (i); and (iii) a fragment of a sequence of (i). In another embodiment the test condition is selected from the group consisting of contacting the cell with a test compound, exposing the cell to an environmental condition and inducing or repressing expression of one or more genes in the cell. In another embodiment the test condition comprises removing a compound from the culture media in which the cell grown. In another embodiment the test condition comprises contacting the cell with a test compound selected from: (1) a small organic molecule; (2) a nucleic acid derivative (e.g., a small interfering RNA, micro RNA mimic or micro RNA inhibitor); and (3) an expression construct that contains an open reading frame of a gene. In another embodiment the test condition comprises exposing the cell to an environmental condition selected from hyperthermia, hypothermia, hypoxia, osmotic stress, oxidative stress, radiation, or changes in atmospheric conditions. In another embodiment each expression construct is comprised in a different cell. In another embodiment the at least one cell comprises a plurality of the expression constructs, wherein each expression construct comprises a transcription regulatory sequence of a different gene of Table 1, wherein the transcription regulatory sequences of the different genes are biomarkers of the same biological response. In another embodiment the at least one cell comprises a plurality of the expression constructs, wherein each expression construct comprises a transcription regulatory sequence of a different gene of Table 1, wherein the transcription regulatory sequences of the different genes are biomarkers of different biological responses. In another embodiment the at least one cell comprises a plurality of the expression constructs, wherein each expression construct comprises a transcription regulatory sequence of a different gene of Table 1, wherein the transcription regulatory sequences of the different genes comprise at least three different biomarkers of each of a plurality different biological responses. In another embodiment the biological responses are responses selected from (1) the hypoxia response, (2) the response to estrogens; (3) the response to androgens; (4) the response mediated by the p53 protein; (5) the response to inhibitors or activators of cholesterol biosynthesis; (6) the interferon-mediated response; (7) the CREB-mediated response; (8) the response to glucocorticoids; (9) the PPAR-mediated response; (10) the RAR-mediated response; (11) the inflammation response induced by TNFa; (12) the heat shock response; and (13) the serum response. In another embodiment the method comprises contacting the test compound with a plurality of sets of different cell types, wherein each expression construct is comprised in each of the cell types. In another embodiment the method further comprises exposing a control cell to the test condition, wherein the control cell comprises an expression construct comprising a control transcriptional regulatory sequence operatively linked with a heterologous sequence encoding a reporter, wherein the control transcriptional regulatory sequence is a transcriptional regulatory sequence of a gene whose activity is not correlated with a biological response correlated with the activity of transcriptional control sequence of the gene of Table 1. In another embodiment the expression construct is comprised in a plasmid, a virus, or an artificial chromosome vector or a transposon vector. In another embodiment the expression construct is integrated into a chromosome in the cell or maintained as a stable episomal vector. In another embodiment the reporter is a light-emitting reporter, a fluorescent reporter or a colorimetric reporter. In another embodiment the reporter comprises luciferase. In another embodiment the method further comprises exposing the cell to a condition that induces the biological response for which the transcription regulatory sequence is a biomarker. In another embodiment correlating comprises correlating a change in biomarker activity with induction of the biological response. In another embodiment correlating comprises correlating a change in biomarker activity with inhibition of the biological response. In another embodiment the method further comprises inducing the biological response and wherein correlating comprises correlating inhibition of the biomarker with inhibition of the biological response. In another embodiment the method further comprises inhibiting the biological response and wherein correlating comprises correlating inhibition of the biomarker with induction of the biological response.

In another aspect this invention provides a method comprising: a) exposing at least one cell to a test condition, wherein the at least one cell comprises at least one expression construct comprising a transcriptional regulatory sequence operatively linked with a heterologous sequence encoding a reporter, wherein the transcription regulatory sequence is a transcription regulatory sequence of a gene of Table 1; b) measuring expression of the reporter; and if the measurement is at a target level; c) exposing at least one second cell to the test condition, wherein the at least one second cell comprises at least one expression construct comprising a transcriptional regulatory sequence operatively linked with a heterologous sequence encoding a reporter, wherein the transcription regulatory sequence is a transcription regulatory sequence of a different gene of the same biological response of Table 1; and; d) measuring expression of the reporter sequence in the at least one second cell. In one embodiment the method further comprises: e) correlating the measurement with the biological response.

In another aspect this invention provides a method of determining whether a test condition modulates a biological response. In one embodiment the method comprises exposing a cell comprising an expression construct of this invention to the test condition and determining whether test condition modulates the activity of the biomarker promoter, wherein modulation of the activity of the biomarker promoter indicates that that the test condition modulates the biological response for which the biomarker promoter is a biomarker. In another embodiment this method comprises exposing a cell comprising an expression construct of this invention to conditions that induce or repress the biological response for which the biomarker promoter is a biomarker; exposing the cell to the test condition and determining whether the test condition modulates the activity of the biomarker promoter, wherein modulation of the activity indicates that the test condition modulates the activity of the biological response. The activity of the biomarker promoter can be positively or negative correlated with the activity of the biological response. In the case of positive correlation, induction of the biomarker promoter is correlated with induction of the response and/or repression of the biomarker promoter is correlated with repression of the biological response. In the case of negative correlation, repression of activity of the promoter is correlated with induction of the biological response and induction of activity of the promoter is correlated with repression of the biological response.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1. presents Table 1 showing biomarkers for various biological responses. The table is divided into Part I and Part II. Each Part is divided into sections. Each major section (e.g., Section 1, Section 2, etc.) relates to a particular biological response. Part B of Table 1 presents other biomarkers of biological responses, again divided into subsections grouped as "Section 1a", "Section 2a", etc. In certain embodiments, biomarkers for a biological response in Part I are preferred to those in Part II, e.g., biomarkers in Part I, Section 1 may be preferred to those in Part II, section 1a.

DETAILED DESCRIPTION OF THE INVENTION

1. Biomarkers

This invention provides nucleic acid molecules comprising transcription regulatory sequences for genes useful as biomarkers of a variety of biological responses or biological pathways. The genes and the biological responses/pathways are identified in Table 1. Certain transcription regulatory sequences of these genes also are identified in Table 1 and provided in the sequence listing. This invention also provides expression constructs comprising biomarker transcription control sequences, devices including them and methods of use. The biomarker transcription expression control sequences are useful, among other things, for identifying test conditions that modulate activity of the biological response or pathway. Modulation includes changing the activity of a pathway, including increasing and decreasing activity.

Biomarkers exhibit different activity or expression under different conditions or states. A biomarker is differentially active or present between states if the mean or median activity or expression level of the biomarker in the different states is calculated to be statistically significant. Common tests for statistical significance include, among others, t-test, ANOVA, Kruskal-Wallis, Wilcoxon, Mann-Whitney and odds ratio. As such, the activity of a biomarker is correlated with a state and the biomarker is useful in classification algorithms to classify an entity as belonging to one or another category. In the present context, activity of a biomarker expression control sequence in a cell indicates whether a biological response or pathway is active in the cell. Cells that contain expression constructs comprising a biomarker expression control sequence operatively linked to a reporter sequence can be subject to a test condition. Activity of the biomarker expression control sequence provides an indication of whether the test condition elicits activity of the biological response or pathway for which the transcription regulatory sequence is a biomarker. For example, a cell comprising an expression construct of this invention can be exposed to a drug candidate to determine whether the drug candidate elicits or inhibits a desired or undesired response, or to an environmental stimulus or condition to determine whether the stimulus or condition elicits or inhibits the response.

2. Biological Responses and Pathways

Biological responses are often characterized by the change in expression of sets of genes. A set of genes whose expression is activated (or turned off) as part of the biological response is referred to as a "pathway." One goal is to identify compounds that modulate or mimic a biological response, or activate or inhibit activity of genes in a pathway. A number of genes have been identified that have promoters whose activity is highly correlated with particular biological responses. Therefore, promoters of these genes function as biomarkers of the biological response. The genes are identified in Table 1, along with specific transcriptional regulatory sequences that were determined to function as biomarkers of the response. In general, a transcriptional regulatory sequence functions as a biomarker if the induction ratio (the ratio between activity with induction of the response and the activity without induction of the response) is at least 2, at least 4, at least 10, at least 25 or at least 50.

Biomarkers have been identified for the following biological responses: (1) the hypoxia response, (2) the response to estrogens; (3) the response to androgens; (4) the response mediated by the p53 protein; (5) the response to inhibitors or activators of cholesterol biosynthesis; (6) the interferon-mediated response; (7) the CREB-mediated response; (8) the response to glucocorticoids; (9) the PPAR-mediated response; (10) the RAR-mediated response; (11) the inflammation response induced by TNFa; (12) the heat shock response; and (13) the serum response.

This invention provides collections of these biomarker promoters, expression constructs in which they are operably linked with sequences encoding reporters, cells that contain these expression constructs, devices that contain the expression constructs and methods of using expression constructs, in particular to determine whether any test condition can modulate the activity of particular biological responses, based on its ability to regulate the activity of the biomarker expression control sequences.

A biological response biomarker is positively correlated with the biological response if its activity is induced or activated when a biological response is active, or if its activity is repressed when the biological response is repressed. A biological response biomarker is negatively correlated with the biological response if its activity is repressed when a biological response is active, or if its activity is induced or activated when the biological response is repressed.

Identifying test conditions that induce or repress the activity of biomarker promoters is useful to evaluate test conditions, such as test compositions, for the ability to induce or inhibit the biological response with which the biomarker activity is correlated. A test condition that induces activity of a biological response biomarker promoter positively correlated with the response is presumed to induce the biological response in full or in part, e.g., to cause a response that mimics the biological response, and its action is correlated positively with the biological response. A test condition that inhibits activity of a biological response biomarker promoter positively correlated with the response when cells are exposed to conditions that induce the biological response is presumed to inhibit the biological response, e.g., to inhibit events correlated with the biological response, and its action is correlated negatively with the biological response.

Alternatively, a test condition that inhibits activity of a biological response biomarker promoter negatively correlated with the response is presumed to induce the biological response in full or in part, e.g., to cause a response that mimics the biological response, and its action is correlated positively with the biological response. A test condition that induces activity of a biological response biomarker promoter negatively correlated with the response when cells are exposed to conditions that induce the biological response is presumed to inhibit the biological response, e.g., to inhibit events correlated with the biological response, and its action is correlated negatively with the biological response.

A method for identifying a test condition that elicits a biological response can comprise providing a cell comprising an expression construct comprising a biological response biomarker promoter operably linked to a reporter gene and exposing the cell to a test condition. The activity of a biological response biomarker promoter in response to the test condition can be measured. The measurement can be correlated with the biological response. Conditions resulting in activity of a desired correlation (e.g., induction of activity of a positively correlated biomarker, or inhibition of the activity a negatively correlated biomarker) can be identified as conditions that elicit the biological response.

A method for identifying a test condition that inhibits a biological response can comprise providing a cell comprising an expression construct comprising a biological response biomarker promoter operably linked to a reporter gene, exposing the cell to a condition that elicits a biological response (or to a condition that induces expression of a biological response biomarker promoter) and exposing the cell to a test condition. The activity of a biological response biomarker promoter in response to the test condition can be measured. The measurement can be correlated with the biological response. Conditions resulting in activity of a desired correlation (e.g., inhibition of the inducible activity of a positively correlated biomarker, or induction of activity of a negatively correlated biomarker) can be identified as conditions that inhibit the biological response.

In each situation, the test condition can be tested further. For example, the ability of the test condition to modulate activity of at least one or a plurality of different biomarkers for the biological response can be tested. The activity of these promoters can be correlated with the biological response. The test condition also can be tested for the ability to modulate a different biological response than the one originally tested.

2.1 Biological Response to Hypoxia

Several promoters have been identified, the activity of each of which is positively correlated with the biological response to hypoxia ("hypoxia response biomarker promoter"). These hypoxia response biomarker promoters are identified in Table 1, section 1 and section 1a. Hypoxia response biomarker promoters generally have inducible activities ranging from 2 to 10-fold typically in this assay. The conditions used to induce the biological response to hypoxia included exposing cells to a 1% oxygen environment and 100 micromolar deferoxamine (DFO) for 24 hrs. The experimental conditions are set forth more completely in Example 1.

More specifically, transcription regulatory sequences have been found that are induced when exposed to low oxygen conditions. Low oxygen conditions induce the hypoxia response. One can use such a promoter in an assay to determine whether a test compound induces the hypoxia response. This is done, for example, by exposing a cell containing an expression construct comprising the transcription regulatory sequence operatively linked with a reporter sequence to a test compound. If the compound induces activity of the promoter, this means the compound induces the hypoxia response. Also, one can use the promoter in an assay to determine whether a test compound inhibits the hypoxia response. This is done, for example, by exposing a cell containing the expression construct to a condition that induces the hypoxia response (for example, exposing the cell to low oxygen conditions) and exposing the cell to the test compound. If the compound inhibits the inducible activity of the promoter, this means the compound inhibits the hypoxia response.

The biological response to hypoxia (or, "hypoxia response") involves a number of events at the phenotypic, cellular and molecular level. These events include increasing the expression of genes involved in cellular respiration and promotion of vascularization and oxygen uptake. The activity of hypoxia response biomarker promoters is, in turn, also correlated with these events.

In certain situations it may be useful to induce a hypoxia response. For example, hypoxia occurs under ischemic conditions, e.g., heart disease, transient ischemic attack, cerebrovascular accident, ruptured arteriovenous malformation and peripheral artery occlusive disease. Under such conditions, cells and tissue can be damaged. For example, a subject can experience cell death in the ischemic area. Pharmaceutical drugs that induce hypoxia may provide protection in situations of ischemia-induced hypoxia.

In certain situations it may be useful to inhibit a hypoxia response. For example, tumor growth results in hypoxic conditions. Under such conditions, it may be beneficial to block the hypoxia response in order to slow or stop tumor growth. Pharmaceutical drugs that inhibit or prevent the results of tumor-induced hypoxia are useful in treating such conditions.

Conditions can be tested for their ability to induce or inhibit the hypoxia response, as discussed above. Hypoxia conditions to which cells can be exposed for these tests include, for example, exposure of cells to an environment in which oxygen is present at no more than about 10%, no more than about 5%, no more than about 3%, no more than about 2%, no more than about 1% or below about 1%. Furthermore, small molecule inhibitors of the cells ability to make or use ATP also elicit the hypoxia response, e.g., or treating with deferoxamine (DFO) for 24 hrs. DFO is a known inhibitor of mitochondria and inducer of hypoxia. Also, cells can be exposed to any condition that induces expression of a hypoxia response biomarker promoter.

2.2 Biological Response to Estrogen (e.g., β-Estradiol)

Several promoters have been identified, the activity of each of which is positively correlated with the biological response to estrogen ("estrogen response biomarker promoter"). These estrogen response biomarker promoters are identified in Table 1, section 2 and section 2a. The condition used to induce the biological response to estrogen was exposing cells to a 10 nanomolar environment of β-estradiol for 24 hrs. The experimental conditions are set forth more completely in Example 2.

More specifically, transcription regulatory sequences have been found that are induced when exposed to estrogens. β-estradiol induces the estrogen receptor protein that regulates the estrogen response. One can use such a promoter in an assay to determine whether a test compound induces the estrogen response. This is done, for example, by exposing a cell containing an expression construct comprising the transcription regulatory sequence operatively linked with a reporter sequence to a test compound. If the compound induces activity of the promoter, this means the compound induces the estrogen response. Also, one can use the promoter in an assay to determine whether a test compound inhibits the estrogen response. This is done, for example, by exposing a cell containing the expression construct to a condition that induces the estrogen response and exposing the cell to the test compound. If the compound inhibits the inducible activity of the promoter, this means the compound inhibits the estrogen response.

The biological response to estrogen (or, "estrogen response") involves a number of events at the cellular and molecular level. These events include cell proliferation and lipid metabolism. The activity of estrogen response biomarker promoters is, in turn, also correlated with these events.

In certain situations it is useful to elicit an estrogen response. For example, estrogens are administered as drugs in a variety of situations. In a form of hormone replacement therapy, estrogen is administered to pen-menopausal and post-menopausal women to counter the effects of diminished estrogen levels, such as osteoperosis. The estrogen response biomarker promoters of this invention are useful in discovering and evaluating pharmaceutical drugs and other conditions for the ability to elicit an estrogen response.

Also, in certain situations it is desirable to inhibit an estrogen response. For example, certain cancers, e.g., certain breast cancers, are hormone receptor positive. That is, cancer cells grow faster in the presence of estrogen. Drugs that lower the amount of estrogen, or that inhibit the activity of estrogen, such as tamoxifen, are used to treat such cancers. The estrogen response biomarker promoters of this invention are useful in discovering and evaluating pharmaceutical drugs and other conditions for the ability to inhibit an estrogen response.

Furthermore, it is known than many environmental toxins and other small molecules can act as estrogen mimics Therefore, an estrogen response biomarker promoter can serve as a useful tool for establishing which toxins or other small molecules can serve as estrogen mimics by, for example, exposing a recombinant cell of this invention to the compound and determining whether it induces activity of an estrogen biomarker promoter.

Conditions can be tested for their ability to induce or inhibit the estrogen response, as discussed above. Estrogen conditions to which cells can be exposed for these tests include, for example, exposure of cells to an environment comprising an estrogen at a concentration of least 100 picomolar, at least 1 nM or at least 10 nM or at least 1 uM. Any estrogen can be used to induce this response. Also, cells can be exposed to any condition that induces expression of an estrogen response biomarker promoter.

2.3 Biological Response to Androgen (e.g., Methyltrienolone)

Several promoters have been identified, the activity of each of which is positively correlated with the biological response to androgen ("androgen response biomarker promoter"). These androgen response biomarker promoters are identified in Table 1, section 3 and section 3a. The condition used to induce the biological response to androgen was exposing cells to a 10 nanomolar environment of methyltrienolone (R1881) for 24 hrs. The experimental conditions are set forth more completely in Example 3.

More specifically, transcription regulatory sequences have been found that are induced when exposed to androgens. Methyltrienolone induces the androgen receptor protein that regulates the androgen response. One can use such a promoter in an assay to determine whether a test compound induces the androgen response. This is done, for example, by exposing a cell containing an expression construct comprising the transcription regulatory sequence operatively linked with a reporter sequence to a test compound. If the compound induces activity of the promoter, this means the compound induces the androgen response. Also, one can use the promoter in an assay to determine whether a test compound inhibits the androgen response. This is done, for example, by exposing a cell containing the expression construct to a condition that induces the androgen response and exposing the cell to the test compound. If the compound inhibits the inducible activity of the promoter, this means the compound inhibits the androgen response.

The biological response to androgen (or, "androgen response") involves a number of events at the cellular and molecular level. These events include regulating gene expression patterns that result in the formation of male secondary sex characteristics in vertebrates. The activity of androgen response biomarker promoters is, in turn, also correlated with these events.

In certain situations it is useful to elicit an androgen response. For example, in a form of hormone replacement therapy, androgen is administered to older men to counter the effects of diminished androgen levels. The androgen response biomarker promoters of this invention are useful in discovering and evaluating pharmaceutical drugs and other conditions for the ability to elicit an androgen response.

Also, in certain situations it is desirable to inhibit an androgen response. For example, androgen ablation can be used as an effective therapy in prostate cancer. The androgen response biomarker promoters of this invention are useful in discovering and evaluating pharmaceutical drugs and other conditions for the ability to inhibit an androgen response.

Furthermore, it is known than many environmental toxins and other small molecules can act as androgen mimics Therefore, an androgen response biomarker promoter can serve as a useful tool for establishing which toxins or other small molecules can serve as androgen mimics.

Androgen conditions to which cells can be exposed for these tests include, for example, exposure of cells to an environment comprising an androgen at a concentration of least 100 picomolar, at least 1 nM or at least 10 nM. Androgens include natural and artificial androgens, such as testosterones, methyltrienolone, and others. Also, cells can be exposed to any condition that induces expression of an androgen response biomarker promoter.

2.4 Biological Response to p53 Activation

Several promoters have been identified, the activity of each of which is positively correlated with the biological response to the activation of the p53 tumor suppressor protein ("p53 response biomarker promoter"). These p53 biomarker promoters are identified in Table 1, section 4 and section 4a. The conditions used to induce the biological response to p53 was exposing cells to a 10 micromolar environment of nutlin for 24 hrs or treatment with doxorubicin at 200 ng/mL final concentration. The experimental conditions are set forth more completely in Example 4.

More specifically, transcription regulatory sequences have been found that are induced when exposed to activators of p53. Nutlin induces the p53 protein by inhibiting the MDM2 protein that is responsible for the degradation of the p53 protein. Doxorubicin is an antibiotic that interacts with DNA by intercalation. This in turn activates p53. One can use such a promoter in an assay to determine whether a test compound induces the p53 response. This is done, for example, by exposing a cell containing an expression construct comprising the transcription regulatory sequence operatively linked with a reporter sequence to a test compound. If the compound induces activity of the promoter, this means the compound induces the p53 response. Also, one can use the promoter in an assay to determine whether a test compound inhibits the p53 response. This is done, for example, by exposing a cell containing the expression construct to a condition that induces the p53 response and exposing the cell to the test compound. If the compound inhibits the inducible activity of the promoter, this means the compound inhibits the p53 response.

p53 is a master tumor suppressor gene that controls a number of critical events at the cellular and molecular level. The p53 protein is a transcription factor that directly binds to DNA and regulates the expression of genes involved in the cell cycle, the DNA repair pathway, and can initiate apoptosis if DNA damage is irreparable. The activity of p53-responsive biomarker promoters, in turn, also correlate with these events.

p53 is critical to proper functioning of cells. A large number of cancers develop from cells that have inactivated the p53 protein. The p53 response biomarker promoters of this invention are useful in discovering and evaluating pharmaceutical drugs and other conditions for the ability to activate the p53 response. Test conditions that stimulate the p53 response may be useful in treating cancer.

Conditions can be tested for their ability to induce or inhibit the p53 response, as discussed above. Conditions to which cells can be exposed for these tests include, for example, exposure of cells to an environment that induces DNA damage, apoptosis, or other disruptions to the cell cycle. Also, cells can be exposed to any condition that induces expression of an p53 response biomarker promoter.

2.5 Biological Response to Cholesterol and Other Molecules that Modulate the Cholesterol Biosynthesis Pathway Several promoters have been identified, the activity of which are positively or negatively correlated with the biological response to the activity of the cholesterol biosynthesis pathway ("cholesterol biomarker promoter"). These cholesterol response biomarker promoters are identified in Table 1, section 5 and section 5a. The conditions used to induce the cholesterol response were exposing cells to a 1 micromolar environment of lovastatin for 24 hrs (negatively correlated with activation of the pathway or positively correlated with inhibition of the pathway), U18666A at 1 micromolar for 24 hrs (negatively correlated with activation of the pathway or positively correlated with inhibition of the pathway), or synthecol at 5 ug/mL for 24 hrs (positively correlated with activation of the pathway). The experimental conditions are set forth more completely in Example 5.

More specifically, transcription regulatory sequences have been found that are induced or repressed when the cholesterol biosynthesis is either inhibited or induced. Lovastatin is a known inhibitor of the HMG-coA reductase protein that is a critical enzyme in the synthesis of cholesterol. U18666A is a known inhibitor of intracellular cholesterol transport. Synthecol is a synthetic form of cholesterol. One can use such a promoter in an assay to determine whether a test compound affects the cholesterol response. This is done, for example, by exposing a cell containing an expression construct comprising the transcription regulatory sequence operatively linked with a reporter sequence to a test compound. If the compound induces activity of biomarker promoters positively correlated with inhibition of cholesterol biosynthesis (negatively correlated with cholesterol biosynthesis), this means the compound inhibits activity of the cholesterol biosynthesis pathway. If the compound induces activity of biomarker promoters positively correlated with cholesterol biosynthesis this means it induces activity of the cholesterol biosynthesis pathway. Similarly, one can induce or repress the cholesterol synthesis response and determine whether a test condition has the opposite effect, e.g., repressing activity of a biomarker positively correlated with the response or inducing activity of a biomarker negatively correlated with the response.

The cholesterol biosynthesis pathway includes a number of events at the cellular and molecular level. These events include the sensing of intracellular cholesterol in the endoplasmic reticulum by the SREBP protein. SREBP is a transcription factor that directly binds DNA and regulates the transcription of the HMG-CoA reductase and LDL receptor genes. The activity of cholesterol biomarker promoters is, in turn, also correlated with these events.

In certain situations it is useful to inhibit cholesterol biosynthesis as high levels of cholesterol are strongly associated with cardiovascular disease. For example, statins are some of the most widely prescribed drugs that inhibit the activity of HMG-CoA reductase, a key enzyme in the cholesterol biosynthesis pathway. The cholesterol biomarker promoters of this invention are useful in discovering and evaluating pharmaceutical drugs and other conditions for the ability to inhibit cholesterol biosynthesis.

Also, in certain situations it may be desirable to activate the cholesterol biosynthesis pathway. There are rare cases of individuals that suffer from hypocholesterolemia, or abnormally low levels of cholesterol. The cholesterol biomarker promoters of this invention are useful in discovering and evaluating pharmaceutical drugs and other conditions for the ability to activate cholesterol biosynthesis.

Conditions can be tested for their ability to induce or inhibit the cholesterol biosynthesis pathway, as discussed above. Conditions to which cells can be exposed for these tests include, for example, exposure of cells to any condition that inhibits the production of cholesterol or the uptake of cholesterol. Statins are examples of cholesterol synthesis inhibitors. Also, cells can be exposed to any condition that induces expression of a cholesterol response biomarker promoter.

2.6 Biological Response to Interferons

Several promoters have been identified, the activity of each of which is positively correlated with the biological response to interferons ("interferon biomarker promoter"). These interferon response biomarker promoters are identified in Table 1, section 6 and section 6a. The conditions used to induce the interferon response were exposing cells to 500 units/mL of interferon alpha for 8 hrs, or interferon gamma at 100 ng/mL for 8 hrs. The experimental conditions are set forth more completely in Example 6. Certain of these biomarkers are correlated with the alpha and/or gamma interferon responses.

More specifically, transcription regulatory sequences have been found that are induced when exposed to interferons, e.g., interferon alpha or interferon gamma. Interferon alpha and gamma induce an interferon-mediated response. One can use such a promoter in an assay to determine whether a test compound induces the interferon-mediated response. This is done, for example, by exposing a cell containing an expression construct comprising the transcription regulatory sequence operatively linked with a reporter sequence to a test compound. If the compound induces activity of the promoter, this means the compound induces the interferon-mediated response. Also, one can use the promoter in an assay to determine whether a test compound inhibits the interferon-mediated response. This is done, for example, by exposing a cell containing the expression construct to a condition that induces the interferon-mediated response (for example, exposing the cell to interferon alpha) and exposing the cell to the test compound. If the compound inhibits the inducible activity of the promoter, this means the compound inhibits the interferon-mediated response.

The biological response to interferons includes a number of events at the cellular and molecular level. Interferons are produced by a wide variety of cells and are key signaling molecules in the inflammation response and in response to the presence of double-stranded RNA viruses. Interferons assist the immune response by inhibiting viral replication within host cells, activating natural killer cells and macrophages, increasing antigen presentation to lymphocytes, and inducing the resistance of host cells to viral infection. The STAT family of transcription factors directly bind DNA and regulate the transcription of target genes in response to interferon signaling. The activity of interferon biomarker promoters is, in turn, also correlated with these events.

In certain situations it is useful to inhibit interferon activity. For example, inhibiting interferon activity may help in cases of acute or chronic inflammation. The interferon biomarker promoters of this invention are useful in discovering and evaluating pharmaceutical drugs and other conditions for the ability to inhibit interferon activity.

Also, in certain situations it may be desirable to activate interferon activity. For example, interferons have antiviral and antioncogenic properties and are used to treat viral infection and cancer. The interferon biomarker promoters of this invention are useful in discovering and evaluating pharmaceutical drugs and other conditions for the ability to activate interferon activity.

Conditions can be tested for their ability to induce or inhibit interferon activity, as discussed above. Conditions to which cells can be exposed for these tests include, for example, exposure of cells to interferon alpha or interferon gamma, or any condition that inhibits or activates the production of interferon proteins, such as a viral infection. Also, cells can be exposed to any condition that induces expression of an interferon biomarker promoter.

2.7. CREB-Mediated Response and Cyclic AMP Signaling

Several promoters have been identified, the activity of each of which is positively correlated with the biological response to cAMP or CREB signaling ("CREB biomarker promoter"). These CREB response biomarker promoters are identified in Table 1, section 7 and section 7a. The conditions used to induce the cholesterol response were exposing cells to 20 micromolar of forskolin for 4 hrs, or phorbol 12-myristate 13-acetate (PMA) at 100 nanomolar for 4 hrs. The experimental conditions are set forth more completely in Example 7.

More specifically, transcription regulatory sequences have been found that are induced when exposed to conditions that activate the CREB signaling cascade. Forskolin is a known activator of protein kinase A that raises cellular cyclic AMP (cAMP) levels. The CREB protein is a transcription factor that is activated by protein kinase A and directly binds DNA to activate target genes. PMA is a known activator of protein kinase C that also activates the CREB signaling cascade. One can use such a promoter in an assay to determine whether a test compound induces a CREB-mediated response. This is done, for example, by exposing a cell containing an expression construct comprising the transcription regulatory sequence operatively linked with a reporter sequence to a test compound. If the compound induces activity of the promoter, this means the compound induces a CREB-mediated response. Also, one can use the promoter in an assay to determine whether a test compound inhibits a CREB-mediated response. This is done, for example, by exposing a cell containing the expression construct to a condition that induces a CREB-mediated response (for example, exposing the cell to forskolin) and exposing the cell to the test compound. If the compound inhibits the inducible activity of the promoter, this means the compound inhibits the CREB-mediated response.

The biological response to CREB-mediated cyclic AMP signaling includes a number of events at the cellular and molecular level. cAMP is a secondary messenger used for intracellular signaling that ultimately activates the CREB transcription factor. CREB-mediated cyclic AMP signaling is involved in many biological functions including regulating the effects of glucagons and adrenaline. The activity of CREB biomarker promoters is, in turn, also correlated with these events.

In certain situations it may be useful to inhibit certain aspects of CREB activity. For example, inhibiting CREB activity may help in cases of metabolic disorders or signaling through certain G-protein coupled receptor (GPCR) pathways. The CREB biomarker promoters of this invention are useful in discovering and evaluating pharmaceutical drugs and other conditions for the ability to inhibit CREB activity.

Also, in certain situations it may be desirable to activate CREB activity. For example, activating CREB activity may help in cases of metabolic disorders or signaling through certain GPCR pathways. The CREB biomarker promoters of this invention are useful in discovering and evaluating pharmaceutical drugs and other conditions for the ability to activate CREB activity.

Conditions can be tested for their ability to induce or inhibit CREB activity, as discussed above. Conditions to which cells can be exposed for these tests include, for example, exposure of cells to any conditions that change cAMP levels within the cell, the stimulation of any GPCR protein, or other ways of activating the CREB protein e.g., exposing cells to biogenic amines, chemokines, or peptide hormones. Also, cells can be exposed to any condition that induces expression of a CREB biomarker promoter.

2.8. Glucocorticoid Response

Several promoters have been identified, the activity of each of which is positively correlated with the biological response to glucocorticoid receptor (GR) signaling ("GR biomarker promoter"). These GR response biomarker promoters are identified in Table 1, section 8 and section 8a. The conditions used to induce the GR response were exposing cells to 100 nanomolar dexamethasone, 1 micromolar prednisone, and 1 micromolar cortisone, each for 4 hrs. The experimental conditions are set forth more completely in Example 8.

More specifically, transcription regulatory sequences have been found that are induced when exposed to conditions that induce the GR-mediated response. Dexamethasone, prednisone, and cortisone are known ligands and activators of the GR protein. GR is a ligand-mediated transcription factor that binds directly to the DNA of target genes in the genome when it is bound to an activating ligand. Dexamethasone and prednisone are also potent anti-inflammatory therapeutic compounds. Activating GR with synthetic ligands is known to inhibit the inflammatory response, and is therefore, GR is an important drug target. One can use such a promoter in an assay to determine whether a test compound induces a GR-mediated response. This is done, for example, by exposing a cell containing an expression construct comprising the transcription regulatory sequence operatively linked with a reporter sequence to a test compound. If the compound induces activity of the promoter, this means the compound induces a GR-mediated response. Also, one can use the promoter in an assay to determine whether a test compound inhibits a GR-mediated response. This is done, for example, by exposing a cell containing the expression construct to a condition that induces a GR-mediated response (for example, exposing the cell to dexamethasone) and exposing the cell to the test compound. If the compound inhibits the inducible activity of the promoter, this means the compound inhibits the GR-mediated response.

The biological response to ligands for GR (or, "GR response") involves a number of events at the cellular and molecular level. These events include GR-mediated expression of genes controlling development, metabolism, and the immune response. The activity of GR response biomarker promoters is, in turn, also correlated with these events.

In certain situations it is useful to activate a GR response. Activating GR activity is known to have potent anti-inflammatory effects. The GR response biomarker promoters of this invention are useful in discovering and evaluating pharmaceutical drugs and other conditions for the ability to elicit a GR response.

Also, in certain situations it is desirable to inhibit a GR response. For example, inhibiting GR may help in cases of metabolic disorders. The GR response biomarker promoters of this invention are useful in discovering and evaluating pharmaceutical drugs and other conditions for the ability to inhibit a GR response.

Furthermore, it is known than many environmental toxins and other small molecules can act as synthetic mimics of GR ligands. Therefore, an GR response biomarker promoter can serve as a useful tool for establishing which toxins or other small molecules can serve as GR ligand mimics by, for example, exposing a recombinant cell of this invention to the compound and determining whether it induces activity of an GR biomarker promoter.

Conditions can be tested for their ability to induce or inhibit the GR response, as discussed above. GR activating conditions to which cells can be exposed for these tests include, for example, any compound or condition that simulates GR binding to its natural ligands.

2.9. PPAR-Mediated Response

Several promoters have been identified, the activity of each of which is positively correlated with the biological response to peroxisome proliferator-activated receptor (PPAR) signaling ("PPAR biomarker promoter"). These PPAR response biomarker promoters are identified in Table 1, section 9 and section 9a. The conditions used to induce the PPAR response were exposing cells to PPAR alpha and 75 micromolar of WY14643, PPAR gamma and 10 micromolar of ciglitazone, or PPAR delta and 100 nanomolar of GW501516 for 24 hrs. The experimental conditions are set forth more completely in Example 9.

More specifically, transcription regulatory sequences have been found that are induced when the PPAR-mediated response is activated. WY14643, ciglitazone and GW501516 are known ligands and activators of the PPAR alpha, gamma, and delta proteins, respectively. The PPAR family of transcription factors is a family of ligand-mediated transcription factors that binds directly to the DNA of target genes in the genome when it is bound to an activating ligand. One can use such a promoter in an assay to determine whether a test compound induces a PPAR-mediated response. This is done, for example, by exposing a cell containing an expression construct comprising the transcription regulatory sequence operatively linked with a reporter sequence to a test compound. If the compound induces activity of the promoter, this means the compound induces a PPAR-mediated response. Also, one can use the promoter in an assay to determine whether a test compound inhibits a PPAR-mediated response. This is done, for example, by exposing a cell containing the expression construct to a condition that induces a PPAR-mediated response (for example, exposing the cell to ciglitazone) and exposing the cell to the test compound. If the compound inhibits the inducible activity of the promoter, this means the compound inhibits the PPAR-mediated response.

The biological response to ligands binding to and activating PPAR (or "PPAR response") involves a number of events at the cellular and molecular level. These events include PPAR-mediated expression of genes that play essential roles in the regulation of cellular differentiation, development, lipid metabolism, and tumorigenesis in higher organisms. The activity of PPAR response biomarker promoters is, in turn, also correlated with these events.

In certain situations it is useful to activate a PPAR response. Activating PPAR activity is known to have anti-diabetic effects. The PPAR response biomarker promoters of this invention are useful in discovering and evaluating pharmaceutical drugs and other conditions for the ability to elicit a PPAR response.

Also, in certain situations it is desirable to inhibit a PPAR response. For example, inhibiting PPAR may help in cases of metabolic disorders. The PPAR response biomarker promoters of this invention are useful in discovering and evaluating pharmaceutical drugs and other conditions for the ability to inhibit a PPAR response.

Furthermore, it is known than many environmental toxins and other small molecules can act as synthetic mimics of PPAR ligands. Therefore, a PPAR response biomarker promoter can serve as a useful tool for establishing which toxins or other small molecules can serve as PPAR ligand mimics by, for example, exposing a recombinant cell of this invention to the compound and determining whether it induces activity of an PPAR biomarker promoter.

Conditions can be tested for their ability to induce or inhibit the PPAR response, as discussed above. PPAR activating conditions to which cells can be exposed for these tests include, for example, any compound or condition that simulates PPAR binding to its ligand binding domain.

2.10 RAR-Mediated Response

Several promoters have been identified, the activity of each of which is positively correlated with the biological response to retinoic acid receptor (RAR) signaling ("RAR biomarker promoter"). These RAR response biomarker promoters are identified in Table 1, section 10 and section 10a. The conditions used to induce the RAR response was exposing cells to the RAR beta protein and 100 nanomolar of adapalene for 24 hrs. The experimental conditions are set forth more completely in Example 10.

More specifically, transcription regulatory sequences have been found that are induced when upon activation of the RAR-mediated response. Adapalene is a known ligand and activator of the RAR beta protein. RAR is a ligand-mediated transcription factor that binds directly to the DNA of target genes in the genome when it is bound to an activating ligand. One can use such a promoter in an assay to determine whether a test compound induces a RAR-mediated response. This is done, for example, by exposing a cell containing an expression construct comprising the transcription regulatory sequence operatively linked with a reporter sequence to a test compound. If the compound induces activity of the promoter, this means the compound induces a RAR-mediated response. Also, one can use the promoter in an assay to determine whether a test compound inhibits a RAR-mediated response. This is done, for example, by exposing a cell containing the expression construct to a condition that induces a RAR-mediated response (for example, exposing the cell to adapalene) and exposing the cell to the test compound. If the compound inhibits the inducible activity of the promoter, this means the compound inhibits the RAR-mediated response.

The biological response to ligands binding to and activation RAR (or, "RAR response") involves a number of events at the cellular and molecular level. These events include RAR-mediated expression of genes that play essential roles in the regulation of cellular differentiation and development. The activity of RAR response biomarker promoters is, in turn, also correlated with these events.

In certain situations it is useful to activate a RAR response. Activating RAR activity through various retinoids is known to play roles in vision, cell proliferation, bone growth, and immune function. The RAR response biomarker promoters of this invention are useful in discovering and evaluating pharmaceutical drugs and other conditions for the ability to elicit a RAR response.

Also, in certain situations it is desirable to inhibit a RAR response. For example, inhibiting RAR may help in cases of carcinogenesis or tumor growth. The RAR response biomarker promoters of this invention are useful in discovering and evaluating pharmaceutical drugs and other conditions for the ability to inhibit a RAR response.

Furthermore, it is known than many environmental toxins and other small molecules can act as synthetic mimics of retinoids or other RAR ligands. Therefore, a RAR response biomarker promoter can serve as a useful tool for establishing which toxins or other small molecules can serve as RAR ligand mimics by, for example, exposing a recombinant cell of this invention to the compound and determining whether it induces activity of an RAR biomarker promoter.

Conditions can be tested for their ability to induce or inhibit the RAR response, as discussed above. RAR activating conditions to which cells can be exposed for these tests include, for example, any compound or condition that simulates RAR binding to its ligand binding domain.

2.11. Biological Response to TNFa and NFkB Activation

Several promoters have been identified, the activity of each of which is positively correlated with the biological response to tumor necrosis factor, alpha (TNFa) that is mediated by nuclear factor kappa-light-chain-enhancer of activated B cells (NFkB) ("NFkB biomarker promoter"). These NFkB biomarker promoters are identified in Table 1, section 11 and section 11a. The conditions used to induce the NFkB response was exposing cells to 20 ng/mL of TNFa for 8 hrs. The experimental conditions are set forth more completely in Example 11.

More specifically, transcription regulatory sequences have been found that are induced when exposed to TNFa. TNFa is a cytokine involved in systemic inflammation and is a member of a group of cytokines that stimulate the acute phase reaction. NFkB is a heterodimeric transcription factor that translocates to the nucleus and mediates the transcription of a vast array of proteins involved in cell survival and proliferation, inflammatory response, and anti-apoptotic factors and is activated by TNFa. One can use such a promoter in an assay to determine whether a test compound induces a NFkB-mediated response. This is done, for example, by exposing a cell containing an expression construct comprising the transcription regulatory sequence operatively linked with a reporter sequence to a test compound. If the compound induces activity of the promoter, this means the compound induces a NFkB-mediated response. Also, one can use the promoter in an assay to determine whether a test compound inhibits a NFkB-mediated response. This is done, for example, by exposing a cell containing the expression construct to a condition that induces a NFkB-mediated response (for example, exposing the cell to TNFa) and exposing the cell to the test compound. If the compound inhibits the inducible activity of the promoter, this means the compound inhibits the NFkB-mediated response.

The biological response to TNFa the "inflammation response induced by TNFa" involves a number of events at the cellular and molecular level. These events include NFkB-mediated expression of genes controlling systemic inflammation. The activity of NFkB response biomarker promoters is, in turn, also correlated with these events.

In certain situations it is useful to activate an NFkB response. Activating NFkB activity is known to stimulate the immune system. The NFkB response biomarker promoters of this invention are useful in discovering and evaluating pharmaceutical drugs and other conditions for the ability to elicit an NFkB response.

Also, in certain situations it is desirable to inhibit a NFkB response. For example, inhibiting NFkB may inhibit the effects of chronic inflammation. The NFkB response biomarker promoters of this invention are useful in discovering and evaluating pharmaceutical drugs and other conditions for the ability to inhibit a NFkB response.

Conditions can be tested for their ability to induce or inhibit the NFkB response, as discussed above. NFkB activating conditions to which cells can be exposed for these tests include, for example, any compound or condition that simulates NFkB binding to genomic targets and affecting transcription of those target genes.

2.12. Heat Shock Response

Several promoters have been identified, the activity of each of which is positively correlated with the biological response to hyperthermia or heat shock signaling ("heat shock biomarker promoter"). These heat shock response biomarker promoters are identified in Table 1, section 12 and section 12a. The conditions used to induce the heat shock response was exposing cells to 43 degrees celsius for 8 hrs. The experimental conditions are set forth more completely in Example 12.

More specifically, transcription regulatory sequences have been found that are induced when exposed to heat shock. When cells are exposed to elevated temperatures or other conditions that result in misfolded proteins, they respond by increasing the expression of chaperone proteins that help to stabilize proteins at higher temperatures. This response is mediated by the family of heat shock transcription factors. One can use such a promoter in an assay to determine whether a test compound induces the heat shock response. This is done, for example, by exposing a cell containing an expression construct comprising the transcription regulatory sequence operatively linked with a reporter sequence to a test compound. If the compound induces activity of the promoter, this means the compound induces a heat shock response. Also, one can use the promoter in an assay to determine whether a test compound inhibits a heat shock response. This is done, for example, by exposing a cell containing the expression construct to a condition that induces a heat shock response (for example, exposing the cell to 43 degrees C.) and exposing the cell to the test compound. If the compound inhibits the inducible activity of the promoter, this means the compound inhibits the heat shock response.

The biological response to heat shock ("heat shock response") involves a number of events at the cellular and molecular level. These events include heat shock transcription factor-mediated expression of genes encoding molecular chaperones. The activity of heat shock response biomarker promoters is, in turn, also correlated with these events.

In certain situations it is useful to activate the heat shock response. Activating chaperone proteins may serve as a protection in conditions that may otherwise denature proteins. The heat shock response biomarker promoters of this invention are useful in discovering and evaluating pharmaceutical drugs and other conditions for the ability to elicit a heat shock response.

Also, in certain situations it is desirable to inhibit the heat shock response. For example, inhibiting heat shock may inhibit the effects of chronic inflammation. The heat shock response biomarker promoters of this invention are useful in discovering and evaluating pharmaceutical drugs and other conditions for the ability to inhibit a heat shock response.

Conditions can be tested for their ability to induce or inhibit the heat shock response, as discussed above. Heat shock activating conditions to which cells can be exposed for these tests include, for example, any compound or condition that denatures or otherwise affects native protein folding.

2.13. Serum Response

Several promoters have been identified, the activity of each of which is correlated with the biological response to serum ("serum response biomarker promoter"). These serum response biomarker promoters are identified in Table 1, section 13 and section 13a. The conditions used to induce the serum response was exposing cells to 20% fetal bovine serum for 8 hrs. The experimental conditions are set forth more completely in Example 13.

More specifically, transcription regulatory sequences have been found that are induced when exposed to serum. When cells are exposed to serum, they activate the serum response transcription factor that directly regulates a set of target genes. One can use such a promoter in an assay to determine whether a test compound induces the serum response. This is done, for example, by exposing a cell containing an expression construct comprising the transcription regulatory sequence operatively linked with a reporter sequence to a test compound. If the compound induces activity of the promoter, this means the compound induces a serum response. Also, one can use the promoter in an assay to determine whether a test compound inhibits a serum response. This is done, for example, by exposing a cell containing the expression construct to a condition that induces a serum response (for example, exposing the cell to fetal bovine serum) and exposing the cell to the test compound. If the compound inhibits the inducible activity of the promoter, this means the compound inhibits the serum response.

The biological response to serum involves a number of events at the cellular and molecular level. These events include serum response transcription factor-mediated expression of genes involved in cell-cycle regulation, development, and muscle growth. The activity of serum response biomarker promoters is, in turn, also correlated with these events.

In certain situations it is useful to activate the serum response. The serum response in some cases may stimulate muscle growth when needed. The serum response biomarker promoters of this invention are useful in discovering and evaluating pharmaceutical drugs and other conditions for the ability to elicit a serum response.

Also, in certain situations it is desirable to inhibit the serum response. For example, inhibiting serum may inhibit tumorigenesis or unregulated cell division. The serum response biomarker promoters of this invention are useful in discovering and evaluating pharmaceutical drugs and other conditions for the ability to inhibit a serum response.

Conditions can be tested for their ability to induce or inhibit the serum response, as discussed above. Serum response activating conditions to which cells can be exposed for these tests include, for example, any compound or condition that simulates the signaling molecules found in serum.

3. Expression Constructs

An expression construct is a recombinant nucleic acid molecule comprising at least one expression control sequence operatively linked with another nucleotide sequence. A recombinant nucleic acid molecule is a nucleic acid molecule comprising two sequences that are not naturally attached to one another, for example, sequences from different species. Two sequences are operably linked when they are placed in a functional relationship with each other so that activity of a first sequence results in an action on the other part. An expression control sequence is operatively linked with a nucleotide sequence when expression of the nucleotide sequence is regulated by the action of the expression control sequence. Expression control sequences include those that regulate transcription of a nucleotide sequence, stability of the transcript or translation of the transcript.

This invention provides expression constructs comprising a biomarker transcription regulatory sequence operatively linked with a reporter sequence. The expression constructs of this invention can be incorporated into a vector or integrated, stably or transiently, into a host cell chromosome.

3.1. Transcription Regulatory Sequences

Transcription regulatory sequences are nucleotide sequences that up- or down-regulate transcription of another nucleotide sequence to which they are operatively linked, e.g., a gene.

3.1.1. Promoters

Promoters are the best-characterized transcriptional regulatory sequences because of their predictable location immediately upstream of transcription start sites. Promoters include sequences that modulate the recognition, binding and transcription initiation activity of the RNA polymerase. These sequences can be cis acting or can be responsive to trans acting factors. Promoters, depending upon the nature of the regulation, can be constitutive or regulated. They are often described as having two separate segments: core and extended promoter regions.

The core promoter includes sequences that are sufficient for RNA polymerase recognition, binding and transcription initiation. The core promoter includes the transcriptional start site, an RNA polymerase binding site and other general transcription binding sites and is where the pre-initiation complex forms and the general transcription machinery assembles. It is generally within 50 nucleotides (nt) of the transcription start site (TSS).

The extended promoter region includes the so-called proximal promoter, which extends to about 250 nucleotides upstream of the transcriptional start site (i.e., −250 nt). It includes primary regulatory elements such as specific transcription factor binding sites. It has been found that many genes have transcription regulatory elements located further up-stream. In particular, a fragment that includes most of the transcription regulatory elements of a gene can extend up to 700 nt or more up-stream of the transcription start site. (See, e.g., U.S. 2007-0161031.) In certain genes, transcription regulatory sequences have been found thousands of nucleotides upstream of the transcriptional start site.

3.1.2. Other Transcription Regulatory Sequences

Transcription regulatory sequences include nucleotide sequences that confer inducible expression of a gene (i.e., that require a substance or stimulus for increased transcription). When an inducer is present, or present at increased concentration, gene expression increases. Regulatory regions also include sequences that confer repression of gene expression (i.e., a substance or stimulus decreases transcription). When a repressor is present or at increased concentration, gene expression decreases. Regulatory regions typically bind one or more trans-acting or cis-acting proteins. Enhancers are known to influence gene expression when positioned 5' or 3' of the gene, or when positioned in or a part of an exon or an intron. Enhancers also can function at a significant distance from the gene, for example, at a distance from about 3 Kb, 5 Kb, 7 Kb, 10 Kb, 15 Kb or more.

Regulatory regions also include, in addition to transcription regulatory sequences, sequences in DNA or RNA molecules that regulate transcript stability, transcript localization, facilitate translation, splicing signals for introns, maintenance of the correct reading frame of the gene to permit in-frame translation of mRNA and, stop codons, leader sequences and fusion partner sequences, internal ribosome binding sites (IRES) elements for the creation of multigene, or polycistronic, messages, polyadenylation signals to provide proper polyadenylation of the transcript of a gene of interest and stop codons and can be optionally included in an expression vector.

3.1.3. Biomarker Transcription Regulatory Sequences

This invention provides isolated nucleic acid sequences that function as biomarker transcriptional regulatory sequences. As is well understood, DNA can be double stranded. The sequences of both strands, that is, one strand and its complement, are considered sequences useful in this invention.

Expression constructs comprising the sequences of the SEQ ID NOs of Table 1 operatively linked with a reporter sequence (e.g., a sequence encoding luciferase) were found to have activity correlated with the biological response indicated. Thus, transcription regulatory sequences that regulate transcription of genes identified in Table 1 are useful as biomarker transcription regulatory sequences for those responses or pathways.

The sequences of Table 1 were selected from transcription regulatory sequences derived from an analysis of the human genome. The analysis is based, in part, on work described in Cooper et al., Trinklein et al., US 2007-0161031 and US 2009-0018031. In short, full-length cDNAs from the Mammalian Gene Collection were aligned against the human genome. Sequences with less than 95% sequence identity, those with more than 200 bases at the 5' end of the cDNA that do not align with the genome, those that align to random sequence not assembled into reference chromosome sequences and those that represent alignment artifacts were filtered out. Alignment artifacts are identified as intronless (ungapped) alignments represented by a small number of independent cDNAs from existing cDNA libraries, as pseudogenes and as single exon genes. More specifically, a library of genetic sequences, such as GenBank, contains a number of molecules reported as cDNAs. When these sequences are aligned against the sequence of the genome, certain locations of the genome are mapped by many reported cDNAs, so that the alignment cannot be considered random: One can be highly confident that these locations represent biologically relevant cDNAs and that the upstream sequences are active transcription regulatory sequences. Other locations in the genome are mapped by few reported cDNAs or none. If the cDNA sequences are unspliced (that is they contain no introns) and the number of cDNAs mapping to a location in the genome is no more than what one would expect under a random model, then these alignments are considered artifacts. Sequences upstream of the 5' end of these cDNAs (the transcription start site) were selected as transcription regulatory sequence.

Individual genes can have more than one transcriptional start site, and in turn multiple promoters containing different transcriptional regulatory sequences. Therefore in many cases we experimentally tested multiple promoters for each gene to identify the precise promoter that regulates the biological response of interest.

Each sequence identified in Table 1 by SEQ ID NO is useful as biomarker regulatory sequence of this invention. For example, the transcription regulatory sequence can be the entire sequence of the given SEQ ID NO. Alternatively, transcription regulatory sequence can be comprised within a longer sequence from the genome from which the sequence of the SEQ ID NO is taken. For example, this sequence can be upstream of the 5' end indicated in the SEQ ID NO. The sequences of Table 1 are human sequences. In other embodiments, the transcription regulatory sequence can comprise a fragment of a sequence of Table 1. Such fragments can comprise at least 25 nt, at least 50 nt, at least 100 nt, at least 250 nt, at least 500 nt, at least 600 nt, at least 700 nt or at least 900 nt of the sequence of the provided SEQ ID NO.

Any transcription regulatory sequence of a biomarker gene of Table 1 can be used in the expression constructs of this invention. This includes, for example, the transcription start site, the core promoter, the extended promoter, an enhancer region, an inducer region, a repressor region, insulators, suppressors or transcription factor binding site. For example, the transcription regulatory sequence can comprise a sequence sufficient to initiate transcription of a second sequence to which it is operatively linked.

In certain embodiments, the sequence includes a sequence extending at least 250 nucleotides up-stream of the transcription start site. However, closer fidelity of activity to the natural environment can be achieved by including transcription regulatory sequences that are further up-stream of the transcription start site, e.g., those that exist in the extended promoter region. For example, the sequence can extend at least or no more than any of −300 nt, −400 nt, −500 nt, −600 nt, −700 nt, −800 nt, −900 nt, −1000 nt, −1200 nt, −1500 nt, −1800 nt, −2000 nt or −3000 nt from a transcription start site. Also, the sequence can comprise sequence downstream of the transcription start site. For example, up to +10 nt, +20 nt, up to +50 nt, up to +100 nt or more than +100 nt. All combinations of these ranges are contemplated. So, for example, the transcription regulatory sequence can include, consist essentially of, or consist of a sequence that spans a range from about +100 to about −3000, about +50 to about −2000, about +20 to about −1800, about +20 to about −1500, about +10 to about −1500, about +10 to about −1200, about +20 to about −1000, about +20 to about −900, about +20 to about −800, about +20 to about −700, about +20 to about −600, about +20 to about −500, about +20 to about −400, or about +20 to about −300, relative to a transcription start site.

The transcription regulatory sequence can be any polymorphic form of a sequence of Table 1. A polymorphic form is one of two or more genetically determined alternative sequences or alleles in a population. The site of the alternative form is referred to as the locus. Polymorphic forms can occur at any frequency in a population. Alleles are those polymorphic forms that occur with a frequency of preferably greater than 1%, greater than 10% or greater than 20% of a population. A polymorphism may comprise one or more base changes, an insertion, a repeat, or a deletion. A polymorphic locus may be as small as one base pair. Polymorphic forms can include single nucleotide polymorphisms (SNPs), insertions, deletions and repeated sequences. For example, polymorphisms include variable number of tandem repeats (VNTR's), hypervariable regions, minisatellites, dinucleotide repeats, trinucleotide repeats, tetranucleotide repeats, simple sequence repeats, and insertion elements such as Alu. The allelic form occurring most frequently in a selected population is sometimes referred to as the wildtype form. It is estimated that there are as many as $3 \times 10^6$ SNPs in the human genome. Diploid organisms may be homozygous or heterozygous for allelic forms. A diallelic polymorphism has two forms. A triallelic polymorphism has three forms. A polymorphism between two nucleic acids can occur naturally, or be caused by exposure to or contact with chemicals, enzymes, or other agents, or exposure to agents that cause damage to nucleic acids, for example, ultraviolet radiation, mutagens or carcinogens.

Polymorphic forms typically will share at least 95% sequence identity, at least 96% sequence identity, at least 97% sequence identity, at least 98% sequence identity, at least 99% sequence identity, at least 99.5% sequence identity, at least 99.75% sequence identity, at least 99.9% sequence identity over a comparison window of at least 200 nucleotides with a sequence of any the SEQ ID NOs given here. Alternatively, the sequence can hybridize under stringent conditions with a sequence of any SEQ ID NO given here. Such a sequence can be at least 200 nt, at least 500 nt, at least 600 nt, at least 700 nt, at least 800 nt, etc.

3.1.4 Sequence Identity and Hybridization

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

A "reference sequence" is a defined sequence used as a basis for a sequence comparison and may be a subset of a larger sequence, e.g., a complete cDNA, protein, or gene sequence.

Because two polynucleotides or polypeptides each may comprise (1) a sequence (i.e., only a portion of the complete polynucleotide or polypeptide sequence) that is similar between the two polynucleotides, or (2) a sequence that is divergent between the two polynucleotides, sequence comparisons between two (or more) polynucleotides or polypeptides are typically performed by comparing sequences of the two polynucleotides over a "comparison window" to identify and compare local regions of sequence similarity.

A "comparison window" refers to a conceptual segment of typically at least 12 consecutive nucleotides or 4 consecutive amino acid residues that is compared to a reference sequence. The comparison window frequently has a length of at least 15 or at least 25 nucleotides or at least 5 or at least 8 amino acids. The comparison window may comprise additions or deletions (i.e., gaps) of about 20 percent or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Dr., Madison, Wis.) or by inspection, and the best alignment (i.e., resulting in the highest percentage of homology over the comparison window) generated by any of the various methods is selected.

A subject nucleotide sequence or amino acid sequence is "identical" to a reference sequence if the two sequences are the same when aligned for maximum correspondence over the length of the nucleotide or amino acid sequence.

The "percentage of sequence identity" between two sequences is calculated by comparing two optimally aligned sequences over a comparison window, determining the number of positions at which the identical nucleotide or amino acid occurs in both sequences to yield the number of matched positions, dividing the number of matched positions by the total number of positions in the window of comparison (i.e., the window size), and multiplying the result by 100 to yield the percentage of sequence identity.

Unless otherwise specified, the comparison window used to compare two sequences is the length of the shorter sequence.

Methods are described further in Natl. Acad. Sci. USA 85:2444; Higgins & Sharp (1988) Gene 73:237-244; Higgins & Sharp, CABIOS 5:151-153 (1989); Corpet et al. (1988) Nucleic Acids Research 16:10881-90; Huang et al. (1992) Computer Applications in the Biosciences 8:155-65; and Pearson et al. (1994) Methods in Molecular Biology 24:307-31. Alignment is also often performed by inspection and manual alignment.

A subject nucleotide sequence or amino acid sequence is "substantially identical" to a reference sequence if the subject amino acid sequence or nucleotide sequence has at least 80% sequence identity over a comparison window. Thus, sequences that have at least 85% sequence identity, at least 90% sequence identity, at least 95% sequence identity, at least 98% sequence identity or at least 99% sequence identity with the reference sequence are also "substantially identical. Two sequences that are identical to each other are, of course, also "substantially identical".

"Hybridizing specifically to" or "specific hybridization" or "selectively hybridize to", refers to the binding, duplexing, or hybridizing of a nucleic acid molecule preferentially to a particular nucleotide sequence under stringent conditions when that sequence is present in a complex mixture (e.g., total cellular) DNA or RNA.

The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) Laboratory Techniques in Biochemistry and Molecular Biology—Hybridization with Nucleic Acid Probes part I chapter 2 "Overview of principles of hybridization and the strategy of nucleic acid probe assays", Elsevier, New York.

Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook et al. for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. In general, a signal to noise ratio of 2× (or higher) than that observed for an unrelated probe in the particular hybridization assay indicates detection of a specific hybridization.

3.1.5 Collections

In certain embodiments, this invention provides collections that comprise the biomarker transcription regulatory sequences of this invention. The collections include isolated nucleic acids, that is, nucleic acids isolated away from their natural environment or existing in a composition in which the nucleic acid is the predominant species of organic or non-solvent molecule. The collections also include expression constructs of this invention and cells comprising the expression constructs of this invention.

In certain embodiments, the transcription regulatory sequences of the collection consist of or consist essentially of the biomarker transcription regulatory sequences of this invention. In other embodiments, at least 20%, at least 30%, at least 40%, at least 50%, at least 60%, at least 70%, at least 90%, at least 95%, at least 97% or at least 99% of the transcription regulatory sequences of the collection are transcription regulatory sequences of this invention. So, for example, at least 20% of the transcription regulatory sequences of the collection can be biomarkers selected from a selected from a section of Table 1, which are biomarkers for the same biological response. Alternatively, the at least 20% can be selected from biomarker transcription regulatory sequences of at least 2, at least 3, at least 4, at least 5, at least 6, at least 7, at least 8, at least 9, at least 10, at least 11, at least 12 or at least 13 different biological responses, e.g., different sections of Table 1, in which case, biomarkers for a plurality of different biological responses will be represented. The collections can comprise no more than 2, no more than 5, no more than 10, no more than 50, no more than 100, no more than 500, no more than 1000 or no more than 5000 transcription regulatory sequences.

3.2. Reporters

In certain embodiments, a transcription regulatory sequence is operatively linked with a heterologous reporter sequence. A reporter sequence is heterologous if it is not naturally under transcriptional regulatory control of the transcription regulatory sequence. For example the transcription regulatory sequence and the reporter can be from different species or the reporter can be an artificially constructed sequence.

A reporter sequence can be any sequence that allows for the detection of a molecule of interest, such as a protein expressed by a cell, or a biological particle. Typical reporter sequences include, include, for example, those encoding light emitting proteins (e.g., luciferase (see, e.g., U.S. Pat. No. 5,292,658), fluorescent proteins (e.g., red, blue and green fluorescent proteins (see, e.g., U.S. Pat. No. 6,232, 107, which provides GFPs from *Renilla* species and other species and U.S. Pat. No. 5,625,048), lacZ (e.g., from *E. coli*), alkaline phosphatase, secreted embryonic alkaline phosphatase (SEAP), chloramphenicol acetyl transferase (CAT), hormones and cytokines and other such well-known proteins. For expression in cells, a nucleic acid encoding the reporter sequence can be expressed as a fusion protein with a protein of interest or under to the control of a promoter of interest. The expression of these reporter genes can also be monitored by measuring levels of mRNA transcribed from these genes or from detection of the translated polypeptide.

In collections using proteins that emit a detectable signal it may be useful, but not essential, for all of the reporter proteins to emit the same signal. This simplifies detection during high-throughput methods.

Alternatively, the expression constructs in the collection can contain different reporter sequences that emit different detectable signals. For example, each reporter sequence can be a light emitting reporter that emits light of a different, distinguishable color. Alternatively, the reporter sequence in each of the constructs can be a unique, pre-determined nucleotide barcode. This allows assaying a large number of the nucleic acid segments in the same batch or receptacle of cells. In an embodiment, in each construct a unique promoter sequence is cloned upstream of a unique barcode reporter sequence yielding a unique promoter/barcode reporter combination. The active promoter can drive the production of a transcript containing the unique barcode sequence. Thus, in a collection of expression constructs, each promoter's activity produces a unique transcript whose level can be measured. Since each reporter is unique, the library of expression constructs can be transfected into one large pool of cells (as opposed to separate wells) and all of the RNAs may be harvested as a pool. The levels of each of the barcoded transcripts can be detected using a microarray with the complementary barcode sequences. So the amount of fluorescence on each array spot corresponds to the strength of the promoter that drove the nucleotide barcode's transcription.

In certain embodiments of this invention, a cell or collection of cells can comprise a plurality of expression constructs of this invention which include biomarker expression control sequences of a plurality of different biological responses. In this case, it may be useful to use reporters for each expression control sequence that can be distinguished from each other, e.g., by emitting a different color or having a different bar code.

Optionally, an expression construct can contain both a first reporter sequence and a second reporter sequence. The first reporter sequence and a second reporter sequence are preferred to be different. For example, the first reporter sequence may encode the same reporter protein (e.g., luciferase or GFP), and the second reporter sequence may be a unique nucleotide barcode. In this way, transcription can yield a hybrid transcript of a reporter protein coding region and a unique barcode sequence. Such a construct could be used either in a receptacle-by-receptacle approach for reading out the signal emitted by the reporter protein (e.g., luminescence) and/or in a pooled approach by reading out the barcodes.

By using the unique, molecular barcode for each member of the collection, a large collection can be assayed in a single receptacle (such as a vial or a well in a plate) rather than in thousands of individual receptacles. This approach is more efficient and economic as it can reduce costs at all levels: reagents, plasticware, and labor.

3.3 Vectors and Chromosomes

The recombinant nucleic acid molecule can be further comprised within a vector that can be used to either infect or transiently or stably transfect cells and that may be capable of replicating inside a cell. Expression constructs can be made part of vectors, such as plasmids, cosmids, viral genomes, bacterial artificial chromosomes and the like. They also can be integrated stably into a chromosome of a host cell.

Any suitable vector can be used. There are many known in the art. Examples of vectors that can be used include, for example, plasmids or modified viruses. The vector is typically compatible with a given host cell into which the vector is introduced to facilitate replication of the vector and expression of the encoded reporter. Examples of specific vectors that may be useful in the practice of the present invention include, but are not limited to, *E. coli* bacteriophages, for example, lambda derivatives, or plasmids, for example, pBR322 derivatives or pUC plasmid derivatives; phage DNAs, e.g., the numerous derivatives of phage 1, e.g., NM989, and other phage DNA, e.g., M13 and filamentous single stranded phage DNA; yeast vectors such as the 2 mu plasmid or derivatives thereof; vectors useful in eukaryotic cells, for example, vectors useful in insect cells, such as baculovirus vectors, vectors useful in mammalian cells such as retroviral vectors, adenoviral vectors, adenovirus viral vectors, adeno-associated viral vectors, SV40 viral vectors, herpes simplex viral vectors and vaccinia viral vectors; vectors derived from combinations of plasmids and phage DNAs, plasmids that have been modified to employ phage DNA or other expression control sequences; and the like.

4. Cells Containing Expression Constructs

In another aspect this invention provides recombinant cells comprising the expression constructs of this invention. Two different embodiments are contemplated in particular.

In a first embodiment each cell or group of cells comprises a different member of the expression library. Such a library of cells is particularly useful with the arrays of this invention. Typically, the library is indexed. For example, each different cell harboring a different expression vector can be maintained in a separate container that indicates the identity of the genomic segment within. The index also can indicate the particular gene or genes that is/are under the transcriptional regulatory control of the sequences naturally in the genome.

In a second embodiment, a culture of cells is transfected with a library of expression constructs so that all of the members of the library exist in at least one cell and each cell has at least one member of the expression library. In this embodiment, a cell can comprise more than one different expression constructs (e.g., having transcription regulatory sequences of different genes). The second embodiment is particularly useful with libraries in which the reporter sequences are unique sequences that can be detected independently.

As used herein the term cells and grammatical equivalents herein in meant any cell, preferably any prokaryotic or eukaryotic cell.

Suitable prokaryotic cells include, but are not limited to, bacteria such as *E. coli*, various *Bacillus* species, and the extremophile bacteria such as thermopiles, etc.

Suitable eukaryotic cells include, but are not limited to, fungi such as yeast and filamentous fingi, including species of *Aspergillus, Trichoderma*, and *Neurospora*; plant cells including those of corn, sorghum, tobacco, canola, soybean, cotton, tomato, potato, alfalfa, sunflower, etc.; and animal cells, including fish, birds and mammals. Suitable fish cells include, but are not limited to, those from species of salmon, trout, tulapia, tuna, carp, flounder, halibut, swordfish, cod and zebrafish. Suitable bird cells include, but are not limited to, those of chickens, ducks, quail, pheasants and turkeys, and other jungle foul or game birds. Suitable mammalian cells include, but are not limited to, cells from horses, cows, buffalo, deer, sheep, rabbits, rodents such as mice, rats, hamsters and guinea pigs, goats, pigs, primates, marine mammals including dolphins and whales, as well as cell lines, such as human cell lines of any tissue or stem cell type, and stem cells, including pluripotent and non-pluripotent, and non-human zygotes.

Useful cell types include primary and transformed mammalian cell lines. Suitable cells also include those cell types implicated in a wide variety of disease conditions, even while in a non-diseased state. Accordingly, suitable cell types include, but are not limited to, tumor cells of all types (e.g. melanoma, myeloid leukemia, carcinomas of the lung, breast, ovaries, colon, kidney, prostate, pancreas and testes), cardiomyocytes, dendritic cells, endothelial cells, epithelial cells, lymphocytes (T-cell and B cell), mast cells, eosinophils, vascular intimal cells, macrophages, natural killer cells, erythrocytes, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. In some embodiments, the cells used with the methods described herein are primary disease state cells, such as primary tumor cells. Suitable cells also include known research cell lines, including, but not limited to, Jurkat T cells, NIH3T3 cells, CHO, COS, HT1080 human fibrosarcoma cells, HepG2 hepatocarcinoma cells, HeLa cells, etc. See the ATCC cell line catalog, hereby expressly incorporated by reference.

In some embodiments the cells used in the present invention are taken from an individual. In some embodiments the individual is a mammal, and in other embodiments the individual is human.

Exogenous DNA may be introduced to cells by lipofection, electroporation, or infection. Libraries in such cells may be maintained in growing cultures in appropriate growth media or as frozen cultures supplemented with Dimethyl Sulfoxide and stored in liquid nitrogen.

4.1. Transient Expression

In certain embodiments this invention provides transiently transformed cells. In this embodiment, vector DNA is delivered to living cells using a transfection reagent such as a lipofection compound. The cells express the content of this vector construct but the cell does not incorporate the vector sequence in its genome. A typical transient transfection experiment involves seeding cells in a plate or dish, then 24 hours later transfecting the vector DNA, then 12-24 hrs later applying a stimulus of interest, and then recording the reporter signal.

4.2. Stably Transformed Cells

In other embodiments, this invention provides stably transformed cells. In this embodiment, the vector DNA contains a gene for a mammalian selectable marker such as hygromycin. The vector is delivered to living cells using a transfection reagent such as a lipofection compound or in the form of a virus, and the cells are grown in the presence of the selecting antibiotic. Over the course of 5-20 or more cell passages, only cells that have integrated the vector DNA into their genome are selected for.

5. Devices and Kits

This invention provides kits and devices. The kits can include all reagents necessary to transiently transfect, infect, or transduce cells and perform assays. For example, the kits can include one or more containers comprising one or more expression constructs of this invention. They also can contain a container comprising a substrate for a reporter molecule made by the expression construct. The kit also can contain containers comprising appropriate solutions for carrying out the assay, such as appropriate buffers. The kit also can contain instructions on how to carry out the assay. The kit can also contain a container comprising cells to be transfected by the expression construct. In certain embodiments, the cells will be stably transformed to contain the expression construct. In certain embodiments, the kit contains microtiter plates, such as those having wells in multiples of 96, which are typically used in research.

6. Methods 6.1 Test Conditions

Certain methods of this invention involve exposing cells to test conditions. A test condition can be any condition different than a control condition to which a cell is exposed. Test conditions include, for example, contacting the cell with a test composition, exposing the cell to a test environmental condition, over-expressing or knocking down expression of a particular gene of interest in the cell, or combinations of these.

Test compositions include individual compounds and mixtures of compounds, e.g., a library of compounds. A compound can be any element or molecule, for example, small organic molecules and biopolymers. Drug candidates useful as test compositions in this invention include small organic molecules and biological molecules, e.g., biologics. Organic molecules used as pharmaceuticals generally are small organic molecules typically having a size up to about 5000 Da, up to about 2000 Da, or up to about 1000 Da. Certain hormones are small organic molecules. Organic biopolymers also are used as test compositions. These include, for example, polypeptides (e.g., peptides and proteins), polynucleotides (e.g., oligonucleotides or nucleic acids (e.g., inhibitory polynucleotides, such as ribozymes, antisense molecules or interfering RNA molecules), carbohydrates, lipids and molecules that combine these, for example glycoproteins, glycolipids and lipoproteins. Certain hormones are biopolymers. Antibodies find increasing use as biological pharmaceuticals. U.S. publication 2009-0035216 provides a list of antibody drugs. This list includes, for example herceptin, bevacizumab, avastin, erbitux and synagis (cell adhesion molecules).

6.2 Assays

This invention provides assays for determining whether and to what extent a test condition modulates a biological response. In certain embodiments, the methods involve exposing a recombinant cell of this invention to a test condition and measuring the amount of activity of a biological response biomarker promoter of this invention. In certain embodiments, the cells tested do not exhibit the biological response, and the methods involve exposing the cells to a test condition and determining whether the response is invoked. In other embodiments, the cells are exhibiting the biological response, e.g., by exposing the cells to conditions that elicit the response and then exposing the cells to the test condition. The expression of the reporter indicates the activity of the biomarker expression control sequence. The activity of the biomarker, in turn, indicates the activity of the biological response for which it is a biomarker.

Measuring a response includes quantitative and qualitative determinations. Qualitative measurement includes measuring a response or lack of response, regardless of intensity. A quantitative response generally involves measuring the intensity of a response.

The assays rely in part on the correlation between the activity of biomarker promoters and the activity of biological responses. This correlation can be positive (e.g., stimulation of biomarker activity correlates with activation of the response, or inhibition of the biomarker correlates with inhibition of the response) or the correlation can be negative (e.g., stimulating activity of the biomarker correlates with inhibition of the response, or inhibition of biomarker activity correlates with activation of the biological response). Thus, biomarker activity (its induction or inhibition of induction) functions as a proxy for the activity of the biological response. This, in turn, allows one to determine whether a test condition modulates (e.g., activates or inhibits) a biological response, based on the ability of the test condition to modulate activity of the biomarker promoter and the correlation of activity of the biomarker promoter with the activity of the biological response. A test condition that modulates or alters activity of a biomarker transcription regulatory sequence, by extension, modulates or alters activity of the biological response for which the transcription regulatory sequence is a biomarker.

This invention contemplates a number of different types of assays. In one assay, a cell comprising an expression construct of this invention is exposed to a test condition and the activity of the biomarker expression control sequence is determined based on expression of the reporter sequence. In another assay, a biomarker expression control sequence for a single biological response is exposed to a plurality of different test conditions, e.g., a plurality of different test compositions, and the effect of each test condition on the activity of the biomarker is determined. This can be, for example, a high throughput assay in which tens, hundreds or thousands of conditions are tested. In another embodiment, a single test condition is tested for the ability to modulate activity of one or more biomarkers for a plurality of different biological responses. For example, one can test biomarkers for at least 2, at least 5, at least 10 or at least 13 different biological responses.

A container (e.g., a multiwell plate array) containing cells harboring an expression construct of this invention is useful for high-throughput screening of promoter activity. A cell comprising an expression construct that comprises a biological response biomarker promoter operably linked with a reporter gene is exposed to a test condition under conditions chosen by the operator. Cells in which the promoters are "turned on" will express the reporter sequences under their transcriptional control. The investigator then checks each well of the device to measure the amount of reporter transcribed. Generally, this involves measuring the signal produced by a reporter protein encoded by the reporter sequence. For example, if the reporter protein is a light emitting reporter, then the amount of light produced in each cell is measured. In the case of a fluorescent protein, light can be directed to each well to induce fluorescence. The amount of signal measured is a function of the expression of the reporter sequence which, in turn, is a function of the activity of the transcriptional regulatory sequences. In certain methods, the assay is multiplexed. A number of compounds, e.g., a library of compounds can be tested. This can involve testing each compound against a recombinant cell of this invention.

The choice of a proper detection system for a particular application is well within the abilities of one of skill in the art. Exemplary detection means include, but are not limited to, detection by unaided eye, light microscopy using the eye or an optical sensor as the detector, confocal microscopy, laser scanning confocal microscopy, imaging using quantum dot color, fluorescence spectrum or other quantum dot property and wide-field imaging with a 2D CCD camera. In an exemplary embodiment, the device is a fluorescent plate reader. For example, the assay can be performed in a multiwell plate, e.g., a plate with multiples of 96 wells (e.g., 96-well plate, 384-well plate, 1536-well plate). In assays in which the reporter is luminescent or fluorescent molecule, the reporter may have to be induced to produce light. For example, in assays involving luciferase, a substrate for the enzyme is provided. In the case of fluorescent proteins, light of an exciting wavelength is provided. Commercially available microplate luminometers can be used to detect the signal. These are available from, for example, Tecan, Molecular Devices and Berthold.

Assays can involve creation of a standard curve against which measurements are compared to quantify the amount of expression.

It also can be useful to identify differences in transcription regulatory sequence activity in two cell types. For example gene expression differs when cells transform from normal to cancerous. Promoters that are overactive in cancer cells may be targets of pharmacological intervention. The arrays of this invention are useful to identify such transcription regulatory sequences. Accordingly, the investigator provides two sets of arrays comprising expression constructs in the wells. Once cell type is used for transformation in a first device and a second cell type, for transformation in a second device. The expression of reporter sequences between the two devices is compared to identify those expressed differently in the two cell types.

Using expression constructs in which the transcription regulatory sequences are operably linked to unique reporter sequences opens the possibility of performing tests without the use of multiwell plates. In such situations a single culture of cells contains the entire expression library distributed among the cells. The culture can be incubated under conditions chosen by the investigator. Then the expression products are isolated. Reporters that emit different colors can be used. As described, if the reporter is a barcode, because each expression vector has a unique nucleotide sequence tag or barcode associated with its partner nucleic acid segment, the amount of each of the reporter sequences can be measured by measuring the amount of transcript comprising each unique sequence. For example, the molecules can be detected on a DNA array that contains probes complementary to the unique sequences. The amount of hybridization to each probe indicates the amount of the reporter sequence expressed, which, in turn, reflects the activity of the transcription regulatory sequences.

EXAMPLES

1. Biological Responses 1.1 Biological Response to Hypoxia

Transient transfection assays were conducted in HT1080 human fibrosarcoma cells (ATCC, Manassas, Va.) in 96-well white plates. After 5,000 cells per well were seeded in culture medium for 24 hr, 50 ng of plasmid DNA per well was transfected with Fugene-6 transfection reagent (Roche Diagnostics, Indianapolis, Ind.) according to Fugene standard protocols. After 16 hrs, the transfection medium was removed and fresh culture medium was added into each well, and 3 replicates of each construct were moved into a chamber containing 1% oxygen, 5% $CO_2$, and 94% nitrogen. Cells were kept in the low oxygen condition for 24 hrs. In addition, 3 replicates of each construct were treated with 100 uM DFO for 24 hrs. Furthermore, 3 replicates of each construct remained in normal oxygen conditions and were not treated with DFO to serve as untreated control replicates. After induction, 100 uL of Steady-Glo (Promega) was added into each well, incubated at room temperature for 30 min, and then read in a standard plate luminometer (Molecular Devices, Sunnyvale, Calif.). Each treatment was assayed in triplicate, and the average of the 3 replicates without hypoxia induction and the average of the 3 replicates with hypoxia induction were recorded.

Transcription regulatory sequences, the activity of which is highly correlated with the hypoxia response in this assay, and that can be used as biomarkers for the hypoxia response, are identified in Table 1, section 1 and section 1a.

1.2. Biological Response to Estrogen (β-Estradiol)

Transient transfection assays were conducted in HT1080 human fibrosarcoma cells (ATCC, Manassas, Va.) in 96-well white plates. First, 10,000 cells per well were seeded in charcoal stripped culture medium for 24 hr. Next, 50 ng of reporter plasmid DNA and 10 ng of an ER cDNA expression plasmid (Origene) per well were transfected with Fugene-6 transfection reagent (Roche Diagnostics, Indianapolis, Ind.) according to Fugene standard protocols. After 16 hrs, the transfection medium was removed and fresh culture medium with or without the addition of an inducing compound was added to each well. For the no treatment control, only fresh media was added to the wells. β-estradiol (Sigma) was added to the media of the treated samples at a final concentration of 10 nM. Cells were incubated for 24 hrs after induction. After 24 hrs, 100 uL of Steady-Glo (Promega) was added into each well, incubated at room temperature for 30 min, and then read in a standard plate luminometer (Molecular Devices, Sunnyvale, Calif.). Each treatment for each reporter construct was assayed in triplicate, and the average of the 3 replicates without treatment and the average of the 3 replicates with treatment were recorded.

Transcription regulatory sequences, the activity of which is highly correlated with the estrogen response in this assay, and that can be used as biomarkers for the estrogen response, are identified in Table 1, section 2 and section 2a.

1.3. Biological Response to Artificial Androgen (Methyltrienolone)

Transient transfection assays were conducted in HT1080 human fibrosarcoma cells (ATCC, Manassas, Va.) in 96-well white plates. First, 10,000 cells per well were seeded in charcoal stripped culture medium for 24 hr. Next, 50 ng of reporter plasmid DNA and 10 ng of an AR cDNA expression plasmid (Origene) per well were transfected with Fugene-6 transfection reagent (Roche Diagnostics, Indianapolis, Ind.) according to Fugene standard protocols. After 16 hrs, the transfection medium was removed and fresh culture medium with or without the addition of an inducing compound was added to each well. For the no treatment control, only fresh media was added to the wells. Methyltrienolone (R1881) was added to the media of the treated samples at a final concentration of 10 nM. Cells were incubated for 24 hrs after induction. After 24 hrs, 100 uL of Steady-Glo (Promega) was added into each well, incubated at room temperature for 30 min, and then read in a standard plate luminometer (Molecular Devices, Sunnyvale, Calif.). Each treatment for each reporter construct was assayed in triplicate, and the average of the 3 replicates without treatment and the average of the 3 replicates with treatment were recorded.

Transcription regulatory sequences, the activity of which is highly correlated with the androgen response in this assay, and that can be used as biomarkers for the androgen response, are identified in Table 1, section 3 and section 3a.

1.4 Biological Response Mediated by p53

Transient transfection assays were conducted in HT1080 human fibrosarcoma cells (ATCC, Manassas, Va.) in 96-well white plates. First, 5,000 cells per well were seeded in standard culture medium for 24 hr. Next, 50 ng of reporter plasmid DNA per well was transfected with Fugene-6 transfection reagent (Roche Diagnostics, Indianapolis, Ind.) according to Fugene standard protocols. After 16 hrs, the transfection medium was removed and fresh culture medium with or without the addition of an inducing compound was added to each well. For the no treatment control, only fresh media was added to the wells. The p53 protein was induced by two separate treatments: nutlin (Sigma) was added to the media at a final concentration of 10 uM, and doxorubicin (Calbiochem) was added to the media at a final concentration of 200 ng/ml. Cells were incubated for 24 hrs after induction. After 24 hrs, 100 uL of Steady-Glo (Promega) was added into each well, incubated at room temperature for 30 min, and then read in a standard plate luminometer (Molecular Devices, Sunnyvale, Calif.). Each treatment for each reporter construct was assayed in triplicate, and the average of the 3 replicates without treatment and the average of the 3 replicates with treatments were recorded.

Transcription regulatory sequences, the activity of which is highly correlated with the p53 activation response in this assay, and that can be used as biomarkers for the p53 activation response, are identified in Table 1, section 4 and section 4a.

1.5 Biological Response to Inhibitors or Activators of Cholesterol Biosynthesis

Transient transfection assays were conducted in HepG2 hepatocarcinoma cells (ATCC, Manassas, Va.) in 96-well white plates. First, 10,000 cells per well were seeded in delipidated culture medium for 24 hr. Next, 100 ng of reporter plasmid DNA per well was transfected with Fugene-6 transfection reagent (Roche Diagnostics, Indianapolis, Ind.) according to Fugene standard protocols. After 16 hrs, the transfection medium was removed and fresh culture medium with or without the addition of an inducing compound was added to each well. For the no treatment control, only fresh media was added to the wells. Inductions were done by three separate treatments: lovastatin (Sigma) (HMG-CoA reductase inhibitor) was added to the media at a final concentration of 1 uM, synthechol (Sigma) (activator of cholesterol utilization pathway) was added to the media at a final concentration of 5 ug/ml, and U1866A (Sigma) (inhibitor of intracellular cholesterol transport) was added to the media at a final concentration of 1 uM. Cells were incubated for 24 hrs after induction. After 24 hrs, 100 uL of Steady-Glo (Promega) was added into each well, incubated at room temperature for 30 min, and then read in a standard plate luminometer (Molecular Devices, Sunnyvale, Calif.). Each treatment for each reporter construct was assayed in triplicate, and the average of the 3 replicates without treatment and the average of the 3 replicates with treatments were recorded.

Transcription regulatory sequences, the activity of which is highly correlated with the cholesterol response in this assay, and that can be used as biomarkers for the cholesterol response, are identified in Table 1, section 5 and section 5a.

1.6 Biological Response to Interferons

Transient transfection assays were conducted in Hela cells (ATCC, Manassas, Va.) in 96-well white plates. First, 10,000 cells per well were seeded in a starvation medium (phenol-free Opti-MEM) for 24 hr. Next, 100 ng of reporter plasmid DNA per well was transfected with Fugene-6 transfection reagent (Roche Diagnostics, Indianapolis, Ind.) according to Fugene standard protocols. After 16 hrs, the transfection medium was removed and fresh culture medium with or without the addition of an inducing compound was added to each well. For the no treatment control, only fresh media was added to the wells. Inductions were done by two separate treatments: interferon alpha (Calbiochem) was added to the media at a final concentration of 500 U/ml, and interferon gamma (Sigma) was added to the media at a final concentration of 100 ng/ml. Cells were incubated for 8 hrs after induction. After 8 hrs, 100 uL of Steady-Glo (Promega) was added into each well, incubated at room temperature for 30 min, and then read in a standard plate luminometer (Molecular Devices, Sunnyvale, Calif.). Each treatment for each reporter construct was assayed in triplicate, and the average of the 3 replicates without treatment and the average of the 3 replicates with treatments were recorded.

Transcription regulatory sequences, the activity of which is highly correlated with the interferon response in this assay, and that can be used as biomarkers for the interferon response, are identified in Table 1, section 6 and section 6a.

1.7 Biological Response to CREB Activation

Transient transfection assays were conducted in Hela cells (ATCC, Manassas, Va.) in 384-well white plates. First, 4,000 cells per well were seeded in standard culture medium for 24 hr. Next, 50 ng of reporter plasmid DNA per well was transfected with Fugene-6 transfection reagent (Roche Diagnostics, Indianapolis, Ind.) according to Fugene standard protocols. After 16 hrs, the transfection medium was removed and fresh culture medium with or without the addition of an inducing compound was added to each well. For the no treatment control, only fresh media was added to the wells. Inductions were done by two separate treatments: forskolin (Sigma) (protein kinase A activator) was added to the media at a final concentration of 20 uM, and phorbol 12-myristate 13-acetate (Promega) (protein kinase C activator) was added to the media at a final concentration of 100 nM. Cells were incubated for 4 hrs after induction. After 4 hrs, 100 uL of Steady-Glo (Promega) was added into each well, incubated at room temperature for 30 min, and then read in a standard plate luminometer (Molecular Devices, Sunnyvale, Calif.). Each treatment for each reporter construct was assayed in triplicate, and the average of the 3 replicates without treatment and the average of the 3 replicates with treatments were recorded.

Transcription regulatory sequences, the activity of which is highly correlated with the CREB activation response in this assay, and that can be used as biomarkers for the CREB activation response, are identified in Table 1, section 7 and section 7a.

1.8 Biological Response to Glucocorticoid Receptor Ligands

Transient transfection assays were conducted in HT1080 cells (ATCC, Manassas, Va.) in 96-well white plates. First, 5,000 cells per well were seeded in standard culture medium for 24 hr. Next, 50 ng of reporter plasmid DNA was transfected with Fugene-6 transfection reagent (Roche Diagnostics, Indianapolis, Ind.) according to Fugene standard protocols. After 16 hrs, the transfection medium was removed and fresh culture medium with or without the addition of an inducing compound was added to each well. For the no treatment control, only fresh media was added to the wells. Inductions were done by three separate treatments: dexamethasone (Sigma) was added to the media of the treated samples at a final concentration of 100 nM, prednisone (Sigma) was added to the media of the treated samples at a final concentration of 1 uM, and cortisone (Sigma) was added to the media of the treated samples at a final concentration of 1 uM. Cells were incubated for 4 hrs after induction. After 4 hrs, 100 uL of Steady-Glo (Promega) was added into each well, incubated at room temperature for 30 min, and then read in a standard plate luminometer (Molecular Devices, Sunnyvale, Calif.). Each treatment for each reporter construct was assayed in triplicate, and the average of the 3 replicates without treatment and the average of the 3 replicates with treatment were recorded.

Transcription regulatory sequences, the activity of which is highly correlated with the glucocorticoid-mediated response in this assay, and that can be used as biomarkers for the glucocorticoid-mediated response, are identified in Table 1, section 8 and section 8a.

1.9 Biological Response to PPAR Ligands

Transient transfection assays were conducted in HepG2 cells (ATCC, Manassas, Va.) in 96-well white plates. First, 10,000 cells per well were seeded in charcoal stripped culture medium for 24 hr. Next, 100 ng of reporter plasmid DNA and 20 ng of a PPAR cDNA expression plasmid (Origene) per well were transfected with Fugene-6 transfection reagent (Roche Diagnostics, Indianapolis, Ind.) according to Fugene standard protocols. After 16 hrs, the transfection medium was removed and fresh culture medium with or without the addition of an inducing compound was added to each well. For the no treatment control, only fresh media was added to the wells. Inductions were done by three separate treatments: WY14643 (Cayman) was added to the media of the treated samples at a final concentration of 75 uM to induce PPAR alpha, ciglitazone (Biomol) was added to the media of the treated samples at a final concentration of 10 uM to induce PPAR gamma, and GW501516 (Alexis) was added to the media of the treated samples at a final concentration of 100 nM to induce PPAR delta. Cells were incubated for 24 hrs after induction. After 24 hrs, 100 uL of Steady-Glo (Promega) was added into each well, incubated at room temperature for 30 min, and then read in a standard plate luminometer (Molecular Devices, Sunnyvale, Calif.).

Each treatment for each reporter construct was assayed in triplicate, and the average of the 3 replicates without treatment and the average of the 3 replicates with treatment were recorded.

Transcription regulatory sequences, the activity of which is highly correlated with the PPAR-mediated response in this assay, and that can be used as biomarkers for the PPAR-mediated response, are identified in Table 1, section 9 and section 9a.

1.10 Biological Response to RAR Ligands

Transient transfection assays were conducted in HepG2 cells (ATCC, Manassas, Va.) in 96-well white plates. First, 10,000 cells per well were seeded in charcoal stripped culture medium for 24 hr. Next, 100 ng of reporter plasmid DNA and 20 ng of a RAR cDNA expression plasmid (Origene) per well were transfected with Fugene-6 transfection reagent (Roche Diagnostics, Indianapolis, Ind.) according to Fugene standard protocols. After 16 hrs, the transfection medium was removed and fresh culture medium with or without the addition of an inducing compound was added to each well. For the no treatment control, only fresh media was added to the wells. Inductions were done by two separate treatments: AM-580 (Biomol) was added to the media of the treated samples at a final concentration of 100 nM for RAR alpha and adapalene (Biomol) was added to the media of the treated samples at a final concentration of 100 nM for RAR beta. Cells were incubated for 24 hrs after induction. After 24 hrs, 100 uL of Steady-Glo (Promega) was added into each well, incubated at room temperature for 30 min, and then read in a standard plate luminometer (Molecular Devices, Sunnyvale, Calif.). Each treatment for each reporter construct was assayed in triplicate, and the average of the 3 replicates without treatment and the average of the 3 replicates with treatment were recorded.

Transcription regulatory sequences, the activity of which is highly correlated with the RAR-mediated response in this assay, and that can be used as biomarkers for the RAR-mediated response, are identified in Table 1, section 10 and section 10a.

1.11 Biological Response to TNFa and NFkB Activation

Transient transfection assays were conducted in HT1080 cells (ATCC, Manassas, Va.) in 96-well white plates. First, 5,000 cells per well were seeded in standard culture medium for 24 hr. Next, 50 ng of reporter plasmid DNA was transfected with Fugene-6 transfection reagent (Roche Diagnostics, Indianapolis, Ind.) according to Fugene standard protocols. After 16 hrs, the transfection medium was removed and fresh culture medium with or without the addition of an inducing compound was added to each well. For the no treatment control, only fresh media was added to the wells. TNFa (Abcam) was added to the media of the treated samples at a final concentration of 20 ng/ml. Cells were incubated for 8 hrs after induction. After 8 hrs, 100 uL of Steady-Glo (Promega) was added into each well, incubated at room temperature for 30 min, and then read in a standard plate luminometer (Molecular Devices, Sunnyvale, Calif.). Each treatment for each reporter construct was assayed in triplicate, and the average of the 3 replicates without treatment and the average of the 3 replicates with treatment were recorded.

Transcription regulatory sequences, the activity of which is highly correlated with the TNFa-mediated response in this assay, and that can be used as biomarkers for the TNFα-mediated response, are identified in Table 1, section 11 and section 11a.

1.12 Biological Response to Heat Shock

Transient transfection assays were conducted in HT1080 cells (ATCC, Manassas, Va.) in 96-well white plates. First, 5,000 cells per well were seeded in standard culture medium for 24 hr. Next, 50 ng of reporter plasmid DNA was transfected with Fugene-6 transfection reagent (Roche Diagnostics, Indianapolis, Ind.) according to Fugene standard protocols. After 16 hrs, three replicates of each transfected construct was moved to 43 degrees C., and three replicates were kept at 37 degrees C. Cells were incubated for 8 hrs at their respective temperatures. After 8 hrs, 100 uL of Steady-Glo (Promega) was added into each well, incubated at room temperature for 30 min, and then read in a standard plate luminometer (Molecular Devices, Sunnyvale, Calif.). Each treatment for each reporter construct was assayed in triplicate, and the average of the 3 replicates without treatment and the average of the 3 replicates with treatment were recorded.

Transcription regulatory sequences, the activity of which is highly correlated with the heat shock response in this assay, and that can be used as biomarkers for the heat shock response, are identified in Table 1, section 12 and section 12a.

1.13 Biological Response to Serum

Transient transfection assays were conducted in HT1080 cells (ATCC, Manassas, Va.) in 96-well white plates. First, 7,500 cells per well were seeded in a starvation medium (phenol-free Opti-MEM) for 24 hr. Next, 50 ng of reporter plasmid DNA per well was transfected with Fugene-6 transfection reagent (Roche Diagnostics, Indianapolis, Ind.) according to Fugene standard protocols. After 16 hrs, the transfection medium was removed and fresh culture medium with or without the addition of fetal bovine serum was added to each well. For the no treatment control, only fresh media was added to the wells. Inductions were done by adding fetal bovine serum to the media at a final concentration of 20%. Cells were incubated for 8 hrs after induction. After 8 hrs, 100 uL of Steady-Glo (Promega) was added into each well, incubated at room temperature for 30 min, and then read in a standard plate luminometer (Molecular Devices, Sunnyvale, Calif.). Each treatment for each reporter construct was assayed in triplicate, and the average of the 3 replicates without treatment and the average of the 3 replicates with treatments were recorded.

Transcription regulatory sequences, the activity of which is highly correlated with the serum response in this assay, and that can be used as biomarkers for the serum response, are identified in Table 1, section 13 and section 13a.

REFERENCES

U.S. 2007-0161031, Jul. 12, 2007, TRINKLEIN, N. D. et al.
U.S. 2009-0018031, Jan. 15, 2009, TRINKLEIN, N. D. et al.
COOPER, S. J. et al., Genome Res., 2006, 16:1-10
GUILLEM, K. et al., Cell, 1997 89:9-12
TRINKLEIN, N. D. et al., Genome Res., 2003, 13:308-312
TRINKLEIN, N. D. et al., Genome Res., 2004, 14:62-66

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10663455B2). An electronic copy of the "Sequence Listing" will also be available from the USPTO upon request and payment of the fee set forth in 37 CFR 1.19(b)(3).

What is claimed is:

1. A method for determining whether a test compound activates cholesterol biosynthesis in a cell comprising:
   a) exposing a plurality of no more than 100 collections of cells to a test compound, wherein the cells in each collection comprise an expression construct comprising a promoter operatively linked with a heterologous sequence encoding a reporter, wherein the promoter within each collection is the same and each collection has a different promoter, wherein a plurality of the promoters are cholesterol biomarker promoters of different genes and are selected from the group consisting of:
   (1) SEQ ID NO: 61 (LSS); SEQ ID NO: 63 (LDLR); SEQ ID NO: 64 (INSIG1); SEQ ID NO: 67; SEQ ID NO: 70 (FASN); SEQ ID NO: 76 (MVD); SEQ ID NO: 77 (SQLE); and SEQ ID NO: 78 (IDI1);
   (2) a sequence of at least 500 nucleotides having at least 98% sequence identity to a sequence of (1); and
   (3) a fragment of at least 500 nucleotides of a sequence of (1);
   and the collections include a promoter from each of at least three different genes from the group;
   b) measuring expression of the reporter; and
   c) correlating the measurement with cholesterol biosynthesis, wherein increased expression of the reporter compared to a control, indicates that the test compound induces cholesterol biosynthesis and decreased expression of the reporter compared with a control indicates that the test compound inhibits cholesterol biosynthesis.

2. The method of claim 1, wherein (a)(2) is a sequence and (a)(3) is a fragment of at least 700 nucleotides.

3. The method of claim 1, wherein (a)(2) is a sequence and (a)(3) is a fragment of at least 900 nucleotides.

4. The method of claim 1, wherein the sequence identity is at least 99.5%.

5. The method of claim 1, wherein the plurality is no more than 50 collections of cells.

6. The method of claim 1 further comprising
   i) measuring the activity of the reporter in the absence of the test compound or under a control compound;
   ii) measuring the activity of the reporter in the presence of the test compound;
   iii) measuring the difference or ratio of reporter activity between the cells exposed to the test compound and cells that were not; and
   iv) correlating the difference or ratio between treated and untreated measurements with an cholesterol-mediated response.

7. The method of claim 1 wherein the test compound is a small organic molecule having a size up to about 5000 Da.

8. The method of claim 1 wherein the test compound is a nucleic acid derivative selected from a small interfering RNA, a micro RNA mimic and a micro RNA inhibitor.

9. The method of claim 1 wherein the expression construct is comprised in a plasmid, a virus, a transposon vector, or an artificial chromosome vector.

10. The method of claim 1 wherein the expression construct is integrated into a chromosome in the cell.

11. The method of claim 1 wherein the reporter is a light-emitting reporter, a fluorescent reporter or a colorimetric reporter.

12. The method of claim 1 wherein the reporter is luciferase.

13. The method of claim 1 wherein one of the cholesterol biomarker promoters is selected from:
   (I) SEQ ID NO: 61 (LSS);
   (II) a sequence of at least 500 nucleotides having at least 98% sequence identity to a sequence of (I); and
   (III) a fragment of at least 500 nucleotides of a sequence of (I).

14. The method of claim 1 wherein one of the cholesterol biomarker promoters is SEQ ID NO: 61 (LSS).

15. The method of claim 1 wherein one of the cholesterol biomarker promoters is selected from:
   (I) SEQ ID NO: 63 (LDLR);
   (II) a sequence of at least 500 nucleotides having at least 98% sequence identity to a sequence of (I); and
   (III) a fragment of at least 500 nucleotides of a sequence of (I).

16. The method of claim 1 wherein one of the cholesterol biomarker promoters is SEQ ID NO: 63 (LDLR).

17. The method of claim 1 wherein one of the cholesterol biomarker promoters is selected from:
   (I) SEQ ID NO: 64 (INSIG1);
   (II) a sequence of at least 500 nucleotides having at least 98% sequence identity to a sequence of (I); and
   (III) a fragment of at least 500 nucleotides of a sequence of (I).

18. The method of claim 1 wherein one of the cholesterol biomarker promoters is SEQ ID NO: 64 (INSIG1).

19. The method of claim 1 wherein one of the cholesterol biomarker promoters is selected from:
   (I) SEQ ID NO: 67;
   (II) a sequence of at least 500 nucleotides having at least 98% sequence identity to a sequence of (I); and
   (III) a fragment of at least 500 nucleotides of a sequence of (I).

20. The method of claim 1 wherein one of the cholesterol biomarker promoters is SEQ ID NO: 67.

21. The method of claim 1 wherein one of the cholesterol biomarker promoters is selected from:

(I) SEQ ID NO: 70 (FASN);
(II) a sequence of at least 500 nucleotides having at least 98% sequence identity to a sequence of (I); and
(III) a fragment of at least 500 nucleotides of a sequence of (I).

22. The method of claim 1 wherein one of the cholesterol biomarker promoters is SEQ ID NO: 70 (FASN).

23. The method of claim 1 wherein one of the cholesterol biomarker promoters is selected from:
(I) SEQ ID NO: 76 (MVD);
(II) a sequence of at least 500 nucleotides having at least 98% sequence identity to a sequence of (I); and
(III) a fragment of at least 500 nucleotides of a sequence of (I).

24. The method of claim 1 wherein one of the cholesterol biomarker promoters is SEQ ID NO: 76 (MVD).

25. The method of claim 1 wherein one of the cholesterol biomarker promoters is selected from:
(I) SEQ ID NO: 77 (SQLE);
(II) a sequence of at least 500 nucleotides having at least 98% sequence identity to a sequence of (I); and
(III) a fragment of at least 500 nucleotides of a sequence of (I).

26. The method of claim 1 wherein one of the cholesterol biomarker promoters is SEQ ID NO: 77 (SQLE).

27. The method of claim 1 wherein one of the cholesterol biomarker promoters is selected from:
(I) SEQ ID NO: 78 (IDI1);
(II) a sequence of at least 500 nucleotides having at least 98% sequence identity to a sequence of (I); and
(III) a fragment of at least 500 nucleotides of a sequence of (I).

28. The method of claim 1 wherein one of the cholesterol biomarker promoters is SEQ ID NO: 78 (IDI1).

29. The method of claim 1 comprising at least 5 different cholesterol biomarker promoters.

30. The method of claim 1 wherein the selected expression constructs comprise an expression control sequence from each of the genes: LSS, LDLR, INSIG1, FASN, MVD, SQLE and IDI1.

31. The method of claim 1, wherein the cholesterol biomarker promoters are selected from (1) SEQ ID NO: 61 (LSS), SEQ ID NO: 63 (LDLR), SEQ ID NO: 64 (INSIG1), SEQ ID NO: 67, SEQ ID NO: 70 (FASN), SEQ ID NO: 76 (MVD), SEQ ID NO: 77 (SQLE) and SEQ ID NO: 78 (IDI1).

* * * * *